US009334467B2

(12) United States Patent
Shaw et al.

(10) Patent No.: US 9,334,467 B2
(45) **Date of Patent: *May 10, 2016**

(54) USE AND PRODUCTION OF STORAGE-STABLE NEUTRAL METALLOPROTEASE

(71) Applicant: Danisco US Inc., Palo Alto, CA (US)

(72) Inventors: Andrew Shaw, San Francisco, CA (US); Louise Wallace, Menlo Park, CA (US); David A. Estell, San Francisco, CA (US); Ronaldus W. J. Hommes, Haarlem (NL); Sang-Kyu Lee, Palo Alto, CA (US); Hiroshi Oh, Cincinnati, OH (US); Eugene S. Sadlowski, Cincinnati, OH (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/037,883

(22) Filed: Sep. 26, 2013

(65) Prior Publication Data

US 2014/0134708 A1 May 15, 2014

Related U.S. Application Data

(60) Division of application No. 13/345,547, filed on Jan. 6, 2012, now Pat. No. 8,574,884, which is a continuation of application No. 12/473,735, filed on May 28, 2009, now Pat. No. 8,114,656, which is a continuation of application No. 11/581,102, filed on Oct. 12, 2006, now abandoned.

(60) Provisional application No. 60/726,448, filed on Oct. 12, 2005.

(51) Int. Cl.

| | |
|---|---|
| ***C12N 9/54*** | (2006.01) |
| ***C12N 9/50*** | (2006.01) |
| ***C12P 21/06*** | (2006.01) |
| ***C12P 19/34*** | (2006.01) |
| ***C12N 15/00*** | (2006.01) |
| ***C12N 1/20*** | (2006.01) |
| ***C11D 3/00*** | (2006.01) |
| ***C07H 21/04*** | (2006.01) |
| ***C07K 1/00*** | (2006.01) |
| ***C11D 3/386*** | (2006.01) |

(52) U.S. Cl.
CPC ............ *C11D 3/38663* (2013.01); *C11D 3/386* (2013.01); *C12N 9/54* (2013.01)

(58) Field of Classification Search
CPC ....... C11D 3/386; C11D 3/38663; C12N 9/54
USPC ......... 435/221, 219, 69.1, 91.1, 320.1, 252.3, 435/264, 263, 262, 265, 267; 510/392; 536/23.1, 23.2; 530/350
See application file for complete search history.

(56) References Cited

U.S. PATENT DOCUMENTS

| | | | |
|---|---|---|---|
| 4,430,243 | A | 2/1984 | Bragg |
| 4,515,705 | A | 5/1985 | Moedell |
| 4,515,707 | A | 5/1985 | Brooks |
| 4,537,706 | A | 8/1985 | Severson |
| 4,550,862 | A | 11/1985 | Barker et al. |
| 4,561,998 | A | 12/1985 | Wertz et al. |
| 4,597,898 | A | 7/1986 | Vandermeer |
| 4,683,195 | A | 7/1987 | Mullis et al. |
| 4,683,202 | A | 7/1987 | Mullis |
| 4,965,188 | A | 10/1990 | Mullis et al. |
| 4,968,451 | A | 11/1990 | Scheibel et al. |
| 4,977,252 | A | 12/1990 | Chiu |
| 5,354,559 | A | 10/1994 | Morehouse |
| 5,486,303 | A | 1/1996 | Capeci et al. |
| 5,489,392 | A | 2/1996 | Capeci et al. |
| 5,496,710 | A | 3/1996 | Nagao et al. |
| 5,516,448 | A | 5/1996 | Capeci et al. |
| 5,565,145 | A | 10/1996 | Watson et al. |

(Continued)

FOREIGN PATENT DOCUMENTS

| | | |
|---|---|---|
| AU | 2001235626 | 8/2001 |
| WO | WO97/11151 | 3/1997 |
| WO | WO00/32601 | 6/2000 |
| WO | WO02/14490 | 2/2002 |
| WO | WO2004/011619 | 2/2004 |
| WO | WO2007/044993 | 4/2007 |

OTHER PUBLICATIONS

Altschul, S.F., et al., "Basic Local Alignment Search Tool." *J. Mol. Biol.*, 215:403-410, 1990.

Altschul, S.F., et al., "Local Alignment Statistics." *Meth. Enzymol.* 266:460-480, 1996.

Broun, P., et al., "Catalytic plasticity of fatty acid modification enzymes underlying chemical diversity of plant lipids." *Science*, 282: 1315-1317, 1998.

(Continued)

*Primary Examiner* — Ganapathirama Raghu
(74) *Attorney, Agent, or Firm* — Danisco US Inc.

(57) ABSTRACT

The present invention provides methods and compositions comprising at least one neutral metalloprotease enzyme that has improved storage stability. In some embodiments, the neutral metalloprotease finds use in cleaning and other applications. In some particularly preferred embodiments, the present invention provides methods and compositions comprising neutral metalloprotease(s) obtained from *Bacillus* sp. In some more particularly preferred embodiments, the neutral metalloprotease is obtained from *B. amyloliquefaciens*. In still further preferred embodiments, the neutral metalloprotease is a variant of the *B. amyloliquefaciens* neutral metalloprotease. In yet additional embodiments, the neutral metalloprotease is a homolog of the the *B. amyloliquefaciens* neutral metalloprotease. The present invention finds particular use in applications including, but not limited to, cleaning, bleaching and disinfecting.

19 Claims, 21 Drawing Sheets

(56) References Cited

U.S. PATENT DOCUMENTS

| | | | |
|---|---|---|---|
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,691,297 A | 11/1997 | Nassano et al. | |
| 5,692,650 A | 12/1997 | Wolter et al. | |
| 5,739,023 A | 4/1998 | Harada et al. | |
| 5,879,584 A | 3/1999 | Bianchetti et al. | |
| 5,929,022 A | 7/1999 | Velazquez | |
| 5,935,826 A | 8/1999 | Bhue et al. | |
| 6,225,464 B1 | 5/2001 | Hiler et al. | |
| 6,294,514 B1 | 9/2001 | Welling | |
| 6,306,812 B1 | 10/2001 | Perkins et al. | |
| 6,326,348 B1 | 12/2001 | Vinson et al. | |
| 6,376,445 B1 | 4/2002 | Bettiol et al. | |
| 7,098,017 B2 | 8/2006 | von der Osten et al. | |
| 8,114,656 B2 | 2/2012 | Shaw et al. | |
| 8,574,884 B2 * | 11/2013 | Shaw et al. | 435/221 |

OTHER PUBLICATIONS

Chamberlin, M., et al. "New RNA Polymerase from *Escherichia coli* infected with Bacteriophage T7." *Nature* 228: 227-231, 1970.

Chang, S., et al., "High Frequency Transformation of *Bacillus subtilis* Protoplasts by Plasmid DNA." *Mol. Gen. Genet*., 168: 111-115, 1979.

Chica, R.A., et al., "Semi-rational approaches to engineering enzyme activity: combining the benefits of directed evolution and rational design." *Curr. Opin. Biotechnol*., vol. 16: 378-384, 2005.

Cho, S.-J., et al., "Purification and Characterization of Proteases from Bacillus amyloliquefaciens Isolated from Traditional Soybean Fermentation Starter." *J. Agric. Food Chem*. 51, 7664-7670, 2003.

Dahlquist, F.W., et al., "Role of Calcium in the Thermal Stability of Thermolysin." Biochem., 15: 1103-1111, 1976.

Devereux, J., et al., "A Comprehensive set of sequence analysis programs for the VAX." *Nucl. Acid Res*., 12: 387-395, 1984.

Devos, D., et al., "Practical limits of function prediction." *Proteins: Structure, Function, and Genetics*, vol. 41: 98-107, 2000.

Dürrschmidt, P., et al., "An Engineered dislude bridge mimics the effects of calcium to protect neutral protease against local unfolding." *FEBS J*., 272: 1523-1534, 2005.

Feng, D.-F., et al. "Progessive Sequences Alignment as a Prerequisite to Correct Phylogenetic Trees." *J. Mol. EvoL*., 35:351-360, 1987.

Ferrari, E., et al., *Genetics*. In Harwood, *Bacillus*, Plenum Publishing Corporation, pp. 57-72, 1989.

Galante, Y.M., "Enzyme Applications in Detergency and in Manufacturing Industries." *Curr. Organic Chem*. 7, 1399-1422, 2003.

Guo, H.H., et al., "Protein tolerance to random amino acid change." *PNAS*. 101(25): 9205-9210, 2004.

Gryczan, T.J., et al., "Characterization of *Staphylococcus aureus* Plasmids Introduced by Transformation into *Bacillus subtilis*." *Bacteriol*., 134: 318-329, 1978.

Henikoff, S., et al., "Amino acid substitution matrices from protein blocks." *Proc. Natl. Acad. Sci. USA*, 89: 10915-10919, 1992.

Higgins, D.G., et al. "Clustal: a package for performing multiple sequence alignment on a microcomputer." *CABIOS* 5: 151-153, 1989.

Higgins, D.G., "Fast and sensitive multiple sequence alignments on a microcomputer." *Gene* 73: 237-244,1988.

Holmquist, B., "Metal Substitutions and Inhibition of Thermolysin: Spectra of the Cobalt Enzyme." *J. Biol. Chem*., 249: 4601-4607, 1974.

Kacian, D.L., et al., "Replicating RNA Molecule Suitable for a Detailed Analysis of Extracellular Evolution and Replication."*Proc. Natl. Acad. Sci. USA* 69: 3038-3042, 1972.

Karlins, S., et al., "Applications and statistics for multiple high-scoring segments in molecular sequences." *Proc. Natl. Acad. Sci. USA* 90: 5873-5787, 1993.

Mansfield, J., et al., "Extreme Stabilization of a Thermolysib-like Protease by an Engineered Disulfide Bond." *J. Biol. Chem*., 272: 11152-11156, 1997.

Needleman, S.B., "A General Method Applicable to the Search for Similarities in the Amino Acid Sequence of Two Proteins." *J. Mol. Biol*., 48: 443-453, 1970.

Neidhardt, F.C., et al., "Culture Medium for Enterobacteria." *J. Bacteriol*., 119(3): 736-747, 1974.

Pearson, W.R., et al., "Improved tools for biological sequence comparison." *Proc. Natl. Acad. Sci. USA* 85: 2444-2448, 1988.

Schallmey, M., et al., "Developments in the use of Bacillus species for industrial production." *Can. J. Microbiol*. 50: 1-17, 2004.

Seffernick, J.A., et al., "Melamine deaminase and Atrazine chlorohydrolase: 98 percent identical but functionally different." *J. Bacteriol*. 183(8): 2405-2410, 2001.

Sen, S., et al., "Developments in directed evolution for improving enzyme functions." *Appl. Biochem. Biotechnol*. 143: 212-223, 2007.

Shimada, H., et al., "The nucleotide sequence and some properties of the neutral protease gene of *Bacillus amyloliquefaciens*." *J. Biotechnol*., 2: 75-85, 1985.

Smith, T.F., et al., "Comparison of Biosequences." *Adv. Appl. Math*. 2: 482-489, 1981.

Springman, E.B., et al.,"Zinc Content and Function in Human Fibroblast Collagenase." *Biochemistry* 34, 15713-15720, 1995.

Strongin, A., et al., Sequence regions of Bacilli metalloproteinases that can affect enzyme thermostability, *Protein Seq. Data Anal*, 4: 355-361, 1991.

Van Den Berg, B., et al., "Characterization of a novel stable biocatalyst obtained by protein engineering." *Biotechnol. Appl. Biochem*. 30: 35-40, 1999.

Vasantha, N., et al., "Genes for Alkaline Protease and Neutral Protease from *Bacillus amyloliquefaciens* Contain a Large Open Reading Frame Between the Regions Coding for Signal Sequence and Mature Protein." *J. of Bacteriology*, 159(3): 811-819, 1984.

Vriend, G., et al., "Prediction and analysis of structure, stability and unfolding of thermolysin-like proteases." *J. of Computer-Aided Molecular Design*, 7: 367-396, 1993.

Whisstock, J.C., et al., "Prediction of protein function from protein sequence." *Q. Rev. Biophysics*. 36 (3): 307-340, 2003.

Willenbrock, F., et al., "The second zinc atom in the matrix metalloproteinase catalytic domain is absent in the full-length enzymes: a possible role for the C-terminal domain." *FEBS Lett*. 358:189-192, 1995.

Witkowski, A., et al., "Conversion of β-Ketoacyl Synthase to a Malonyl Decarboxylase by replacement of the active cysteine with glutamine." *Biochemistry* 38: 11643-11650, 1999.

Wu, D, et al. "The Litigation Amplification Reaction (LAR)-Amplification of Specific DNA Sequences Using Sequential Rounds of Template-Dependent Ligation." *Genomics* 4:560, 1989.

International Search Report for International Publication No. WO 2007/044993, Apr. 19, 2007.

European Search Report for European Patent Application No. EP 11 16 5353 dated Nov. 2, 2011.

Frigerio, et al., "Cumulative stabilizing effects of hydrophobic interactions on the surface of the neutral protease from Bacillus subtilis", Protein Eng., 1996, 9:439-45.

Hardy, et al., "Stabilization of Bacillus stearothermophilus neutral protease by introduction of prolines", FEBS Lett, 1993, 317:89-92.

Van Den Burg, et al., "Engineering an enzyme to resist boiling", Proc Natl Acad Sci, 1998, 95:2056-60.

GenBank Accession No. AAA22621, Apr. 26, 1993, Takagi, M., et al., Thermostable Neutral Protease (nprT) [Geobacillus stearothermophilus], www.ncbi.nlm.nih.gov/protein/aaa22621.

GenBank Accession No. AAA22670, Apr. 26, 1993, Shimada, et al.

GenBank Accession No. AAB05346, Apr. 26, 1993, Vasantha, N., et al., Preproneutral Protease (gtg start codon) [Bacillus amyloliquefaciens]; www.ncbi.nlm.nih.gov/protein/AAB05346.1?report=gpwithparts&log@=seqview.

GenBank Accession No. AAV30844, Aug. 15, 2006, Niu, et al. http://www.ncbi.nlm.nih.gov/protein/AAV30844.

GenBank Accession No. AAW59490.1, Jan. 24, 2005, Tian, B.Y., et al., Extracellular Neutral Protease Precursor [Brevibacillus laterosporus]; www.ncbi.nlm.nih.gov/protein/aaw59490.

GenBank Accession No. ABC49679, Apr. 30, 2006, Bai, et al.

GenBank Accession No. AY867791.1, Jan. 20, 2005, Tian, et al.

GenBank Accession No. DQ291130.1, Apr. 30, 2006, Bai, et al.

* cited by examiner

```
B.amylo_nprE    ---------MGLGKKLSVAVAASFMSLTISLPGVQAAENPQLKENLTNFVPKHSLVQSEL
B.sub_nprE      ---------MGLGKKLSVRVAASFMSLSISLPGVQAAEGHQLKENQTNFLSKKPIAQSEL
S.aur_aur       -----------------MRKFSRYAFTSMATVTLLSSLTPAALASDTNHKPATSDINFEI
B.ste_nprT      ------MNKRAMLGAIGLAFGLLAAPIGASAKGESIVWNEQWKTPSFVSGSLLNGGEQAL
B.cal_npr       ------MNKRAMLGAIGLAFGLMAWPFGASAKGKSMVWNEQWKTPSFVSGSLLG---RCS
B.thu_nprB      MKKKSLALVLATGMAVTTFGGTGSAFADSKNVLSTKKYNETVQSPEFVSGDLTEATGKKA
B.cer_nprC      MKKKSLALVLATGMAVTTFGGTGSAFADSKNVLSTKKYNETVQSPEFISGDLTEATGKKA
B.sub_nprB      --MRNLTKTSLLLAGLCTAAQMVFVTHASAEESIEYDHTYQTPSYIIEKSPQKPVQNTTQ
B.cerE33L_npr   --MKNKKNFVKIGLTTGVMLSVIMPYGDAYAATEDLKVETKEDTFRTGNLTVPSQKSAEN

B.amylo_nprE    PSVSDKAIKQYLKQNGKVFKGNPSERLKLIDQTTDDLGYKHFRYVPVVNGVPVKDSQVII
B.sub_nprE      SAPNDKAVKQFLKKNSNIFKGDPSKSVKLVESTTDALGYKHFRYAPVVNGVPIKDSQVIV
S.aur_aur       TQKSD-AVKALKELPKSENVKNHYQDYSVTDVKTDKKGFTHYTLQPSVDGVHAPDKEVKV
B.ste_nprT      EELVYQYVDRENGTFRLGGRARDRLALI--GKQTDELGHTVMRFEQRHHGIPVYGTMLAA
B.cal_npr       QELVYRYLDQEKNTFQLGGQARERLSLI--GNKLDELGHTVMRFEQAIAASLCMGAVLVA
B.thu_nprB      ESVVFDYLNAAKGDYKLGEKSAQDCFKVKQAKKDAVTDSTVLRLQQVYEGVPVWGSTQVA
B.cer_nprC      ESVVFDYLNAAKGDYKLGEKSAQDSFKVKQVKKDAVTDSTVVRMQQVYEGVPVWGSTQVA
B.sub_nprB      KESLFSYLDKHQTQFKLKGNANSHFRVSK-TIKDPKTKQTFFKLTEVYKGIPIYGFEQAV
B.cerE33L_npr   VAKDALKGKTEQALSSKQVNTESKVNYNVTQSRKSYDGTTLVRLQQTYEGRDVYGYQLTA
                        .                              .         .    .

B.amylo_nprE    HVDKSNNVYAINGELNNDVSAKTANSKKLSANQALDHAYKAIGKSPEAVSNGTVANKNKA
B.sub_nprE      HVDKSDNVYAVNGELHNQSAAKTDNSQKVSSEKALALAFKAIGKSPDAVSNGAAKNSNKA
S.aur_aur       HADKSGKVVLING----DTDAKKVKPTNKVTLSKDEAADKAFNAVKIDKNKAKNLQDDVI
B.ste_nprT      HV-KDGELIALSGSLIPNLDGQPRLKKAKTVTVQQAEAIAEQDVTETVTKERPITENGER
B.cal_npr       HV-NDGELSSLSGTLIPNLD-KRTLKTEAAISIQQAEMIAKQDVADRVTKERPAAEEGKP
B.thu_nprB      HVSKDGSLKVLSGTVAPDLDKKEKLKNKNKIEGAKAIEIAQKDLGIT-----PKYEVEPK
B.cer_nprC      HVSKDGSLKVLSGTVAPDLDKKEKLKNKNKIEGAKAIEIAQQDLGVT-----PKYEVEPK
B.sub_nprB      AMKENKQVKSFFGKVHPQIKDVSVTPSISEKKAIHTARRELEASIGKI----EYLDGEPK
B.cerE33L_npr   HINDDGVLTSVSGDSAQDLQQQEDLKQPITLSEEDAKKQLFKIYGDNLT---FVEEPEIK
                   ..  :  . *    :                                     :

B.amylo_nprE    ELKAAATKDGKYRLAYDVTIRYIEPEPANWEVTVDAETGKILKKQNKVE-----------
B.sub_nprE      ELKAIETKDGSYRLAYDVTIRYVEPEPANWEVLVDAETGSILKQQNKVE-----------
S.aur_aur       KENKVEIDGDSNKYIYNIELITVTPEISHWKVKIDADTGAVVEKTNLVK-----------
B.ste_nprT      TRLVIYPTDGTARLAYEVNVRFLTPVPGNWVYIIDATDGAILNKFNQID-----------
B.cal_npr       TRLVIYPDEETPRLAYEVNVRFLTPVPGNWIYMIDAADGKVLNKWNQMD-----------
B.thu_nprB      ADLYVYQNGEETTYAYVVNLNFLDPSPGNYYYFIEADSGKVLNKYNKLDHVANEDKSPVK
B.cer_nprC      ADLYVYQNGEETTYAYVVNLNFLDPSPGNYYYFIEADSGKVLNKFNTIDHVTNDDKSPVK
B.sub_nprB      GELYIYPHDGEYDLAYLVRLSTSEPEPGYWHYFIDAKNGKVIESFNAIH-----------
B.cerE33L_npr   QVVYVDENTNKATSAYQITFSASTPEYVSGTVLIDAFVGDLLKELVQKLGIQVDSSI---
                               * : .    *        ::*  * :::.

B.amylo_nprE    ----------------HAATTGTGTTLKGKTVSLNISSESGKYVLRDLSKPTGTQIITYD
B.sub_nprE      ----------------HAAATGSGTTLKGATVPLNISYEGGKYVLRDLSKPTGTQIITYD
S.aur_aur       ----------------EAAATGTGKGVLGDTKDININSIDGGFSLEDLTHQGKLSAYNFN
B.ste_nprT      -----SRQPGGGQPVAGASTVGVGRGVLGDQKYINTTYSSYYGYYYLQDNTRGSGIFTYD
B.cal_npr       -----EAKPGGAQPVAGTSTVGVGRGVLGDQKYINTTYSSYYGYYYLQDNTRGSGIFTYD
B.thu_nprB      QEAPKQEVKPAVKPVTGTNAVGTGKGVLGDTKSLNTTLSS--SSYYLQDNTRGATIFTYD
B.cer_nprC      QEAPKQDAKAVVKPVTGTNKVGTGKGVLGDTKSLNTTLSG--SSYYLQDNTRGATIFTYD
B.sub_nprB      ------------------EAAGTGIGVSGDEKSFDVTEQN--GRFYLADETRGKGINTFD
B.cerE33L_npr   -----VQSATSNKSQDPSKLIGTGKDDLGMNRTFGISQRS-DGTYILADYSRGKGIETYT
                                    .* *    *    :. .  .                 .:
```

*FIG. 3A*

```
B.amylo_nprE     LQNREY-------NLPGTLVSSTTNQFTTSSQRAAVDAHYNLGKVYDYFYQKFNRNSYDN
B.sub_nprE       LQNRQS-------RLPGTLVSSTTKIFTSSSQRAAVDAHYNLGKVYDYFYSNFKRNSYDN
S.aur_aur        DQTGQ-----------ATLITNEDENFVKDDQRAGVDANYYAKQTYDYYKNTFGRESYDN
B.ste_nprT       GRNR--------TVLPGSLWTDGDNQFTASYDAAAVDAHYYAGVVYDYYKNVHGRLSYDG
B.cal_npr        GRNR--------TVLPGSLWADGDNQFFASYDAAAVDAHYYAGVVYDYYKNVHGRLSYDG
B.thu_nprB       AKNR--------TTLPGTLWVDADNVFNAAYDAAAVDAHYYAGKTYDYYKATFNRNSIND
B.cer_nprC       AKNR--------STLPGTLWADADNVFNAAYDAAAVDAHYYAGKTYDYYKATFNRNSIND
B.sub_nprB       AKNLNETLFTLLSQLIGYTGKEIVSGTSVFNEPAAVDAHANAQAVYDYYSKTFGRDSFDQ
B.cerE33L_npr    ANYKDYNNYR--RNIWGYLDDLVTSNSTNFTDPKAVSAHYLATKVYDFYQEKYSRNSFDN
                  .              .       .      :  .*.*:     .**::   . * * :

B.amylo_nprE     KGGKIVSSVHYG----------SRYNNAAWIGDQMIYGDGDGSFFSPLSGSMDVTAHEMT
B.sub_nprE       KGSKIVSSVHYG----------TQYNNAAWTGDQMIYGDGDGSFFSPLSGSLDVTAHEMT
S.aur_aur        HGSPIVSLTHVNHYGGQ-----DNRNNAAWIGDKMIYGDGDGRTFTNLSGANDVVAHELT
B.ste_nprT       SNAAIRSTVHYG----------RGYNNAFWNGSQMVYGDGDGQTFLPFSGGIDVVGHELT
B.cal_npr        SNAAIRSTVHYG----------RGYNNAFWNGSQMVYGDGDGQTFLPFSGGIDVVGHELT
B.thu_nprB       AGAPLKSTVHYG----------SKYNNAFWNGSQMVYGDGDGVTFTSLSGGIDVIGHELT
B.cer_nprC       AGAPLKSTVHYG----------SNYNNAFWNGSQMVYGDGDGVTFTSLSGGIDVIGHELT
B.sub_nprB       NGARIITSTVHVG----------KQWNNAAWNGVQMVYGDGDGSKFKPLSGSLDIVAHEIT
B.cerE33L_npr    NGQKVISVVHGWNTNGTNKGNPKQWFNAFSNGAMLVYGD-------PIVRAFDVAGHEFT
                  .  : * .*                **   *  ::***        :  . *: .**:*

B.amylo_nprE     HGVTQETANLNYENQPGALNESFSDVFGYFND-----TEDWDIGEDITVSQPALRSLSNP
B.sub_nprE       HGVTQETANLIYENQPGALNESFSDVFGYFND-----TEDWDIGEDITVSQPALRSLSNP
S.aur_aur        HGVTQETANLEYKDQSGALNESFSDVFGYFVD-----DEDFLMGEDVYTPGKEGDALRSM
B.ste_nprT       HAVTDYTAGLVYQNESGAINEAMSDIFGTLVEFYANRNPDWEIGEDIYTPGVAGDALRSM
B.cal_npr        HAVTDYTAGLVYQNESGAINEAMSDIFGTLVEFYANRNPDWEIGEDIYTPGVAGDALRSM
B.thu_nprB       HAVTEYSSDLIYQNESGALNEAISDVFGTLVEFYDNRNPDWEIGEDIYTPGKAGDALRSM
B.cer_nprC       HAVTENSSNLIYQNESGALNEAISDIFGTLVEFYDNRNPDWEIGEDIYTPGKAGDALRSM
B.sub_nprB       HAVTQYSAGLLYQGEPGALNESISDIMGAMAD-----RDDWEIGEDVYTPGIAGDSLRSL
B.cerE33L_npr    HAVTRNESGLEYAGEAGAINEAISDILGVAVEKYANNGKFNWTMGEQSGRIFRDMKNPSS
                 *.**   :.* * .:.**:**::**::*   :             :            .

B.amylo_nprE     TKYGQPDNFKNYKNLPNITDAGDYGGVHTNSGIPNKAAYN----------TITKIGVNKAE
B.sub_nprE       TKYNQPDNYANYRNLPNTDEGDYGGVHTNSGIPNKAAYN----------TITKLGVSKSQ
S.aur_aur        SNPEQFGQPSHMKDYVYTEK-DNGGVHTNSGIPNKAAYN----------VIQAIGKSKSE
B.ste_nprT       SDPAKYGDPDHYSKRYTGTQ-DNGGVHTNSGIINKAAYLLSQGGVHYGVSVNGIGRDKMG
B.cal_npr        SDPAKYGDPDHYSKRYTGTQ-DNGGVHTNSGIINKAAYLLSQGGVHYGVSVTGIGRDKMG
B.thu_nprB       SDPTKYGDPDHYSKRYTGTS-DNGGVHTNSGIINKQAYLLANGGTHYGVTVTGIGKDKLG
B.cer_nprC       SDPTKYGDPDHYSKRYTGSS-DNGGVHTNSGIINKQAYLLANGGTHYGVTVTGIGKDKLG
B.sub_nprB       EDPSKQGNPDHYSNRYTGTE-DYGGVHINSSIHNKAAYLLAEGGVHHGVQVEGIGREASE
B.cerE33L_npr    ISSRYPEDYRHYNNLPIDAAHDHGGVHTNSSIINKVAYLIASGGNHNGVNVQGIGEDKMF
                  .     :  :  .       * **** **.* ** **            :  :* .

B.amylo_nprE     QIYYRALTVYLTPSSTFKDAKAALIQSARDLYG--SQDAASVEAAWNAVGL- (SEQ ID NO:173)
B.sub_nprE       QIYYRALTTYLTPSSTFKDAKAALIQSARDLYG--STDAAKVEAAWNAVGL- (SEQ ID NO:174)
S.aur_aur        QIYYRALTEYLTSNSNFKDCKDALYQAAKDLYD-EQTAEQVYEAWNEVGVE  (SEQ ID NO:175)
B.ste_nprT       KIFYRALVYYLTPTSNFSQLRAACVQAAADLYGSTSQEVNSVKQAFNAVGVY (SEQ ID NO:176)
B.cal_npr        KIFYRALVYYLTPTSNFSQLRAACVQAAADLYGSTSQEVNSVKQAFNAVGVY (SEQ ID NO:177)
B.thu_nprB       AIYYRANTQYFTQSTTFSQARAGAVQAAADLYGANSAEVNAVKQSFSAVGIN (SEQ ID NO:178)
B.cer_nprC       AIYYRANTQYFTQSTTFSQARAGAVQAAADLYGANSAEVAAVKQSFSAVGVN (SEQ ID NO:179)
B.sub_nprB       QIYYRALTYYVTASTDFSMMKQAAIEAANDLYGEGSKQSASVEKAYEAVGIL (SEQ ID NO:180)
B.cerE33L_npr    DIFYYANTDELNMTSDFKELKEACIRVATNLYGKDSSEVQAVQQAFKAAYI- (SEQ ID NO:181)
                  *:* * .  .. .: *.  : .  . * :**.  .     *  ::. . :
```

FIG. 3B

```
Thermolysin             ITGTSTVGVGRGVLGDQKNINTTYSTYY---YLQDNTR--GNGIFTYDAK
B. stearothermophilus   ITGTSTVGVGRGVLGDQKNINTTYSTYY---YLQDNTR--GNGIFTYDAK
B. caldoyticus          VAGTSTVGVGRGVLGDQKYINTTYSSYYGYYYLQDNTR--GSGIFTYDGR
B. cereus               VTGTNKVGTGKGVLGDTKSLNTTLSGSS--YYLQDNTR--GATIFTYDAK
B. brevis               VTAT-----GKGVLGDTKQFETTKQGST--YMLKDTTR--GKGIETYTAN
B. polymyxa             -------ATGKGVLGDSKSFTTTASGSS--YQLKDTTR--GNGIVTYTAS
B. pumilus              ---AAATGSGTTLKGATVPLNISYEGGK--YVLRDLSKPTGTQIITYDLQ
B. subtilis var.        ---AAATGSGTTLKGATVPLNISYEGGK--YVLRDLSKPTGTQIITYDLQ
B. subtilis             --------------------------------------------------
B. amyloliquefaciens    ---AATTGTGTTLKGKTVSLNISSESGK--YVLRDLSKPTGTQIITYDLQ

                                                                        94
Thermolysin             YRTT-LPGSLWADADNQFFASYDAPAVDAHYYAGVTYDYYKNVHNRLSYD
B. stearothermophilus   YRTT-LPGSLWADADNQFFASYDAPAVDAHYYAGVTYDYYKNVHNRLSYD
B. caldoyticus          NRTV-LPGSLWADGDNQFFASYDAAAVDAHYYAGVVYDYYKNVHGRLSYD
B. cereus               NRST-LPGTLWADADNVFNAAYDAAAVDAHYYAGKTYDYYKATFNRNSIN
B. brevis               NRTS-LPGTLMTDSDNYWT---DGAAVDAHAHAQKTYDYFRNVHNRNSYD
B. polymyxa             NRQS-IPGTLLTDADNVWN---DPAGVDAHAYAAKTYDYYKSKFGRNSID
B. pumilus              NRQSRLPGTLVSSTTKTFTSSSQRAAVDAHYNLGKVYDYFYSNFKRNSYD
B. subtilis var.        NRQSRLPGTLVSSTTKTFTSSSQRAAVDAHYNLGKVYDYFYSNFKRNSYD
B. subtilis             -------------------------AVDAHYNLGKVYDYFYSNFKRNSYD
B. amyloliquefaciens    NREYNLPGTLVSSTTNQFTTSSQRAAVDAHYNLGKVYDYFYQKFNRNSYD
                                                 .****     .***:  .  * * :

                                                                       142
Thermolysin             GNNAAIRSSVHYSQGYNNAFWNGSQMVYGDGDG--QTFIPLSGGIDVVAH
B. stearothermophilus   GNNAAIRSSVHYSQGYNNAFWNGSQMVYGDGDG--QTFIPLSGGIDVVAH
B. caldoyticus          GSNAAIRSTVHYGRGYNNAFWNGSQMVYGDGDG--QTFLPFSGGIDVVGH
B. cereus               DAGAPLKSTVHYGSNYNNAFWNGSQMVYGDGDG--VTFTSLSGGIDVIGH
B. brevis               GNGAVIRSTVHYSTRYNNAFWNGSQMVYGDGDG--TTFLPLSGGLDVVAH
B. polymyxa             GRGLQLRSTVHYGSRYNNAFWNGSQMTYGDGDGDGSTFIAFSGDPDVVGH
B. pumilus              NKGSKIVSSVHYGTQYNNAAWTGDQMIYGDGDG--SFFSPLSGSLDVTAH
B. subtilis var.        NKGSKIVSSVHYGTQYNNAAWTGDQMIYGDGDG--SFFSPLSGSLDVTAH
B. subtilis             NKGSKIVSSVHYGTQYNNAAWTGDQMIYGDGDG--SFFSPLSGSLDVTAH
B. amyloliquefaciens    NKGGKIVSSVHYGSRYNNAAWIGDQMIYGDGDG--SFFSPLSGSMDVTAH
                        . .  : *:***.  **** * *.** ******    * .:**. ** .*

                                                                       192
Thermolysin             ELTHAVTDYTAGLIYQNESGAINEAISDIFGTLVKFYANKNPDWEIGEDV
B. stearothermophilus   ELTHAVTDYTAGLIYQNESGAINEAISDIFGTLVEFYANKNPDWEIGEDV
B. caldoyticus          ELTHAVTDYTAGLVYQNESGAINEAMSDIFGTLVEFYANRNPDWEIGEDI
B. cereus               ELTHAVTENSSNLIYQNESGALNEAISDIFGTLVEFYDNRNPDWEIGEDI
B. brevis               ELTHAVTERTAGLVYQNESGALNESMSDIFGAMVD-----NDDWLMGEDI
B. polymyxa             ELTHGVTEYTSNLEYYGESGALNEAFSDVIGNDIQ-----RKNWLVGDDI
B. pumilus              EMTHGVTQETANLIYENQPGALNESFSDVFGYFND-----TEDWDIGEDI
B. subtilis var.        EMTHGVTQETANLIYENQPGALNESFSDVFGYFND-----TEDWDIGEDI
B. subtilis             EMTHGVTQETANLIYENQPGALNESFSDVFGYFND-----TEDWDIGEDI
B. amyloliquefaciens    EMTHGVTQETANLNYENQPGALNESFSDVFGYFND-----TEDWDIGEDI
                        *:**.**: ::.* * .:.**:**::**::*   .       :* :*:*:

                                                                       238
Thermolysin             YTPGISGDSLRSMSDPAKYGDPDHYSKR----YTGTQDNGGVHINSGIIN
B. stearothermophilus   YTPGISGDSLRSMSDPAKYGDPDHYSKR----YTGTQDNGGVHINSGIIN
B. caldoyticus          YTPGVAGDALRSMSDPAKYGDPDHYSKR----YTGTQDNGGVHTNSGIIN
B. cereus               YTPGKAGDALRSMSDPTKYGDPDHYSKR----YTGSSDNGGVHTNSGIIN
B. brevis               YTPGRSGDALRSLQDPAAYGDPDHYSKR----YTGSQDNGGVHTNSGINN
B. polymyxa             YTPNICGDALRSMSNPTLYDQPHHYSNL----YKGSSDNGGVHTNSGIIN
B. pumilus              T---VSQPALRSLSNPTKYNQPDNYANYRNLPNTDEGDYGGVHTNSGIPN
B. subtilis var.        T---VSQPALRSLSNPTKYNQPDNYANYRNLPNTDEGDYGGVHTNSGIPN
B. subtilis             T---VSQPALRSLSNPTKYNQPDNYANYRNLPNTDEGDYGGVHTNSGIPN
B. amyloliquefaciens    T---VSQPALRSLSNPTKYGQPDNFKNYKNLPNTDAGDYGGVHTNSGIPN
                             .  :***:.:*: *.:*.:: :      ..  * **** **** *
```

FIG. 4A

```
                                                                         288
Thermolysin           KAAYLISQGGTHYGVSVVGIGRDKLGKIFYRALTQYLTPTSNFSQLRAAA
B. stearothermophilus KAAYLISQGGTHYGVSVVGIGRDKLGKIFYRALTQYLTPTSNFSQLRAAA
B. caldoyticus        KAAYLLSQGGVHYGVSVTGIGRDKMGKIFYRALVYYLTPTSNFSQLRAAC
B. cereus             KQAYLLANGGTHYGVTVTGIGKDKLGAIYYRANTQYFTQSTTFSQARAGA
B. brevis             KAAYLLAEGGTHYGVRVNGIGRTDTAKIYYHALTHYLTPYSNFSAMRRAA
B. polymyxa           KAYYLLAQGGTFHGVTVNGIGRDAAVQIYYSAFTNYLTSSSDFSNARAAV
B. pumilus            KAAYN----------TITKLGVSKSQQIYYRALTTYLTPSSTFKDAKAAL
B. subtilis var.      KAAYN----------TITKLGVSKSQQIYYRALTTYLTPSSTFKDAKAAL
B. subtilis           KAAYN----------TITKLGVSKSQQIYYRALTTYLTPSSTFKDAKAAL
B. amyloliquefaciens  KAAYN----------TITKIGVNKAEQIYYRALTVYLTPSSTFKDAKAAL
                      *  *            :  :*      *:* * . *:*  : *.  : .

                                                316
Thermolysin           VQSATDLYGSTSQEVASVKQAFDAVGVK (SEQ ID NO:182)
B. stearothermophilus VQSATDLYGSTSQEVASVKQAFDAVGVK (SEQ ID NO:183)
B. caldoyticus        VQAAADLYGSTSQEVNSVKQAFNAVGVY (SEQ ID NO:184)
B. cereus             VQAAADLYGANSAEVAAVKQSFSAVGVN (SEQ ID NO:185)
B. brevis             VLSATDLFGANSRQVQAVNAAYDAVGVK (SEQ ID NO:186)
B. polymyxa           IQAAKDLYGANSAEATAAAKSFDAVG-  (SEQ ID NO:187)
B. pumilus            IQSARDLYGST--DAAKVEAAWNAVGL- (SEQ ID NO:188)
B. subtilis var.      IQSARDLYGST--DAAKVEAAWNAVGL- (SEQ ID NO:189)
B. subtilis           IQSARDLYGST--DAAKVEAAWNAVGL- (SEQ ID NO:190)
B. amyloliquefaciens  IQSARDLYGSQ--DAASVEAAWNAVGL- (SEQ ID NO:191)
                      : :* **:*:   :.  .  ::.***
```

FIG. 4B

```
NprE      ---AATTGTGTTLK--GKTVSLNISSESGKYVLRDLSKPTGTQIITYDLQNREYNLPGT-
1BQB.A    ---AAATGTGKGVL--GDTKDININSIDGGFSLEDLT--HQGKLSAYNFNDQTGQ--AT-
1EZM      ----AEAGGPGGNQKIGKYTYGSDYGPLIVNDRCEMD---DGNVITVDMNSSTDDSKTTP
1NPC      VTGTNKVGTGKGVL--GDTKS--LNTTLSGSSYYLQDNTRGATIFTYDAKNRS-TLPGT-

NprE      LVSSTTNQFTTSS---QRAAVDAHYNLGKVYDYFYQKFNRNSYDNKGGKIVSSVHYGS--
1BQB.A    LITNEDENFVKDD---QRAGVDANYYAKQTYDYYKNTFGRESYDNHGSPIVSLTHVNHYG
1EZM      FRFACPTNTYKQVNGAYSPLNDAHF-FGGVVFKLYRDWFGTSPLT--HKLYMKVHYGR--
1NPC      LWADADNVFNAAY---DAAAVDAHYYAGKTYDYYKATFNRNSINDAGAPLKSTVHYGS-

NprE      ---RYNNAAWIGDQMIYGDGDGSFFSPLSGSMDVTAHEMTHGVTQETANLNYENQPGALN
1BQB.A    GQDNRNNAAWIGDKMIYGDGDGRTFTNLSGANDVVAHEITHGVTQQTANLEYKDQSGALN
1EZM      ---SVENAYWDGTAMLFGDGAT-MFYPLV-SLDVAAHEVSHGFTEQNSGLIYRGQSGGMN
1NPC      ---NYNNAFWNGSQMVYGDGDGVTFTSLSGGIDVIGHELTHAVTENSSNLIYQNESGALN

NprE      ESFSDVFGYFND-----TEDWDIGEDITVS---QPALRSLSNPTKYG-QPDNFKNYKNLP
1BQB.A    ESFSDVFGYFVD-----DEDFLMGEDVYTPGKEGDALRSMSNPEQFG-QPSHMKDYVY--
1EZM      EAFSDMAGEAAEFYMRGKNDFLIGYDIKKG---SGALRYMDQPSRDGRSIDNASQYYNG-
1NPC      EAISDIFGTLVEFYDNRNPDWEIGEDIYTPGKAGDALRSMSDPTKYG-DPDHYSKRYTGS

NprE      NTDAGDYGGVHTNSGIPNKAAYNTIT----------KIGVN--KAEQIYYRALTVYLTPS
1BQB.A    --TEKDNGGVHTNSGIPNKAAYNVIQ----------AIGKS--KSEQIYYRALTEYLTSN
1EZM      -------IDVHHSSGVYNRAFYLLAN----------SPGWDTRKAFEVFVDANRYYWTAT
1NPC      ----SDNGGVHTNSGIINKQAYLLANGGTHYGVTVTGIGKD-KLGAIYYRANTQYFTQS

NprE      STFKDAKAALIQSARDLYG--SQDAASVEAAWNAVGL- (SEQ ID NO:192)
1BQB.A    SNFKDLKDALYQAAKDLYE-QQTAEQVYEAWNEVGVE  (SEQ ID NO:193)
1EZM      SNYNSGACGVIRSAQNRNY-SAADVTRAFSTVGVTCP  (SEQ ID NO:194)
1NPC      TTFSQARAGAVQAAADLYGANSAEVAAVKQSFSAVGVN (SEQ ID NO:195)
```

FIG. 5

Fragment 1:
*AATTGTGTTL*KGKTVSLNISSESGKYVLRDLSKPTGTQIITYDLQNREYNLPGTLVSSTTNQFTT SSQRAAVDAHYNLGKVYDYFYQKFNRNSYDNKGGKIVSSVHYGSRYNNAAWIGDQMIYGDGDGSF FSPLSGSMDVTAHEMTHGVTQETANLNYENQPGALNESFSDVFGYFNDTEDWDIGEDITVSQPAL RSLSNPTKYGQPDNFKNYKNLPNT (SEQ ID NO:222)

Fragment 2 (Frayed):
*DAGDYGGVHT*NSGIPNKAAYNTITKIGVNKAEQIYYRALTVYLTPSSTFKDAKAALIQSARDLYG SQDAASVEAAWNAVGL (SEQ ID NO:223)

Fragment 3:
*AATTGTGTTL*KGKTVSLNISSESGKYVLRDLSKPTGTQIITYDLQNREYNLPGTLVSSTTNQFTT SSQRAAVDAHYNLGKVYDYFYQKFNRNSYDNKGGKIVSSVHYGSRYNNAAWIGDQMIYGDGDGSF FSPLSGSMDVTAHEMTHGVTQETANLNYENQPGALNESFSDVFGYFNDTEDWDIGEDITVSQPALRS (SEQ ID NO:224)

Fragment 4 (Deduced based on size):
*AATTGTGTTL*KGKTVSLNISSESGKYVLRDLSKPTGTQIITYDLQNREYNLPGTLVSSTTNQFTT SSQRAAVDAHYNLGKVYDYFYQKFNRNSYDNKGGKIVSSVHYGSRYNNAAWIGDQMIYGDGDGSF FSPLSGS*MDV* (SEQ ID NO:225)

Fragment 5:
*LSNPTKYGQP*DNFKNYKNLPNTDAGDYGGVHTNSGIPNKAAYNTITKIGVNKAEQIYYRALTVYL TPSSTFKDAKAALIQSARDLYGSQDAASVEAAWNAVGL (SEQ ID NO:226)

*FIG. 35*

USE AND PRODUCTION OF STORAGE-STABLE NEUTRAL METALLOPROTEASE

CROSS REFERENCE TO RELATED APPLICATIONS

The present application is a Divisional of U.S. application Ser. No. 13/345,547, filed Jan. 6, 2012, now U.S. Pat. No. 8,574,884, which is a Continuation of U.S. application Ser. No. 12/473,735, filed on May 28, 2009, now U.S. Pat. No. 8,114,656, which is a Continuation of Ser. No. 11/581,102, filed Oct. 12, 2006 (Abandoned), which claims priority to U.S. Provisional Patent Application Ser. No. 60/726,448, filed Oct. 12, 2005.

SEQUENCE LISTING

The sequence listing submitted via EFS, in compliance with 37 C.F.R. §1.52(e), is incorporated herein by reference. The sequence listing text file submitted via EFS contains the file "GC889-2-C2-SEQLIST.txt", created on Dec. 12, 2013, which is 151,552 bytes in size.

FIELD OF THE INVENTION

The present invention provides methods and compositions comprising at least one neutral metalloprotease enzyme that has improved storage stability. In some embodiments, the neutral metalloprotease finds use in cleaning and other applications. In some particularly preferred embodiments, the present invention provides methods and compositions comprising neutral metalloprotease(s) obtained from *Bacillus* sp. In some more particularly preferred embodiments, the neutral metalloprotease is obtained from *B. amyloliquefaciens*. In still further preferred embodiments, the neutral metalloprotease is a variant of the *B. amyloliquefaciens* neutral metalloprotease. In yet additional embodiments, the neutral metalloprotease is a homolog of the the *B. amyloliquefaciens* neutral metalloprotease. The present invention finds particular use in applications including, but not limited to cleaning, bleaching and disinfecting.

BACKGROUND OF THE INVENTION

Detergent and other cleaning compositions typically include a complex combination of active ingredients. For example, most cleaning products include a surfactant system, enzymes for cleaning, bleaching agents, builders, suds suppressors, soil-suspending agents, soil-release agents, optical brighteners, softening agents, dispersants, dye transfer inhibition compounds, abrasives, bactericides, and perfumes. Despite the complexity of current detergents, there are many stains that are difficult to completely remove. Furthermore, there is often residue build-up, which results in discoloration (e.g., yellowing) and diminished aesthetics due to incomplete cleaning. These problems are compounded by the increased use of low (e.g., cold water) wash temperatures and shorter washing cycles. Moreover, many stains are composed of complex mixtures of fibrous material, mainly incorporating carbohydrates and carbohydrate derivatives, fiber, and cell wall components (e.g., plant material, wood, mud/clay based soil, and fruit). These stains present difficult challenges to the formulation and use of cleaning compositions.

In addition, colored garments tend to wear and show appearance losses. A portion of this color loss is due to abrasion in the laundering process, particularly in automated washing and drying machines. Moreover, tensile strength loss of fabric appears to be an unavoidable result of mechanical and chemical action due to use, wearing, and/or washing and drying. Thus, a means to efficiently and effectively wash colored garments so that these appearance losses are minimized is needed.

In sum, despite improvements in the capabilities of cleaning compositions, there remains a need in the art for detergents that remove stains, maintain fabric color and appearance, and prevent dye transfer. In addition, there remains a need for detergent and/or fabric care compositions that provide and/or restore tensile strength, as well as provide anti-wrinkle, anti-bobbling, and/or anti-shrinkage properties to fabrics, as well as provide static control, fabric softness, maintain the desired color appearance, and fabric anti-wear properties and benefits. In particular, there remains a need for the inclusion of compositions that are capable of removing the colored components of stains, which often remain attached to the fabric being laundered. In addition, there remains a need for improved methods and compositions suitable for textile bleaching.

SUMMARY OF THE INVENTION

The present invention provides methods and compositions comprising at least one neutral metalloprotease enzyme that has improved storage stability. In some embodiments, the neutral metalloprotease finds use in cleaning and other applications. In some particularly preferred embodiments, the present invention provides methods and compositions comprising neutral metalloprotease(s) obtained from *Bacillus* sp. In some more particularly preferred embodiments, the neutral metalloprotease is obtained from *B. amyloliquefaciens*. In still further preferred embodiments, the neutral metalloprotease is a variant of the *B. amyloliquefaciens* neutral metalloprotease. In yet additional embodiments, the neutral metalloprotease is a homolog of the the *B. amyloliquefaciens* neutral metalloprotease. The present invention finds particular use in applications including, but not limited to cleaning, bleaching and disinfecting.

The present invention provides novel neutral metalloproteases, novel genetic material encoding the neutral metalloprotease enzymes, and neutral metalloprotease proteins obtained from *Bacillus* sp., in particular, *B. amyloliquefaciens*, and variant proteins developed therefrom. In particular, the present invention provides neutral metalloprotease compositions obtained from *Bacillus* sp., particularly *B. amyloliquefaciens*, DNA encoding the protease, vectors comprising the DNA encoding the neutral metalloprotease, host cells transformed with the vector DNA, and an enzyme produced by the host cells. The present invention also provides cleaning compositions (e.g., detergent compositions), animal feed compositions, and textile and leather processing compositions comprising neutral metalloprotease(s) obtained from a *Bacillus* species, in particular, *B. amyloliquefaciens*. In alternative embodiments, the present invention provides mutant (i.e., variant) neutral metalloproteases derived from the wild-type neutral metalloproteases described herein. These mutant neutral metalloproteases also find use in numerous applications.

The present invention provides isolated neutral metalloproteases obtained from a *Bacillus* species, in particular, *B. amyloliquefaciens*. In further embodiments, the neutral metalloprotease comprises the amino acid sequence set forth in SEQ ID NO:3. In additional embodiments, the present invention provides isolated neutral metalloproteases comprising at least 45% amino acid identity with the neutral metalloprotease comprising SEQ ID NO:3. In some embodiments, the isolated neutral metalloproteases comprise at least 50% identity, preferably at least 55%, more preferably at least 60%, yet more preferably at least 65%, even more preferably at least 70%, more preferably at least 75%, still more preferably at least 80%, more preferably 85%, yet more preferably 90%, even more preferably at least 95%, and most preferably 99% identity with the neutral metalloprotease comprising SEQ ID NO:3.

The present invention also provides isolated neutral metalloproteases having immunological cross-reactivity with the metalloprotease obtained from *B. amyloliquefaciens*, as well as compositions comprising these neutral metalloproteases. In alternative embodiments, the neutral metalloproteases have immunological cross-reactivity with neutral metalloproteases comprising the amino acid sequence set forth in SEQ ID NO:3 and/or SEQ ID NO:18. In still further embodiments, the neutral metalloproteases have cross-reactivity with fragments (i.e., portions) of the neutral metalloprotease of *B. amyloliquefaciens*, and/or neutral metalloprotease comprising the amino acid sequence set forth in SEQ ID NO:3 and/or SEQ ID NO:18. Indeed, it is intended that the present invention encompass fragments (e.g., epitopes) of the *B. amyloliquefaciens* metalloprotease that stimulate an immune response in animals (including, but not limited to humans) and/or are recognized by antibodies of any class. The present invention further encompasses epitopes on metalloproteases that are cross-reactive with *B. amyloliquefaciens* metalloprotease epitopes. In some embodiments, the metalloprotease epitopes are recognized by antibodies, but do not stimulate an immune response in animals (including, but not limited to humans), while in other embodiments, the metalloprotease epitopes stimulate an immune response in at least one animal species (including, but not limited to humans) and are recognized by antibodies of any class. The present invention also provides means and compositions for identifying and assessing cross-reactive epitopes.

In some embodiments, the present invention provides the amino acid sequences set forth in SEQ ID NO:3 and/or SEQ ID NO:4. In alternative embodiments, the sequence comprises substitutions at least one amino acid position in SEQ ID NO:3 and/or SEQ ID NO:4. In some preferred embodiments, the present invention provides neutral metalloprotease variants having an amino acid sequence comprising at least one substitution of an amino acid made at a position equivalent to a position in a *B. amyloliquefaciens* neutral metalloprotease comprising the amino acid sequence set forth in SEQ ID NO:3 and/or SEQ ID NO:4. In alternative embodiments, the present invention provides neutral metalloprotease variants having an amino acid sequence comprising at least one substitution of an amino acid made at a position equivalent to a position in a *B. amyloliquefaciens* neutral metalloprotease comprising at least a portion of SEQ ID NO:3 and/or SEQ ID NO:4. In some alternative preferred embodiments, the neutral metalloproteases comprise multiple mutations in at least a portion of SEQ ID NO:3, 4 and/or 18.

In yet additional embodiments, the present invention provides the amino acid sequence set forth in SEQ ID NO:13. In alternative embodiments, the sequence comprises substitutions at least one amino acid position in SEQ ID NO:13. In some preferred embodiments, the present invention provides neutral metalloprotease variants having an amino acid sequence comprising at least one substitution of an amino acid made at a position equivalent to a position in a *B. amyloliquefaciens* neutral metalloprotease comprising the amino acid sequence set forth in SEQ ID NO:13. In alternative embodiments, the present invention provides neutral metalloprotease variants having an amino acid sequence comprising at least one substitution of an amino acid made at a position equivalent to a position in a *B. amyloliquefaciens* neutral metalloprotease comprising at least a portion of SEQ ID NO:13. In some alternative preferred embodiments, the neutral metalloproteases comprise multiple mutations in at least a portion of SEQ ID NO:13.

In some particularly preferred embodiments, these variants have improved performance as compared to wild-type *B. amyloliquefaciens* neutral metalloprotease. The present invention also provides neutral metalloprotease variants having at least one improved property as compared to the wild-type neutral metalloprotease. In some additional particularly preferred embodiments, these variants have improved stability as compared to wild-type *B. amyloliquefaciens* neutral metalloprotease. In some further preferred embodiments, these variants have improved thermostability as compared to wild-type *B. amyloliquefaciens* neutral metalloprotease. In yet additional preferred embodiments, these variants have improved performance under lower or higher pH conditions, as compared to wild-type *B. amyloliquefaciens* neutral metalloprotease.

The present invention also provides neutral metalloproteases comprising at least a portion of the amino acid sequence set forth in SEQ ID NO:3, 4 and/or 18. In some embodiments, the nucleotide sequences encoding these neutral metalloproteases comprise a nucleotide sequence selected from SEQ ID NOS:1, 2, 12, and/or 13. In some embodiments, the neutral metalloproteases are variants having amino acid sequences that are similar to that set forth in SEQ ID NO:3 and/or SEQ ID NO:4. In yet additional embodiments, the neutral metalloproteases are variants and/or homologs. In still further embodiments, the neutral metalloproteases are those set forth in any of FIGS. 3 through 5. In other embodiments, the neutral metalloproteases are variants of those set forth in FIGS. 3, 4 and/or 5.

The present invention also provides expression vectors comprising a polynucleotide sequence encoding at least a portion of the neutral metalloprotease set forth in SEQ ID NO:3. The present invention further provides expression vectors comprising a polynucleotide sequences that encode at least one neutral metalloprotease variant having amino acid sequence(s) comprising at least one substitution of an amino acid made at a position equivalent to a position in a *Bacillus* neutral metalloprotease comprising the amino acid sequence set forth in SEQ ID NO:3. In further embodiments, the present invention provides host cells comprising these expression vectors. In some particularly preferred embodiments, the host cells are selected from the group consisting of *Bacillus* sp. The present invention also provides the neutral metalloproteases produced by the host cells.

The present invention also provides compositions comprising at least a portion of an isolated neutral metalloprotease of obtained from a *Bacillus* sp., particularly, *B. amyloliquefaciens*, wherein at least a portion of the neutral metalloprotease is encoded by a polynucleotide sequence selected from SEQ ID NOS:1, 2, 12 and/or 13. In further embodiments, the present invention provides host cells comprising these expression vectors. In some particularly preferred embodiments, the host cells are *Bacillus* sp. The present invention also provides the neutral metalloproteases produced by the host cells.

The present invention also provides variant neutral metalloproteases, wherein the neutral metalloproteases comprise at least one substitution corresponding to the amino acid positions in SEQ ID NO:3 and/or SEQ ID NO:18, and wherein variant metalloproteases have better performance in at least one property, as compared to wild-type *B. amyloliquefaciens* metalloprotease.

The present invention also provides variant amino acids, wherein the variants comprise at least one substitution of an amino acid made at a position equivalent to a position in a neutral metalloprotease comprising the amino acid set forth in SEQ ID NO:18, wherein the position(s) is or are selected from positions 1, 3, 4, 5, 6, 11, 12, 13, 14, 16, 21, 23, 24, 25, 31, 32, 33, 35, 36, 38, 44, 45, 46, 47, 48, 49, 50, 51, 54, 55, 58, 59, 60, 61, 62, 63, 65, 66, 69, 70, 76, 85, 86, 87, 88, 90, 91, 92, 96, 97, 98, 99, 100, 102, 109, 110, 111, 112, 113, 115, 117, 119, 127, 128, 129, 130, 132, 135, 136, 137, 138, 139, 140, 146, 148, 151, 152, 153, 154, 155, 157, 158, 159, 161, 162, 169, 173, 178, 179, 180, 181, 183, 184, 186, 190, 191, 192, 196, 198, 199, 200, 202, 203, 204, 205, 210, 211, 214, 215, 216, 217, 218, 219, 220, 221, 222, 223, 224, 228, 229, 237, 239, 240, 243, 244, 245, 248, 252, 253, 260, 261, 263, 264, 265, 267, 269, 270, 273, 277, 280, 282, 283, 284, 285, 286, 288, 289, 290, 292, 293, 296, 297, and 299.

The present invention also provides isolated neutral metalloprotease variants having an amino acid sequence comprising at least one substitution of an amino acid made at a position equivalent to a position in a neutral metalloprotease comprising the amino acid sequence set forth in SEQ ID NO:18. In some embodiments, the isolated neutral metalloprotease variants have substitutions that are made at positions equivalent to positions 1, 3, 4, 5, 6, 11, 12, 13, 14, 16, 21, 23, 24, 25, 31, 32, 33, 35, 36, 38, 44, 45, 46, 47, 48, 49, 50, 51, 54, 55, 58, 59, 60, 61, 62, 63, 65, 66, 69, 70, 76, 85, 86, 87, 88, 90, 91, 92, 96, 97, 98, 99, 100, 102, 109, 110, 111, 112, 113, 115, 117, 119, 127, 128, 129, 130, 132, 135, 136, 137, 138, 139, 140, 146, 148, 151, 152, 153, 154, 155, 157, 158, 159, 161, 162, 169, 173, 178, 179, 180, 181, 183, 184, 186, 190, 191, 192, 196, 198, 199, 200, 202, 203, 204, 205, 210, 211, 214, 215, 216, 217, 218, 219, 220, 221, 222, 223, 224, 228, 229, 237, 239, 240, 243, 244, 245, 248, 252, 253, 260, 261, 263, 264, 265, 267, 269, 270, 273, 277, 280, 282, 283, 284, 285, 286, 288, 289, 290, 292, 293, 296, 297, and 299 of a neutral metalloprotease comprising an amino acid sequence set forth in SEQ ID NO:18.

In additional embodiments, the isolated neutral metalloprotease variant comprise comprises at least one mutation selected from T004C, T004E, T004H, T004I, T004K, T004L, T004M, T004N, T004P, T004R, T004S, T004V, T004W, T004Y, G012D, G012E, G012I, G012K, G012L, G012M, G012Q, G012R, G012T, G012V, G012W, K013A, K013C, K013D, K013E, K013F, K013G, K013H, K013I, K013L, K013M, K013N, K013Q, K013S, K013T, K013V, K013Y, T014F, T014G, T014H, T014I, T014K, T014L, T014M, T014P, T014Q, T014R, T014S, T014V, T014W, T014Y, S023A, S023D, S023F, S023G, S023I, S023K, S023L, S023M, S023N, S023P, S023Q, S023R, S023S, S023T, S023V, S023W, S023Y, G024A, G024D, G024F, G024G, G024H, G024I, G024K, G024L, G024M, G024N, G024P, G024R, G024S, G024T, G024V, G024W, G024Y, K033H, Q045C, Q045D, Q045E, Q045F, Q045H, Q045I, Q045K, Q045L, Q045M, Q045N, Q045P, Q045R, Q045T, Q045W, N046A, N046C, N046E, N046F, N046G, N046H, N046I, N046K, N046L, N046M, N046P, N046Q, N046R, N046S, N046T, N046V, N046W, N046Y, R047E, R047K, R047L, R047M, R47Q, R047S, R047T, Y049A, Y049C, Y049D, Y049E, Y049F, Y049H, Y049I, Y049K, Y049L, Y049N, Y049R, Y049S, Y049T, Y049V, Y049W, N050D, N050F, N050G, N050H, N050I, N050K, N050L, N050M, N050P, N050Q, N050R, N050W, N050Y, T054C, T054D, T054E, T054F, T054G, T054H, T054I, T054K, T054L, T054M, T054N, T054P, T054Q, T054R, T054S, T054V, T054W, T054Y, S058D, S058H, S058I, S058L, S058N, S058P, S058Q, T059A, T059C, T059E, T059G, T059H, T059I, T059K, T059L T059M, T059N, T059P, T059Q, T059R, T059S, T059V, T059W, T060D, T060F, T060I, T060K, T060L, T060N, T060Q, T060R, T060V, T060W, T060Y, T065C, T065E, T065F, T065H, T065I, T065K, T065L, T065M, T065P, T065Q, T065R, T065V, T065Y, S066C, S066D, S066E, S066F, S066H, S066I, S066K, S066L, S066N, S066P, S066Q, S066R, S066T, S066V, S066W, S066Y, Q087A, Q087D, Q087E, Q087H, Q087I, Q087K, Q087L, Q087M, Q087N, Q087R, Q087S, Q087T, Q087V, Q087W, N090C, N090D, N090E, N090F, N090G, N090H, N090K, N090L, N090R, N090T, N096G, N096H, N096K, N096R, K097H, K097Q, K097W, K100A, K100D, K100E, K100F, K100H, K100N, K100P, K100Q, K100R, K100S, K100V, K100Y, R110A, R110C, R110E, R110H, R110K, R110L, R110M, R110N, R110Q, R110S, R110Y, D119E, D119H, D119I, D119L, D119Q, D119R, D119S, D119T, D119V, D119W, G128C, G128F, G128H, G128K, G128L, G128M, G128N, G128Q, G128R, G128W, G128Y, S129A, S129C, S129D, S129F, S129G, S129H, S129I, S129K, S129L, S129M, S129Q, S129R, S129T, S129V, S129W, S129Y, F130I, F130K, F130L, F130M, F130Q, F130R, F130T, F130V, F130Y, S135P, G136I, G136L, G136P, G136V, G136W, G136Y, S137A, M138I, M138K, M138L, M138Q, M138V, D139A, D139C, D139E, D139G, D139H, D139I, D139K, D139L, D139M, D139P, D139R, D139S, D139V, D139W, D139Y, V140C, Q151I, E152A, E152C, E152D, E152F, E152G, E152H, E152L, E152M, E152N, E152R, E152S, E152W, N155D, N155K, N155Q, N155R, D178A, D178C, D178G, D178H, D178K, D178L, D178M, D178N, D178P, D178Q, D178R, D178S, D178T, D178V, D178W, D178Y, T179A, T179F, T179H, T179I, T179K, T179L, T179M, T179N, T179P, T179Q, T179R, T179S, T179V, T179W, T179Y, E186A, E186C, E186D, E186G, E186H, E186K, E186L, E186M, E186N, E186P, E186Q, E186R, E186S, E186T, E186V, E186W, E186Y, V190H, V190I, V190K, V190L, V190Q, V190R, S191F, S191G, S191H, S191I, S191K, S191L, S191N, S191Q, S191R, S191W, L198M, L198V, S199C, S199D, S199E, S199F, S199I, S199K, S199L, S199N, S199Q, S199R, S199V, Y204H, Y204T, G205F, G205H, G205L, G205M, G205N, G205R, G205S, G205Y, K211A, K211C, K211D, K211G, K211M, K211N, K211Q, K211R, K211S, K211T, K211V, K214A, K214C, K214E, K214I, K214L, K214M, K214N, K214Q, K214R, K214S, K214V, L216A, L216C, L216F, L216H, L216Q, L216R, L216S, L216Y, N218K, N218P, T219D, D220A, D220E, D220H, D220K, D220N, D220P, A221D, A221E, A221F, A221I, A221K, A221L, A221M, A221N, A221S, A221V, A221Y, G222C, G222H, G222N, G222R, Y224F, Y224H, Y224N, Y224R, T243C, T243G, T243H, T243I, T243K, T243L, T243Q, T243R, T243W, T243Y, K244A, K244C, K244D, K244E, K244F, K244G, K244L, K244M, K244N, K244Q, K244S, K244T, K244V, K244W, K244Y, V260A, V260D, V260E, V260G, V260H, V260I, V260K, V260L, V260M, V260P, V260Q, V260R V260S, V260T, V260W, V260Y, Y261C, Y261F, Y261I, Y261L, T263E, T263F, T263H, T263I, T263L, T263M, T263Q, T263V, T263W, T263Y, S265A, S265C, S265D, S265E, S265K, S265N, S265P, S265Q, S265R, S265T, S265V, S265W, K269E, K269F, K269G, K269H, K269I, K269L, K269M, K269N, K269P, K269Q, K269S, K269T, K269V, K269W, K269Y, A273C, A273D, A273H, A273I, A273K, A273L, A273N, A273Q, A273R, A273Y, R280A, R280C, R280D, R280E, R280F, R280G, R280H, R280K, R280L, R280M, R280S, R280T, R280V, R280W, R280Y, L282F, L282G, L282H, L282I, L282K, L282M, L282N, L282Q, L282R, L282V, L282Y, S285A, S285C, S285D, S285E, S285K, S285P, S285Q, S285R, S285W, Q286A, Q286D, Q286E, Q286K, Q286P, Q286R, A289C, A289D, A289E, A289K, A289L, A289R, A293C, A293R, N296C, N296D, N296E, N296K, N296R, N296V, A297C, A297K, A297N, A297Q, A297R, and G299N.

In still further embodiments the present invention provides isolated variant neutral metalloproteases, wherein the metalloprotease comprises multiple mutations selected from S023W/G024M, T004V/S023W/G024W, S023W/G024Y/A288V, T004L/S023W/G024Y, N046Q/N050F/T054L, N050Y/T059R/S129Q, S023W/G024W, A273H/S285P/E292G, S023Y/G024Y, S023Y/G024W, T004S/S023Y/G024W, N046Q/T054K, S023W/G024Y, T004V/S023W, T059K/S066N, N046Q/N050W/T054H/T153A, T004V/S023W/G024Y, L282M/Q286P/A289R, N046Q/R047K/N050Y/T054K, L044Q/T263W/S285R, T004L/S023W/G024W, R047K/N050F/T054K, A273H/S285R, N050Y/T059K/S066Q, T054K/Q192K, N046Q/N050W, L282M/Q286K, T059K/S066Q, T004S/S023W, L282M/Q286R/A289R/K011N, L282M/A289R, N046Q/N050W/T054H, T059K/S129Q, T004S/S023N/G024Y/F210L, T004V/S023W/G024M/A289V, L282M/Q286K/A289R/S132T, N050W/T054H, L282M/Q286R, L282F/Q286K/A289R, T059R/S066Q, R047K/N050W/T054H, S265P/L282M/Q286K/A289R, L282M/Q286R/T229S, L282F/Q286K, T263W/S285R, S265P/L282M/Q286K, T263H/A273H/S285R, T059R/S129V, S032T/T263H/A273H/S285R, T059R/S066Q/S129Q, T004S/G024W, T004V/S023W/G024M, T059K/S066Q/S129Q, L282M/Q286K/A289R/I253V, T004V/S023Y/G024W, T059R/S066N/S129Q, N050F/T054L, T004S/S023N/G024W, T059R/S066N, T059R/S066N/S129V, Q286R/A289R, N046Q/R047K/N050F/T054K, S265P/L282M/Q286P/A289R, S265P/L282M/Q286R/A289R Q062K/S066Q/S129I, S023N/G024W, N046Q/R047K/N050W/T054H, R047K/T054K, T004L/G024W, T014M/T059R/S129V, T059R/S066Q/N092S/S129I, R047K/N050W/T054K, T004V/G024W, N047K/N050F/T054K, S265P/L282F/Q286K/N061Y, L282F/Q286K/E159V, T004V/S023Y/G024M, S265P/L282F/A289R/T065S, T059K/F063L/S066N/S129V, T004L/S023W, N050F/T054H, T059R/S066Q/S129V, V190I/D220E/S265W/L282F, T004S/S023Y/G024M, T004L/S023N/G024Y, T059K/S066N/S129I, T059R/S066N/S129I, L282M/Q286R/A289R/P162S, N046Q/N050F/T179N, T059K/Y082C/S129V, T059K/S129I, N050Y/T054K, T059K/S066Q/V102A/S129Q, T059R/S066Q/S129I, T059W/S066N/S129V/S290R, T059R/S129I, T059K/S066Q/S129I, T059K/S066Q/S129V, S265P/L282M/Q286R/A289R/T202S/K203N, T004V/S023N/G024W, S265P/Q286K, S265P/L282F/A289R, D220P/S265W, L055F/T059W/S129V, T059R/S129Q/S191R, N050W/T054K, T004S/S023W/G024M, R047K/N050F/T054H, T059K/S066N/K088E, T059K/S066Q/S129I/V291L, L282M/Q286R/A289R, T059R/S066N/F085S/S129I, L282F/Q286P/A289R, L282F/Q286R/A289R, G099D/S265P/L282F/Q286K/A289R, N046Q/N050F, N050Y/T059W/S066N/S129V, T009I/D220P/S265N, V190F/D220P/S265W, N157Y/T263W/A273H/S285R, T263W/A273H/S285R, T263W/S285W, T004V/S023Y, N046Q/R047K/N050W, N050W/T054L, N200Y/S265P/L282F/Q286P/A289R, T059R/S066Q/P264Q, T004V/G024Y, T004L/G024Y, N050Y/S191I, N050Y/T054L, T004L/S023W/G024Y/N155K, F169I/L282F/Q286R/A289R, L282M/Q286K/A289R, F130L/M138L/E152W/D183N, N046Q/R047K/N050Y/T054H, T004V/G024M, N050Y/T059W/S066Q/S129V, S023N/G024Y, T054H/P162Q, T004S/S023W/G024Y, N050Y/T054H, L282F/Q286R/A289R/F169I, R047K/N050W, V190F/D220P, L282M/F173Y, T004L/S023Y, N050W/A288D, V190I/D220P/S265Q, S265P/L282F/Q286P/A289R, S265P/L282F/Q286R/A289R, N046Q/N050Y/T054K, T059W/S066Q, T263W/A273H/S285W T263W/A273H/S285P, S023Y/G024M, T004L/S023N/G024W, T004V/S023N/G024Y, T059W/S066N/S129Q, T004S/S023Y, T004S/S023N/G024M, T059W/S066N/A070T, T059W/S066Q/S129Q, T263W/A273H, A273H/285P, N046Q/R047K/N050Y/T054L, N046Q/R047K/N050Y, R047K/N050Y, T263H/S285W, R047K/N050F, N046Q/R047K/N050F/T054H, S023N/G024M, T004S/G024Y, R047K/N050Y/T054H, T059W/S066N/S129I, R047K/T054L, T004S/S023W/G024W, M138L/E152F/T146S, D220P/S265N, T004S/G024M, T004V/S023N, N046Q/N050F/T054K, N046Q/N050Y/T054H, Q062H/S066Q/S129Q, T059W/S129Q, T059W/S129V, N050F/T054K, R047K/N050F/T054L, V190I/D220P/S265W, N112I/T263H/A273H/S285R, T059W/S066N/S129V, T059W/S066Q/S129I, T059W/S129I, T263W/S285P, V190I/D220P, A289V/T263H/A273H, T263H/A273H/S285P, N90S/A273H/S285P, R047K/N050Y/T054L, T004S/S023N, T059R/S129Q, N046Q/R047K/T054H, T059W/S066Q/S129V, E152W/T179P, N050Y/S066Q/S129V, T202S/T263W/A273H, T263W/A273H/S285P, M138L/E152W/T179P, N046Q/R047K, N046Q/T054H/F176L, T004L/G024M, T004S/L282M, T263H/A273H, T263H/A273H/S285W, T004L/S023Y/G024M, L282F/Q286P, T004V/S023Y/G024Y, V190F/S265W, M138L/E152F, V190F/D220E/S265W, N046Q/N050F/T054H, N157Y/S285W, T004F/S023Y/G024M, T004V/S023N/G024M, L198I/D220E/S265Q, N046Q/N050Y/T054K/A154T, S016L/D220E/S265W, D220E/S265W, D220E/A237S/S265W, S066Q/S129Q, V190F/D220E/S265Q/T267I, L282M/F173Y/T219S, E152F/T179P, V190I/S265W, M138L/S066Q, M138L/E152W, T059W/S066Q/A070T/S129I, V190F/D220E/S265N, V190F/S265N, N046Q/N050Y, and M138L/E152F/T179P.

In yet further embodiments, the present invention provides isolated variant neutral metalloproteases, wherein the metalloprotease comprises multiple mutations selected from V190I/D220P, V190I/D220P/S265Q, V190L/D220E, V190I/D220E/S265Q, V190I/D220E/S265W/L282F, V190L/D220E/S265Q, V190I/D220E/S265W, V190L/D220E/S265N, T059R/S066Q/S129I, V190I/D220E/S265N, V190L/D220E/S265W, V190I/D220E, T059W/S066N/S129V, T059K/S066Q/S129V, T059K/Y082C/S129V, T059R/S066N/S129I, S066Q/S129V, T059R/S066Q/S129V, T059R/S129I, N050Y/T059W/S066N/S129V, D220P/S265N, S066Q/S129I, T059W/S066Q/S129V, T059K/S066Q/S129I, T059R/S129V, N050Y/S066Q/S129V, T059W/S066Q/S129I, N050Y/T059W/S066Q/S129V, T059K/S129I, D220P/S265W, F130L/M138L/T179P, S066N/S129I, T059R/S066N/S129V, F130I/M138L/T179P, T059R/S066Q/N092S/S129I, S066N/S129V, D220E/S265Q, F130L/M138L/E152W/T179P, T059W/S129V, S265P/L282M/Q286R/A289R, S265P/L282F/Q286R/A289R, T059W/S066N/S129I, V190I/D220P/S265W, F130L/E152W/T179P, F130L/M138L/E152F/T179P, Q062K/S066Q/S129I, T059K/S066N/S129I, E152H/T179P, S265P/L282M/Q286K/A289R, F130L/M138L/E152H/T179P, T263W/A273H/S285R, D220E/S265N, F130I/M138L/E152H/T179P, F130V/M138L/E152W/T179P, F130I/M138L/E152W/T179P, T059W/S129I, D220E/S265W, F130V/M138L/T179P, F130L/E152V/T179P, T059R/S129Q, T263W/S285P, F130I/M138L/E152F/T179P, E152W/T179P, V190L/S265Q, F130L/E152F/T179P, L282M/Q286R/A289R/P162S, D220P/S265Q, M138L/E152F/T179P, F130I/E152H/T179P, M138L/E152W/T179P, F130L/T179P, F130L/M138L/E152W/T179P/Q286H, F130L/M138L/E152H, T263W/A273H/S285W, S265P/Q286K, T059W/S066Q/S129Q, T263W/S285R, T059W/S066N/S129Q, T263W/S285W, T059R/S066N/S129Q, S265P/L282M/Q286R/A289R/T202S/K203N, T059W/S129Q, Q062H/S066Q/S129Q, L282M/Q286R/A289R, V190L/D220E/S265N/V291I, V190L/S265N, F130L/M138L/E152W, N050Y/T059R/S129Q, F130I/T179P, T059K/S066Q/S129Q, T059K/S129Q, S265P/L282M/Q286P/A289R, S265P/L282F/Q286P/A289R, T263W/A273H/S285P, S265P/L282M/Q286K, S016L/D220E/S265W, S066Q/S129Q, S265P/L282M/Q286P, L282F/Q286R/A289R, F130V/E152W/T179P, L044Q/T263W/S285R L055F/T059W/S129V, V190L/S265W, Q286R/A289R, G99D/S265P/L282F/Q286K/A289R, F130L/M138L/E152F, T059R/S066Q/S129Q, F130L/E152H, S066N/S129Q, T004S/S023N/G024M/K269N, S265P/L282M, E152F/T179P, T059W/S066N/S129V/S290R, L282F/Q286K/A289R, F130L/M138L, F130I/M138L/E152W, S265P/L282F, F130I/M138L/E152H, F130V/M138L/E152H, V190I/S265Q, M138L/E152M, S265P/L282F/Q286P, M138L/E152H, T059K/S066N/K088E, V190I/S265W, F130L/E152W, L282M/Q286K/A289R, L282M/Q286K/A289R/I253V, T263W/A273H, V190I/S265N, M138L/E152W, A273H/S285R, F130I/M138L, F130L/E152F, F130V/M138L/E152W, T059K/S066Q/V102A/S129Q, F130V/E152H/T179P, F130I/M138L/E152F, F130V/M138L/E152F, M138L/E152F, L282M/Q286R, F130I/E152H, S265P/L282F/A289R/T065S, T263H/A273H/S285R, F130V/M138L, T014M/T059R/S129V, L282M/Q286R/A289R/K11N, A273H/S285P, L282M/Q286K/A289R/S132T, T263H/A273H/S285W, F130V/E152W, S265P/L282F/Q286K/N061Y, F130I/E152W, L198I/D220E/S265Q, V190I/S265L, T263H/S285W, S265P/L282F/A289R, M138L/S066Q, F130I/E152F, N90S/A273H/S285P, S032T/T263H/A273H/S285R, L282F/Q286P/A289R, N157Y/T263W/A273H/S285R, V105A/S129V, T263H/A273H/S285P, S129Q/L282H, T059W/S066Q, F130V/E152H, S023W/G024Y, T004V/S023N, T059R/S066Q, N050W/T054L, L282M/Q286P/A289R, A115V/V190L/S265W, L282M/Q286K, T059R/S066N, L282F/Q286P, T004V/S023W/G024M, S265P/L282F/Q286R/L78H, L282F/Q286K, T004V/S023W/G024Y, S023W/G024M, T059R/R256S, F130V/E152F, T004V/G024W, N050W/T054K, S023Y/G024M, T004V/S023Y, T004V/S023Y/G024M, N050Y/T054H, S023W/G024W, T004V/S023Y/G024Y, T004V/S023N/G024W, F130L/M138L/E152F/T179P/V291I, N050Y/T059K/S066Q, T004V/S023Y/G024W, T059K/S066N, T004V/S023N/G024Y, S023Y/G024W, N050F/T054L, R047K/T054K, S023N/G024W, L282M/A289R, S023Y/G024Y, T004V/G024M, R047K/N050F/T054K, N050F/T054K, T059K/S066Q, S023N/G024M, S023N/G024Y, T004L/S023N, R047K/N050W/T054H, T004L/S023W/G024Y, T004S/S023W, N046Q/N050W/T054H/A142T, T004L/S023Y, T004V/S023W, N050W/T054H, T004S/S023N, T004S/L282M, T004L/S023W, N050F/T054H, N050Y/T054L, and R047K/N050W/T054K.

In yet further embodiments, the present invention provides isolated neutral metalloproteases comprising multiple mutations selected from S066Q/S129V, S066Q/S129I, N050Y/S066Q/S129V, S066N/S129I, T059K/S066Q/S129V, S066N/S129V, F130L/E152W/T179P, S265P/L282M/Q286R/A289R, F130L/E152V/T179P, T059K/S066Q/S129I, T263W/S285P, T059K/S066N/S129I, T263W/A273H/S285P, S265P/L282F/Q286R/A289R, F130V/E152W/T179P, T263W/A273H/S285R, V190I/D220P/S265W, F130L/E152H, S066N/S129Q, S265P/L282M/Q286K/A289R, V190I/D220E, T059R/S066N/S129I, V190I/D220E/S265W, T059K/S129I, T059R/S066Q/S129I, F130I/M138L/E152H/T179P, F130I/T179P, T263W/A273H/S285W, S016L/D220E/S265W, S066Q/S129Q, V190I/D220E/S265Q, T059R/S066Q/S129V, D220E/S265N, V190L/D220E, D220E/S265W, V190I/D220P, V190L/D220E/S265N, L044Q/T263W/S285R, S265P/L282M/Q286P/A289R, F130L/M138L/E152H/T179P, T263W/S285R, L282M/Q286R/A289R, T263W/S285W, F130I/E152H/T179P, V190I/D220E/S265N, V190L/D220E/S265W, V190I/D220P/S265Q, T059R/S066N/S129V, V190L/D220E/S265Q, E152H/T179P, F130L/M138L/E152F/T179P, Q062H/S066Q/S129Q, T059R/S129V, V190I/D220E/S265W/L282F, V190I/S265Q, F130L/E152F/T179P, D220E/S265Q, E152W/T179P, T059K/S066Q/S129Q, F130L/M138L/T179P, F130I/M138L/E152F/T179P, F130L/M138L/E152W/T179P, N050Y/T059W/S066Q/S129V, S265P/L282M/Q286K, T059R/S129I, F130V/E152H/T179P, D220P/S265N, S265P/L282M/Q286P, F130I/E152H, T059R/S066Q/N092S/S129I, F130L/T179P, G99D/S265P/L282F/Q286K/A289R, T263W/A273H, V190I/S265N, D220P/S265W, F130L/E152W, F130L/M138L/E152H, S265P/L282M, V190I/S265Q, F130L/E152F, T059K/S129Q, Q286R/A289R, M138L/E152W/T179P, F130I/M138L/E152H, D220P/S265Q, V190L/S265N, F130I/M138L/E152W, S265P/Q286K, V190L/S265Q, V190I/S265W, F130L/M138L/E152F, F130V/E152H, E152F/T179P, N050Y/T059W/S066N/S129V, T059R/S066N/S129Q, F130I/E152W, F130V/E152W, T059R/S066Q/S129Q, T263H/A273H/S285P, N90S/A273H/S285P, V190L/D220E/S265N/V291I, T059R/S129Q, A273H/S285P, F130I/M138L/E152W/T179P, F130V/M138L/E152F, N050Y/T059R/S129Q, T059W/S066Q/S129I, F130V/M138L/T179P, F130V/M138L/E152W/T179P, V190L/S265W, F130V/M138L/E152W, T059W/S066Q/S129V, V190I/S265Q, F130V/M138L/E152H, F130I/E152F, N157Y/T263W/A273H/S285R, T263H/S285W, M138L/E152F/T179P, A115V/V190L/S265W, M138L/E152M, T263H/A273H/S285W, F130L/M138L/E152W, T059K/S066N/K088E, F130I/M138L/E152F, F130I/M138L/T179P, T004V/S023N, T059K/S066Q/V102A/S129Q, F130L/M138L, N047K/N050F/T054K, T263H/A273H/S285R, F130L/M138L/E152W/T179P/Q286H, M138L/E152H, M138L/S066Q, L282M/Q286R/A289R/P162S, L282F/Q286R/A289R, Q062K/S066Q/S129I, A273H/S285R, S265P/L282F/Q286P, S265P/L282F/Q286P/A289R, S265P/L282M/Q286R/A289R/T202S/K203N, T059W/S066N/S129I, V190I/S265L, T059W/S066N/S129V, F130I/M138L, L282M/Q286K/A289R/I253V, R047K/N050F/T054K, M138L/E152F, N050W/T054K, L198I/D220E/S265Q, L282F/Q286K/A289R, N050F/T054K, L282M/Q286R, M138L/E152W, S265P/L282F, F130V/E152F, T059W/S066N/S129Q, F130V/M138L, T263H/A273H, L282M/Q286K/A289R, N046Q/N050W/T054H/A142T, T059W/S066Q/S129Q, S265P/L282F/A289R/T065S, N050F/T054H, S129Q/L282H, L282M/Q286K/A289R/S132T, L282M/Q286R/A289R/K11N, T059K/S066N, R047K/N050W/T054K, T059K/S066Q, T004V/S023Y, T059W/S066N/S129V/S290R, N050Y/T059K/S066Q, and R047K/N050Y.

The present invention also provides isolated polynucleotides comprising a nucleotide sequence (i) having at least 70% identity to SEQ ID NOS:1, 2, 12 and/or 13, or (ii) being capable of hybridizing to a probe derived from any of the nucleotide sequence set forth herein, including the primer sequences provided in the Examples, under conditions of intermediate to high stringency, or (iii) being complementary to the nucleotide sequence set forth in SEQ ID NOS:1, 2, 12, and/or 13. In some embodiments, the present invention provides expression vectors encoding at least one such polynucleotide. In further embodiments, the present invention provides host cells comprising these expression vectors. In some particularly preferred embodiments, the host cells are *Bacillus* sp. The present invention also provides the neutral metalloproteases produced by the host cells. In further embodiments, the present invention provides polynucleotides that are complementary to at least a portion of the sequence set forth in SEQ ID NOS:1, 2, 12, and/or 13.

The present invention also provides methods of producing an enzyme having neutral metalloprotease activity, comprising: transforming a host cell with an expression vector comprising a polynucleotide having at least 70% sequence identity to SEQ ID NO:1, 2, 12 and/or 13; cultivating the transformed host cell under conditions suitable for the host cell. In some preferred embodiments, the host cell is a *Bacillus* species.

The present invention also provides probes comprising 4 to 150 nucleotide sequence substantially identical to a corresponding fragment of SEQ ID NOS:1, 2, 12, and/or 13, wherein the probe is used to detect a nucleic acid sequence coding for an enzyme having metalloproteolytic activity. In some embodiments, the nucleic acid sequence is obtained from a *Bacillus* sp.

The present invention also provides cleaning compositions comprising at least one neutral metalloprotease obtained from a *Bacillus* sp. In some embodiments, at least one neutral metalloprotease is obtained from *B. amyloliquefaciens*. In some particularly preferred embodiments, at least one neutral metalloprotease comprises the amino acid sequence set forth in SEQ ID NO:3, 4, and/or 18. In some further embodiments, the present invention provides isolated neutral metalloproteases comprising at least 45% amino acid identity with neutral metalloprotease comprising SEQ ID NO:3, 4 and/or 18. In some embodiments, the isolated neutral metalloproteases comprise at least 50% identity, preferably at least 55%, more preferably at least 60%, yet more preferably at least 65%, even more preferably at least 70%, more preferably at least 75%, still more preferably at least 80%, more preferably 85%, yet more preferably 90%, even more preferably at least 95%, and most preferably 99% identity with SEQ ID NO:3, 4, and/or 18.

The present invention further provides cleaning compositions comprising at least one neutral metalloprotease, wherein at least one of the neutral metalloproteases has immunological cross-reactivity with the neutral metalloprotease obtained from a *Bacillus* sp. In some preferred embodiments, the neutral metalloproteases have immunological cross-reactivity with neutral metalloprotease obtained from *B. amyloliquefaciens*. In alternative embodiments, the neutral metalloproteases have immunological cross-reactivity with neutral metalloprotease comprising the amino acid sequence set forth in SEQ ID NO:3, 4 and/or 18. In still further embodiments, the neutral metalloproteases have cross-reactivity with fragments (i.e., portions) of a *Bacillus* sp. neutral metalloprotease and/or the neutral metalloprotease comprising the amino acid sequence set forth in SEQ ID NO:3, 4, and/or 18. The present invention further provides cleaning compositions comprising at least one neutral metalloprotease, wherein the neutral metalloprotease is a variant neutral metalloprotease having an amino acid sequence comprising at least one substitution of an amino acid made at a position equivalent to a position in a *Bacillus* sp. neutral metalloprotease having an amino acid sequence set forth in SEQ ID NO:3, 4 and/or 18, particularly *B. amyloliquefaciens* neutral metalloprotease.

In yet additional embodiments, the cleaning compositions contain at least one neutral metalloprotease comprising a set of mutations in SEQ ID NO:3, 4 and/or 18. In some particularly preferred embodiments, the variant neutral metalloproteases comprise at least one substitution corresponding to the amino acid positions in SEQ ID NO:3, 4, and/or 18, and wherein the variant neutral metalloproteases have better performance in at least one property, as compared to wild-type *B. amyloliquefaciens* neutral metalloprotease.

The present invention also provides cleaning compositions comprising a cleaning effective amount of a metalloproteolytic enzyme, the enzyme comprising an amino acid sequence having at least 70% sequence identity to SEQ ID NO:3, 4, and/or 18, and a suitable cleaning formulation. In some preferred embodiments, the cleaning compositions further comprise one or more additional enzymes or enzyme derivatives selected from the group consisting of proteases, amylases, lipases, mannanases, pectinases, cutinases, oxidoreductases, hemicellulases, and cellulases.

The present invention also provides compositions comprising at least one neutral metalloprotease obtained from a *Bacillus* sp., in particular *B. amyloliquefaciens*, wherein the compositions further comprise at least one stabilizer. In some embodiments, the stabilizer is selected from borax, glycerol, zinc ions, calcium ions, and calcium formate. In some embodiments, the present invention provides competitive inhibitors suitable to stabilize the enzyme of the present invention to anionic surfactants. In some embodiments, at least one neutral metalloprotease is obtained from a *Bacillus* sp. In some particularly preferred embodiments, at least one neutral metalloprotease is obtained from *B. amyloliquefaciens*. In some particularly preferred embodiments, at least one neutral metalloprotease comprises the amino acid sequence set forth in SEQ ID NO:3, 4, and/or 18.

The present invention further provides compositions comprising at least one neutral metalloprotease obtained from a *Bacillus* sp., wherein the neutral metalloprotease is an autolytically stable variant. In some embodiments, at least one variant neutral metalloprotease is obtained from *B. amyloliquefaciens*. In some particularly preferred embodiments, at least one variant neutral metalloprotease comprises the amino acid sequence set forth in SEQ ID NO:3, 4, and/or 18.

The present invention also provides cleaning compositions comprising at least 0.0001 weight percent of the neutral metalloprotease of the present invention, and optionally, an adjunct ingredient. In some embodiments, the composition comprises an adjunct ingredient. In some preferred embodiments, the composition comprises a sufficient amount of a pH modifier to provide the composition with a neat pH of from about 3 to about 5, the composition being essentially free of materials that hydrolyze at a pH of from about 3 to about 5. In some particularly preferred embodiments, the materials that hydrolyze comprise a surfactant material. In additional embodiments, the cleaning composition is a liquid composition, while in other embodiments, the cleaning composition is a solid composition and in still further embodiments, the cleaning composition is a gel. Indeed, it is not intended that the present invention be limited to any particular formulation and/or composition, as various formulations and/or compositions find use in the present invention. In further embodiments, the surfactant material comprises a sodium alkyl sulfate surfactant that comprises an ethylene oxide moiety.

The present invention additionally provides cleaning compositions that in addition to at least one neutral metalloprotease of the present invention, further comprise at least one acid stable enzyme, the cleaning composition comprising a sufficient amount of a pH modifier to provide the composition with a neat pH of from about 3 to about 5, the composition being essentially free of materials that hydrolyze at a pH of from about 3 to about 5. In further embodiments, the materials that hydrolyze comprise a surfactant material. In some preferred embodiments, the cleaning composition being a liquid composition. In yet additional embodiments, the surfactant material comprises a sodium alkyl sulfate surfactant that comprises an ethylene oxide moiety. In some embodiments, the cleaning composition comprises a suitable adjunct ingredient. In some additional embodiments, the composition comprises a suitable adjunct ingredient. In some preferred embodiments, the composition comprises from about 0.001 to about 0.5 weight % of neutral metalloprotease.

In some alternatively preferred embodiments, the composition comprises from about 0.01 to about 0.1 weight percent of neutral metalloprotease.

The present invention also provides methods of cleaning, the comprising the steps of: a) contacting a surface and/or an article comprising a fabric with the cleaning composition comprising the neutral metalloprotease of the present invention at an appropriate concentration; and b) optionally washing and/or rinsing the surface or material. In alternative embodiments, any suitable composition provided herein finds use in these methods. In some embodiments, the fabric comprises at least one grass stain. In some particularly preferred embodiments, the cleaning compositions of the present invention find use in removing grass and other stains from fabrics.

The present invention also provides animal feed comprising at least one neutral metalloprotease obtained from a *Bacillus* sp. In some embodiments, at least one neutral metalloprotease is obtained from *B. amyloliquefaciens*. In some particularly preferred embodiments, at least one neutral metalloprotease comprises the amino acid sequence set forth in SEQ ID NO:18.

The present invention provides an isolated polypeptide having metalloproteolytic activity, (e.g., a neutral metalloprotease) having the amino acid sequence set forth in SEQ ID NO:18. In some embodiments, the present invention provides isolated polypeptides having approximately 40% to 98% identity with the sequence set forth in SEQ ID NO:18. In some preferred embodiments, the polypeptides have approximately 50% to 95% identity with the sequence set forth in SEQ ID NO:18. In some additional preferred embodiments, the polypeptides have approximately 60% to 90% identity with the sequence set forth in SEQ ID NO:3. In yet additional embodiments, the polypeptides have approximately 65% to 85% identity with the sequence set forth in SEQ ID NO:3, 4, and/or 18. In some particularly preferred embodiments, the polypeptides have approximately 90% to 95% identity with the sequence set forth in SEQ ID NO:3, 4, and/or 18.

The present invention further provides isolated polynucleotides that encode neutral metalloproteases comprise an amino acid sequence comprising at least 40% amino acid sequence identity to SEQ ID NO:3, 4, and/or 18. In some embodiments, the neutral metalloproteases have at least 50% amino acid sequence identity to SEQ ID NO:3, 4 and/or 18. In some embodiments, the neutral metalloproteases have at least 60% amino acid sequence identity to SEQ ID NO:3, 4 and/or 18. In some embodiments, the neutral metalloproteases have at least 70% amino acid sequence identity to SEQ ID NO:3, 4, and/or 18. In some embodiments, the neutral metalloproteases have at least 80% amino acid sequence identity to SEQ ID NO:3, 4, and/or 18. In some embodiments, the neutral metalloproteases have at least 90% amino acid sequence identity to SEQ ID NO:3, 4, and/or 18. In some embodiments, the neutral metalloproteases have at least 95% amino acid sequence identity to SEQ ID NO:3, 4, and/or 18. The present invention also provides expression vectors comprising any of the polynucleotides provided above.

The present invention further provides host cells transformed with the expression vectors of the present invention, such that at least one neutral metalloprotease is expressed by the host cells. In some embodiments, the host cells are bacteria, while in other embodiments, the host cells are fungi.

The present invention also provides isolated polynucleotides comprising a nucleotide sequence (i) having at least 70% identity to SEQ ID NO:1, 2, 12 and/or 13, or (ii) being capable of hybridizing to a probe derived from the nucleotide sequence of SEQ ID NO:1, 2, 12, and/or 13, under conditions of medium to high stringency, or (iii) being complementary to the nucleotide sequence of SEQ ID NO:1, 2, 12, and/or 13. In some embodiments, the present invention provides vectors comprising such polynucleotide. In further embodiments, the present invention provides host cells transformed with such vectors.

The present invention further provides methods for producing at least one enzyme having neutral metalloprotease activity, comprising: the steps of transforming a host cell with an expression vector comprising a polynucleotide comprising at least 70% sequence identity to SEQ ID NO:1, 2, 12, and/or 13, cultivating the transformed host cell under conditions suitable for the host cell to produce the neutral metalloprotease; and recovering the neutral metalloprotease. In some preferred embodiments, the host cell is a *Bacillus* sp, while in some alternative embodiments, the host cell is *B. amyloliquefaciens.*

The present invention also provides fragments (i.e., portions) of the DNA encoding the neutral metalloproteases provided herein. These fragments find use in obtaining partial length DNA fragments capable of being used to isolate or identify polynucleotides encoding mature neutral metalloprotease enzyme described herein from *B. amyloliquefaciens*, or a segment thereof having proteolytic activity. In some embodiments, portions of the DNA provided in SEQ ID NO:2 find use in obtaining homologous fragments of DNA from other species which encode a neutral metalloprotease or portion thereof having metalloproteolytic activity.

The present invention further provides at least one probe comprising a polynucleotide substantially identical to a fragment of SEQ ID NOS:1, 2, 6, 7, 8, 9, 10, 11, 12, 13, 14, 15, and/or any primer sequence set forth herein, wherein the probe is used to detect a nucleic acid sequence coding for an enzyme having metalloproteolytic activity, and wherein the nucleic acid sequence is obtained from a bacterial source. In some embodiments, the bacterial source is a *Bacillus* sp. In some preferred embodiments, the bacterial source is *B. amyloliquefaciens.*

The present invention further provides compositions comprising at least one of the neutral metalloproteases provided herein. In some preferred embodiments, the compositions are cleaning compositions. In some embodiments, the present invention provides cleaning compositions comprising a cleaning effective amount of at least one neutral metalloprotease comprising an amino acid sequence having at least 40% sequence identity to SEQ ID NO:18 at least 90% sequence identity to SEQ ID NO:18, and/or having an amino acid sequence of SEQ ID NO:18. In some embodiments, the cleaning compositions further comprise at least one suitable cleaning adjunct. In some embodiments, the neutral metalloprotease is derived from a *Bacillus* sp. In some preferred embodiments, the *Bacillus* sp., is *B. amyloliquefaciens.*

In still further embodiments, the cleaning composition further comprises at least one additional enzymes or enzyme derivatives selected from the group consisting of proteases, amylases, lipases, mannanases, and cellulases.

The present invention also provides isolated naturally occurring neutral metalloproteases comprising an amino acid sequence having at least 45% sequence identity to SEQ ID NO:18, at least 60% sequence identity to SEQ ID NO:18, at least 75% sequence identity to SEQ ID NO:18, at least 90% sequence identity to SEQ ID NO:18, at least 95% sequence identity to SEQ ID NO:18, and/or having the sequence identity of SEQ ID NO:18, the neutral metalloprotease being isolated from a *Bacillus* sp. In some embodiments, the neutral metalloprotease is isolated from *B. amyloliquefaciens.*

In additional embodiments, the present invention provides engineered variants of the neutral metalloproteases of the present invention. In some embodiments, the engineered variants are genetically modified using recombinant DNA technologies, while in other embodiments, the variants are naturally occurring. The present invention further encompasses engineered variants of homologous enzymes, as well as isolated enzyme homologs. In some embodiments, the engineered variant homologous neutral metalloproteases are genetically modified using recombinant DNA technologies, while in other embodiments, the variant homologous neutral metalloproteases are naturally occurring.

The present invention also provides methods for producing neutral metalloproteases, comprising: (a) transforming a host cell with an expression vector comprising a polynucleotide having at least 70% sequence identity to SEQ ID NO:2, at least 95% sequence identity to SEQ ID NO:2, and/or having a polynucleotide sequence of SEQ ID NO:2; (b) cultivating the transformed host cell under conditions suitable for the host cell to produce the neutral metalloprotease; and (c) recovering the neutral metalloprotease. In some embodiments, the host cell is a *Bacillus* species (e.g., *B. subtilis, B. clausii*, or *B. licheniformis*). In alternative embodiments, the host cell is a *B. amyloliquefaciens*

In further embodiments, the present invention provides means to produce host cells that are capable of producing the neutral metalloproteases of the present invention in relatively large quantities. In particularly preferred embodiments, the present invention provides means to produce neutral metalloprotease with various commercial applications where degradation or synthesis of polypeptides are desired, including cleaning compositions, as well as food and/or feed components, textile processing, leather finishing, grain processing, meat processing, cleaning, preparation of protein hydrolysates, digestive aids, microbicidal compositions, bacteriostatic compositions, fungistatic compositions, personal care products (e.g., oral care, hair care, and/or skin care).

The present invention also provides variant neutral metalloproteases having improved performance as compared to wild-type *B. amyloliquefaciens* neutral metalloprotease. In some preferred embodiments, the improved performance comprises improved thermostability, as compared to wild-type *B. amyloliquefaciens* neutral metalloprotease. In alternative preferred embodiments, the improved performance comprises improved performance under lower or higher pH conditions, as compared to wild-type *B. amyloliquefaciens* neutral metalloprotease. In additional preferred embodiments, the improved performance comprises improved autolytic stability, as compared to wild-type *B. amyloliquefaciens* neutral metalloprotease. In some particularly preferred embodiments, the enzyme compositions of the present invention have comparable or improved wash performance, as compared to presently used neutral metalloproteases. Other objects and advantages of the present invention are apparent herein.

DESCRIPTION OF THE FIGURES

FIGS. 3A and 3B provide a sequence alignment of various metalloprotease homologues (SEQ ID NOS:173-181) that find use in the present invention.

FIGS. 4A and 4B provide a sequence alignment of various metalloprotease homologues (SEQ ID NOS:182-191) that find use in the present invention. In this Figure, the numbering is for thermolysin (*B. thermoproteolyticus*). As in FIG. 3, the "*" indicates conserved residues, ":" indicates conservatively replaced residues, and "." indicates similar residues.

FIG. 5 provides a sequence alignment of various metalloprotease homologues (SEQ ID NOS:192-195) identified through homology modeling.

FIG. 35 provides the amino acid sequences (SEQ ID NOS: 222-226) for the citrate-induced autolytic fragments of NprE highlighting the autolysis sites. Fragment 1 and 2 are the first clip, Fragment 3-5 represent the second clip. The italicized letters represent the sequenced N-termini and bold letters highlight the peptides that were identified from the in-gel digestion of the respective fragments.

DESCRIPTION OF THE INVENTION

Figure 1:
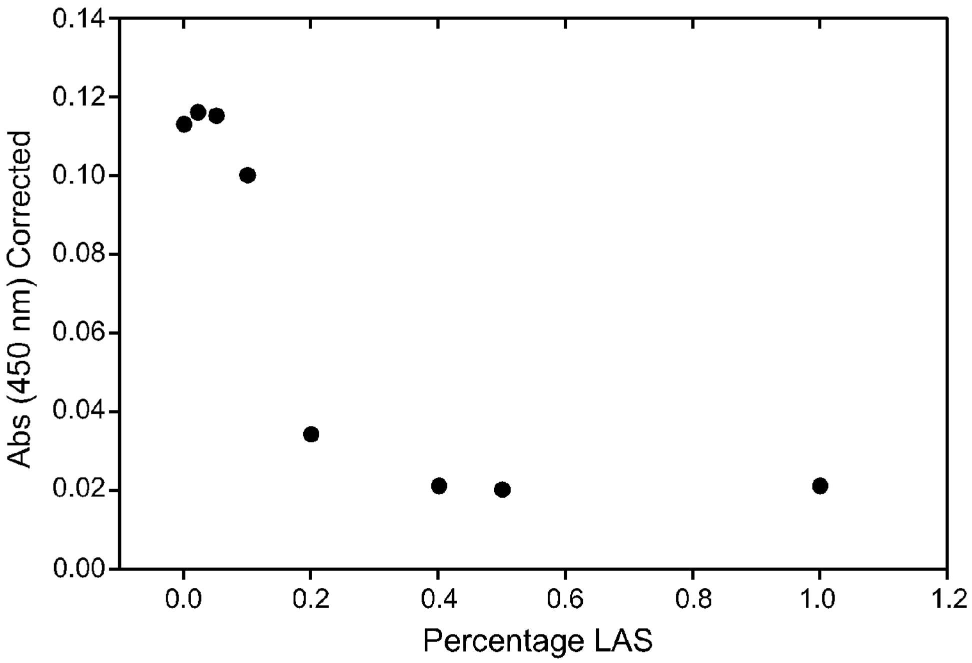
FIG. 1 provides a graph showing the results from the determination of the affinity constants of purified MULTIFECT® neutral binding protein for zinc and calcium cations using the fluorescent dyes Fluo-Zn3 and Fluo-3, respectively.

The present invention provides methods and compositions comprising at least one neutral metalloprotease enzyme that has improved storage stability. In some embodiments, the neutral metalloprotease finds use in cleaning and other applications. In some particularly preferred embodiments, the present invention provides methods and compositions comprising neutral metalloprotease(s) obtained from *Bacillus* sp. In some more particularly preferred embodiments, the neutral metalloprotease is obtained from *B. amyloliquefaciens*. In still further preferred embodiments, the neutral metalloprotease is a variant of the *B. amyloliquefaciens* neutral metalloprotease. In yet additional embodiments, the neutral metalloprotease is a homolog of the the *B. amyloliquefaciens* neutral metalloprotease. The present invention finds particular use in applications including, but not limited to cleaning, bleaching and disinfecting.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used herein. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "multimer" refers to two or more proteins or peptides that are covalently or non-covalently associated and exist as a complex in solution. A "dimer" is a multimer that contains two proteins or peptides; a "trimer" contains three proteins or peptides, etc. As used herein, "octamer" refers to a multimer of eight proteins or peptides.

As used herein, "personal care products" means products used in the cleaning, bleaching and/or disinfecting of hair, skin, scalp, and teeth, including, but not limited to shampoos, body lotions, shower gels, topical moisturizers, toothpaste, and/or other topical cleansers. In some particularly preferred embodiments, these products are utilized on humans, while in other embodiments, these products find use with non-human animals (e.g., in veterinary applications).

As used herein, "cleaning compositions" and "cleaning formulations," unless otherwise indicated, refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the neutral metalloprotease and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to neutral metalloprotease, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "Applicant Enzyme" refers to the neutral metalloproteases of the present invention.

As used herein, "enhanced performance" in a detergent is defined as increasing cleaning of bleach-sensitive stains (e.g., grass, tea, wine, blood, dingy, etc.), as determined by usual evaluation after a standard wash cycle. In particular embodiments, the neutral metalloprotease of the present invention provides enhanced performance in the removal of colored stains and soils. In further embodiments, the enzyme of the present invention provides enhanced performance in the removal and/or decolorization of stains.

As used herein the term "hard surface cleaning composition," refers to detergent compositions for cleaning hard surfaces such as floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the neutral metalloprotease to such an extent that the neutral metalloprotease is not effective as desired during normal use situations. Specific cleaning composition materials are exemplified in detail hereinafter.

As used herein, "effective amount of enzyme" refers to the quantity of enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, personal care cleaning compositions (e.g., oral cleaning compositions, denture cleaning compositions, personal cleansing compositions, etc.), and compositions suitable for use in the pulp and paper industry.

As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like.

As used herein, the term "transferase" refers to an enzyme that catalyzes the transfer of functional compounds to a range of substrates.

As used herein, "leaving group" refers to the nucleophile which is cleaved from the acyl donor upon substitution by another nucleophile.

As used herein, the term "enzymatic conversion" refers to the modification of a substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the phrase "detergent stability" refers to the stability of a detergent composition. In some embodiments, the stability is assessed during the use of the detergent, while in other embodiments, the term refers to the stability of a detergent composition during storage.

As used herein, the phrase, "stability to proteolysis" refers to the ability of a protein (e.g., an enzyme) to withstand proteolysis. It is not intended that the term be limited to the use of any particular protease to assess the stability of a protein.

As used herein, "oxidative stability" refers to the ability of a protein to function under oxidative conditions. In particular, the term refers to the ability of a protein to function in the presence of various concentrations of $H_2O_2$ and/or peracid. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (i.e., around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a mutant when exposed to a different temperature (i.e., higher or lower) than optimum temperature for enzymatic activity. However, it is not intended that the present invention be limited to any temperature stability level nor temperature range.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the phrase "neutral metalloprotease activity improvement" refers to the relative improvement of neutral metalloprotease activity, in comparison with a standard enzyme. In some embodiments, the term refers to an improved rate of product formation, while in other embodiments, the term encompasses compositions that produce less hydrolysis product. In additional embodiments, the term refers to neutral metalloprotease compositions with altered substrate specificity.

As used herein, the phrase "alteration in substrate specificity" refers to changes in the substrate specificity of an enzyme. In some embodiments, a change in substrate specificity is defined as a difference between the $K_{cat}/K_m$ ratio observed with an enzyme compared to enzyme variants or other enzyme compositions. Enzyme substrate specificities vary, depending upon the substrate tested. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios for particular substrates of interest. However, it is not intended that the present invention be limited to any particular substrate composition nor any specific substrate specificity.

As used herein, "surface property" is used in reference to an electrostatic charge, as well as properties such as the hydrophobicity and/or hydrophilicity exhibited by the surface of a protein.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C. Here the three R groups may be: AAA, BBB, CCC, AAB, AAC, BBA, BBC, CCA, CCB, or ABC.

In reference to chemical compositions, the term "substituted" as used herein, means that the organic composition or radical to which the term is applied is:

(a) made unsaturated by the elimination of at least one element or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties which may replace hydrogen as described in (b) immediately above, that contain only carbon and hydrogen atoms, are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

As used herein, the terms "purified" and "isolated" refer to the removal of contaminants from a sample. For example, neutral metalloprotease are purified by removal of contaminating proteins and other compounds within a solution or preparation that are not neutral metalloprotease. In some embodiments, recombinant neutral metalloprotease are expressed in bacterial or fungal host cells and these recombinant neutral metalloproteases are purified by the removal of other host cell constituents; the percent of recombinant neutral metalloprotease polypeptides is thereby increased in the sample. In particularly preferred embodiments, the metalloprotease of the present invention is substantially purified to a level of at least about 99% of the protein component, as determined by SDS-PAGE or other standard methods known in the art. In alternative preferred embodiments, the metalloprotease of the present invention comprise at least about 99% of the protease component of the compositions. In yet alternative embodiments, the metalloprotease is present in a range of about at least 90-95% of the total protein and/or protease.

As used herein, "protein of interest," refers to a protein (e.g., an enzyme or "enzyme of interest") which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide" and polypeptide are used interchangeably herein. Wherein a peptide is a portion of a protein, those skilled in the art understand the use of the term in context.

As used herein, functionally and/or structurally similar proteins are considered to be "related proteins." In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the neutral metalloprotease of the present invention). For example, the present invention encompasses such homologs as those provided in FIGS. 3-5. Additional homologs are contemplated, including but not limited to metalloprotease enzymes obtained from *B. cereus, B. cereus* E33L, *B. caldolyticus, B. pumulis, B. megaterium, B. subtilis amylosacchariticus, Brevibacillus brevis, Paenibacillus polymyxa* (*Bacillus polymyxa*), *B. stearothermophilus, B. thuringiensis, B. subtilis* and *S. aureus*, as well as aureolysin, extracellular elastase, and neutral protease B. In further embodiments, the term encompasses proteins that are immunologically cross-reactive.

As used herein, the term "derivative" refers to a protein which is derived from a protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

Related (and derivative) proteins comprise "variant proteins." In some preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means suitable and is preferably based on the assessment of properties of interest. For example, pH and/or temperature, as well as detergent and for oxidative stability is/are determined in some embodiments of the present invention. Indeed, it is contemplated that enzymes having various degrees of stability in one or more of these characteristics (pH, temperature, proteolytic stability, detergent stability, and/or oxidative stability) will find use.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

In some preferred embodiments, the neutral metalloprotease gene is ligated into an appropriate expression plasmid. The cloned neutral metalloprotease gene is then used to transform or transfect a host cell in order to express the neutral metalloprotease gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the neutral metalloprotease gene. In some embodiments, a selection gene such as an antibiotic resistance gene that enables continuous cultural maintenance of plasmid-infected host cells by growth in antimicrobial-containing media is also included.

The following cassette mutagenesis method may be used to facilitate the construction of the neutral metalloprotease variants of the present invention, although other methods may be used. First, as described herein, a naturally-occurring gene encoding the neutral metalloprotease is obtained and sequenced in whole or in part. Then, the sequence is scanned for a point at which it is desired to make a mutation (deletion, insertion or substitution) of one or more amino acids in the encoded neutral metalloprotease. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the neutral metalloprotease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "analogous sequence" refers to a sequence within a protein that provides similar function, tertiary structure, and/or conserved residues as the protein of interest (i.e., typically the original protein of interest). For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some preferred embodiments, the tertiary structure and/or conserved residues of the amino acids in the protein of interest are located at or near the segment or fragment of interest. Thus, where the segment or fragment of interest contains, for example, an alpha-helix or a beta-sheet structure, the replacement amino acids preferably maintain that specific structure.

As used herein, "homologous protein" refers to a protein (e.g., neutral metalloprotease) that has similar action and/or structure, as a protein of interest (e.g., an neutral metalloprotease from another source). It is not intended that homologs (also referred to herein as "homologues") be necessarily related evolutionarily. Thus, it is intended that the term encompass the same or similar enzyme(s) (i.e., in terms of structure and function) obtained from different species. In some preferred embodiments, it is desirable to identify a homolog that has a quaternary, tertiary and/or primary structure similar to the protein of interest, as replacement for the segment or fragment in the protein of interest with an analogous segment from the homolog will reduce the disruptiveness of the change.

As used herein, "homologous genes" refers to at least a pair of genes from different species, which genes correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'S, N'-4, and a comparison of both strands.

As used herein, "percent (%) nucleic acid sequence identity" is defined as the percentage of nucleotide residues in a candidate sequence that is identical with the nucleotide residues of the sequence.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, it is typically desirable to use relatively stringent conditions to form the hybrids (e.g., relatively low salt and/or high temperature conditions are used).

The phrases "substantially similar and "substantially identical" in the context of at least two nucleic acids or polypeptides typically means that a polynucleotide or polypeptide comprises a sequence that has at least about 40% identity, more preferable at least about 50% identity, yet more preferably at least about 60% identity, preferably at least about 75% identity, more preferably at least about 80% identity, yet more preferably at least about 90%, still more preferably about 95%, most preferably about 97% identity, sometimes as much as about 98% and about 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad. Sci. USA 89:10915 [1989]; Karin et al., Proc. Natl. Acad. Sci USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "equivalent residues" refers to proteins that share particular amino acid residues. For example, equivalent resides may be identified by determining homology at the level of tertiary structure for a protein (e.g., neutral metalloprotease) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

As used herein, the terms "hybrid neutral metalloproteases" and "fusion neutral metalloproteases" refer to proteins that are engineered from at least two different or "parental" proteins. In preferred embodiments, these parental proteins are homologs of one another. For example, in some embodiments, a preferred hybrid neutral metalloprotease or fusion protein contains the N-terminus of a protein and the C-terminus of a homolog of the protein. In some preferred embodiment, the two terminal ends are combined to correspond to the full-length active protein.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electro oration, naked DNA and the like as known in the art. (See, Chang and Cohen, Mol. Gen. Genet., 168:111-115 [1979]; Smith et al., Appl. Env. Microbiol., 51:634 [1986]; and the review article by Ferrari et al., in Harwood, *Bacillus*, Plenum Publishing Corporation, pp. 57-72 [1989]).

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a marker, gene or a vector encoding a gene which permits the amplification of that gene under appropriate growth conditions.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to amplification methods (e.g., the polymerase chain reaction), refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195, 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

DETAILED DESCRIPTION OF THE PRESENT INVENTION

The present invention provides methods and compositions comprising at least one neutral metalloprotease enzyme that has improved storage stability. In some embodiments, the neutral metalloprotease finds use in cleaning and other applications. In some particularly preferred embodiments, the present invention provides methods and compositions comprising neutral metalloprotease(s) obtained from *Bacillus* sp.

In some more particularly preferred embodiments, the neutral metalloprotease is obtained from *B. amyloliquefaciens*. In still further preferred embodiments, the neutral metalloprotease is a variant of the *B. amyloliquefaciens* neutral metalloprotease. In yet additional embodiments, the neutral metalloprotease is a homolog of the the *B. amyloliquefaciens* neutral metalloprotease. The present invention finds particular use in applications including, but not limited to cleaning, bleaching and disinfecting.

Also as described in more detail in the Examples below, the present invention provides many advantages for cleaning of a wide range of objects, including but not limited to clothing, fabrics, medical devices, etc. In addition, the present invention provides compositions that are effective in cleaning, bleaching, and disinfecting, over a range of wash temperatures and pHs.

In general, proteases hydrolyze amide linkages of proteins via addition of a water molecule to the peptide bond(s). Cleavage occurs at the carbonyl-group of the peptide bond. In bacterial species such as *Bacillus*, there are two main classes of extracellular proteases namely, alkaline or serine proteases and neutral metalloproteases.

Neutral metalloendopeptidases (i.e., neutral metalloproteases) (EC 3.4.24.4) belong to a protease class that has an absolute requirement for zinc ions for catalytic activity. These enzymes are optimally active at neutral pH and are in the 30 to 40 kDa size range. Neutral metalloproteases bind between two and four calcium ions that contribute to the structural stability of the protein. The bound metal ion at the active site of metalloproteases is an essential feature that allows the activation of a water molecule. The water molecule then functions as the nucleophile and cleaves the carbonyl group of the peptide bond.

The neutral zinc-binding metalloprotease family includes the bacterial enzyme thermolysin, and thermolysin-like proteases ("TLPs"), as well as carboxypeptidase A (a digestive enzyme), and the matrix metalloproteases that catalyze the reactions in tissue remodeling and degradation. The only well characterized of these proteases, with respect to stability and function, is thermolysin and its variants (TLPs). Indeed, much research has been focused on the engineering *Bacillus subtilis* neutral proteases to increase the thermal stability of the enzyme (See e.g., Vriend et al., In, Tweel et al. (eds), *Stability and Stabilization of enzymes*, Elsevier, pp. 93-99 [1993]).

Most effort has been focused on increasing the stability of the protease by altering structural determinants identified through the use of molecular modeling suggested to prevent local unfolding processes that would result in autolysis of the protein and cause the neutral protease to denature at high temperatures (See e.g., van den Burg et al., in Hopsu-Havu et al., (eds), *Proteolysis in Cell Functions Manipulating the Autolytic Pathway of a Bacillus Protease*. Biomedical and Health Research Vol. 13, IOS Press [1997] p. 576).

Compositions and methods to engineer neutral metalloproteases with improved characteristics are provided herein. As indicated herein, calcium ions have been reported for other proteases such as thermolysin to prevent autolysis. The *B. stearothermophilus* neutral protease has been stabilized against autolysis and proteolytic degradation by addition of calcium (See, Dürrschmidt et al., FEBS J., 272:1523-1534 [2005]).

Indeed, the present invention provides compositions and methods suitable for the engineering of neutral metalloproteases that are independent of calcium in order to maintain their structural stability. In some embodiments, engineering prevents the local unfolding in a particular secondary structural element that may prevent proteolysis.

Natural and engineered proteases, such as subtilisin are often expressed in *Bacillus subtilis* and several have been applied in detergent formulations to remove proteinaceous stains. Others have been applied for example in the baking industry (e.g., thermolysin from *Bacillus thermoproteolyticus*; See e.g., Galante and Formantici, Curr. Organic Chem., 7, 1399-1422 [2003]). In general, the serine proteases have been more widely utilized in detergents, at least partially due to the relative ease with which these proteases can be stabilized.

Indeed, metalloproteases are less frequently used in industry, and particularly in the detergent industry for a number of reasons. These enzymes involve more complex protein systems, as the enzymes have the absolute requirement for calcium and zinc ions for stability and function, respectively. Further, the detergent solution as well as the water used in the laundry process often contains components that often interfere with the binding of the ions by the enzyme or chelate these ions, resulting in a decrease or loss of proteolytic function and destabilization of the protease.

In contrast to the currently used metalloprotease enzyme systems, the present invention provides neutral metalloproteases that are sufficiently stabilized to facilitate long-term shelf storage in liquid laundry detergent compositions. In particularly preferred embodiments, the metalloprotease stability and activity are preserved through complexing the enzyme with its obligatory active-site zinc molecule. Importantly, the combination of calcium and zinc ions does not have a deleterious effect on the enzyme's function. In some embodiments, the neutral metalloprotease stabilized is the wild-type metalloprotease from *Bacillus amyloliquefaciens* (e.g., purified MULTIFECT® Neutral; "PMN"). In alternative preferred embodiments, recombinant neutral metalloprotease (e.g., *Bacillus amyloliquefaciens* neutral metalloprotease cloned into *Bacillus subtilis* ("nprE")). In additional embodiments, metalloproteases with improved stability encompass enzymes with increased affinity for one or more of the calcium binding sites of the enzyme. In preferred embodiments, the neutral metalloproteases of the present invention find use in general detergent applications, including but not limited to cold water temperatures, grass stains, and/or low pH conditions.

The present invention provides conditions that stabilize zinc-binding neutral metalloprotease for increased storage stability in detergent bases and/or compositions. In preferred embodiments, the detergent compositions comprise at least one metalloprotease (e.g., any *Bacillus* neutral metalloprotease) that is stabilized against autolysis and unfolding, by the inclusion within the detergent formulation of the essential zinc and/or calcium ions. In some particularly preferred embodiments, the neutral metalloprotease from *Bacillus amyloliquefaciens* (PMN) and the recombinant form expressed in *Bacillus subtilis* (nprE) that bind zinc ion with 10-fold greater affinity than the calcium ion find use in the present invention. The stabilized protease in the presence of essential zinc ions has improved stability against proteolysis when compared to the same proteases with in the absence of ions.

Although some experimental results indicated that nprE loses some proteolytic activity (~20%) after one hour of adding the detergent base, nprE incubated at 32° C. in the presence of zinc ions showed significant stabilization over the test conditions with no additional salts or calcium ions. The presence of both calcium and zinc ions did not show an additive effect. At zinc ion concentrations lower than 15 mM neutral metalloprotease is sufficiently stable over approximately 4 weeks. Thus, the present invention provides compositions comprising the addition of zinc to increase the storage life of neutral metalloprotease in the presence of detergent components.

Furthermore, in alternative embodiments, the zinc cation is replaced with $Co^{2+}$, $Mn^{2+}$ or $Fe^{2+}$, since all of these ions have been shown to bind and restore the protease activity of neutral metalloproteases. However, it was determined that $Mn^{2+}$ and $Fe^{2+}$ do not restore all of the native activity. While $Co^{2+}$ restores the highest percentage of the activity, it is apparently less firmly bound than $Zn^{2+}$. The zinc cation is an essential feature in the active site of all neutral metalloproteases, as it is known to play a role in substrate binding and enzyme catalysis (See e.g., Holmquist and Vallee, J. Biol. Chem., 249:4601-4607 [1974]). The relatively tight affinity of the neutral metalloprotease for the zinc cation (~μM range) and the approximately 10-fold greater affinity for this ion relative to calcium, suggest that zinc functions as a stabilizer, thereby preventing autolysis, proteolysis and unfolding. However, it is not intended that the present invention be limited to any particular mechanisms.

The present invention provides extremely beneficial opportunities for application in the production and development of industrial detergents. Many detergents are available with high specificity towards the removal of protein, starch and grease stains. In particular, the better wash performance of PMN or neutral metalloprotease from *B. amyloliquefaciens* on Equest Grass (Warwick) indicates that the neutral metalloproteases of the present invention in a detergent base that also contains zinc finds use in improved detergent compositions.

Detailed Description of Cleaning and Detergent Formulations of the Present Invention Unless otherwise noted, all component or composition levels provided herein are made in reference to the active level of that component or composition, and are exclusive of impurities, for example, residual solvents or by-products, which may be present in commercially available sources.

Enzyme components weights are based on total active protein.

All percentages and ratios are calculated by weight unless otherwise indicated. All percentages and ratios are calculated based on the total composition unless otherwise indicated.

In the exemplified detergent compositions, the enzymes levels are expressed by pure enzyme by weight of the total composition and unless otherwise specified, the detergent ingredients are expressed by weight of the total compositions.

Cleaning Compositions Comprising Neutral Metalloprotease

The stabilized neutral metalloproteases of the present invention are useful in formulating various detergent compositions. The cleaning composition of the present invention may be advantageously employed for example, in laundry applications, hard surface cleaning, automatic dishwashing applications, as well as cosmetic applications such as dentures, teeth, hair and skin. However, due to the unique advantages of increased effectiveness in lower temperature solutions and the superior color-safety profile, the enzymes of the present invention are ideally suited for laundry applications such as the bleaching of fabrics. Furthermore, the enzymes of the present invention find use in both granular and liquid compositions.

The enzymes of the present invention also find use in cleaning additive products. A cleaning additive product including at least one enzyme of the present invention is ideally suited for inclusion in a wash process when additional bleaching effectiveness is desired. Such instances include, but are not limited to low temperature solution cleaning applications. The additive product may be, in its simplest form, one or more neutral metalloprotease enzyme as provided by the present invention. In some embodiments, the additive is packaged in dosage form for addition to a cleaning process where a source of peroxygen is employed and increased bleaching effectiveness is desired. In some embodiments, the single dosage form comprises a pill, tablet, gelcap or other single dosage unit including pre-measured powders and/or liquids. In some embodiments, filler and/or carrier material(s) are included, in order to increase the volume of such composition. Suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol. In some embodiments, the compositions comprise from about 5% to about 90% of such materials. In additional embodiments, acidic fillers are used to reduce the pH of the composition. In some alternative embodiments, the cleaning additive includes at least one activated peroxygen source as described below and/or adjunct ingredients as more fully described below.

The cleaning compositions and cleaning additives of the present invention require an effective amount of neutral metalloprotease enzyme as provided in the present invention. In some embodiments, the required level of enzyme is achieved by the addition of one or more species of neutral metalloprotease provided by the present invention. Typically, the cleaning compositions of the present invention comprise at least 0.0001 weight percent, from about 0.0001 to about 1, from about 0.001 to about 0.5, or even from about 0.01 to about 0.1 weight percent of at least one neutral metalloprotease provided by the present invention.

In some preferred embodiments, the cleaning compositions provided herein are typically formulated such that, during use in aqueous cleaning operations, the wash water has a pH of from about 5.0 to about 11.5, or in alternative embodiments, even from about 6.0 to about 10.5. In some preferred embodiments, liquid product formulations are typically formulated to have a neat pH from about 3.0 to about 9.0, while in some alternative embodiments the formulation has a neat pH from about 3 to about 5. In some preferred embodiments, granular laundry products are typically formulated to have a pH from about 8 to about 11. Techniques for controlling pH at recommended usage levels include the use of buffers, alkalis, acids, etc., and are well known to those skilled in the art.

In some particularly preferred embodiments, when at least one neutral metalloprotease is employed in a granular composition or liquid, the neutral metalloprotease is in the form of an encapsulated particle to protect the enzyme from other components of the granular composition during storage. In addition, encapsulation also provides a means of controlling the availability of the neutral metalloprotease(s) during the cleaning process and may enhance performance of the neutral metalloprotease(s). It is contemplated that the encapsulated neutral metalloproteases of the present invention will find use in various settings. It is also intended that the neutral metalloprotease be encapsulated using any suitable encapsulating material(s) and method(s) known in the art.

In some preferred embodiments, the encapsulating material typically encapsulates at least part of the neutral metalloprotease catalyst. In some embodiments, the encapsulating material is water-soluble and/or water-dispersible. In some additional embodiments, the encapsulating material has a glass transition temperature (Tg) of 0° C. or higher (See e.g., WO 97/11151, particularly from page 6, line 25 to page 7, line 2, for more information regarding glass transition temperatures).

In some embodiments, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. In some embodiments in which the encapsulating material is a carbohydrate, it is selected from the group consisting of monosaccharides, oligosaccharides, polysaccharides, and combinations thereof. IN some preferred embodiments, the encapsulating material is a starch (See e.g., EP 0 922 499; U.S. Pat. No. 4,977,252. U.S. Pat. No. 5,354,559, and U.S. Pat. No. 5,935,826, for descriptions of some exemplary suitable starches).

In additional embodiments, the encapsulating material comprises a microsphere made from plastic (e.g., thermoplastics, acrylonitrile, methacrylonitrile, polyacrylonitrile, polymethacrylonitrile and mixtures thereof; commercially available microspheres that find use include, but are not limited to EXPANCEL® [Casco Products, Stockholm, Sweden], PM 6545, PM 6550, PM 7220, PM 7228, EXTENDOSPHERES®, and Q-CEL® [PQ Corp., Valley Forge, Pa.], LUXSIL® and SPHERICELL® [Potters Industries, Inc., Carlstadt, N.J. and Valley Forge, Pa.]).

Processes of Making and Using of Applicants' Cleaning Composition

In some preferred embodiments, the cleaning compositions of the present invention are formulated into any suitable form and prepared by any process chosen by the formulator, (See e.g., U.S. Pat. No. 5,879,584, U.S. Pat. No. 5,691,297, U.S. Pat. No. 5,574,005, U.S. Pat. No. 5,569,645, U.S. Pat. No. 5,565,422, U.S. Pat. No. 5,516,448, U.S. Pat. No. 5,489,392, and U.S. Pat. No. 5,486,303, for some non-limiting examples). In some embodiments in which a low pH cleaning composition is desired, the pH of such composition is adjusted via the addition of an acidic material such as HCl.

Adjunct Materials

While not essential for the purposes of the present invention, in some embodiments, the non-limiting list of adjuncts described herein are suitable for use in the cleaning compositions of the present invention. Indeed, in some embodiments, adjuncts are incorporated into the cleaning compositions of the present invention. In some embodiments, adjunct materials assist and/or enhance cleaning performance, treat the substrate to be cleaned, and/or modify the aesthetics of the cleaning composition (e.g., perfumes, colorants, dyes, etc.). It is understood that such adjuncts are in addition to the neutral metalloproteases of the present invention. The precise nature of these additional components, and levels of incorporation thereof, depends on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to those provided explicitly herein, additional examples are known in the art (See e.g., U.S. Pat. Nos. 5,576,282, 6,306,812 B1 and 6,326,348 B1). In some embodiments, the aforementioned adjunct ingredients constitute the balance of the cleaning compositions of the present invention.

Surfactants—

In some embodiments, the cleaning compositions of the present invention comprise at least one surfactant or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents.

In some embodiments, the surfactant is present at a level of from about 0.1% to about 60%, while in alternative embodiments, the level is from about 1% to about 50%, while in still further embodiments, the level is from about 5% to about 40%, by weight of the cleaning composition.

Builders—

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

Chelating Agents—

In some embodiments, the cleaning compositions of the present invention contain at least one chelating agent, Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

Deposition Aid—

In some embodiments, the cleaning compositions of the present invention include at least one deposition aid. Suitable deposition aids include, but are not limited to polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

Dye Transfer Inhibiting Agents—

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

Dispersants—

In some embodiments, the cleaning compositions of the present invention contains at least one dispersants. Suitable water-soluble organic materials include, but are not limited to the homo- or co-polymeric acids or their salts, in which the polycarboxylic acid comprises at least two carboxyl radicals separated from each other by not more than two carbon atoms.

Enzymes—

In some embodiments, the cleaning compositions of the present invention comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, B-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with amylase is used.

Enzyme Stabilizers—

In some embodiments of the present invention, the enzymes used in the detergent formulations of the present invention are stabilized. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as. other metal ions (e.g., barium (II), scandium (II), iron (II), manganese (II), aluminum (III), Tin (II), cobalt (II), copper (II), Nickel (II), and oxovanadium (IV)).

Catalytic Metal Complexes—

In some embodiments, the cleaning compositions of the present invention contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephos-phonic acid) and water-soluble salts thereof are used (See e.g., U.S. Pat. No. 4,430,243).

In some embodiments, the cleaning compositions of the present invention are catalyzed by means of a manganese compound. Such compounds and levels of use are well known in the art (See e.g., U.S. Pat. No. 5,576,282).

In additional embodiments, cobalt bleach catalysts find use in the cleaning compositions of the present invention. Various cobalt bleach catalysts are known in the art (See e.g., U.S. Pat. No. 5,597,936, and U.S. Pat. No. 5,595,967). Such cobalt catalysts are readily prepared by known procedures (See e.g., U.S. Pat. No. 5,597,936, and U.S. Pat. No. 5,595,967).

In additional embodiments, the cleaning compositions of the present invention include a transition metal complex of a macropolycyclic rigid ligand ("MRL"). As a practical matter, and not by way of limitation, in some embodiments, the compositions and cleaning processes provided by the present invention are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include, but are not limited to manganese, iron and chromium. Preferred MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See e.g., WO 00/32601, and U.S. Pat. No. 6,225,464).

Processes of Making and Using Cleaning Compositions

The cleaning compositions of the present invention are formulated into any suitable form and prepared by any suitable process chosen by the formulator, (See e.g., U.S. Pat. No. 5,879,584, U.S. Pat. No. 5,691,297, U.S. Pat. No. 5,574,005, U.S. Pat. No. 5,569,645, U.S. Pat. No. 5,565,422, U.S. Pat. No. 5,516,448, U.S. Pat. No. 5,489,392, U.S. Pat. No. 5,486,303, U.S. Pat. No. 4,515,705, U.S. Pat. No. 4,537,706, U.S. Pat. No. 4,515,707, U.S. Pat. No. 4,550,862, U.S. Pat. No. 4,561,998, U.S. Pat. No. 4,597,898, U.S. Pat. No. 4,968,451, U.S. Pat. No. 5,565,145, U.S. Pat. No. 5,929,022, U.S. Pat. No. 6,294,514, and U.S. Pat. No. 6,376,445, all of which are incorporated herein by reference for some non-limiting examples).

Method of Use

In preferred embodiments, the cleaning compositions of the present invention find use in cleaning surfaces and/or fabrics. In some embodiments, at least a portion of the surface and/or fabric is contacted with at least one embodiment of the cleaning compositions of the present invention, in neat form or diluted in a wash liquor, and then the surface and/or fabric is optionally washed and/or rinsed. For purposes of the present invention, "washing" includes, but is not limited to, scrubbing, and mechanical agitation. In some embodiments, the fabric comprises any fabric capable of being laundered in normal consumer use conditions. In preferred embodiments, the cleaning compositions of the present invention are used at concentrations of from about 500 ppm to about 15,000 ppm in solution. In some embodiments in which the wash solvent is water, the water temperature typically ranges from about 5° C. to about 90° C. In some preferred embodiments for fabric cleaning, the water to fabric mass ratio is typically from about 1:1 to about 30:1.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa and AA (amino acid); by (base pair); kb (kilobase pair); kD (kilodaltons); gm (grams); μg and ug (micrograms);

mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{405}$ (optical density at 405 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); LAS (lauryl sodium sulfonate); SDS (sodium dodecyl sulfate); Tris (tris(hydroxymethyl)aminomethane); TAED (N,N,N'N'-tetraacetylethylenediamine); BES (polyesstersulfone); MES (2-morpholinoethanesulfonic acid, monohydrate; f.w. 195.24; Sigma # M-3671); $CaCl_2$ (calcium chloride, anhydrous; f.w. 110.99; Sigma # C-4901); DMF (N,N-dimethylformamide, f.w. 73.09, d=0.95); Abz-AGLA-Nba (2-Aminobenzoyl-L-alanylglycyl-L-leucyl-L-alanino-4-nitrobenzylamide, f.w. 583.65; Bachem # H-6675, VWR catalog #100040-598); SBG1% ("Super Broth with Glucose"; 6 g Soytone [Difco], 3 g yeast extract, 6 g NaCl, 6 g glucose); the pH was adjusted to 7.1 with NaOH prior to sterilization using methods known in the art; w/v (weight to volume); v/v (volume to volume); Npr and npr (neutral metalloprotease); SEQUEST® (SEQUEST database search program, University of Washington); Npr and npr (neutral metalloprotease gene); nprE and NprE (*B. amyloliquefaciens* neutral metalloprotease); PMN (purified MULTIFECT® metalloprotease); MS (mass spectroscopy); SRI (Stain Removal Index); TIGR (The Institute for Genomic Research, Rockville, Md.); AATCC (American Association of Textile and Coloring Chemists); Amersham (Amersham Life Science, Inc. Arlington Heights, Ill.); Corning (Corning International, Corning, N.Y.); ICN (ICN Pharmaceuticals, Inc., Costa Mesa, Calif.); Pierce (Pierce Biotechnology, Rockford, Ill.); Equest (Equest, Warwick International Group, Inc., Flintshire, UK); EMPA (Eidgenossische Material Prufungs and Versuch Anstalt, St. Gallen, Switzerland); CFT (Center for Test Materials, Vlaardingen, The Netherlands); Amicon (Amicon, Inc., Beverly, Mass.); ATCC (American Type Culture Collection, Manassas, Va.); Becton Dickinson (Becton Dickinson Labware, Lincoln Park, N.J.); Perkin-Elmer (Perkin-Elmer, Wellesley, Mass.); Rainin (Rainin Instrument, LLC, Woburn, Mass.); Eppendorf (Eppendorf AG, Hamburg, Germany); Waters (Waters, Inc., Milford, Mass.); Geneart (Geneart GmbH, Regensburg, Germany); Perseptive Biosystems (Perseptive Biosystems, Ramsey, Minn.); Molecular Probes (Molecular Probes, Eugene, Oreg.); BioRad (BioRad, Richmond, Calif.); Clontech (CLONTECH Laboratories, Palo Alto, Calif.); Cargill (Cargill, Inc., Minneapolis, Minn.); Difco (Difco Laboratories, Detroit, Mich.); GIBCO BRL or Gibco BRL (Life Technologies, Inc., Gaithersburg, Md.); New Brunswick (New Brunswick Scientific Company, Inc., Edison, N.J.); Thermoelectron (Thermoelectron Corp., Waltham, Mass.); BMG (BMG Labtech, GmbH, Offenburg, Germany); Greiner (Greiner Bio-One, Kremsmuenster, Austria); Novagen (Novagen, Inc., Madison, Wis.); Novex (Novex, San Diego, Calif.); Finnzymes (Finnzymes OY, Finland) Qiagen (Qiagen, Inc., Valencia, Calif.); Invitrogen (Invitrogen Corp., Carlsbad, Calif.); Sigma (Sigma Chemical Co., St. Louis, Mo.); DuPont Instruments (Asheville, N.Y.); Global Medical Instrumentation or GMI (Global Medical Instrumentation; Ramsey, Minn.); MJ Research (MJ Research, Waltham, Mass.); Infors (Infors AG, Bottmingen, Switzerland); Stratagene (Stratagene Cloning Systems, La Jolla, Calif.); Roche (Hoffmann La Roche, Inc., Nutley, N.J.); Agilent (Agilent Technologies, Palo Alto, Calif.); S-Matrix (S-Matrix Corp., Eureka, Calif.); US Testing (United States Testing Co., Hoboken, N.Y.); West Coast Analytical Services (West Coast Analytical Services, Inc., Santa Fe Springs, Calif.); Ion Beam Analysis Laboratory (Ion Bean Analysis Laboratory, The University of Surrey Ion Beam Centre (Guildford, UK); TOM (Terg-o-Meter); BMI (blood, milk, ink); BaChem (BaChem AG, Bubendorf, Switzerland); Molecular Devices (Molecular Devices, Inc., Sunnyvale, Calif.); Corning (Corning International, Corning, N.Y.); MicroCal (Microcal, Inc., Northhampton, Mass.); Chemical Computing (Chemical Computing Corp., Montreal, Canada); NCBI (National Center for Biotechnology Information); Argo Bioanalytica (Argo Bioanalytica. Inc, New Jersey); Vydac (Grace Vydac, Hesperia, Calif.); Minolta (Konica Minolta, Ramsey, N.J.); and Zeiss (Carl Zeiss, Inc., Thornwood, N.Y.).

In these experiments, a spectrophotometer was used to measure the absorbance of the products formed after the completion of the reactions. A reflectometer was used to measure the reflectance of the swatches. Unless otherwise indicated, protein concentrations were estimated by Coomassie Plus (Pierce), using BSA as the standard.

The following assays were used in the Examples described below.

A. Bradford Assay for Protein Content Determination in 96-Well Microtiter Plates (MTPs)

In these assays, the Bradford dye reagent (Quick Start) assay was used to determine the protein concentration in NprE protease samples on MTP scale.

In this assay system, the chemical and reagent solutions used were:

| | |
|---|---|
| Quick Start Bradford Dye Reagent | BIO-RAD, #500-0205 |
| Dilution buffer | 10 mM NaCl, 0.1 mM CaCl2, 0.005% TWEEN ®-80 |

The equipment used was a Biomek FX Robot (Beckman) and a SpectraMAX (type 340) MTP reader; the MTPs were from Costar (type 9017).

In the test, 200 μl Bradford Dye Reagent was pipetted into each well, followed by 15 μl dilution buffer. Finally 10 μl of filtered culture broth were added to the wells. After thorough mixing, the MTPs were incubated for at least 10 minutes at room temperature. Possible air bubbles were blown away and the ODs of the wells were read at 595 nm.

To determine the protein concentration, the background reading (i.e., from uninoculated wells) was subtracted form the sample readings. The obtained $OD_{595}$ values provide a relative measure of the protein content in the samples. The linearity of the NprE calibration lines between 0 to 5 μg enabled the use of $OD_{595}$ nm values as a relative measure for the protein content. As the expected content of NprE in supernatant was 200-300 μg/ml, the 10 μl sample volume used in the test contains less than 5 μg protein, providing values in the linear range.

B. Microswatch Assay for Testing Protease Performance

The detergents used in this assay did not contain enzymes. The equipment used was a Biomek FX Robot (Beckman) and a SpectraMAX (type 340) MTP reader; the MTPs were from Costar (type 9017).

Detergent Preparation (Cold Water Liquid Detergent; US Conditions):

Milli-Q water was adjusted to 6 gpg water hardness (Ca/Mg=3/1), and 0.78 g/l TIDE® 2007-2× detergent was added.

The detergent solution was vigorously stirred for at least 15 minutes. Then. 5 mM HEPES (free acid) was added and the pH adjusted to 8.2.

Microswatches

Microswatches of ¼" circular diameter were obtained from CFT. Before cutting of the swatches, the fabric (EMPA 116) was washed with water. Two microswatches were placed in each well of a 96-well microtiter plate vertically to expose the whole surface area (i.e., not flat on the bottom of the well).

Test Method

The incubator was set to 20° C. The filtered culture broth samples were tested at an appropriate concentration by dilution with a mixture of 10 mM NaCl, 0.1 mM CaCl2 and 0.005% TWEEN®-80 solution. The desired detergent solution was prepared as described above. Then, 190 μl of detergent solution was added to each well of the MTP, containing microswatches. To this mixture, 10 μl of the diluted enzyme solution were added (to provide a total volume of 200 μl/well). The MTP was sealed with tape and placed in the incubator for 30 minutes, with agitation at 1400 rpm. Following incubation under the appropriate conditions, 100 μl of solution from each well were removed and placed into a fresh MTP. The new MTP containing 100 μl of solution/well was read at 405 nm in a MTP reader. Blank controls, as well as a control containing two microswatches and detergent but no enzyme were also included.

Calculation of the BMI Performance:

The obtained absorbance value was corrected for the blank value (i.e., obtained after incubation of microswatches in the absence of enzyme). The resulting absorbance was a measure for the hydrolytic activity. For each sample (e.g., nprE or variant) the performance index was calculated. The performance index compared the performance of the variant (actual value) and the standard enzyme (theoretical value) at the same protein concentration. In addition, the theoretical values were calculated, using the parameters of the Langmuir equation of the standard enzyme. A performance index (PI) that is greater than 1 (PI>1) identified a better variant (as compared to the standard [e.g., wild-type]), while a PI of 1 (PI=1) identified a variant that performed the same as the standard, and a PI that is less than 1 (PI<1) identified a variant that performed worse than the standard. Thus, the PI identified winners, as well as variants that are less desirable for use under certain circumstances.

C. Citrate Stability Assay for NprE Protease.

Citrate stability was measured after incubation of wild-type NprE and variants in the presence of 50 mM citrate. The initial and residual activity was determined using the DMC hydrolysis assay. In this assay system, the chemical and reagent solutions used were:

| | |
|---|---|
| Citric acid monohydrate | Merck 1.00244 |
| Pipes (free acid) | Sigma P-1851 |
| Tris (free acid) | Sigma T-1378 |
| HEPES (Ultra>99.5%) | Sigma-H7523 |
| TWEEN ®-80 | Sigma P-8074 |
| Dimethylcasein(DMC) | Sigma C-9801 |
| Tris buffer (free acid) | 6.04 g dissolved in 1000 ml water (=50 mM) |
| HEPES buffer | 11.9 g. dissolved in 1000 ml water (=50 mM) |
| Citrate buffer (free acid) | 21.0 g. dissolved in 1000 ml water (=100 mM), |
| PIPES buffer (free acid): | 3.32 g dissolved in about 960 ml water, |
| DMC solution | 1% w/v in 55 mM PIPES buffer, final pH = 6.0 |
| Dilution buffer 1 | 0.1 mM CaCl2/25 mM Tris; pH 8.2 |
| Dilution buffer 2 | 0.1 mM CaCl2/50 mM Citrate/25 mM Tris; pH 8.2 |

The concentrations of these dilution buffers are indicated as final concentrations. The initial concentration was proportionally higher and dependent on the dilution rate. The initial concentration was proportionally higher and dependent on the dilution rate. In alternative experiments, HEPES finds use in exchange for Tris. The equipment used was a Biomek FX Robot (Beckman), and an incubator/shaker (Innova, type 4230; New Brunswick). The PIPES buffer was adjusted to pH 5.8 with 4 N HCl (final concentration of 55 mM). The Tris buffer was adjusted to pH 8.2 with 4 N HCl (final concentration of 25 mM). The 50 mM citrate/25 mM Tris buffer was adjusted to pH 8.2 with 4 N NaOH. The HEPES buffer was adjusted to pH 8.2 with 4 N NaOH (final concentration of 25 mM). The 50 mM citrate/25 mM HEPES buffer was adjusted to pH 8.2 with 4 N NaOH.

Protein Determination

In order to establish the desired dilution rate in the citrate stability assay the protease concentration of the wild-type NprE controls for each plate were determined with the TCA assay. In this method, 25 μl filtered culture broth were added to 200 μl 16.875% (w/v) TCA. After incubation for 10 to 15 minutes at ambient temperature, the light scattering/absorbance at 405 nm was determined. The protein concentration was determined by using a calibration line, constructed with purified NprE.

Test Method

The dilution rate of the filtered culture broth was determined using the TCA assay, as described above.

Stressed Conditions:

The filtered culture broth was diluted with dilution buffer 2. The MTP was covered with tape, shaken for a few seconds and placed in the incubator at 25° C. for 60 minutes at 200 rpm. After incubation, 20 μl of the mixture were taken from each well and transferred into a new MTP, containing 180 μl 1% DMC preheated substrate solution (the substrate was preheated at 25° C.). The MTP was placed directly in the incubator/shaker and incubated at 25° C. for 30 minutes at 200 rpm agitation. The residual protease activity was determined using the dimethylcasein hydrolysis assay, described below.

Unstressed Conditions

The filtered culture broth was diluted with dilution buffer 1 Immediately, 20 μl of the mixture were taken from each well and transferred into a new MTP, containing 180 μl of preheated 1% DMC substrate solution (the substrate was preheated at 25° C.). The MTP was placed directly in the incubator/shaker and incubated for 25° C. for 30 minutes at 200 rpm agitation. The initial protease activity as determined with TNBS, using the dimethylcasein hydrolysis assay, described below.

All residual activity values (determined with the dimethylcasein hydrolysis assay) were calculated using the following equation.

$$\%\ \text{Residual Activity}=OD_{60\ min}\ \text{value}^{*}\ 100/OD_{00\ min}\ \text{value}$$

D. Dimethylcasein Hydrolysis Assay

In this assay system, the chemicals and reagent solutions used were:

| | |
|---|---|
| Dimethylcasein (DMC) | Sigma C-9801 |
| TWEEN ®-80 | Sigma P-8074 |
| PIPES buffer (free acid) | Sigma P-1851; 15.1 g dissolved in about 960 ml water; pH adjusted to 6.0 with 4N NaOH, 1 ml of 5% TWEEN ®-80 added and the volume brought up to 1000 ml. Final concentration of PIPES and TWEEN ®-80: 50 mM and 0.005% respectively. |

-continued

| | |
|---|---|
| Picrylsulfonic acid (TNBS) | Sigma P-2297 (5% solution in water) |
| Reagent A | 45.4 g $Na_2B_4O_7$•10H2O (Merck 6308) and 15 ml of 4N NaOH dissolved together to a final volume of 1000 ml (by heating if needed) |
| Reagent B | 35.2 g $NaH_2PO_4$•$1H_2O$ (Merck 6346) and 0.6 g $Na_2SO_3$ (Merck 6657) dissolved together to a final volume of 1000 ml. |

Method

To prepare the substrate, 4 g dimethylcasein was dissolved in 400 ml PIPES buffer. The filtered culture supernatants were diluted with PIPES buffer. Then, 10 μl of each diluted supernatant were added to 200 μl substrate in the wells of a MTP. The MTP was covered with tape, shaken for a few seconds and placed in an oven at 25° C. for 30 minutes without agitation. About 15 minutes before removal of the $1^{st}$ plate from the oven, the TNBS reagent was prepared by mixing 1 ml TNBS solution per 50 ml of Reagent A. MTPs were filled with 60 μl TNBS Reagent A per well. The incubated plates were shaken for a few seconds, after which 10 μl was transferred to the MTPs with TNBS Reagent A. The plates were covered with tape and shaken for 20 minutes in a bench shaker (BMG Thermostar) at room temperature and 500 rpm. Finally, 200 μl Reagent B was added to the wells, mixed for 1 minute on a shaker, and the absorbance at 405 nm was determined using a MTP reader.

The obtained absorbance value was corrected for the blank value (i.e., substrate without enzyme). The resulting absorbance was a measure of the hydrolytic activity. The (arbitrary) specific activity of a sample was calculated by dividing the absorbance and the determined protein concentration.

E. TIDE® Stability Assay

The stability of NprE and variants was measured after an incubation step in the presence of 25% TIDE® compact detergent. The initial and residual activity was determined using the AGLA-assay described below. The equipment used was a Biomek FX Robot (Beckman), a fluorescence meter (FLUOstar Optima; BMG), an incubator/shaker (iEMS; Thermoelectron) and an incubator/shaker (Innova; New Brunswick (type 4230)); the MTPs were from Costar (type 9017) and from Greiner (black plates, type 655076).

Chemicals and Reagents:

In this assay system, the chemical and reagent solutions used were:

| | |
|---|---|
| TIDE ®-compact detergent | With and without DTPA |
| TIDE ®-compact detergent solution | 125 g TIDE ®-compact dissolved in a mixture of 50 g of 50 mM HEPES pH 8.2 and 275 ml water; concentration of TIDE ® was 27.7%, after dilution with supernatant 25% |
| MES dilution buffer | 52.6 mM MES/NaOH, 2.6 mM $CaCl_2$, 0.005% TWEEN ®-80, pH 6.5 |
| AGLA substrate | BaChem, cat no. H-6675 or American Peptide Company, cat no. 81-0-31 |
| AGLA substrate solution | 451 mg of AGLA dissolved in 16 ml N,N-dimethylformamide; this solution was poured into 304 ml of MES-buffer (52.6 mM MES/NaOH, 2.6 mM $CaCl_2$, 0.005% TWEEN ®-80, pH 6.5) with stirring |

Test Method:

Unstressed Conditions:

First, 20 μl filtered culture broth was diluted with 180 μl MES dilution buffer. Then, 20 μl of this diluted broth was diluted with 180 μl MES dilution buffer. Then, 10 μl of this dilution was diluted with 190 μl AGLA-substrate solution in a pre-warmed plate at 25° C. Any air bubbles present were blown away and the plate was measured according to the AGLA protease assay protocol.

Stressed Conditions:

First, 20 μl filtered culture broth was diluted with 180 μl TIDE®-compact detergent solution without DTPA and after premixing in the iEMS shaker for 5 minutes, were incubated further in the Innova shaker. The plate was incubated for a total of 60 minutes at 32° C., at 200 rpm. In addition, 20 ul filtered culture broth were diluted with 180 ul TIDE®-compact detergent solution with DTPA and after premixing in the iEMS shaker for 5 minutes, were incubated further in the Innova shaker. The plate was incubated for a total of 40 minutes at 20° C., at 200 rpm. Then, 20 μl of either of these solutions were diluted with 180 μl MES dilution buffer and 10 μl of this dilution were diluted with 190 μl AGLA-substrate solution in a pre-warmed plate at 25° C. Any air bubbles present were blown away and the plate was measured according to the AGLA protease assay protocol.

Calculations:

Fluorescence measurements were taken at excitation of 350 nm and emission of 415 nm. The spectrofluorometer software calculated the reaction rates of the increase in fluorescence for each well to a linearly regressed line of milli-RFU/min:

$$\text{Percentage of residual activity: } \frac{(\text{Slope of stressed condition}) * 100}{(\text{Slope of unstressed condition})}$$

F. 2-Aminobenzoyl-L-alanylglycyl-L-leucyl-L-alanino-4-nitrobenzylamide Protease Assay (Abz-AGLA-Nba)

The method provided below provides a degree of technical detail that yields reproducible protease assay data independent of time and place. While the assay can be adapted to a given laboratory condition, any data obtained through a modified procedure must be reconciled with results produced by the original method. Neutral metalloproteases cleave the peptide bond between glycine and leucine of 2-aminobenzoyl-L-alanylglycyl-L-leucyl-L-alanino-4-nitrobenzylamide (Abz-AGLA-Nba). Free 2-aminobenzoyl-L-alanylglycine (Abz-AG) in solution has a fluorescence emission maximum at 415 nm with an excitation maximum of 340 nm. Fluorescence of Abz-AG is quenched by nitrobenzylamide in the intact Abz-AGLA-Nba molecule.

In these experiments, the liberation of Abz-AG by protease cleavage of Abz-AGLA-Nba was monitored by fluorescence spectroscopy (Ex. 340/Em. 415). The rate of appearance of Abz-AG was a measure of proteolytic activity. Assays were performed under non-substrate limited initial rate conditions.

A microplate mixer with temperature control (e.g., Eppendorf Thermomixer) was required for reproducible assay results. The assay solutions were incubated to desired temperature (e.g., 25° C.) in the microplate mixer prior to enzyme addition. Enzyme solutions were added to the plate in the mixer, mixed vigorously and rapidly transferred to the plate reader.

A spectrofluorometer with capability of continuous data recording, linear regression analysis, and with temperature control was required (e.g., SpectraMax M5, Gemini EM, Molecular Devices). The reader was always maintained at the desired temperature (e.g., 25° C.). The reader was set for top-read fluorescence detection and the excitation was set to 350 nm and emission to 415 nm without the use of a cut-off filter. The PMT was set to medium sensitivity and 5 readings per well. Autocalibration was turned on, but only to calibrate before the first reading. The assay was measured for 3 minutes with the reading interval minimized according to the number of wells selected to be monitored. The reader was set to calculate the rate of milli-RFU/min (thousandths of relative fluorescence units per minute). The number of readings used to calculate the rate (Vmax points) was set to the number equivalent to 2 minutes, as determined by the reading interval (e.g., a reading every 10 seconds would use 12 points to calculate the rate). The max RFU was set to 50,000.

All pipeting of enzyme and substrate stock solutions were done with positive displacement pipets (Rainin Microman). Buffer, assay, and enzyme working solutions were pipetted by single or multi-channel air-displacement pipets (Rainin LTS) from tubes, reagent reservoirs or stock microplates. A repeater pipet (Eppendorf) finds use in transferring the assay solution to microplate wells when few wells are used, to minimize reagent loss. Automated pipetting instruments such as the Beckman FX or Cybio Cybi-well also find use in transferring enzyme solutions from a working stock microplate to the assay microplate in order to initiate an entire microplate at once.

Reagents and Solutions:

52.6 mM MES/NaOH, 2.6 mM $CaCl_2$, pH 6.5—MES Buffer

MES acid (10.28 g) and 292 mg anhydrous $CaCl_2$ were dissolved in approximately 900 mL purified water. The solution was titrated with NaOH to pH 6.5 (at 25° C. or with temperature adjustment pH probe). The pH-adjusted buffer was made up to 1 L total volume. The final solution was filtered through a 0.22 gm sterile filter and kept at room temperature.

48 mM Abz-AGLA-Nba in DMF—Abz-AGLA-Nba Stock

Approximately 28 mg of Abz-AGLA-Nba was placed in a small tube. It was dissolved in mL of DMF (volume will vary depending upon Abz-AGLA-Nba massed) and vortexed for several minutes. The solution was stored at room temperature shielded from light.

50 mM MES, 2.5 mM $CaCl_2$, 5% DMF, 2.4 mM Abz-AGLA-Nba pH 6.5—Assay Solution

One mL Abz-AGLA-Nba stock was added to 19 mL MES Buffer and vortexed. The solution was stored at room temperature shielded from light.

50 mM MES, 2.5 mM $CaCl_2$, pH 6.5—Enzyme Dilution Buffer

This buffer was produced by adding 5 mL purified water to 95 mL MES Buffer.

50 mM MES, 2.5 mM $CaCl_2$, 5% DMF, pH 6.5—Substrate Dilution Buffer

Five mL pure DMF were added to 95 mL MES Buffer. This buffer was used to determine kinetic parameters.

Enzyme Solutions

The enzyme stock solutions were diluted with enzyme dilution buffer to a concentration of approximately 1 ppm (1 ug/mL). MULTIFECT® neutral protease (wild-type NprE) was diluted to concentrations below 6 ppm (6 ug/mL). Serial dilutions were preferred. Solutions were stable at room temperature for 1 hour, but for longer term storage, the solutions were maintained on ice.

Procedure

First all buffers, stock, and working solutions were prepared. Each enzyme dilution was assayed in triplicate, unless otherwise indicated. When not completely full, the enzyme working solution stock microplate was arranged in full vertical columns starting from the left of the plate (to accommodate the plate reader). The corresponding assay plate was similarly set up. The microplate spectrofluorometer was set up as previously described.

First, a 200 uL aliquot of assay solution were placed in the wells of a 96-well microplate. The plate was incubated for 10 min at 25° C. in a temperature controlled microplate mixer, shielded from light. The assay was initiated by transferring 10 uL of the working enzyme solutions from the stock microplate to the assay microplate in the mixer. Optimally, 96-well pipetting head finds use, or an 8-well multi-channel pipet was used to transfer from the left-most column first. The solutions were vigorously mixed for 15 seconds (900 rpm in Eppendorf Thermomixer) Immediately, the assay microplate was transferred to the microplate spectrofluorometer and recording of fluorescence measurements at excitation of 350 nm and emission of 415 nm were begun. The spectrofluorometer software calculated the reaction rates of the increase in fluorescence for each well to a linearly regressed line of milli-RFU/min. In some experiments, a second plate was placed in the microplate mixer for temperature equilibration while the first plate was being read.

The rate initial velocities were linear with respect to product concentration (i.e., liberated 2-aminobenzoyl fluorescence) up to 0.3 mM product, which corresponded to approximately 50,000 RFU in a solution starting at 2.3 mM Abz-AGLA-Nba with background fluorescence of approximately 22,000 RFU. Abz-AGLA-Nba was dissolved in DMF and was been used the day it was prepared.

Detergent Compositions:

In the exemplified detergent compositions, the enzymes levels are expressed by pure enzyme by weight of the total composition and unless otherwise specified, the detergent ingredients are expressed by weight of the total compositions. The abbreviated component identifications therein have the following meanings:

| Abbreviation | Ingredient |
|---|---|
| LAS | Sodium linear $C_{11-13}$ alkyl benzene sulfonate. |
| NaC16-17HSAS | Sodium $C_{16-17}$ highly soluble alkyl sulfate |
| TAS | Sodium tallow alkyl sulphate. |
| CxyAS | Sodium $C_{1x}$-$C_{1y}$ alkyl sulfate. |
| CxyEz | $C_{1x}$-$C_{1y}$ predominantly linear primary alcohol condensed with an average of z moles of ethylene oxide. |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2$•N + $(CH_3)_2(C_2H_4OH)$ with $R_2$ = $C_{12}$-$C_{14}$. |
| Silicate | Amorphous Sodium Silicate ($SiO_2$:$Na_2O$ ratio = 1.6-3.2:1). |
| Metasilicate | Sodium metasilicate ($SiO_2$:$Na_2O$ ratio = 1.0). |
| Zeolite A | Hydrated Aluminosilicate of formula $Na_{12}(AlO_2SiO_2)_{12}$•$27H_2O$ |
| SKS-6 | Crystalline layered silicate of formula $\delta$-$Na_2Si_2O_5$. |
| Sulfate | Anhydrous sodium sulphate. |
| STPP | Sodium Tripolyphosphate. |
| MA/AA | Random copolymer of 4:1 acrylate/maleate, average molecular weight about 70,000-80,000. |
| AA | Sodium polyacrylate polymer of average molecular weight 4,500. |
| Polycarboxylate | Copolymer comprising mixture of carboxylated monomers such as acrylate, maleate and methyacrylate with a MW ranging between 2,000-80,000 such as Sokolan commercially available from BASF, being a copolymer of acrylic acid, MW4,500. |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate. |
| PB4 | Sodium perborate tetrahydrate of nominal formula $NaBO_3$•$4H_2O$. |

-continued

| Abbreviation | Ingredient |
|---|---|
| Percarbonate | Sodium percarbonate of nominal formula $2Na_2CO_3 \cdot 3H_2O_2$. |
| TAED | Tetraacetyl ethylene diamine. |
| NOBS | Nonanoyloxybenzene sulfonate in the form of the sodium salt. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane. |
| DETBCHD | 5,12-diethyl-1,5,8,12-tetraazabicyclo [6,6,2] hexadecane, dichloride, Mn(II) SALT |
| PAAC | Pentaamine acetate cobalt(III) salt. |
| Paraffin | Paraffin oil sold under the tradename Winog 70 by Wintershall. |
| Paraffin Sulfonate | A Paraffin oil or wax in which some of the hydrogen atoms have been replaced by sulfonate groups. |
| Aldose oxidase | Oxidase enzyme sold under the tradename Aldose Oxidase by Novozymes A/S |
| Galactose oxidase | Galactose oxidase from Sigma |
| nprE | The recombinant form of neutral metalloprotease expressed in *Bacillus subtilis*. |
| PMN | Purified neutral metalloprotease from *Bacillus amyloliquefacients*. |
| Amylase | Amylolytic enzyme sold under the tradename PURAFECT ® Ox described in WO 94/18314, WO96/05295 sold by Genencor; NATALASE ®, TERMAMYL ®, FUNGAMYI ® and DURAMYL ™, all available from Novozymes A/S. |
| Lipase | Lipolytic enzyme sold under the tradename LIPOLASE ®, LIPOLASE ® Ultra by Novozymes A/S and Lipomax ™ by Gist-Brocades. |
| Cellulase | Cellulytic enzyme sold under the tradename Carezyme, Celluzyme and/or Endolase by Novozymes A/S. |
| Pectin Lyase | PECTAWAY ® and PECTAWASH ® available from Novozymes A/S. |
| PVP | Polyvinylpyrrolidone with an average molecular weight of 60,000 |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Silicone antifoam | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| SRP 1 | Anionically end capped poly esters. |
| PEG X | Polyethylene glycol, of a molecular weight of x. |
| PVP K60 ® | Vinylpyrrolidone homopolymer (average MW 160,000) |
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG. |
| DC3225C | Silicone suds suppresser, mixture of Silicone oil and Silica from Dow Corning. |
| TEPAE | Tetreaethylenepentaamine ethoxylate. |
| BTA | Benzotriazole. |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids. |

-continued

| Abbreviation | Ingredient |
|---|---|
| Clay | A hydrated aluminumu silicate in a general formula $Al_2O_3SiO_2 \cdot xH_2O$. Types: Kaolinite, mont-morillonite, atapulgite, illite, bentonite, halloysite. |
| pH | Measured as a 1% solution in distilled water at 20° C. |

Example 1

Cloning of the Neutral Metalloprotease Gene from *B. amyloliquefaciens*

In this Example, methods used to clone the *B. amyloliquefaciens* neutral metalloprotease gene are described. The gene-encoding neutral metalloprotease was cloned from *B. amyloliquefaciens* using well-established methods in this art. The non-exempt (i.e., the strain carries extrageneric DNA (besides the chloramphenicol selectable marker which is allowed in an exempt strain), specifically the plasmid pJM102 sequences) strain BC91504 (aprE/nprE-pJM102 in BG3594::comK) carries the *B. subtilis* aprE promoter and signal sequence fused to *B. amyloliquefaciens* nprE propeptide/mature gene in integrating plasmid pJM102.

The following two sequences (SEQ ID NO:1 and SEQ ID NO:2) of *B. subtilis* and *B. amyloliquefaciens* were generated via PCR with the oligonucleotide primers corresponding to the underlined sequences.

*B. subtilis* chromosomal EcoRI restriction site (GAATTC) and aprE start codon (GTG) and *B. amyloliquefaciens* nprE stop codon are shown in the following sequences in boldface type as well as a synthetically introduced HindIII restriction site (ΔΔGCTT) designed into primer #4.

The *B. amyloliquefaciens* aprE 5' upstream sequence, promoter and signal sequence coding region are shown in the following sequence (SEQ ID NO:1). Primer 1 (apr-f; GAGCTGGGTAΔΔGCCTATGAAT; SEQ ID NO:5) is shown underlined, at the beginning of the sequence, while the aprE portion of primers 2 and 3 (npr-f and npr-r; GTTCAG-CAACATGTCTGCGCAGGCT; SEQ ID NO:6) are shown double underlined at the end of the sequence.

```
                                                (SEQ ID NO: 1)
GAGCTGGGTAAAGCCTATGAATTCTCCATTTTCTTCTGCTATCAAAATAA

CAGACTCGTGATTTTCCAAACGAGCTTTCAAAAAAGCCTCTGCCCCTTGC

AAATCGGATGCCTGTCTATAAAATTCCCGATATTGGTTAAACAGCGGCGC

AATGGCGGCCGCATCTGATGTCTTTGCTTGGCGAATGTTCATCTTATTTC

TTCCTCCCTCTCAATAATTTTTTCATTCTATCCCTTTTCTGTAAAGTTTA

TTTTTCAGAATACTTTTATCATCATGCTTTGAAAAAATATCACGATAATA

TCCATTGTTCTCACGGAAGCACACGCAGGTCATTTGAACGAATTTTTTCG

ACAGGAATTTGCCGGGACTCAGGAGCATTTAACCTAAAAAAGCATGACAT

TTCAGCATAATGAACATTTACTCATGTCTATTTTCGTTCTTTTCTGTATG

AAAATAGTTATTTCGAGTCTCTACGGAAATAGCGAGAGATGATATACCTA

AATAGAGATAAAATCATCTCAAAAAAATGGGTCTACTAAAATATTATTCC

ATCTATTACAATAAATTCACAGAATAGTCTTTTAAGTAAGTCTACTCTGA

ATTTTTTTAAAAGGAGAGGGTAAAGAGTGAGAAGCAAAAAATTGTGGATC
```

-continued

AGCTTGTTGTTTGCGTTAACGTTAATCTTTACGATGGC

GTTCAGCAACATGTCTGCGCAGGCT

The sequence of the *B. amyloliquefaciens* propeptide and mature nprE coding sequence and transcription terminator are provided in the sequence below. In this sequence, the nprE portion of primers 2 and 3 is underlined (GCTGAGAATC-CTCAGCTTAΔΔGAAAACCTG; SEQ ID NO:7), while the npr-r portion of primer 4 (GGCTTCACCATGATCATATAT-GTCΔΔGCTTGGGGGG; SEQ ID NO:8) is shown double underlined.

(SEQ ID NO: 2)

GCTGAGAATCCTCAGCTTAAAGAAAACCTGACGAATTTTGTACCGAAGCA

TTCTTTGGTGCAATCAGAATTGCCTTCTGTCAGTGACAAAGCTATCAAGC

AATACTTGAAACAAAACGGCAAAGTCTTTAAAGGCAATCCTTCTGAAAGA

TTGAAGCTGATTGACCAAACGACCGATGATCTCGGCTACAAGCACTTCCG

TTATGTGCCTGTCGTAAACGGTGTGCCTGTGAAAGACTCTCAAGTCATTA

TTCACGTCGATAAATCCAACAACGTCTATGCGATTAACGGTGAATTAAAC

AACGATGTTTCCGCCAAAACGGCAAACAGCAAAAAATTATCTGCAAATCA

GGCGCTGGATCATGCTTATAAAGCGATCGGCAAATCACCTGAAGCCGTTT

CTAACGGAACCGTTGCAAACAAAAACAAAGCCGAGCTGAAAGCAGCAGCC

ACAAAAGACGGCAAATACCGCCTCGCCTATGATGTAACCATCCGCTACAT

CGAACCGGAACCTGCAAACTGGGAAGTAACCGTTGATGCGGAAACAGGAA

AAATCCTGAAAAAGCAAAACAAAGTGGAGCATGCCGCCACAACCGGAACA

GGTACGACTCTTAAAGGAAAAACGGTCTCATTAAATATTTCTTCTGAAAG

CGGCAAATATGTGCTGCGCGATCTTTCTAAACCTACCGGAACACAAATTA

TTACGTACGATCTGCAAAACCGCGAGTATAACCTGCCGGGCACACTCGTA

TCCAGCACCACAAACCAGTTTACAACTTCTTCTCAGCGCGCTGCCGTTGA

TGCGCATTACAACCTCGGCAAAGTGTATGATTATTTCTATCAGAAGTTTA

ATCGCAACAGCTACGACAATAAAGGCGGCAAGATCGTATCCTCCGTTCAT

TACGGCAGCAGATACAATAACGCAGCCTGGATCGGCGACCAAATGATTTA

CGGTGACGGCGACGGTTCATTCTTCTCACCTCTTTCCGGTTCAATGGACG

TAACCGCTCATGAAATGACACATGGCGTTACACAGGAAACAGCCAACCTG

AACTACGAAAATCAGCCGGGCGCTTTAAACGAATCCTTCTCTGATGTATT

CGGGTACTTCAACGATACTGAGGACTGGGATATCGGTGAAGATATTACGG

TCAGCCAGCCGGCTCTCCGCAGCTTATCCAATCCGACAAAATACGGACAG

CCTGATAATTTCAAAAATTACAAAAACCTTCCGAACACTGATGCCGGCGA

CTACGGCGGCGTGCATACAAACAGCGGAATCCCGAACAAAGCCGCTTACA

ATACGATTACAAAAATCGGCGTGAACAAAGCGGAGCAGATTTACTATCGT

GCTCTGACGGTATACCTCACTCCGTCATCAACTTTTAAAGATGCAAAAGC

CGCTTTGATTCAATCTGCGCGGGACCTTTACGGCTCTCAAGATGCTGCAA

GCGTAGAAGCTGCCTGGAATGCAGTCGGATTGTAAACAAGAAAAGAGACC

GGAAATCCGGTCTCTTTTTTATATCTAAAAACATTTCACAGT

GGCTTCACCATGATCATATATGTCAAGCTTGGGGGG

The amino acid sequence of the full-length NprE (pre-, pro- and mature sequence) is provided below:

(SEQ ID NO: 3)

MGLGKKLSVAVAASFMSLTISLPGVQAAENPQLKENLTNFVPKHSLVQSE

LPSVSDKAIKQYLKQNGKVKGNPSERLKLIDQTTDDLGYKHFRYVPVVNG

VPVKDSQVIIHVDKSNNVYAINGELNNDVSAKTANSKKLSANQALDHAYK

AIGKSPEAVSNGTVANKNKAELKAAATKDGKYRLAYDVTIRYIEPEPANV

WEVTVDAETGKILKKQNKVEHAATTGTGTTLKGKTVSLNISSESGKYVLR

DLSKPTGTQIITYDLQNREYNLPGTLVSSTTNQFTTSSQRAAVDAHYNLG

KVYDYFYQKFNRNSYDNKGGKIVSSVHYGSRYNNAAWIGDQMIYGDGDGS

FFSPLSGSMDVTAHEMTHGVTQETANLNYENQPGALNESFSDVFGYFNDT

EDWDIGEDITVSQPALRSLSNPTKYGQPDNFKNYKNLPNTDAGDYGGVHT

NSGIPNKAAYNTITKIGVNKAEQIYYRALTVYLTPSSTFKDAKAALIQSA

RDLYGSQDAASVEAAWNAVGL

In some alternative embodiments, the following NprE sequence finds use in the present invention.

(SEQ ID NO: 4)

VRSKKLWISLLFALTLIFTMAFSNMSAQAAENPQLKENLTNFVPKHSLVQ

SELPSVSDKAIKQYLKQNGKVFKGNPSERLKLIDQTTDDLGYKHFRYVPV

VNGVPVKDSQVIIHVDKSNNVYAINGELNNDVSAKTANSKKLSANQALDH

AYKAIGKSPEAVSNGTVANKNKAELKAAATKDGKYRLAYDVTIRYIEPEP

ANWEVTVDAETGKILKKQNKVEHAATTGTGTTLKGKTVSLNISSESGKYV

LRDLSKPTGTQIITYDLQNREYNLPGTLVSSTTNQFTTSSQRAAVDAHYN

LGKVYDYFYQKFNRNSYDNKGGKIVSSVHYGSRYNNAAWIGDQMIYGDGD

GSFFSPLSGSMDVTAHEMTHGVTQETANLNYENQPGALNESFSDVFGYFN

DTEDWDIGEDITVSQPALRSLSNPTKYGQPDNFKNYKNLPNTDAGDYGGV

HTNSGIPNKAAYNTITKIGVNKAEQIYYRALTVYLTPSSTFKDAKAALIQ

SARDLYGSQDAASVEAAWNAVGL

The primer sequences used in these PCR experiments are provided below:

| Primers Used in PCR Experiments | | |
|---|---|---|
| Primer Number | Sequence | SEQ ID NO: |
| 1 | 5'-GAGCTGGGTAAAGCCTATGAAT-3' | SEQ ID NO: 5 |
| 2 | 5'-CAGGTTTTCTTTAAGCTGAGGATTCTCAGC-AGCCTGCGCAGACATGTTGCTGAAC-3' | SEQ ID NO: 9 |
| 3 | 5'-GTTCAGCAACATGTCTGCGCAGGCT-GCTGAGAATCCTCAGCTTAAAGAAAACCTG-3' | SEQ ID NO: 10 |

-continued

| Primers Used in PCR Experiments | | |
|---|---|---|
| Primer Number | Sequence | SEQ ID NO: |
| 4 | 5'CCCCCCAAGCTTGACATATATGATCATGGTGAAGCC-3' | SEQ ID NO: 11 |

Primers 2 and 3 are reverse complements of each other and correspond to either non-coding (#2) or coding (#3) strands of the chromosomal DNAs. For the coding strand, they correspond to the last 25 base pairs of the aprE signal sequence and the first 30 base pairs of the nprE propeptide. Primer #4 is the reverse complement to the underlined sequence, comprising 24 base pairs 3' of the nprE stop codon and terminator with an introduced HindIII site preceded by six dCTP residues, to provide a so-called "clamp," allowing more efficient cleavage with HindIII restriction endonuclease, as some restriction enzymes cleave inefficiently if their recognition sequence is located at the very ends of DNA fragments.

The two PCR fragments were generated with the following protocol and reagents (except DNA template and oligonucleotide primers) from Applied Biosystems' rTTH DNA Polymerase, XL Kit:

40.6 μl $H_2O$
30 μl 3.3× rTth PCR buffer
10 μl 2 mM dNTP mix
4.4 μl 25 mM Mg-acetate
5 μl 50 μM primer #1 or #3 (forward primers)
5 μl 50 μM primer #2 or #4 (reverse primers)
2 μl *B. subtilis* or *B. amyloliquefaciens* chromosomal DNA
2 μl rTth polymerase
1 μl Pfu Turbo polymerase
100 μl total reaction volume The PCR conditions used in these experiments were (95° C., 30 sec./58° C., 30 sec/68° C., 1 min.)×30 cycles followed by rapid cooling to 4° C. Reactions were run on 1.2% agarose/TBE preparative gels, the appropriately-sized fragments excised and purified using the QIAGEN® Gel Extraction Kit. In a second fusion, PCR reactions were conducted in which chromosomal DNAs were replaced by 1 ul each of the two separate fragments and only outside primers #s 1 and #2 were used. The same PCR conditions as described above were used. Due to the complementary ends formed on the two fragments from the use of complementary primers 2 and 3 in the first PCRs, the two fragments were precisely fused.

The fusion fragment was digested with EcoRI and HindIII and gel purified as described above. The integration plasmid pJM102 was also digested with EcoRI and HindIII, and the linear plasmid was then gel purified and ligated by standard techniques to the digested apr/npr fusion fragment. This ligation reaction was subsequently used to directly transform a xylose-induced *B. subtilis* strain.

After purification, the two fragments were generated by PCR with primers 1 and 2 from wild-type *B. subtilis* chromosomal DNA, and with primers 3 and 4 from chromosomal DNA from a *B. amyloliquefaciens* strain. This fragment was again purified as descried above, followed by cutting with EcoRI and HindIII as in the same digestion of the integrating plasmid pJM102 and subsequent ligation of the fusion fragment to the plasmid. Several transformants had the fusion sequenced from the chromosome to verify the absence of any PCR-derived mutations. One of these was then amplified stepwise from 5-25 mg/mL chloramphenicol, the selectable marker on pJM102, to co-amplify the linked expression cassette.

The selected sequence verified transformant was obtained by selection for pJM102's chloramphenicol (CMP) resistance marker on LB/agar plates containing 5 mg/ml CMP. This was then inoculated into LB broth at 10 mg/ml CMP overnight at 37° C., with shaking at 250 RPM. This culture was then streaked onto LB/agar plates with 10 mg/ml CMP to isolate single colonies. One colony was then inoculated into LB broth at 25 mg/ml CMP overnight at 37° C., with shaking at 250 RPM. This culture was then streaked to LB/agar plates with 25 mg/ml CMP to isolate single colonies. These colonies were harvested and stored in glycerol at −70° C. until use, as known in the art.

The deletion of the two non-essential proteases present in *B. subtilis* (aprE and nprE), as well as amylase, reduced the total extracellular protease level during the production of metalloprotease. The DNA encoding the neutral metalloprotease was cloned into an amylase-deleted host. The inducible comK for competence development was inserted in the middle of the amylase locus, making the strain "amy$^-$." The secretion of the expressed protein was ensured by insertion of the nucleotides encoding the signal sequence prior to the coding sequence of the gene.

Example 2

Expression and Fermentation of the Purified MULTIFECT® Neutral and Recombinant Neutral Metalloprotease (nprE)

The recombinant *Bacillus subtilis* produced as described in Example 1 was cultivated by conventional batch fermentation in a nutrient medium as described below. One glycerol vial (prepared as described in Example 1) of *B. subtilis* culture containing the *B. amyloliquefaciens* neutral metalloprotease was used to inoculate 600 ml of SBG1% medium containing 200 mg/L chloramphenicol. The cultures were grown for 48 hours at 37° C., after which time, the culture fluid was recovered by centrifugation at 12,000 rpm, as known in the art. This procedure was done in duplicate. The final enzyme concentrations obtained were in the range of about 1.4 and 2 g/L.

Example 3

Purification and Characterization of Neutral Metalloprotease

This Example describes the methods used to purify the neutral metalloprotease expressed by the organisms described in Example 2. After 36 hours of incubation at 37° C., the fermentation broth was recovered and centrifuged at 12 000 rpm (SORVALL® centrifuge model RCSB). The secreted neutral metalloproteases were isolated from the culture fluid and concentrated approximately 10-fold using an Amicon filter system 8400 with a BES (polyethersulfone) 10 kDa cutoff.

The concentrated supernatant was dialyzed overnight at 4° C. against 25 mM MES buffer, pH 5.4, containing 10 mM NaCl. The dialysate was then loaded onto a cation-exchange column Porous HS20 (total volume ~83 mL; binding capacity ~4.5 g protein/mL column; Waters) as described below. The column was pre-equilibrated with 25 mM MES buffer, pH 5.4, containing 10 mM NaCl. Then, approximately 200-300 mL of sample was loaded onto the column. The bound protein was eluted using a pH gradient from 5.4 to 6.2 over 10-column volumes of MES buffer. Elution of the protein was between pH 5.82 and 6.0, and was assessed using proteolytic activity as described herein and 10% (w/v) NUPAGE® SDS-PAGE (Novex). The neutral protease containing fractions were then pooled. Calcium and zinc chloride salts in the ratio of 3:1 were added prior to the adjustment of the pH to 5.8. The Perceptive Biosystems BIOCAD® Vision (GMI) was used for protein purification.

The purified protein, assessed using a 10% (w/v) NUPAGE® SDS-PAGE, was determined to homogenous, with greater than 95% purity. Typically, less than 1% of the purified preparations showed serine protease activity when assessed using the standard protease assay with the small substrate, suc-p-AAPF-pNA (N-succinyl-L-Ala-L-Ala-L-Pro-L-Phe-p-nitroanilide) (Sigma). This assay was performed in microtiter plate format (96 well) using a 100 mM Tris-HCl buffer, pH 8.5, containing 10 mM $CaCl_2$ and 0.005% TWEEN®-80. The substrate (p-AAPF NA) was prepared by making a 160 mM stock in DMSO (dimethylsulfoxide) (100 mg/me and diluting this stock 100-fold with the Tris-HCl buffer containing $CaCl_2$ and 0.005% TWEEN®-80. Then, 10 uL of diluted protease solution (dilutions were prepared using 100 mM Tris-HCl buffer, pH 8.5, containing 10 mM $CaCl_2$ and 0.005% TWEEN-80) was added to 190 uL 1 mg/ml p-AAPF solution. The assay was mixed for 5 minutes and the kinetic change at 410 nm was read over 2 to 5 minutes. The slope of the response was measured and used as an indication of the amount of serine protease, activity. The protein was formulated for storage using 25 mM MES buffer, pH 5.8, containing 1 mM zinc chloride, 4 mM calcium chloride, and 40% propylene glycol.

Example 4

Affinity of Purified MULTIFECT® Neutral Metalloprotease (PMN) for Calcium and Zinc Cations In this Example, methods to determine the affinity of the neutral metalloprotease (PMN) prepared as described in the above Examples are described. The affinities of PMN for calcium and zinc ions were performed using the fluorescent indicators Fluo-3 and FluoZin-3, respectively obtained from Molecular Probes. All fluorescence measurements were recorded on a LS50B Luminescence spectrophotometer (Perkin-Elmer). The binding of Fluo-3 was monitored by excitation at 500 nm and the emission spectra were recorded from 505 to 550 nm. Similarly, the binding of FluoZin-3 was monitored by excitation at 495 nm and the emission spectra were collected from 500 to 550 nm. The excitation and emission slit width were both set at 2.5 nm.

In these determinations, 100 uM neutral metalloprotease in 50 mM Tris-HCl buffer, pH 8.4, was titrated with increasing amounts of the relevant indicator. The titration curves are shown in FIG. 1. In this Figure, the triangles represent the curve binding data obtained for $Zn^{2+}$, using the Fluo-Zin3 dye monitored at 516 nm, while the circles represent the data obtained for $Ca^{2+}$ using the Fluo-3 dye monitored at 522 nm. The association constants (Ka's) for zinc and calcium (assuming a single binding site) were determined to be 0.401 nM and 0.037 nM, respectively. These results indicate that purified MULTIFECT® neutral metalloprotease bound the zinc ion with approximately 10-fold greater affinity than the calcium ion. Based on the weaker binding of calcium, initial protein engineering experiments are designed to involve either (i) designing tighter calcium binding site(s) and/or (ii) eliminating the structural stability requirement for calcium (e.g., to stabilize the protein to greater than 80%).

Example 5

Storage Stability

In this Example, experiments conducted to assess the storage stability of PMN and recombinant *B. amyloliquefaciens* neutral metalloprotease expressed in *B. subtilis* are described. Proteolysis of these neutral metalloprotease preparations was assessed in the presence of increasing LAS (lauryl sodium sulfate; Sigma) solutions (0% up to an including 10%). Proteolytic fragments generated from the purified MULTIFECT® neutral metalloprotease (PMN) were observed using 10% (w/v) NUPAGE® SDS-PAGE.

The storage stability of the recombinant neutral metalloprotease from *B. amyloliquefaciens* expressed in *B. subtilis* produced as described above, was determined in buffer alone (50 mM Tris-HCl buffer, pH 8.4) and in the presence of detergent base obtained from Procter & Gamble. The buffer and/or detergent base contained zinc ions, calcium ions or a combination thereof. The concentration of both the zinc and calcium ions was varied from 0 to 25 mM. These results were always compared with those for the neutral metalloprotease incubated in buffer alone.

Protease Assays

Azo-Casein Assay:

The azo-casein endpoint assay was used to assess the amount of proteolysis that occurred under certain conditions. In these assays, 75 uL of enzyme were incubated with excess calcium or zinc or both ions added to 250 μl of 1% (w/v) azo-casein (Sigma). The reaction proceeded at 30° C. for 15 minutes, after which 10% (w/v) trichloroacetic acid was added to stop the reaction. The precipitated protein and the unreacted azo-casein were removed by centrifugation for 10 minutes at 14 000 rpm. The color of the azo-group was developed by addition of 750 μL 1 M sodium hydroxide. The development of the color proceeded for 5 minutes, after which the reaction was stopped and the absorbance was measured at 440 nm.

Succinylated-Casein and TNBSA Assay:

The activity of the neutral metalloprotease was determined using the QuantiCleave Protease Assay Kit™ (Pierce). This assay is based on the digestion of succinylated-casein by the enzyme. The primary amino groups formed are then reacted with trinitrobenzene sulfonic acid (TNBSA) and form a colored complex that has maximum absorbance at 450 nm. The assay is performed in 96-well microtiter format. The assay requires a 15-minute incubation with the succinylated casein and a 15-minute reaction with the TNBSA. During both incubations, the samples are placed on a shaker. TPCK-trypsin (Pierce) is the general standard used for overall protease activity determinations. However, optimum conditions for activity for specific proteases require the use of the protease of interest. In the case of the assays performed in these experiments, both trypsin and the protease of interest were used, in order to calibrate the assay. The accuracy of the assay requires that the standard dilutions made of 0.5 mg/mL trypsin always result in absorbance values (at 450 nm) below 0.5.

Every sample was measured relative to a control containing no casein. The reported change in absorbance (ΔAbs(450 nm)) accounts for the interference from the amino groups of casein. Further, any possible interference from primary amino groups in the buffer and/or other components of the detergent was/were also corrected for in this manner. The activity of all samples was determined relative to detergent with no added neutral metalloprotease, as well as for enzyme incubated in BupH™ borate buffer supplied with the kit, for the same length of time and at the same temperature.

This test is an end-point assay, in which 50 mM borate buffer, pH 8.5, was used at 32° C. The protease assays were typically performed in duplicate. In most experiments to determine stability measurements, the protein and detergent were diluted using the above-mentioned buffer by 1:1000, although in some experiments dilutions of were also 1:500 or 1:200, in order to obtain readings where the absorbance of the blanks was less than 0.5. The microtiter spectrophotometer used in these experiments was a SpectraMax250® (Molecular Devices) and all assays were conducted in medium protein-binding 96-well plates (Corning).

The results for the standards protein samples (e.g., trypsin and purified metalloprotease) obtained in these assays indicated that there was a non-linear response (a linear scale may be adequate only in a narrow assay range). Hence, the curve was fitted to a quadratic function where $f=y_0+ax^2+bx$; f is fit to y (SigmaPlot® v. 9; SPSS, Inc.). Thus, if a linear equation was used to quantitate the amount of protein, inaccurate data were obtained; the quadratic equation was found to be required in order to obtain accurate results. It is noted that the manufacturer's (Pierce) kit insert indicates that the results may be fitted with “x” being a log scale.

Example 6

Effect of pH and LAS on Neutral Metalloprotease Activity

The pH optimum of the activity for 0.36 mg/mL of formulated nprE was also determined. The buffers investigated in this study were 50 mM sodium acetate over the pH range 3.5-5.5 (pKa=4.76), 50 mM MES buffer over the pH range 5.5 to 7.0 (pKa=6.10), and 50 mM Tris-HCl buffer at pH 8.4. The pH optimum for formulated nprE was determined to be between 5.5 and 6.0.

Figure 2:
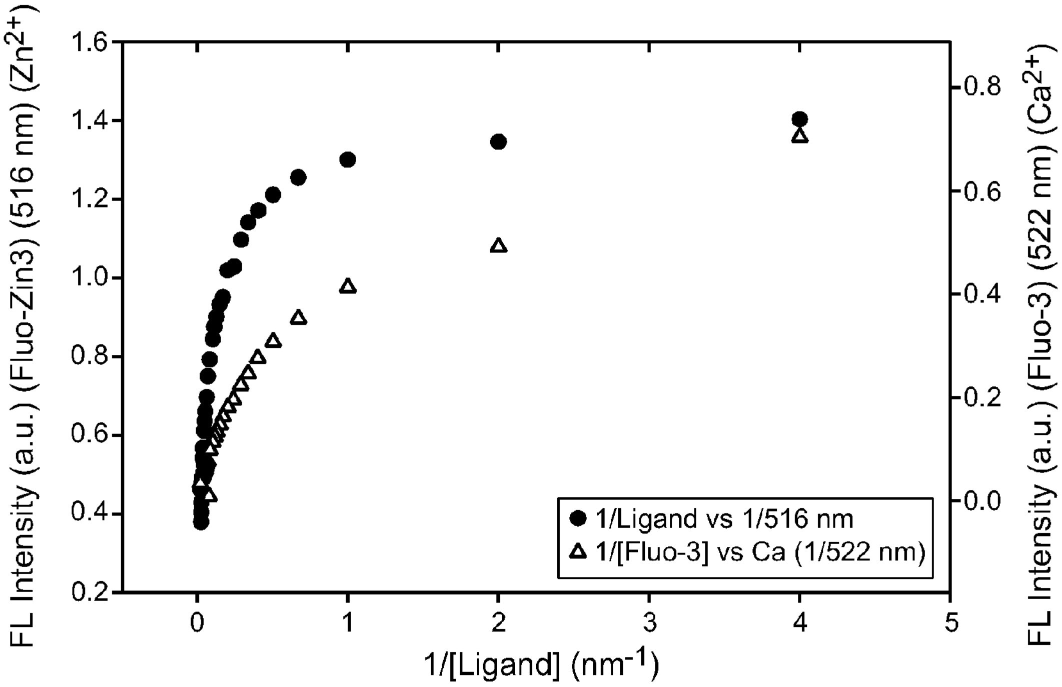
FIG. 2 provides a graph showing inhibition of protease activity of 0.36 mg/ml formulated recombinant *B. amyloliquefaciens* nprE by Linear Alkylbenzene Sulfonate (LAS) assayed using the QuantiCleave™ protease assay.

The effect of the detergent component LAS on the activity of 0.36 mg/ml of formulated nprE was investigated by incubation with 0 to 1% (w/v) LAS. The results are shown in the graph provided at FIG. 2. As these results indicate, the protease is significantly inactivated by the detergent component, thereby necessitating a means to stabilize the protease against this deleterious effect.

In some experiments, the high density liquid detergent (HDL) composition designated as “TIDE® 2005,” provided by Procter & Gamble was used. As supplied, this detergent contained all necessary components, except for the neutral metalloprotease of the present invention.

Storage Stability in Liquid Detergent Base as a Function of Time

The stability test was performed in a mini-storage manner. The conditions to be varied and the various concentrations of calcium and zinc chloride salts to be added were assessed using a matrix designed using the FusionPro™ (S-Matrix) software. The following table summarizes the conditions tested to ascertain the long-term storage stability of neutral metalloprotease from *B. amyloliquefaciens*.

TABLE 6

Long-Term Storage Test Conditions

| Condition | $[CaCl_2]$ (mM) | $[ZnCl_2]$ (mM) |
|---|---|---|
| 1 | 15 | — |
| 2 | 7.5 | 7.5 |
| 3 | — | 15 |
| 4 | — | — |
| 5 | 12 | 3 |
| 6 | — | — |
| 7 | — | 15 |
| 8 | 7.5 | 7.5 |
| 9 | 15 | — |
| 10 | 15 | 15 |
| 11 | 12 | 3 |

The final volume of each tested condition was 1 mL. TIDE® 2005 was dosed with 0.36 mg enzyme/mL. Formulated culture fluid and purified recombinant metalloprotease were incubated in the TIDE® 2005 base at 32° C. over a period of approximately 4 weeks. The storage stability of the metalloprotease in detergent was compared to the stability of the neutral metalloprotease in 50 mM MES buffer, pH 5.8.

Prior to testing, the samples were diluted 5 in 1000 using assay buffer (50 mM borate buffer, pH 8.5). The residual activity was determined and compared relative to the neutral metalloprotease in assay buffer. All measurements were determined in duplicate. Each sample was tested in parallel with appropriate control blanks (i.e., the detergent, buffer and any necessary additives being tested). The samples were then assayed as described in the instructions provided with the QuantiCleave™ Protease Assay Kit (Pierce).

Figure 22:
FIG. 22 provides a diagram showing the construction of strain EL561.

The results of these stability tests conducted over a 3-4 week period are shown in FIG. 22. In TIDE® 2005, the neutral metalloprotease in the absence of ions (i.e., no added salt) rapidly lost all of its proteolytic/hydrolytic activity against casein. Indeed it was determined that less than 20% of the activity remained after less than 1 hour of incubation. In contrast, incubation of nprE in TIDE® 2005 containing zinc ions (up to and including 15 mM) stabilized the protease and prevented proteolysis over a 7-day period. Thus, the presence of zinc ions in this formulation functioned well in maintaining at least 60% of the protease activity. Likewise, a concentration of 7.5 mM zinc ions resulted in a similar stabilization effect. This concentration of zinc ions is exceeding low and is contemplated to find use in a variety of detergent formulations. In these experiments, no added effect was provided by the inclusion of calcium ions. Furthermore, the addition of calcium ions in excess of 15 mM, and up to and including 25 mM, induced precipitation when added to TIDE® 2005 base. Although it is not intended that the present invention be limited to any particular mechanism, it was contemplated that the absence of an effect of added calcium ions on protease stabilization in these experiments was the result of the detergent composition.

For thermolysin, which displays 55% amino acid sequence identity with neutral metalloprotease from *B. amyloliquefaciens* (sequence alignment performed using CLUSTAL W, v. 1.82), it has been clearly shown that zinc ions are essential for activity, whereas the calcium ions and engineering of the calcium binding sites have been shown to play a stabilization role (See e.g., Mansfield., et al., J. Biol. Chem., 272:11152-11156 [1997]; and Van den Berg et al., Biotechnol. Appl. Biochem., 30:35-40 [1999]).

In alternative embodiments, other cations (e.g., $Co^{2+}$, $Mn^{2+}$ and $Fe^{2+}$) find use in the present invention for the stabilization of neutral metalloprotease from *B. amyloliquefaciens*. This is in contrast to prior data that has indicated that none of these ions resulted in 100% restoration of specific activity (Holmquist. and Vallee, J. Biol. Chem., 249:4601-4607 [1974]). It is contemplated that these ions will affect stability by preventing the unfolding and subsequent proteolytic degradation of the metalloprotease. However, it is not intended that the present invention be limited to any particular mechanism of action.

Example 7

NprE Protease Production in *B. subtilis* Using the nprE Expression Vector pUBnprE In this Example, experiments conducted to produce NprE protease in *B. subtilis*, in particular, the methods used in the transformation of plasmid pUBnprE into *B. subtilis* are described. Transformation was performed as known in the art (See e.g., WO 02/14490, incorporated herein by reference). The DNA sequence (nprE leader, nprE pro and nprE mature DNA sequence from *B. amyloliquefaciens*) provided below, encodes the NprE precursor protein:

(SEQ ID NO: 12)

GTGGGTTTAGGTAAGAAATTGTCTGTTGCTGTCGCCGCTTCCTTTATGAG

TTTAACCATCAGTCTGCCGGGTGTTCAGGCCGCTGAGAATCCTCAGCTTA

AAGAAAACCTGACGAATTTTGTACCGAAGCATTCTTTGGTGCAATCAGAA

TTGCCTTCTGTCAGTGACAAAGCTATCAAGCAATACTTGAAACAAAACGG

CAAAGTCTTTAAAGGCAATCCTTCTGAAAGATTGAAGCTGATTGACCAAA

CGACCGATGATCTCGGCTACAAGCACTTCCGTTATGTGCCTGTCGTAAAC

GGTGTGCCTGTGAAAGACTCTCAAGTCATTATTCACGTCGATAAATCCAA

CAACGTCTATGCGATTAACGGTGAATTAAACAACGATGTTTCCGCCAAAA

CGGCAAACAGCAAAAAATTATCTGCAAATCAGGCGCTGGATCATGCTTAT

AAAGCGATCGGCAAATCACCTGAAGCCGTTTCTAACGGAACCGTTGCAAA

CAAAAACAAAGCCGAGCTGAAAGCAGCAGCCACAAAAGACGGCAAATACC

GCCTCGCCTATGATGTAACCATCCGCTACATCGAACCGGAACCTGCAAAC

TGGGAAGTAACCGTTGATGCGGAAACAGGAAAAATCCTGAAAAAGCAAAA

CAAAGTGGAGCATGCCGCCACAACCGGAACAGGTACGACTCTTAAAGGAA

AAACGGTCTCATTAAATATTTCTTCTGAAAGCGGCAAATATGTGCTGCGC

GATCTTTCTAAACCTACCGGAACACAAATTATTACGTACGATCTGCAAAA

CCGCGAGTATAACCTGCCGGGCACACTCGTATCCAGCACCACAAACCAGT

TTACAACTTCTTCTCAGCGCGCTGCCGTTGATGCGCATTACAACCTCGGC

AAAGTGTATGATTATTTCTATCAGAAGTTTAATCGCAACAGCTACGACAA

TAAAGGCGGCAAGATCGTATCCTCCGTTCATTACGGCAGCAGATACAATA

ACGCAGCCTGGATCGGCGACCAAATGATTTACGGTGACGGCGACGGTTCA

TTCTTCTCACCTCTTTCCGGTTCAATGGACGTAACCGCTCATGAAATGAC

ACATGGCGTTACACAGGAAACAGCCAACCTGAACTACGAAAATCAGCCGG

GCGCTTTAAACGAATCCTTCTCTGATGTATTCGGGTACTTCAACGATACT

GAGGACTGGGATATCGGTGAAGATATTACGGTCAGCCAGCCGGCTCTCCG

CAGCTTATCCAATCCGACAAAATACGGACAGCCTGATAATTTCAAAAATT

ACAAAAACCTTCCGAACACTGATGCCGGCGACTACGGCGGCGTGCATACA

AACAGCGGAATCCCGAACAAAGCCGCTTACAATACGATTACAAAAATCGG

CGTGAACAAAGCGGAGCAGATTTACTATCGTGCTCTGACGGTATACCTCA

-continued

CTCCGTCATCAACTTTTAAAGATGCAAAAGCCGCTTTGATTCAATCTGCG

CGGGACCTTTACGGCTCTCAAGATGCTGCAAGCGTAGAAGCTGCCTGGAA

TGCAGTCGGATTGTAA

In the above sequence, bold indicates the DNA that encodes the mature NprE protease, standard font indicates the leader sequence (nprE leader), and underlined indicates the pro sequences (nprE pro). The amino acid sequence (NprE leader, NprE pro and NprE mature DNA sequence) (SEQ ID NO:13) provided below, encodes the NprE precursor protein. In this sequence, underlined indicates the pro sequence and bold indicates the mature NprE protease. SEQ ID NO:17 provides the NprE pro-sequence separately from the mature NprE sequence and SEQ ID NO:18 provides the mature NprE sequence. This sequence was used as the basis for making the variant libraries described herein.

(SEQ ID NO: 13)

MGLGKKLSVAVAASFMSLTISLPGVQAAENPQLKENLTNFVPKHSLVQSE

LPSVSDKAIKQYLKQNGKVFKGNPSERLKLIDQTTDDLGYKHFRYVPVVN

GVPVKDSQVIIHVDKSNNVYAINGELNNDVSAKTANSKKLSANQALDHAY

KAIGKSPEAVSNGTVANKNKAELKAAATKDGKYRLAYDVTIRYIEPEPAN

WEVTVDAETGKILKKQNKVEHAATTGTGTTLKGKTVSLNISSESGKYVLR

DLSKPTGTQIITYDLQNREYNLPGTLVSSTTNQFTTSSQRAAVDAHYNLG

KVYDYFYQKFNRNSYDNKGGKIVSSVHYGSRYNNAAWIGDQMIYGDGDGS

FFSPLSGSMDVTAHEMTHGVTQETANLNYENQPGALNESFSDVFGYFNDT

EDWDIGEDITVSQPALRSLSNPTKYGQPDNFKNYKNLPNTDAGDYGGVHT

NSGIPNKAAYNTITKIGVNKAEQIYYRALTVYLTPSSTFKDAKAALIQSA

RDLYGSQDAASVEAAWNAVGL

(SEQ ID NO: 17)

AENPQLKENLTNFVPKHSLVQSELPSVSDKAIKQYLKQNGKVFKGNPSER

LKLIDQTTDDLGYKHFRYVPVVNGVPVKDSQVIIHVDKSNNVYAINGELN

NDVSAKTANSKKLSANQALDHAYKAIGKSPEAVSNGTVANKNKAELKAAA

TKDGKYRLAYDVTIRYIEPEPANWEVTVDAETGKILKKQNKVEH (SEQ ID NO: 18)

AATTGTGTTLKGKTVSLNISSESGKYVLRDLSKPTGTQIITYDLQNREYN

LPGTLVSSTTNQFTTSSQRAAVDAHYNLGKVYDYFYQKFNRNSYDNKGGK

IVSSVHYGSRYNNAAWIGDQMIYGDGDGSFFSPLSGSMDVTAHEMTHGVT

QETANLNYENQPGALNESFSDVFGYFNDTEDWDIGEDITVSQPALRSLSN

PTKYGQPDNFKNYKNLPNTDAGDYGGVHTNSGIPNKAAYNTITKIGVNKA

EQIYYRALTVYLTPSSTFKDAKAALIQSARDLYGSQDAASVEAAWNAVGL

The pUBnprE expression vector was constructed by amplifying the nprE gene from the chromosomal DNA of *B. amyloliquefaciens* by PCR using two specific primers:

Oligo AB1740:

(SEQ ID NO: 19)

CTGCAGGAATTCAGATCTTAACATTTTTCCCCTATCATTTTTCCCG

Oligo AB1741:

(SEQ ID NO: 20)

GGATCCAAGCTTCCCGGGAAAAGACATATATGATCATGGTGAAGCC

PCR was performed on a thermocycler with Phusion High Fidelity DNA polymerase (Finnzymes. The PCR mixture contained 10 μl 5× buffer (Finnzymes Phusion), 1 μl 10 mM dNTP's, 1.5 μl DMSO, 1 μl of each primer, 1 μl Finnzymes Phusion DNA polymerase, 1 μl chromosomal DNA solution 50 ng/μl, 34.5 μl MilliQ water. The following protocol was used:

PCR Protocol:

1) 30 sec 98° C.;
2) 10 sec 98° C.;
3) 20 sec 55° C.;
4) 1 min 72° C.;
5) 25 cycles of steps 2 to 4; and
6) 5 min 72° C.

Figure 14:
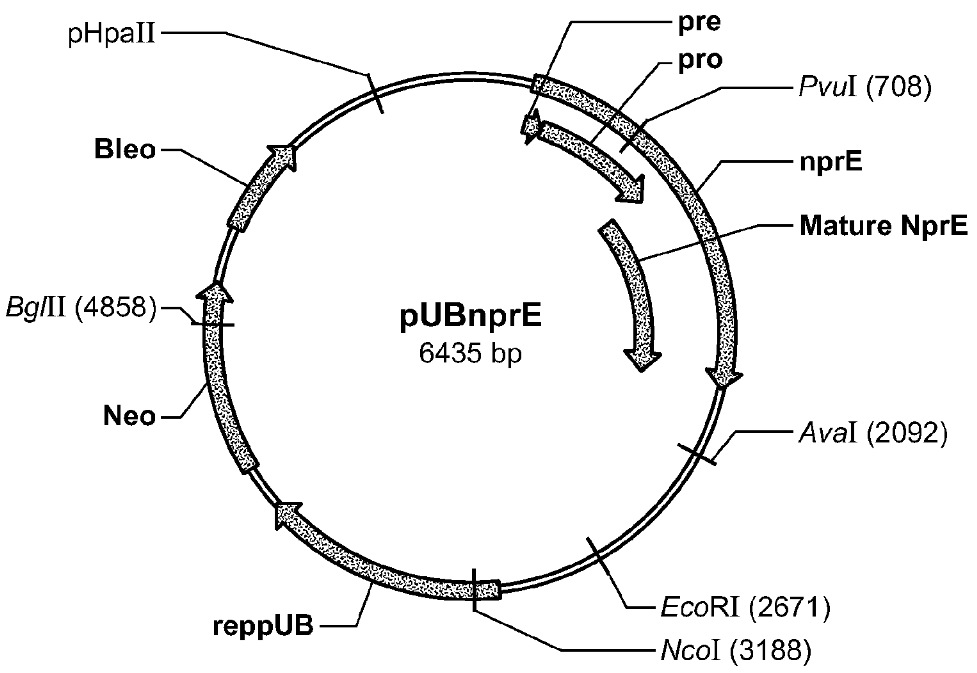
FIG. 14 provides a map of pUBnprE.

This resulted in a 1.9 kb DNA fragment which was digested using BglII and BclI DNA restriction enzymes. The multicopy *Bacillus* vector pUB110 (See e.g., Gryczan, J. Bacteriol., 134:318-329 [1978]) was digested with BamHI. The PCR fragment×BglII×BclI was then ligated in the pUB110 x BamHI vector to form pUBnprE expression vector (See, FIG. 14).

pUBnprE was transformed to a *B. subtilis* (ΔaprE, ΔnprE, oppA, ΔspoIIE, degUHy32, ΔamyE::(xylR,pxylA-comK) strain. Transformation into *B. subtilis* was performed as described in WO 02/14490, incorporated herein by reference. Selective growth of *B. subtilis* transformants harboring the pUBnprE vector was performed in shake flasks containing 25 ml MBD medium (a MOPS based defined medium), with 20 mg/L neomycin. MBD medium was made essentially as known in the art (See, Neidhardt et al., J. Bacteriol., 119: 736-747 [1974]), except that $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The culture was incubated for three days at 37° C. in an incubator/shaker (Infors). This culture resulted in the production of secreted NprE protease with proteolytic activity as demonstrated by protease assays. Gel analysis was performed using NuPage Novex 10% Bis-Tris gels (Invitrogen, Cat.No. NP0301BOX). To prepare samples for analysis, 2 volumes of supernatant were mixed with 1 volume 1M HCl, 1 volume 4×LDS sample buffer (Invitrogen, Cat.No. NP0007), and 1% PMSF (20 mg/me and subsequently heated for 10 minutes at 70° C. Then, 25 μL of each sample were loaded onto the gel, together with 10 μL of SeeBlue plus 2 pre-stained protein standards (Invitrogen, Cat.No.LC5925). The results clearly demonstrated that the nprE cloning strategy described in this example yield active NprE produced by *B. subtilis.*

Example 8

Generation of nprE Site Evaluation Libraries (SELs)

In this Example, methods used in the construction of nprE SELs are described. The pUBnprE vector, containing the nprE expression cassette described above, served as template DNA. This vector contains a unique BglII restriction site, which was utilized in the site evaluation library construction.

The pUBnprE expression vector, primers, synthesized at Invitrogen (desalted, 50 nmol scale) were used to generate the libraries. The sequences of the primers are provided in Table 8-1.

To construct a nprE site evaluation library, three PCR reactions were performed, including two mutagenesis PCRs to introduce the mutated codon of interest in the mature nprE DNA sequence and a third PCR used to fuse the two mutagenesis PCRs in order to construct the pUBnprE expression vector including the desired mutated codon in the mature nprE sequence.

The method of mutagenesis was based on the codon-specific mutation approach, in which the creation of all possible mutations at a time in a specific DNA triplet was performed using a forward and reverse oligonucleotide primer with a length of 25 to 45 nucleotides enclosing a specific designed triple DNA sequence NNS ((A,C,T or G), (A,C,T or G), (C or G)) that corresponded with the sequence of the codon to be mutated and guaranteed random incorporation of nucleotides at that specific nprE mature codon. The number listed in the primer names (See, Table 8-1) corresponds with the specific nprE mature codon position.

Two additional primers used to construct the site evaluation libraries contained the BglII restriction site together with a part of the pUBnprE DNA sequence flanking the BglII restriction site. These primers were produced by Invitrogen (50 nmole scale, desalted) and are listed in Table 8-1.

TABLE 8-1

| Primer Name | Primer Sequence and SEQ ID NO: | |
|---|---|---|
| **Primer Sequences** | | |
| pUB-BglII-FW | GTCAGTCAGATCTTCCTTCAGGTTATGACC | (SEQ ID NO: 21) |
| pUB-BglII-RV | GTCTCGAAGATCTGATTGCTTAACTGCTTC | (SEQ ID NO: 22) |
| **Specific nprE Forward Mutagenesis Primers** | | |
| nprE4F | GTGGAGCATGCCGCCACANNSGGAACAGGTACGACTCTTAA | (SEQ ID NO: 23) |
| nprE12F | CAGGTACGACTCTTAAANNSAAAACGGTCTCATTAAATAT | (SEQ ID NO: 24) |
| nprE13F | GTACGACTCTTAAAGGANNSACGGTCTCATTAAATATTTC | (SEQ ID NO: 25) |
| nprE14F | CGACTCTTAAAGGAAAANNSGTCTCATTAAATATTTC | (SEQ ID NO: 26) |
| nprE23F | CATTAAATATTTCTTCTGAANNSGGCAAATATGTGCTGCG | (SEQ ID NO: 27) |
| nprE24F | TAAATATTTCTTCTGAAAGCNNSAAATATGTGCTGCGCGATC | (SEQ ID NO: 28) |
| nprE33F | GTGCTGCGCGATCTTTCTNNSCCTACCGGAACACAAATTAT | (SEQ ID NO: 29) |
| nprE45F | AAATTATTACGTACGATCTGNNSAACCGCGAGTATAACCTG | (SEQ ID NO: 30) |
| nprE46F | TTATTACGTACGATCTGCAANNSCGCGAGTATAACCTGCC | (SEQ ID NO: 31) |
| nprE47F | CGTACGATCTGCAAAACNNSGAGTATAACCTGCCGGG | (SEQ ID NO: 32) |
| nprE49F | GATCTGCAAAACCGCGAGNNSAACCTGCCGGGCACACTC | (SEQ ID NO: 33) |
| nprE50F | CTGCAAAACCGCGAGTATNNSCTGCCGGGCACACTCGTATC | (SEQ ID NO: 34) |

TABLE 8-1-continued

Primer Sequences

| Primer Name | Primer Sequence and SEQ ID NO: | |
|---|---|---|
| nprE54F | GAGTATAACCTGCCGGGCNNSCTCGTATCCAG CACCAC | (SEQ ID NO: 35) |
| nprE58F | CGGGCACACTCGTATCCNNSACCACAAACCAG TTTAC | (SEQ ID NO: 36) |
| nprE59F | GCACACTCGTATCCAGCNNSACAAACCAGTTT ACAAC | (SEQ ID NO: 37) |
| nprE60F | CACTCGTATCCAGCACCNNSAACCAGTTTACA ACTTC | (SEQ ID NO: 38) |
| nprE65F | CCACAAACCAGTTTACANNSTCTTCTCAGCGC GCTGC | (SEQ ID NO: 39) |
| nprE66F | CAAACCAGTTTACAACTNNSTCTCAGCGCGCT GCCGTTG | (SEQ ID NO: 40) |
| nprE87F | GTGTATGATTATTTCTATNNSAAGTTTAATCG CAACAG | (SEQ ID NO: 41) |
| nprE90F | ATTATTTCTATCAGAAGTTTNNSCGCAACAGC TACGACAATAA | (SEQ ID NO: 42) |
| nprE96F | TTAATCGCAACAGCTACGACNNSAAAGGCGGC AAGATCGTATC | (SEQ ID NO: 43) |
| nprE97F | GCAACAGCTACGACAATNNSGGCGGCAAGATC GTATC | (SEQ ID NO: 44) |
| nprE100F | CTACGACAATAAAGGCGGCNNSATCGTATCCT CCGTTCATTA | (SEQ ID NO: 45) |
| nprE186F | GAGGACTGGGATATCGGTNNSGATATTACGGT CAGCCAG | (SEQ ID NO: 46) |
| nprE196F | GTCAGCCAGCCGGCTCTCNNSAGCTTATCCAA TCCGAC | (SEQ ID NO: 47) |
| nprE211F | GACAGCCTGATAATTTCNNSAATTACAAAAAC CTTCC | (SEQ ID NO: 48) |
| nprE214F | GATAATTTCAAAAATTACNNSAACCTTCCGAA CACTGATG | (SEQ ID NO: 49) |
| nprE228F | GCGACTACGGCGGCGTGNNSACAAACAGCGGA ATCCC | (SEQ ID NO: 50) |
| nprE280F | CTTTGATTCAATCTGCGNNSGACCTTTACGGC TCTCAAG | (SEQ ID NO: 51) |
| **Specific nprE Reverse Mutagenesis Primers** | | |
| nprE4R | TTAAGAGTCGTACCTGTTCCSNNTGGCGGCAT GCTCCAC | (SEQ ID NO: 52) |
| nprE12R | ATATTTAATGAGACCGTTTTSNNTTTAAGAGT CGTACCTG | (SEQ ID NO: 53) |
| nprE13R | GAAATATTTAATGAGACCGTSNNTCCTTTAAG AGTCGTAC | (SEQ ID NO: 54) |
| nprE14R | GAAATATTTAATGAGACSNNTTTTCCTTTAAG AGTCG | (SEQ ID NO: 55) |
| nprE23R | CGCAGCACATATTTGCCSNNTTCAGAAGAAAT ATTTAATG | (SEQ ID NO: 56) |
| nprE24R | GATCGCGCAGCACATATTTSNNGCTTTCAGAA GAAATATTTA | (SEQ ID NO: 57) |
| nprE33R | ATAATTTGTGTTCCGGTAGGSNNAGAAAGATC GCGCAGCAC | (SEQ ID NO: 58) |

TABLE 8-1-continued

Primer Sequences

| Primer Name | Primer Sequence and SEQ ID NO: | |
|---|---|---|
| nprE45R | CAGGTTATACTCGCGGTTSNNCAGATCGTACG TAATAATTT | (SEQ ID NO: 59) |
| nprE46R | GGCAGGTTATACTCGCGSNNTTGCAGATCGTA CGTAATAA | (SEQ ID NO: 60) |
| nprE47R | CCCGGCAGGTTATACTCSNNGTTTTGCAGATC GTACG | (SEQ ID NO: 61) |
| nprE49R | GAGTGTGCCCGGCAGGTTSNNCTCGCGGTTTT GCAGATC | (SEQ ID NO: 62) |
| nprE50R | GATACGAGTGTGCCCGGCAGSNNATACTCGCG GTTTTGCAG | (SEQ ID NO: 63) |
| nprE54R | GTGGTGCTGGATACGAGSNNGCCCGGCAGGTT ATACTC | (SEQ ID NO: 64) |
| nprE58R | GTAAACTGGTTGTGGTSNNGGATACGAGTGTG CCCG | (SEQ ID NO: 65) |
| nprE59R | GTTGTAAACTGGTTTGTSNNGCTGGATACGAG TGTGC | (SEQ ID NO: 66) |
| nprE60R | GAAGTTGTAAACTGGTTSNNGGTGCTGGATAC GAGTG | (SEQ ID NO: 67) |
| nprE65R | GCAGCGCGCTGAGAAGASNNTGTAAACTGGTT TGTGG | (SEQ ID NO: 68) |
| nprE66R | CAACGGCAGCGCGCTGAGASNNAGTTGTAAAC TGGTTTG | (SEQ ID NO: 69) |
| nprE87R | CTGTTGCGATTAAACTTSNNATAGAAATAATC ATACAC | (SEQ ID NO: 70) |
| nprE90R | TTATTGTCGTAGCTGTTGCGSNNAAACTTCTG ATAGAAATAAT | (SEQ ID NO: 71) |
| nprE96R | GATACGATCTTGCCGCCTTTSNNGTCGTAGCT GTTGCGATTAA | (SEQ ID NO: 72) |
| nprE97R | GATACGATCTTGCCGCCSNNATTGTCGTAGCT GTTGC | (SEQ ID NO: 73) |
| nprE100R | TAATGAACGGAGGATACGATSNNGCCGCCTTT ATTGTCGTAG | (SEQ ID NO: 74) |
| nprE186R | CTGGCTGACCGTAATATCSNNACCGATATCCC AGTCCTC | (SEQ ID NO: 75) |
| nprE196R | GTCGGATTGGATAAGCTSNNGAGAGCCGGCTG GCTGAC | (SEQ ID NO: 76) |
| nprE211R | GGAAGGTTTTTGTAATTSNNGAAATTATCAGG CTGTC | (SEQ ID NO: 77) |
| nprE214R | CATCAGTGTTCGGAAGGTTSNNGTAATTTTTG AAATTATC | (SEQ ID NO: 78) |
| nprER | GGGATTCCGCTGTTTGTSNNCACGCCGCCGTA GTCGC | (SEQ ID NO: 79) |
| nprER | CTTGAGAGCCGTAAAGGTCSNNCGCAGATTGA ATCAAAG | (SEQ ID NO: 80) |

Construction of each site evaluation library started with two primary PCR amplifications using the pUB-BglII-FW primer and a specific nprE reverse mutagenesis primer. For the second PCR, the pUB-BglII-RV primer and a specific nprE forward mutagenesis primer (equal nprE mature codon positions for the forward and reverse mutagenesis primers) were used.

The introduction of the mutations in the mature nprE sequence was performed using Phusion High-Fidelity DNA Polymerase (Finnzymes; Cat. no. F-530L). All PCRs were performed according to the Finnzymes protocol supplied with the polymerase. The PCR conditions for the primary PCRs were:

For primary PCR 1:

pUB-BglII-FW primer and a specific NPRE reverse mutagenesis primer—both 1 μL (10 μM);

For primary PCR 2:

pUB-BglII-RV primer and a specific NPRE forward mutagenesis primer—both 1 μL (10 μM); together with

| | | |
|---|---|---|
| 5 x Phusion HF buffer | 10 | μL |
| 10 mM dNTP mixture | 1 | μL |
| Phusion DNA polymerase | 0.75 | μL (2 units/μL) |
| DMSO, 100% | 1 | μL |
| pUBnprE template DNA | 1 | μL (0.1-1 ng/μL) |
| Distilled, autoclaved water | up to 50 | μL |

The PCR program was: 30 seconds 98° C., 30×(10 seconds 98° C., 20 seconds 55° C., 1.5 minute 72° C.) and 5 min 72° C., performed in a PTC-200 Peltier thermal cycle (MJ Research). The PCR experiments result in two fragments of approximately 2 to 3 kB, which had about 30 nucleotide base overlap around the NPRE mature codon of interest. Fragments were fused in a third PCR reaction using these two aforementioned fragments and the forward and reverse BglII primers. The fusion PCR reaction was carried out in the following solution:

pUB-BglII-FW primer and pUB-BglII-RV primer—both 1 μL (10 μM)

| | | |
|---|---|---|
| 5 x Phusion HF buffer | 10 | μL |
| 10 mM dNTP mixture | 1 | μL |
| Phusion DNA polymerase | 0.75 | μL (2 units/μL) |
| DMSO, 100% | 1 | μL |
| primary PCR 1 reaction mix | 1 | μL |
| primary PCR 2 reaction mix | 1 | μL |
| Distilled, autoclaved water | up to 50 | μL |

The PCR fusion program was as follows: 30 seconds 98° C., 30×(10 seconds 98° C., 20 seconds 55° C., 2:40 minute 72° C.) and 5 min 72° C., in a PTC-200 Peltier thermal cycler (MJ Research).

The amplified linear 6.5 Kb fragment was purified using the Qiaquick PCR purification kit (Qiagen, Cat. no. 28106) and digested with BglII restriction enzyme to create cohesive ends on both sides of the fusion fragment:

35 μL purified linear DNA fragment

4 μL REACT® 3 buffer (Invitrogen)

1 μL BglII, 10 units/ml (Invitrogen)

Reaction conditions: 1 hour, 30° C.

Ligation of the BglII digested and purified using Qiaquick PCR purification kit (Qiagen, Cat. no. 28106) fragment results in circular and multimeric DNA containing the desired mutation:

30 μL of purified BglII digested DNA fragment

8 μL T4 DNA Ligase buffer (Invitrogen® Cat. no. 46300-018)

1 μL T4 DNA Ligase, 1 unit/pt (Invitrogen® Cat. no. 15224-017)

Reaction conditions: 16-20 hours, 16°

Subsequently, the ligation mixture was transformed to a *B. subtilis* (ΔaprE, ΔnprE, oppA, ΔspolIE, degUHy32, ΔamyE::(xylR,pxylA-comK) strain. Transformation to *B. subtilis* was performed as described in WO 02/14490, incorporated herein by reference. For each library, 96 single colonies were picked and grown in MOPS media with neomycin and 1.25 g/L yeast extract for sequence analysis (BaseClear) and screening purposes. Each library included a maximum of 19 nprE site-specific variants.

The variants were produced by growing the *B. subtilis* SEL transformants in 96 well MTP at 37° C. for 68 hours in MBD medium with 20 mg/L neomycin and 1.25 g/L yeast extract (See, above).

Example 9

Generation of nprE Combinatorial Libraries (RCLs)

In this Example, methods used to generate nprE combinatorial libraries are described. For this enzyme, one property was chosen as the property that needed to be changed the most. This property is defined herein as the "primary property." All other properties were "secondary properties" for the purpose of combinatorial library design. The basic strategy for improving a protein as used herein, was to combine mutations that improve the primary property and also maintain or improve the secondary properties. The site evaluation data were used to identify those mutations which improved the primary property while maintaining or improving the secondary properties. Mutations that were to be combined were identified by their Performance Index (PI or Pi) and associated $\Delta\Delta G_{app}$ values.

The "Apparent Free Energy Change" ($\Delta\Delta G_{app}$) as used herein is defined as:

$$\Delta\Delta G_{app}=-RT\,\mathrm{Ln}(P_{variant}/P_{parent})$$

where $P_{variant}$ is the performance value for the variant and $P_{parent}$ is the performance value for the parent enzyme under the same conditions. The ratio $P_{variant}/P_{parent}$ is defined as the performance index (Pi) for the property. The $\Delta\Delta G_{app}$ values were expected to behave in a similar fashion to actual ΔΔG values for data distributions and additivity. However, since ΔΔG represents the maximum amount of work that can be carried out by the variant compared to the parent enzyme, the quantity $\Delta\Delta G_{app}$ generally underestimates the ΔΔG and may lead to results that appear synergistic in that the properties of two additive positions may be greater than the value predicted by adding their $\Delta\Delta G_{app}$ values together.

For example, when TIDE® stability is the primary property and BMI activity is the secondary property, mutations that have $\Delta\Delta G_{app}$ values <0 (Pi>1) and BMI $\Delta\Delta G_{app}$ values <0.06 (Pi>0.9) may be chosen for combination. Indeed, these relationships were explored in these experiments.

To produce the variants used in these experiments, synthetic nprE library fragments, containing multiple mutations at multiple nprE mature DNA positions, were produced by GeneArt (Geneart). These 1.5 kB nprE library fragments were digested with DNA restriction enzymes PvuI and AvaI, purified and ligated in the 5 kB pUB vector fragment (also digested with DNA restriction enzymes PvuI and AvaI) by a ligase reaction using T4 DNA Ligase (Invitrogen® Cat. no. 15224-017).

To transform the ligation reaction mix directly into *Bacillus* cells, the library DNA (nprE library fragment mix ligated in pUB vector fragment) was amplified using the TempliPhi kit (Amersham cat. #25-6400). For this purpose, 1 μL of the ligation reaction mix was mixed with 5 μL of sample buffer from the TempliPhi kit and heated for 3 minutes at 95° C. to denature the DNA. The reaction was placed on ice to cool for 2 minutes and then spun down briefly. Next, 5 μL of reaction buffer and 0.2 μL of phi29 polymerase from the TempliPhi kit were added, and the reactions were incubated at 30° C. in an MJ Research PCR machine for 4 hours. The phi29 enzyme was heat inactivated in the reactions by incubation at 65° C. for 10 min in the PCR machine.

For transformation of the libraries into *Bacillus,* 0.1 μL of the TempliPhi amplification reaction product was mixed with 500 μL of competent *B. subtilis* cells (ΔaprE, ΔnprE, oppA, ΔspoIIE, degUHy32, ΔamyE::(xylR,pxylA-comK) followed by vigorous shaking at 37° C. for 1 hour. Then, 100 and 500 μL were plated on HI-agar plates containing 20 mg/L neomycin and 0.5% skim milk. In general, transformation to *B. subtilis* was performed as described in WO 02/14490, incorporated herein by reference. *B. subtilis* nprE combinatorial libraries, constructed by this method are contemplated to contain wild type amino acids at one or more of the positions targeted for mutagenesis.

The variants obtained in these libraries were then tested for their stability in TIDE® and their performance in BMI wash performance tests as described herein. Table 9 provides performance indices for the variants tested in the BMI assay. In this Table, "Pos." indicates the position in the NprE amino acid sequence that was changed, and "AA" indicates the amino acid substitution made for each variant.

TABLE 9

Results (Performance Indices) for Tested Variants

| Pos. | Variant | AA | TIDE (−) | TIDE (−) ΔΔG | TIDE (+) | TIDE (+) ΔΔG | BMI Pi | BMI ΔΔG |
|---|---|---|---|---|---|---|---|---|
| 4 | T004L | L | 0.80 | 0.13 | 1.13 | −0.07 | 1.01 | 0.00 |
| 23 | S023Y | Y | 1.08 | −0.05 | 1.13 | −0.07 | 1.02 | −0.01 |
| 23 | S023W | W | 1.12 | −0.07 | 1.13 | −0.07 | 1.29 | −0.15 |
| 23 | S023N | N | 1.33 | −0.17 | 1.10 | −0.06 | 0.95 | 0.03 |
| 23 | S023T | T | 0.88 | 0.07 | 1.06 | −0.03 | 0.91 | 0.05 |
| 23 | S023G | G | 1.29 | −0.15 | 1.06 | −0.03 | 0.92 | 0.05 |
| 23 | S023R | R | 0.98 | 0.01 | 1.06 | −0.03 | 1.46 | −0.22 |
| 23 | S023L | L | 0.90 | 0.06 | 1.03 | −0.02 | 1.24 | −0.13 |
| 23 | S023M | M | 1.04 | −0.02 | 1.03 | −0.02 | 1.09 | −0.05 |
| 23 | S023V | V | 0.82 | 0.12 | 1.02 | −0.01 | 0.93 | 0.04 |
| 23 | S023K | K | 1.01 | −0.01 | 1.02 | −0.01 | 1.50 | −0.24 |
| 24 | G024Y | Y | 0.60 | 0.30 | 1.11 | −0.06 | 1.10 | −0.06 |
| 24 | G024W | W | 0.36 | 0.60 | 1.10 | −0.06 | 1.20 | −0.11 |
| 24 | G024M | M | 0.71 | 0.20 | 1.09 | −0.05 | 1.12 | −0.07 |
| 24 | G024F | F | 0.50 | 0.41 | 1.08 | −0.04 | 1.19 | −0.10 |
| 24 | G024L | L | 0.49 | 0.42 | 1.07 | −0.04 | 1.22 | −0.12 |
| 24 | G024H | H | 0.80 | 0.13 | 1.05 | −0.03 | 1.17 | −0.09 |
| 24 | G024K | K | 0.55 | 0.35 | 1.04 | −0.02 | 1.55 | −0.26 |
| 24 | G024T | T | 0.57 | 0.33 | 1.03 | −0.02 | 0.94 | 0.04 |
| 24 | G024R | R | 0.56 | 0.34 | 1.02 | −0.01 | 1.47 | −0.23 |
| 46 | N046Q | Q | 0.88 | 0.08 | 1.07 | −0.04 | 1.22 | −0.12 |
| 47 | R047K | K | 1.12 | −0.07 | 1.09 | −0.05 | 1.15 | −0.08 |
| 50 | N050F | F | 1.07 | −0.04 | 1.07 | −0.04 | 1.38 | −0.19 |
| 50 | N050Y | Y | 1.00 | 0.00 | 1.04 | −0.02 | 1.27 | −0.14 |
| 50 | N050W | W | 1.01 | −0.01 | 1.04 | −0.02 | 1.46 | −0.22 |
| 50 | N050P | P | 1.23 | −0.12 | 1.03 | −0.02 | 1.12 | −0.07 |
| 54 | T054H | H | 1.08 | −0.04 | 1.11 | −0.06 | 1.17 | −0.09 |
| 54 | T054K | K | 1.03 | −0.02 | 1.11 | −0.06 | 1.47 | −0.23 |
| 54 | T054L | L | 1.09 | −0.05 | 1.08 | −0.05 | 1.26 | −0.14 |
| 54 | T054N | N | 0.97 | 0.02 | 1.07 | −0.04 | 1.25 | −0.13 |
| 54 | T054Y | Y | 1.14 | −0.08 | 1.07 | −0.04 | 1.08 | −0.04 |
| 54 | T054W | W | 1.02 | −0.01 | 1.07 | −0.04 | 1.22 | −0.12 |
| 54 | T054S | S | 0.99 | 0.01 | 1.05 | −0.03 | 1.03 | −0.02 |
| 54 | T054I | I | 1.09 | −0.05 | 1.04 | −0.02 | 1.34 | −0.17 |
| 54 | T054R | R | 0.96 | 0.02 | 1.04 | −0.02 | 1.46 | −0.22 |
| 54 | T054Q | Q | 1.09 | −0.05 | 1.03 | −0.02 | 1.23 | −0.12 |
| 54 | T054F | F | 0.98 | 0.01 | 1.03 | −0.02 | 1.16 | −0.09 |
| 54 | T054V | V | 1.14 | −0.08 | 1.01 | −0.01 | 1.11 | −0.06 |
| 59 | T059R | R | 0.76 | 0.16 | 1.28 | −0.14 | 1.56 | −0.26 |
| 59 | T059W | W | 0.56 | 0.34 | 1.26 | −0.14 | 1.32 | −0.16 |
| 59 | T059K | K | 0.99 | 0.00 | 1.16 | −0.09 | 1.60 | −0.28 |
| 59 | T059N | N | 0.98 | 0.01 | 1.15 | −0.08 | 1.16 | −0.09 |
| 59 | T059G | G | 0.94 | 0.04 | 1.13 | −0.07 | 1.11 | −0.06 |
| 59 | T059P | P | 1.18 | −0.10 | 1.12 | −0.07 | 1.19 | −0.10 |
| 59 | T059M | M | 1.04 | −0.02 | 1.10 | −0.06 | 1.10 | −0.05 |
| 59 | T059H | H | 0.98 | 0.01 | 1.07 | −0.04 | 1.32 | −0.16 |
| 59 | T059S | S | 1.09 | −0.05 | 1.04 | −0.03 | 0.91 | 0.06 |
| 59 | T059A | A | 1.05 | −0.03 | 1.04 | −0.02 | 0.96 | 0.03 |
| 59 | T059Q | Q | 1.05 | −0.03 | 1.04 | −0.02 | 1.31 | −0.16 |
| 59 | T059I | I | 0.64 | 0.26 | 1.01 | −0.01 | 1.43 | −0.21 |
| 60 | T060N | N | 0.79 | 0.14 | 1.03 | −0.02 | 1.07 | −0.04 |
| 66 | S066Q | Q | 0.75 | 0.17 | 1.01 | −0.01 | 1.12 | −0.07 |
| 66 | S066N | N | 1.08 | −0.05 | 1.01 | −0.01 | 1.00 | 0.00 |
| 110 | R110K | K | 1.08 | −0.04 | 1.04 | −0.02 | 1.05 | −0.03 |
| 119 | D119H | H | 1.03 | −0.02 | 1.15 | −0.08 | 1.16 | −0.09 |
| 129 | S129I | I | 2.32 | −0.49 | 1.68 | −0.30 | 0.98 | 0.01 |
| 129 | S129V | V | 2.34 | −0.50 | 1.55 | −0.26 | 1.01 | 0.00 |
| 129 | S129Q | Q | 1.86 | −0.37 | 1.44 | −0.21 | 0.99 | 0.00 |
| 129 | S129T | T | 1.59 | −0.27 | 1.36 | −0.18 | 1.04 | −0.02 |
| 129 | S129L | L | 1.70 | −0.31 | 1.35 | −0.18 | 1.01 | −0.01 |
| 129 | S129H | H | 1.60 | −0.28 | 1.30 | −0.15 | 1.17 | −0.09 |
| 129 | S129Y | Y | 1.28 | −0.14 | 1.06 | −0.04 | 1.25 | −0.13 |
| 129 | S129A | A | 1.13 | −0.07 | 1.06 | −0.03 | 1.12 | −0.07 |
| 129 | S129K | K | 1.18 | −0.10 | 1.05 | −0.03 | 1.33 | −0.17 |
| 130 | F130L | L | 1.29 | −0.15 | 1.52 | −0.25 | 0.91 | 0.05 |
| 130 | F130I | I | 1.18 | −0.10 | 1.14 | −0.08 | 1.03 | −0.02 |
| 130 | F130V | V | 1.05 | −0.03 | 1.06 | −0.03 | 0.99 | 0.00 |
| 130 | F130K | K | 0.99 | 0.00 | 1.04 | −0.02 | 1.26 | −0.14 |
| 138 | M138L | L | 1.11 | −0.06 | 1.43 | −0.21 | 0.95 | 0.03 |
| 152 | E152H | H | 1.53 | −0.25 | 1.36 | −0.18 | 1.15 | −0.08 |
| 152 | E152W | W | 1.32 | −0.16 | 1.31 | −0.16 | 1.06 | −0.03 |
| 152 | E152F | F | 1.32 | −0.16 | 1.15 | −0.08 | 1.09 | −0.05 |
| 179 | T179P | P | 1.33 | −0.17 | 1.50 | −0.24 | 1.04 | −0.03 |
| 190 | V190I | I | 1.37 | −0.18 | 1.68 | −0.30 | 1.16 | −0.09 |
| 220 | D220P | P | 2.24 | −0.47 | 2.66 | −0.57 | 1.05 | −0.03 |
| 220 | D220E | E | 2.23 | −0.47 | 2.44 | −0.52 | 1.05 | −0.03 |
| 243 | T243I | I | 1.13 | −0.07 | 1.17 | −0.09 | 1.06 | −0.03 |
| 263 | T263W | W | 1.37 | −0.18 | 1.40 | −0.20 | 0.92 | 0.05 |
| 263 | T263H | H | 1.03 | −0.02 | 1.01 | −0.01 | 1.05 | −0.01 |
| 273 | A273H | H | 1.10 | −0.06 | 1.14 | −0.08 | 0.98 | 0.01 |
| 282 | L282M | M | 1.03 | −0.01 | 1.16 | −0.09 | 1.01 | −0.01 |
| 282 | L282F | F | 0.91 | 0.05 | 1.06 | −0.04 | 1.09 | −0.05 |
| 282 | L282Y | Y | 0.83 | 0.11 | 1.04 | −0.02 | 0.92 | 0.05 |
| 285 | S285R | R | 1.08 | −0.04 | 1.38 | −0.19 | 1.23 | −0.12 |
| 285 | S285P | P | 1.11 | −0.06 | 1.30 | −0.16 | 0.98 | 0.01 |
| 285 | S285W | W | 1.08 | −0.05 | 1.28 | −0.14 | 0.95 | 0.03 |
| 285 | S285Q | Q | 1.06 | −0.03 | 1.10 | −0.05 | 0.98 | 0.01 |
| 285 | S285K | K | 0.89 | 0.07 | 1.00 | 0.00 | 1.20 | −0.10 |
| 286 | Q286R | R | 0.95 | 0.03 | 1.18 | −0.10 | 1.14 | −0.08 |
| 286 | Q286P | P | 0.98 | 0.01 | 1.15 | −0.08 | 0.97 | 0.02 |
| 286 | Q286K | K | 0.93 | 0.04 | 1.09 | −0.05 | 1.22 | −0.12 |

Example 10

Alternative Method Generate nprE Site Evaluation Libraries (SELs) Via QuikChange® Mutagenesis In this Example, alternative methods to generate nprE SELs are described. As in Example 8, above, the pUBnprE vector served as the template DNA source for the generation of nprE SELs. The major difference between the two methods is that this method requires amplification of the entire vector using complementary site-directed mutagenic primers.

Materials:

*Bacillus* strain containing the pUBnprE vector

Qiagen Plasmid Midi Kit (Qiagen cat #12143)

Ready-Lyse Lysozyme (Epicentre cat # R1802M)

dam Methylase Kit (New England Biolabs cat # M0222L)

Zymoclean Gel DNA Recovery Kit (Zymo Research cat # D4001)

nprE site-directed mutagenic primers, 100 nmole scale, 5' Phosphorylated, PAGE purified (Integrated DNA Technologies, Inc.)

QuikChange Multi Site-Directed Mutagenesis Kit (Stratagene cat #200514)

MJ Research PTC-200 Peltier Thermal Cycler (Bio-Rad Laboratories)

1.2% agarose E-gels (Invitrogen cat # G5018-01)

TempliPhi Amplification Kit (GE Healthcare cat #25-6400-10)

Competent *B. subtilis* cells (ΔaprE, ΔnprE, oppA, ΔspolIE, degUHy32, ΔamyE::(xylR,pxylA-comK)

Methods:

To obtain the pUBnprE vector, a single colony of a *Bacillus* strain containing the pUBnprE vector was used to inoculate a 5 ml LB+10 ppm neomycin tube. This was the starter culture used in these methods. The culture was grown at 37° C., with shaking at 225 rpm for 6 hours. Then, 100 ml of fresh LB+10 ppm neomycin were inoculated with 1 ml of the starter culture. This culture was grown overnight at 37° C., with shaking at 225 rpm. Following this incubation, the cell pellet was harvested by sufficient centrifugation to provide a cell pellet. The cell pellet was resuspended in 10 ml Buffer P1 (Qiagen Plasmid Midi Kit). Then, 10 ul of Ready-Lyse Lysozyme was added to the resuspended cell pellet and incubated at 37° C. for 30 min. Then, the Qiagen Plasmid Midi Kit protocol was continued (using 10 ml of Buffer P2 and P3 to account for the increased volume of cell culture). After isolation of pUBnprE vector from *Bacillus*, the concentration of pUBnprE vector was quantitated. The vector was then dam methylated using the dam Methylase Kit (New England Biolabs), using the methods set forth in the kit protocols, to methylate approximately 2 ug of pUBnprE vector per tube. The Zymoclean Gel DNA recovery kit was used to purify and concentrate the dam-methylated pUBnprE vector. The dam-methylated pUBnprE vector was quantitated and then diluted to a working concentration of 50 ng/ul. Complementary site-directed mutagenic primers (1 ul of each primer at 10 uM) (See, Table 10-1), were used in a PCR reaction in the QuikChange Multi Site-Directed Mutagenesis Kit (Stratagene), following the manufacturer's protocol (e.g., 1 ul dam methylated pUBnprE vector (50 ng/ul) 1 ul nprE site-directed Forward mutagenic primer (10 uM), 1 ul nprE site-directed Forward mutagenic primer (10 uM), 2.5 ul 10× QuikChange Multi Reaction buffer, 1 ul dNTP Mix, 1 ul QuikChange Multi enzyme blend (2.5 U/ul), and 17.5 ul distilled, autoclaved water, to provide a 25 ul total reaction mix). The nprE site evaluation libraries were amplified using the following conditions: 95° C., for 1 min. (1st cycle only), followed by 95° C. for 1 min., 55° C. for 1 min, 65° C. for 13½ min, and repeat cycling 23 times. The reaction product was stored at 4° C. overnight. Then, the reaction mixture underwent DpnI digest treatment (supplied with QuikChange Multi Site-Directed Mutagenesis Kit) to digest parental pUBnprE vector, using the manufacturer's protocol (i.e., 1.5 ul DpnI restriction enzyme was added to each tube and incubated at 37° C. for 3 hours; 2 ul of DpnI-digested PCR reaction was then analyzed on a 1.2% E-gel for each nprE SEL to ensure PCR reaction worked and that parental template was degraded). TempliPhi rolling circle amplification was then used to generate large amounts of DNA for increasing library size of each nprE SEL, using the manufacturer's protocol (i.e., 1 ul DpnI treated QuikChange Multi Site-Directed Mutagenesis PCR, 5 ul TempliPhi Sample Buffer, 5 ul TempliPhi Reaction Buffer, and 0.2 ul TempliPhi Enzume Mix, for an ~11 ul total reaction; incubated at 30° C. for 3 hours; the TempliPhi reaction was diluted by adding 200 ul distilled, autoclaved water and briefly vortexed. Then, 1.5 ul of diluted TempliPhi material was transformed into competent *B. subtilis* cells, and nprE SELs were selected for using LA+10 ppm Neomycin+1.6% skim milk plates. Table 10-1 provides the names, sequences and SEQ ID NOS for the primers used in these experiments. All of the primers were synthesized by Integrated DNA Technologies, on 100 nmole scale, 5'-phosphorylated, and PAGE purified.

TABLE 10-1

Primers

| PRIMER | SEQUENCE | |
|---|---|---|
| nprE-T4F | GTGGAGCATGCCGCCACANNSGGAACAGGT ACGACTCTTAAAGG | (SEQ ID NO: 81) |
| nprE-G12F | CCGGAACAGGTACGACTCTTAAANNSAAAA CGGTCTCATTAAATATTTCTTCTGAAAGC | (SEQ ID NO: 82) |
| nprE-Q45F | CGGAACACAAATTATTACGTACGATCTGNN SAACCGCGAGTATAACCTGCC | (SEQ ID NO: 83) |
| nprE-Y49F | AAACCGCGAGNNSAACCTGCCGGGCACACT CGTATCC | (SEQ ID NO: 84) |
| nprE-N50F | GTACGATCTGCAAAACCGCGAGTATNNSCT GCCGGGCACACTCGTATCAG | (SEQ ID NO: 85) |
| nprE-T65F | CCAGCACCACAAACCAGTTTACANNSTCTT CTCAGCGCGCTGCCGTTG | (SEQ ID NO: 86) |
| nprE-D119F | GCAGATACAATAACGCAGCCTGGATCGGCN NSCAAATGATTTACGGTGACGGCGAC | (SEQ ID NO: 87) |
| nprE-G128F | CCAAATGATTTACGGTGACGGCGACNNSTC ATTCTTCTCACCTCTTTCCGGTTC | (SEQ ID NO: 88) |
| nprE-F130F | GGTGACGGCGACGGTTCANNSTTCTCACCT CTTTCCGGTCC | (SEQ ID NO: 89) |
| nprE-Q151F | CATGAAATGACACATGGCGTTACANNSGAA ACAGCCAACCTGAACTAC | (SEQ ID NO: 90) |
| nprE-E152F | CATGAAATGACACATGGCGTTACACAGNNS AACGCCAACCTGAACTACG | (SEQ ID NO: 91) |
| nprE-N155F | CATGGCGTTACACAGGAAACAGCCMMSCTG AACTACGAAAATCAGCCG | (SEQ ID NO: 92) |
| nprE-T179F | CTGATGTATTCGGGTACTTCAACGATNNSG AGGACTGGGATATCGGTG | (SEQ ID NO: 93) |
| nprE-Y204F | GCAGCTTATCCAATCCGACAAAANNSGGAC AGCCTGATAATTTCAAAAATTAC | (SEQ ID NO: 94) |
| nprE-G205F | GCAGCTTATCCAATCCGACAAAATACNNSC AGCCTGATAATTTCAAAAATTACAAAAACC | (SEQ ID NO: 95) |
| nprE-Y224F | GAACACTGATGCCGGCGACNNSGGCGGCGT GCATACAAAC | (SEQ ID NO: 96) |
| nprE-T243F | GAACAAAGCCGCTTACAATACGATTNNSAA AATCGGCGTGAACAAAGCG | (SEQ ID NO: 97) |
| nprE-V260F | GCAGATTTACTATCGTGCTCTGACGNNSTA CCTCACTCCGTCATCAACTTTTAAAG | (SEQ ID NO: 98) |
| nprE-Y261F | GATTTACTATCGTGCTCTGACGGTANNSCT CACTCCGTCATCAACTTTTAAAG | (SEQ ID NO: 99) |
| nprE-T263F | GTGCTCTGACGGTATACCTCNNSCCGTCAT CAACTTTTAAAGATGC | (SEQ ID NO: 100) |
| nprE-A273F | CCGTCATCAACTTTTAAAGATGCAAAANNS GCTTTGATTCAATCTGCGCGG | (SEQ ID NO: 101) |
| nprE-L282F | GATTCAATCTGCGCGGGACNNSTACGGCTC TCAAGATGCTGC | (SEQ ID NO: 102) |

TABLE 10-1-continued

Primers

| PRIMER | SEQUENCE | |
|---|---|---|
| nprE-S285F | CGCGGGACCTTTACGGCNNSCAAGATGCTG CAAGCGTAG | (SEQ ID NO: 103) |
| nprE-A289F | CCTTTACGGCTCTCAAGATGCTNNSAGCGT AGAAGCTGCCTGGAATG | (SEQ ID NO: 104) |
| nprE-A293F | CTCAAGATGCTGCAAGCGTAGAANNSGCCT GGAATGCAGTCGGATTG | (SEQ ID NO: 105) |
| nprE-N296F | GCAAGCGTAGAAGCTGCCTGGNNSGCAGTC GGATTGTAAACAAGAAAAG | (SEQ ID NO: 106) |
| nprE-G299F | GAAGCTGCCTGGAATGCAGTCNNSTTGTAA ACAAGAAAAGAGACCGGAAATCC | (SEQ ID NO: 107) |
| nprE-T60F | CACACTCGTATCCAGCACCNNSAACCAGTT TACAACTTCTTCTCAG | (SEQ ID NO: 108) |
| nprE-R110F | CTCCGTTCATTACGGCAGCNNSTACAATAA CGCAGCCTGGATC | (SEQ ID NO: 109) |
| nprE-D139F | CTCACCTCTTTCCGGTTCAATGNNSGTAAC CGCTCATGAAATGACAC | (SEQ ID NO: 110) |
| nprE-T4R | CCTTTAAGAGTCGTACCTGTTCCSNNTGTG GCGGCATGCTCCAC | (SEQ ID NO: 111) |
| nprE-G12R | GCTTTCAGAAGAAATATTTAATGAGACCGT TTTSNNTTTAAGAGTCGTACCTGTTCCGG | (SEQ ID NO: 112) |
| nprE-Q45R | GGCAGGTTATACTCGCGGTTSNNCAGATCG TACGTAATAATTTGTGTTCCG | (SEQ ID NO: 113) |
| nprE-Y49R | GGATACGAGTGTGCCCGGCAGGTTSNNCTC GCGGTTTTGCAGATCGTAC | (SEQ ID NO: 114) |
| nprE-N50R | CTGGATACGAGTGTGCCCGGCAGSNNATAC TCGCGGTTTTGCAGATCGTAC | (SEQ ID NO: 115) |
| nprE-T65R | CAACGGCAGCGCGCTGAGAAGASNNTGTAA ACTGGTTTGTGGTGCTGG | (SEQ ID NO: 116) |
| nprE-D119R | GTCGCCGTCACCGTAAATCATTTGSNNGCC GATCCAGGCTGCGTTATTGTATCTGC | (SEQ ID NO: 117) |
| nprE-G128R | GAACCGGAAAGAGGTGAGAAGAATGASNNG TCGCCGTCACCGTAAATCATTTGG | (SEQ ID NO: 118) |
| nprE-F130R | GGACCGGAAAGAGGTGAGAASNNTGAACCG TCGCCGTCACC | (SEQ ID NO: 119) |
| nprE-Q151R | GTAGTTCAGGTTGGCTGTTTCSNNTGTAAC GCCATGTGTCATTTCATG | (SEQ ID NO: 120) |
| nprE-E152R | CGTAGTTCAGGTTGGCTGTSNNCTGTGTAA CGCCATGTGTCATTTCATG | (SEQ ID NO: 121) |
| nprE-N155R | CGGCTGATTTTCGTAGTTCAGSNNGGCTGTT TCCTGTGTAACGCCATG | (SEQ ID NO: 122) |
| nprE-T179R | CACCGATATCCCAGTCCTCSNNATCGTTGA AGTACCCGAATACATCAG | (SEQ ID NO: 123) |
| nprE-Y204R | GTAATTTTTGAAATTATCAGGCTGTCCSNN TTTTGTCGGATTGGATAAGCTGC | (SEQ ID NO: 124) |
| nprE-G205R | GGTTTTTGTAATTTTTGAAATTATCAGGCT GSNNGTATTTTGTCGGATTGGATAAGCTGC | (SEQ ID NO: 125) |
| nprE-Y224R | GTTTGTATGCACGCCGCCSNNGTCGCCGGC ATCAGTGTTC | (SEQ ID NO: 126) |
| nprE-T243R | CGCTTTGTTCACGCCGATTTTSNNAATCGT ATTGTAAGCGGCTTTGTTC | (SEQ ID NO: 127) |

TABLE 10-1-continued

Primers

| PRIMER | SEQUENCE | |
|---|---|---|
| nprE-V260R | CTTTAAAAGTTGATGACGGAGTGAGGTASN NCGTCAGAGCACGATAGTAAATCTGC | (SEQ ID NO: 128) |
| nprE-Y261R | CTTTAAAAGTTGATGACGGAGTGAGSNNTA CCGTCAGAGCACGATAGTAAATC | (SEQ ID NO: 129) |
| nprE-T263R | GCATCTTTAAAAGTTGATGACGGSNNGAGG TATACCGTCAGAGCAC | (SEQ ID NO: 130) |
| nprE-A273R | CCGCGCAGATTGAATCAAAGCSNNTTTTGC ATCTTTAAAAGTTGATGACGG | (SEQ ID NO: 131) |
| nprE-L282R | GCAGCATCTTGAGAGCCGTASNNGTCCCGC GCAGATTGAATC | (SEQ ID NO: 132) |
| nprE-S285R | CTACGCTTGCAGCATCTTGSNNGCCGTAAA GGTCCCGCG | (SEQ ID NO: 133) |
| nprE-A289R | CATTCCAGGCAGCTTCTACGCTSNNAGCAT CTTGAGAGCCGTAAAGG | (SEQ ID NO: 134) |
| nprE-A293R | CAATCCGACTGCATTCCAGGCSNNTTCTAC GCTTGCAGCATCTTGAG | (SEQ ID NO: 135) |
| nprE-N296R | CTTTTCTTGTTTACAATCCGACTGCSNNCC AGGCAGCTTCTACGCTTGC | (SEQ ID NO: 136) |
| nprE-G299R | GGATTTCCGGTCTCTTTTCTTGTTTACAAS NNGACTGCATTCCAGGCAGCTTC | (SEQ ID NO: 137) |
| nprE-T60R | CTGAGAAGAAGTTGTAAACTGGTTSNNGGT GCTGGATACGAGTGTG | (SEQ ID NO: 138) |
| nprE-R110R | GATCCAGGCTGCGTTATTGTASNNGCTGCC GTAATGAACGGAG | (SEQ ID NO: 139) |
| nprE-D139R | GTGTCATTTCATGAGCGGTTACSNNCATTC AACCGGAAAGAGGTGAG | (SEQ ID NO: 140) |
| nprE-S135F | GCGACGGTTCATTCTTCTCACCTCTTNNSG GTTCAATGGACGTAACCGCTC | (SEQ ID NO: 141) |
| nprE-G136F | GCGACGGTTCATTCTTCTCACCTCTTTCCN NSTCAATGGACGTAACCGCTCATG | (SEQ ID NO: 142) |
| nprE-S137F | CTTCTCACCTCTTTCCGGTNNSATGGACGT AACCGCTCATG | (SEQ ID NO: 143) |
| nprE-V140F | CCTCTTTCCGGTTCAATGGACNNSACGCTC ATGAAATGACAC | (SEQ ID NO: 144) |
| nprE-S197F | CAGCCAGCCGGCTCTCCGCNNSTTATCCAA TCCGACAAAATACGGACAG | (SEQ ID NO: 145) |
| nprE-L198F | CAGCCAGCCGGCTCTCCGCAGCNNSTCCAA TCCGACAAAATACGGACAG | (SEQ ID NO: 146) |
| nprE-S199F | CAGCCAGCCGGCTCTCCGCAGCTTANNSAA TCCGACAAAATACGGACAGCC | (SEQ ID NO: 147) |
| nprE-L216F | CAGCCTGATAATTTCAAAAATTACAAAAAC NNSCCGGAACACTGATGCCGGCGAC | (SEQ ID NO: 148) |
| nprE-P217F | CAGCCTGATAATTTCAAAAATTACAAAAAC CTTNNSAACACTGATGCCGGCGAC | (SEQ ID NO: 149) |
| nprE-N218F | CAGCCTGATAATTTCAAAAATTACAAAAAC CTTCCGNNSACTGATGCCGGCGACTAC | (SEQ ID NO: 150) |
| nprE-T219F | CAGCCTGATAATTTCAAAAATTACAAAAAC CTTCCGAACNNSGATGCCGGCGACTACGG | (SEQ ID NO: 151) |
| nprE-D220F | CAGCCTGATAATTTCAAAAATTACAAAAAC CTTCCGAACACTNNSGCCGGCGACTACGGC GGCG | (SEQ ID NO: 152) |

TABLE 10-1-continued

| Primers | | |
|---|---|---|
| PRIMER | SEQUENCE | |
| nprE-A221F | CAGCCTGATAATTTCAAAAATTACAAAAAC CTTCCGAACACTGATNNSGGCGACTACGGC GGCGTG | (SEQ ID NO: 153) |
| nprE-G222F | CCTTCCGAACACTGATGCCNNSGACTACGG CGGCGTGCATAC | (SEQ ID NO: 154) |
| nprE-Q286F | CGGGACCTTTACGGCTCTNNSGATGCTGCA AGCGTAGAAGCTG | (SEQ ID NO: 155) |
| nprE-A297F | GCGTAGAAGCTGCCTGGAATNNSGTCGGAT TGTAAACAAGAAAAGAGACCGG | (SEQ ID NO: 156) |
| nprE-S135R | GAGCGGTTACGTCCATTGAACCSNNAAGAG GTGAGAAGAATGAACCGTCGC | (SEQ ID NO: 157) |
| nprE-G136R | CATGAGCGGTTACGTCCATTGASNNGGAAA GAGGTGAGAAGAATGAACCGTCGC | (SEQ ID NO: 158) |
| nprE-S137R | CATGAGCGGTTACGTCCATSNNACCGGAAA GAGGTGAGAAG | (SEQ ID NO: 159) |
| nprE-V140R | GTGTCATTTCATGAGCGGTSNNGTCATTGA ACCGGAAAGAGG | (SEQ ID NO: 160) |
| nprE-S197R | CTGTCCGTATTTTGTCGGATTGGATAASNN GCGGAGAGCCGGCTGGCTG | (SEQ ID NO: 161) |
| nprE-L198R | CTGTCCGTATTTTGTCGGATTGGASNNGCT GCGGAGAGCCGGCTGGCTG | (SEQ ID NO: 162) |
| nprE-S199R | GGCTGTCCGTATTTTGTCGGATTSNNTAAG CTGCGGAGAGCCGGCTGGCTG | (SEQ ID NO: 163) |
| nprE-L216R | GTCGCCGGCATCAGTGTTCGGSNNGTTTTT GTAATTTTTGAAATTATCAGGCTG | (SEQ ID NO: 164) |
| nprE-P217R | GTCGCCGGCATCAGTGTTSNNAAGGTTTTT GTAATTTTTGAAATTATCAGGCTG | (SEQ ID NO: 165) |
| nprE-N218R | GTCGTCGCCGGCATCAGTSNNCGGAAGGTT TTTGTAATTTTTGAAATTATCAGGCTG | (SEQ ID NO: 166) |
| nprE-T219R | CCGTAGTCGCCGGCATCSNNGTTCGGAAGG TTTTTGTAATTTTTGAAATTATCAGGCTG | (SEQ ID NO: 167) |
| nprE-D220R | CGCCGCCGTAGTCGCCGGCSNNAGTGTTCG GAAGGTTTTTGTAATTTTTGAAATTATCAG GCTG | (SEQ ID NO: 168) |
| nprE-A221R | CACGCCGCCGTAGTCGCCSNNATCAGTGTT CGGAAGGTTTTTGTAATTTTTGAAATTATC AGGCTG | (SEQ ID NO: 169) |
| nprE-G222R | GTATGCACGCCGCCGTAGTCSNNGGCATCA GTGTTCGGAAGG | (SEQ ID NO: 170) |
| nprE-Q286R | CAGCTTCTACGCTTGCAGCATCSNNAGAGC CGTAAAGGTCCCG | (SEQ ID NO: 171) |
| nprE-A297R | CCGGTCTCTTTTCTTGTTTACAATCCGACS NNATTCCAGGCAGCTTCTACGC | (SEQ ID NO: 172) |

Example 11

Identification of nprE Homologues

In this Example, experiments conducted to identify npr homologues are described. In particular, in this Example, experiments were conducted to clone neutral protease (npr) homologs from different and closely related *Bacillus* species. The different species were chosen in order to explore the diversity and properties from which these different species are isolated.

The various npr homologs explored included:

*B. caldolyticus* npr (P23384)
*B. cereus* nprC (P05806)
*B. cereus* E33L npr (AAY60523)
*B. stearothermophilus* nprT
*B. subtilis* nprB
*B. subtilis* nprE
*B. thuringiensis* nprB (AAK00602)
*S. aureus* aur (P81177)

FIG. 3 provides a sequence alignment of these homologs (SEQ ID NOS:173-181) and FIG. 4 (SEQ ID NOS:182-191) provides another sequence alignment of various other homologs.

Figure 6:
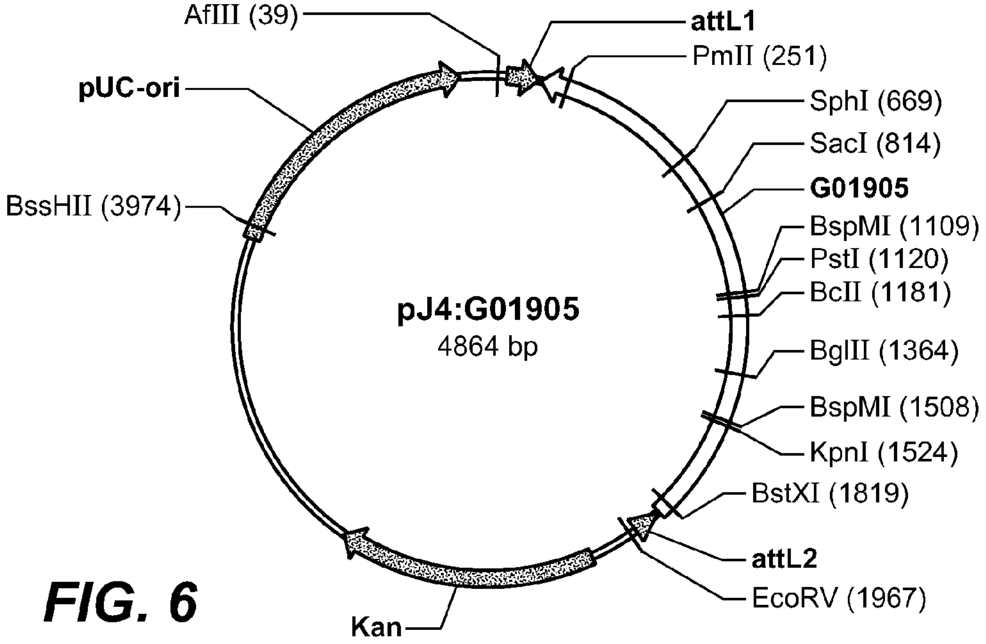
FIG. 6 provides a map of plasmid pJ4:GO1905.
Figure 7:
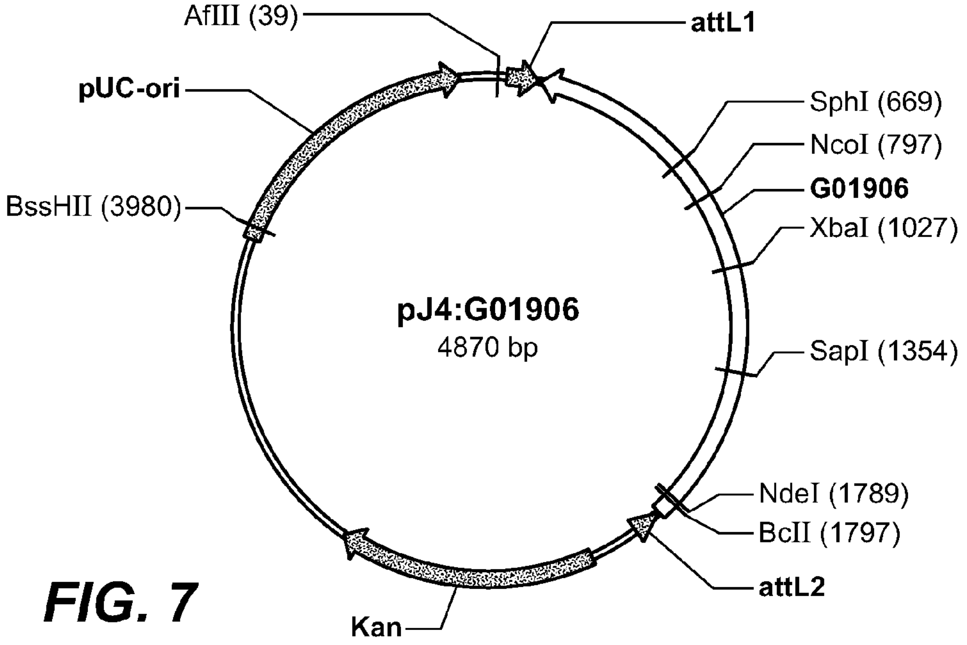
FIG. 7 provides a map of plasmid pJ4: G01906.
Figure 8:
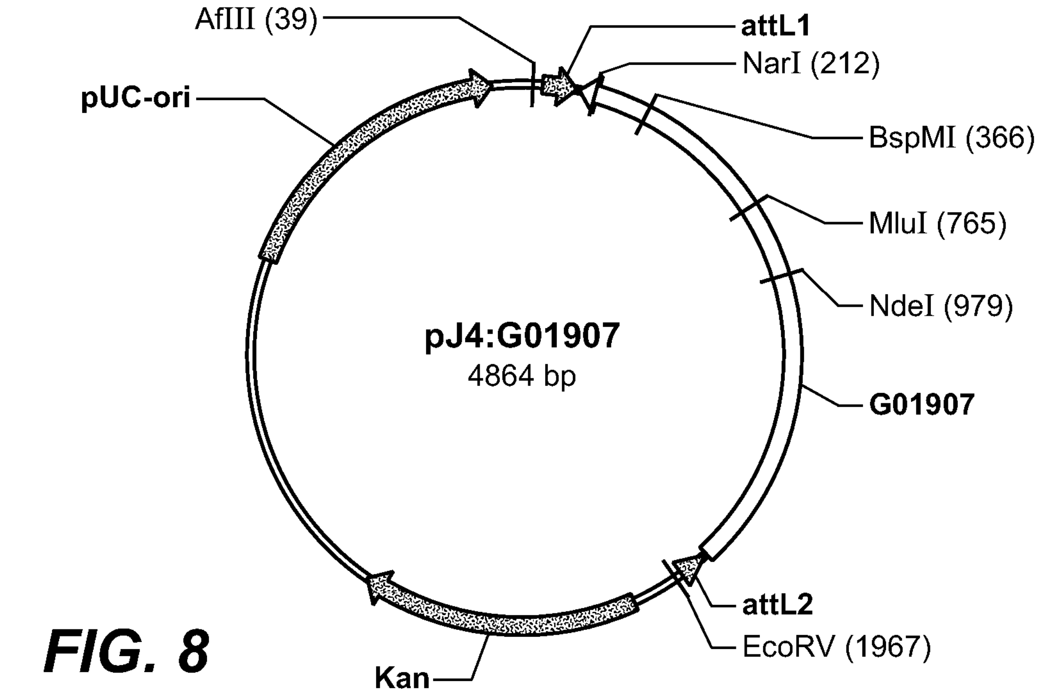
FIG. 8 provides a map of plasmid pJ4:G01907.
Figure 9:
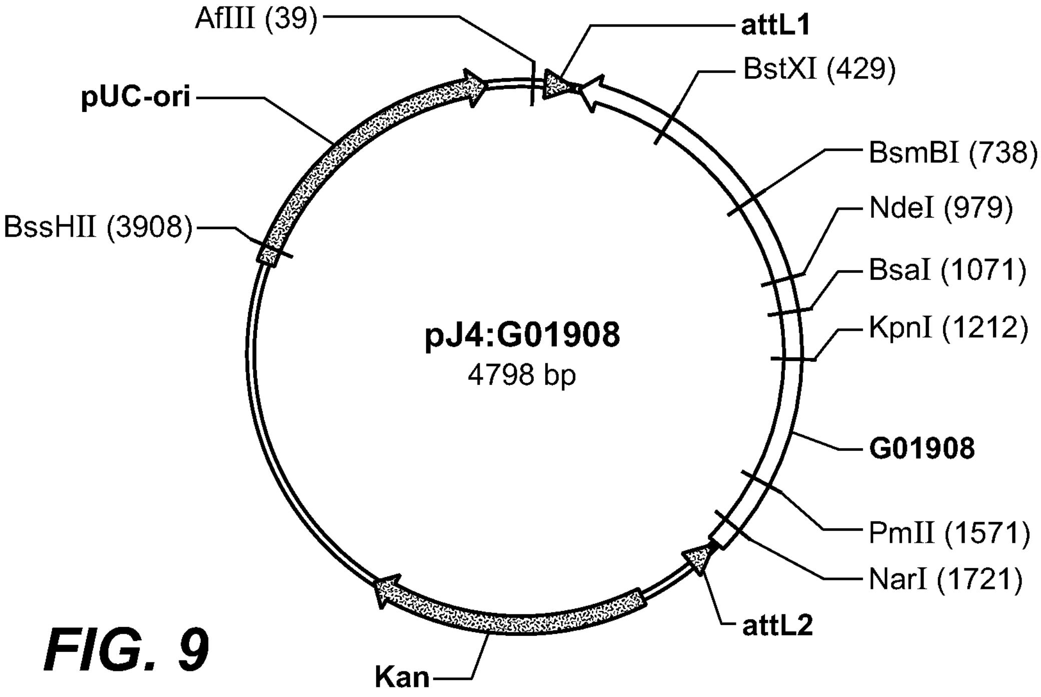
FIG. 9 provides a map of plasmid pJ4:G01908.
Figure 10:
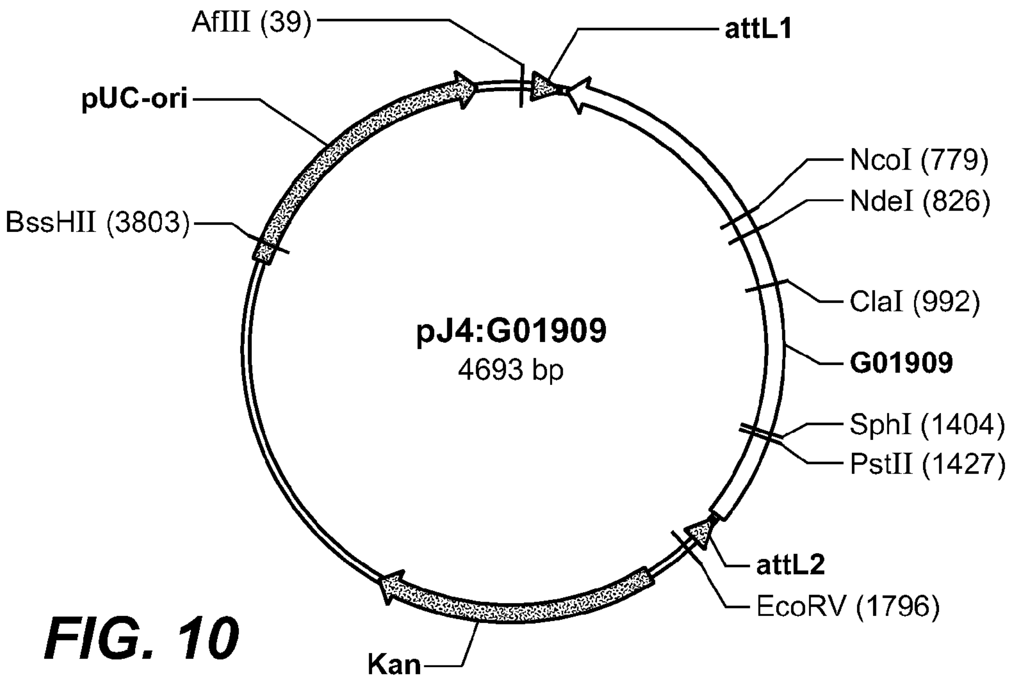
FIG. 10 provides a map of plasmid pJ4:G01909.
Figure 11:
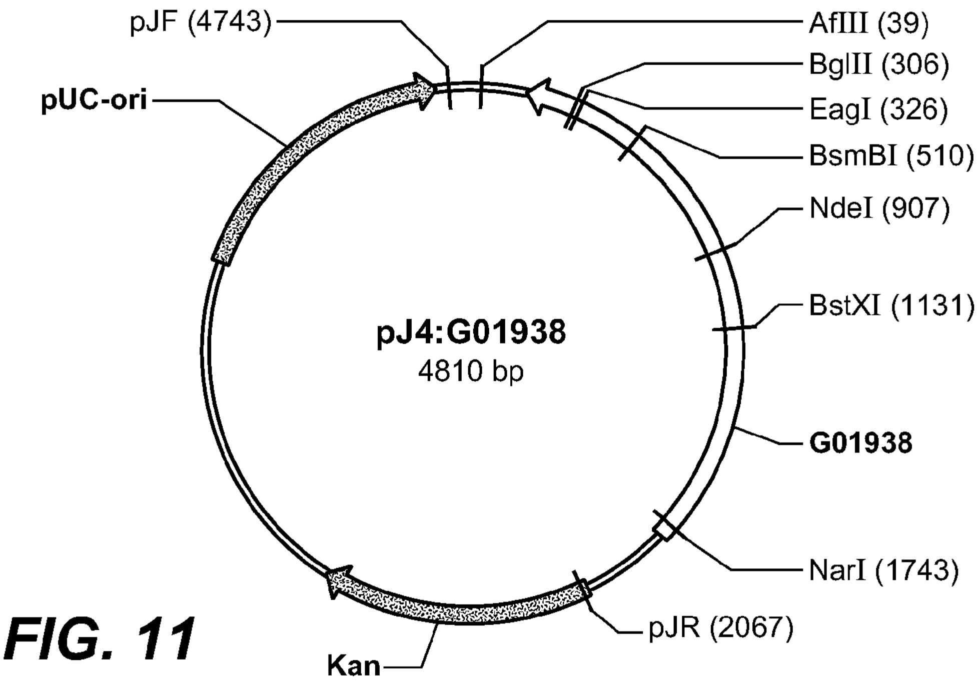
FIG. 11 provides a map of plasmid pJ4:G01938.
Figure 12:
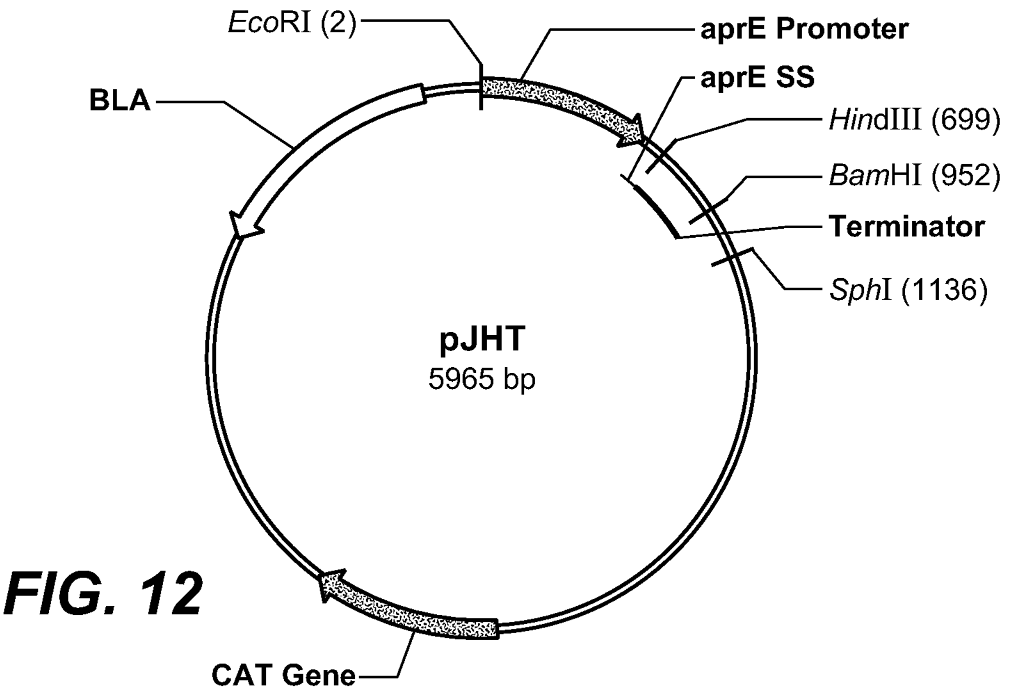
FIG. 12 provides a map of plasmid pJHT.
Figure 13:
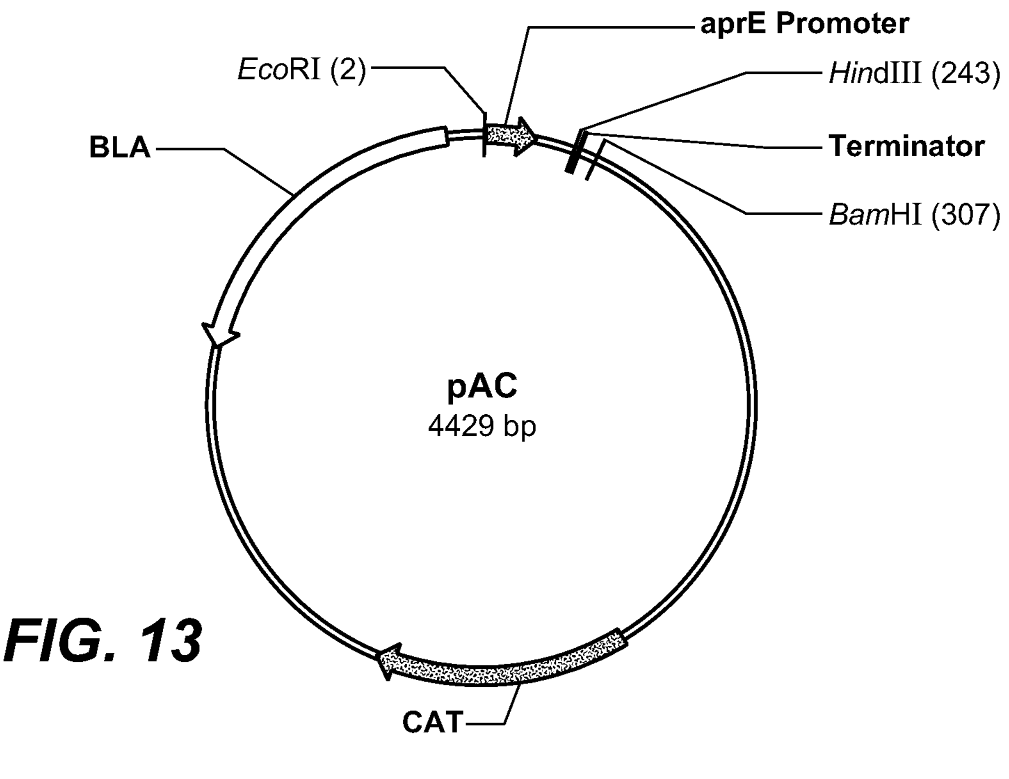
FIG. 13 provides a map of plasmid pAC.

In these experiments, the materials included:

Chromosomal DNA of *B. subtilis* strain 1168
The following DNA plasmids were synthesized at DNA2.0 with *B. subtilis* codon optimization:
pJ4:G01905 (*B. thuringiensis* nprB) (See, FIG. 6)
pJ4:G01906 (*B. cereus* E33L npr) (See, FIG. 7)
pJ4:G01907 (*B. cereus* nprC) (See, FIG. 8)
pJ4:G01908 (*B. caldolyticus* npr) (See, FIG. 9)
pJ4:G01909 (*S. aureus* aur) (See, FIG. 10)
pJ4:G01938 (*S. stearothermophilus* nprT) (See, FIG. 11)
pJHT vector (See, FIG. 12)
pAC vector (See, FIG. 13)
MJ Research PTC-200 Peltier Thermal Cycler (Bio-Rad Laboratories)
Primers (Operon Inc)
PfuUltra II Fusion HS DNA Polymerase (Stratagene)
Restriction endonucleases (Roche)
TOP10 chemically competent *E. coli* cells (Invitrogen)
*B. subtilis* competent cells ((ΔaprE, ΔnprE, oppA, ΔspollE, degUHy32, ΔamyE::(xylR,pxylA-comK)

TABLE 11

| Primers | | |
|---|---|---|
| Primer Name | Primer Sequence and SEQ ID NO: | |
| EL-689 | CGTCTTCAACAATTGTCCATTTTCTTCTGC | (SEQ ID NO: 196) |
| EL-693 | CAGACAATTTCTTACCTAAACCCACTCTTTACCCT CTCCTTTTAAAAAAATCT | (SEQ ID NO: 197) |
| EL-694 | GAATTTTTTTAAAAGGAGAGGGTAAAGAGTGGGTT TAGGTAAGAAATTGTCTG | (SEQ ID NO: 198) |
| EL-695 | GCTTATGGATCCCGTCGTTTCAGCTGAGAGAG | (SEQ ID NO: 199) |
| EL-696 | GATGTCTTGGTCAAGTTGCGCACTCTTTACCCTCT CCTTTTAAAAAAATTC | (SEQ ID NO: 200) |
| EL-697 | GAATTTTTTTAAAAGGAGAGGGTAAAGAGTGCGCA ACTTGACCAAGACATC | (SEQ ID NO: 201) |
| EL-698 | GGCCGGTTTTTTATGTAAGCTTATAGAATGCCGAC AGCCTCATACG | (SEQ ID NO: 202) |
| EL-699 | CGTATGAGGCTGTCGGCATTCTATAAGCTTACATA AAAAACCGGCCTTGG | (SEQ ID NO: 203) |
| EL-700 | AATGGTGCATGCAAGGAAGTGGCG | (SEQ ID NO: 204) |
| EL-755 | CGTCTTCAAGAATTCCTCCATTTTCTTCTGC | (SEQ ID NO: 205) |
| EL-733 | GCACCCAACATTGCACGTTTATTCACTCTTTACCC TCTCCTTTTAAAAAAATTC | (SEQ ID NO: 206) |

TABLE 11-continued

| Primers | | |
|---|---|---|
| Primer Name | Primer Sequence and SEQ ID NO: | |
| EL-734 | GAATTTTTTTAAAAGGAGAGGGTAAAGAGTGAATA AACGTGCAATGTTGGGTGC | (SEQ ID NO: 207) |
| EL-735 | GCTTATAAGCTTAATATACTCCAACCGCGTTG | (SEQ ID NO: 208) |
| EL-739 | CCAGCATAGCGCGTTTGTTCACTCTTTACCCTCTC CTTTTAAAAAAATTC | (SEQ ID NO: 209) |
| EL-740 | GAATTTTTTTAAAAGGAGAGGGTAAAGAGTGAACA AACGCGCTATGCTGG | (SEQ ID NO: 210) |
| EL-741 | GCTTATAAGCTTAATAGACACCCACGGCATTAAAC GCC | (SEQ ID NO: 211) |
| EL-742 | CAGGACAAGAGCTAAGGACTTTTTTTCACTCTTTA CCCTCTCCTTTTAAAAAAATTC | (SEQ ID NO: 212) |
| EL-743 | GAATTTTTTTAAAAGGAGAGGGTAAAGAGTGAAAA AAAAGTCCTTAGCTCTTGTCCTG | (SEQ ID NO: 213) |
| EL-744 | GCTTATAAGCTTAATTAATGCCGACGGCAC | (SEQ ID NO: 214) |

A. Cloning of *B. subtilis* nprE

Figure 15:
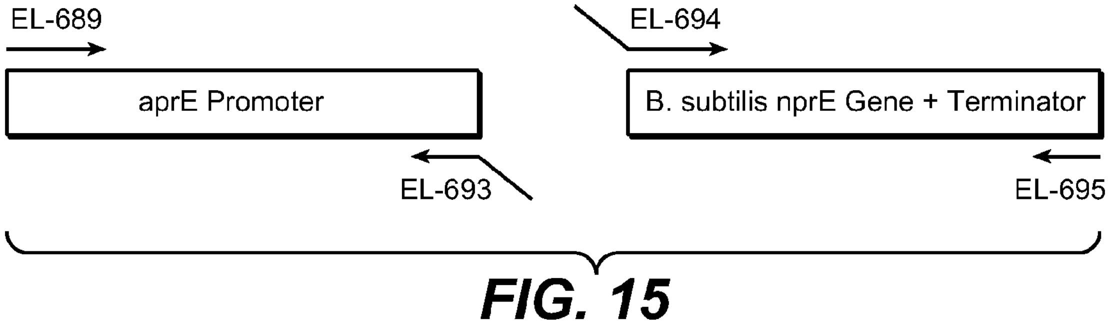
FIG. 15 provides a schematic showing the amplification of the aprE promoter and *B. subtilis* nprE gene fragments.

To construct the *B. subtilis* nprE plasmid, the amplified aprE promoter fragment (from pJHT vector) and *B. subtilis* nprE gene with terminator fragment (from *B. subtilis* strain 1168) were separately prepared. FIG. 15 provides a schematic, illustrating the amplification of the individual DNA fragments.

PCR Splice Overlap Extension (SOE) reaction was used to join the 2 separate DNA fragments together. In this reaction, the following reagents were combined: 1 ul aprE promoter DNA fragment, 1 ul *B. subtilis* nprE gene+Terminator fragment, 1 ul Primer EL-689 (25 uM), 1 ul Primer EL-695 (25 uM), 5 ul 10× PfuUltra II Fusion HS DNA polymerase buffer, 1 ul dNTP (10 mM), 1 ul PfuUltra II Fusion HS DNA polymerase, and 39 ul distilled, autoclaved water to provide a total reaction volume of 50 ul. The PCR cycles were: 95° C. for 2 minutes ($1^{st}$ cycle only), followed by 28 cycles of 95° C. for 30 seconds, 54° C. for 30 seconds, and 72° C. for 0:45 seconds.

Figure 16:
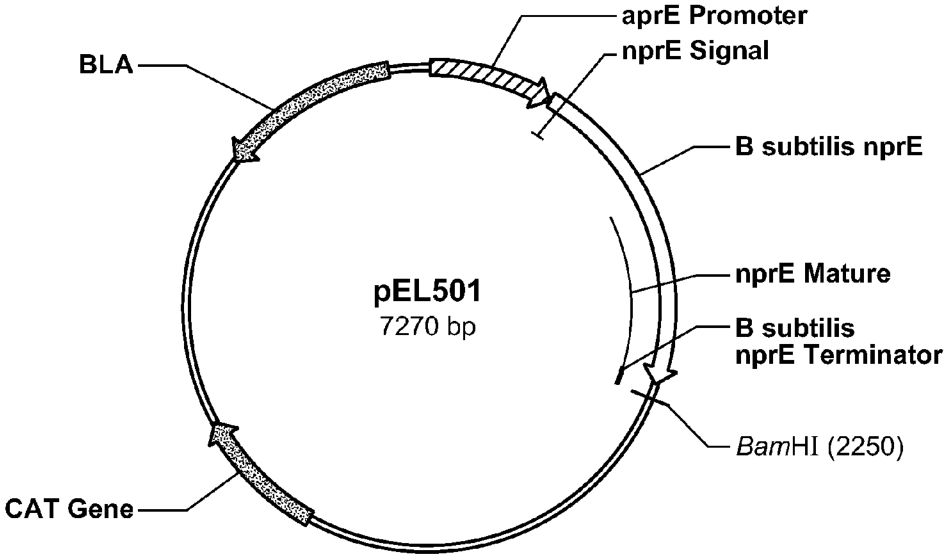
FIG. 16 provides a map of plasmid pEL501.

The PCR fusion fragment of aprE promoter-*B. subtilis* nprE gene+Terminator was digested with MfeI and BamHI restriction endonucleases. The pJHT vector was digested with EcoRI and BamHI restriction endonucleases. The restriction endonuclease digested aprE promoter-*B. subtilis* nprE gene+Terminator DNA fragment was then ligated with the restriction endonuclease digested pJHT vector. The ligation mixture was then transformed into TOP10 chemically competent *E. coli* cells for selection on LA+50 ppm carbenicillin. After identification of plasmids containing the correct DNA construct sequence for plasmid pEL501 (See, FIG. 16), transformed into competent *B. subtilis* cells for integration into aprE promoter locus. Transformants were selected for protease activity (i e skim milk clearing) on LA+5 ppm chloramphenicol+1.6% skim milk plates. Amplified strains were then transferred to LA+25 ppm chloramphenicol+1.6% skim milk plates. Strains were then transferred to LA+25 ppm chloramphenicol+1.6% skim milk plates for amplification.

B. Cloning of *B. subtilis* nprB

Figure 17:
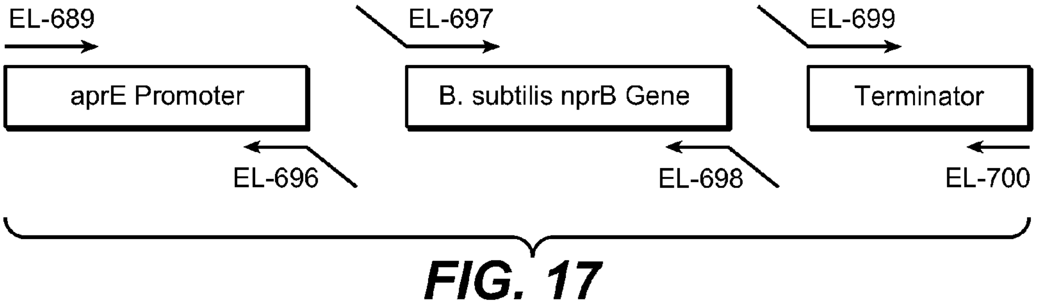
FIG. 17 provides a schematic showing the amplification of the aprE promoter and *B. subtilis* nprB gene fragments.

To construct the *B. subtilis* nprB plasmid, amplified the aprE promoter fragment (from pJHT vector), *B. subtilis* nprB gene fragment (from *B. subtilis* strain 1168), and Terminator fragment (from pJHT vector) were separately prepared. FIG. 17 provides a schematic diagram of the amplification of the individual DNA fragments.

PCR Splice Overlap Extension (SOE) reaction was used to join the three separate DNA fragments together. In this reaction, the following reagents were combined: 1 ul aprE promoter DNA fragment, 1 ul *B. subtilis* nprB gene+Terminator fragment, 1 ul Terminator DNA fragment, 1 ul Primer EL-689 (25 uM), 1 ul Primer EL-700 (25 uM), 5 ul 10× PfuUltra II Fusion HS DNA polymerase buffer, 1 ul dNTP (10 mM), 1 ul PfuUltra II Fusion HS DNA Polymerase, and 38 ul distilled, autoclaved water, for a 50 ul total reaction volume. The PCR cycles were: 95° C. for 2 minutes ($1^{st}$ cycle only), followed by 28 cycles of 95° C. for 30 seconds, 54° C. for 30 seconds, and 72° C. for 0:45 seconds.

Figure 18:
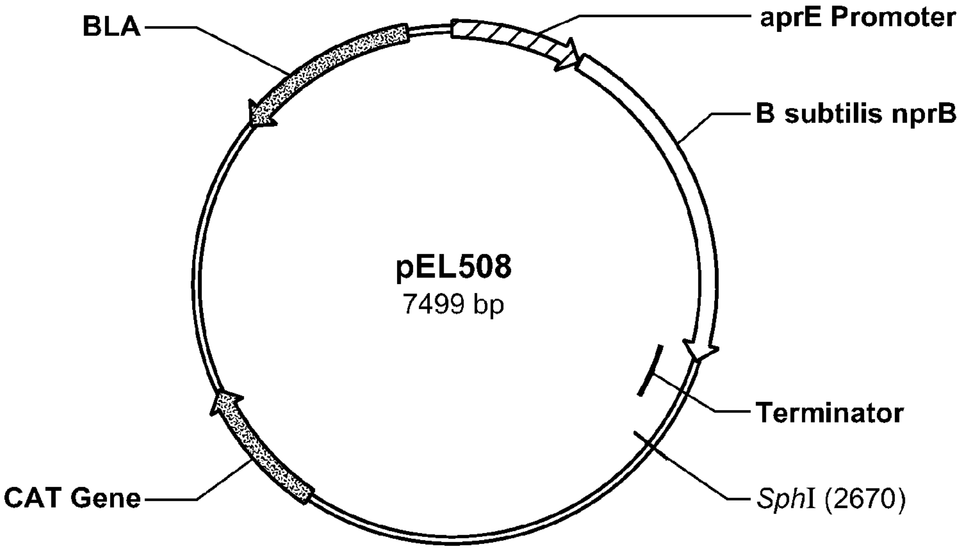
FIG. 18 provides a map of plasmid pEL508.

The PCR fusion fragment of aprE promoter-*B. subtilis* nprB gene+Terminator was digested with MfeI and SphI restriction endonucleases. The pJHT vector was digested with EcoRI and SphI restriction endonucleases. The restriction endonuclease digested aprE promoter-*B. subtilis* nprB gene+Terminator DNA fragment was then ligated with the restriction endonuclease digested pJHT vector. The ligation mixture was then transformed into TOP10 chemically competent *E. coli* cells for selection on LA+50 ppm carbenicillin. After identification of plasmids containing the correct DNA construct sequence for plasmid pEL508 (See, FIG. 18), transformed into competent *B. subtilis* cells for integration into aprE promoter locus. Transformants were selected for protease activity (i e skim milk clearing) on LA+5 ppm chloramphenicol+1.6% skim milk plates. Amplified strains were then transferred to LA+25 ppm chloramphenicol+1.6% skim milk plates. Strains were then transferred to LA+25 ppm chloramphenicol+1.6% skim milk plates for amplification.

C. Cloning of *B. stearothermophilus* nprT

Figure 19:
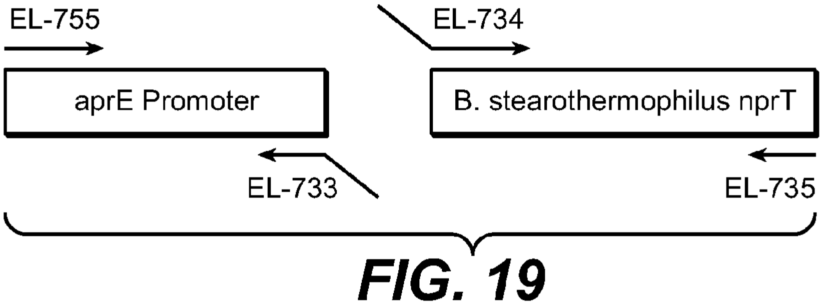
FIG. 19 provides a schematic showing the amplification of the aprE promoter and *B. stearothermophilus* nprT gene fragments, used in the production of strain EL560.

To construct the *B. stearothermophilus* nprT plasmid, the amplified aprE promoter fragment (from pJHT vector) and *B. stearothermophilus* nprT fragment (from plasmid pJ4: G01938) were separately prepared. FIG. 19 provides a schematic diagram of the amplification of the individual DNA fragments.

PCR Splice Overlap Extension (SOE) reaction was used to join the 2 separate DNA fragments together. In this reaction, the following reagents were combined: 1 ul aprE promoter DNA fragment, 1 ul *B. stearothermophilus* nprT gene fragment, 1 ul Primer EL-755 (25 uM), 1 ul Primer EL-735 (25 uM), 5 ul 10× PfuUltra II Fusion HS DNA Polymerase buffer, 1 ul dNTP (10 mM), 1 ul PfuUltra II Fusion HS DNA Polymerase, and 39 ul distilled, autoclaved water, to provide a total reaction volume of 50 ul. The PCR cycles were: 95° C. for 2 minutes ($1^{st}$ cycle only), followed by 28 cycles of 95° C. for 30 seconds, 54° C. for 30 seconds, and 72° C. for 0:45 seconds.

Figure 20:
FIG. 20 provides a diagram showing the construction of strain EL560.

The PCR fusion fragment of aprE promoter-*B. stearothermophilus* nprT gene+Terminator was digested with EcoRI and HindIII restriction endonucleases. The pAC vector was digested with EcoRI and HindIII restriction endonucleases. The restriction endonuclease digested aprE promoter-*B. stearothermophilus* nprT DNA fragment was then ligated with the restriction endonuclease digested pAC vector. TempliPhi rolling circle amplification was then used to generate large amounts of the ligated aprE promoter-*B. stearothermophilus* nprT pAC DNA molecule, using the manufacturer's protocol (i.e., 1 ul aprE promoter-*B. stearothermophilus* nprT pAC ligation reaction, 5 ul TempliPhi Sample Buffer, 5 ul TempliPhi Reaction Buffer, and 0.2 ul TempliPhi Enzume Mix, for an ~11 ul total reaction; incubated at 30° C. for 3 hours). The TempliPhi reaction was then transformed directly into competent *B. subtilis* cells for integration into aprE promoter locus, thereby generating *Bacillus* strain EL560, confirmed by DNA sequencing analysis (See, FIG. 20). Transformants were selected for protease activity (i.e. skim milk clearing) on LA+5 ppm chloramphenicol+1.6% skim milk plates. Strains were then transferred to LA+25 ppm chloramphenicol+1.6% skim milk plates for amplification.

D. Cloning of *B. caldolyticus* npr

Figure 21:
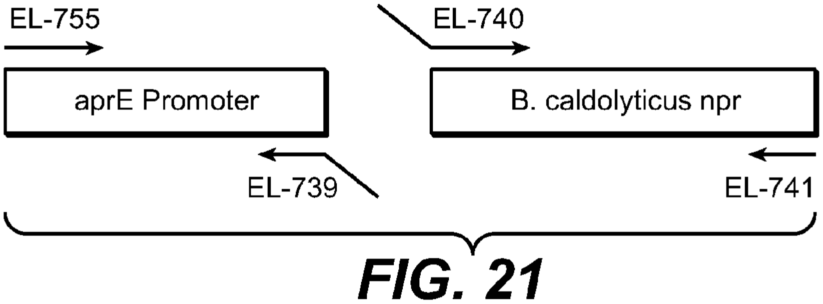
FIG. 21 provides a schematic showing the amplification of the aprE promoter and *B. caldolyticus* npr gene fragments, used in the production of strain EL561.

To construct the *B. caldolyticus* npr plasmid, the amplified aprE promoter fragment (from pJHT vector) and *B. caldolyticus* npr fragment (from plasmid pJ4:G01908) were separately prepared. FIG. 21 provides a schematic diagram of the amplification of the individual DNA fragments.

PCR Splice Overlap Extension (SOE) reaction was used to join the 2 separate DNA fragments together. In this reaction, the following reagents were combined: 1 ul aprE promoter DNA fragment, 1 ul *B. caldolyticus* npr gene fragment, 1 ul Primer EL-755 (25 uM), 1 ul Primer EL-741 (25 uM), 5 ul 10× PfuUltra II Fusion HS DNA Polymerase buffer, 1 ul dNTP (10 mM), 1 ul PfuUltra II Fusion HS DNA Polymerase, and 39 ul distilled, autoclaved water, to provide a total reaction volume of 50 ul. The PCR cycles were: 95° C. for 2 minutes ($1^{st}$ cycle only), followed by 28 cycles of 95° C. for 30 seconds, 54° C. for 30 seconds, and 72° C. for 0:45 seconds.

The PCR fusion fragment of aprE promoter-*B. caldolyticus* npr gene+Terminator was digested with EcoRI and HindIII restriction endonucleases. The pAC vector was digested with EcoRI and HindIII restriction endonucleases. The restriction endonuclease digested aprE promoter-*B. caldolyticus* npr DNA fragment was then ligated with the restriction endonuclease digested pAC vector. TempliPhi rolling circle amplification was then used to generate large amounts of the ligated aprE promoter-*B. caldolyticus* npr pAC DNA molecule, using the manufacturer's protocol (i.e., 1 ul aprE promoter-*B. caldolyticus* npr pAC ligation reaction, 5 ul TempliPhi Sample Buffer, 5 ul TempliPhi Reaction Buffer, and 0.2 ul TempliPhi Enzume Mix, for an ~11 ul total reaction; incubated at 30° C. for 3 hours). The TempliPhi reaction was then transformed directly into competent *B. subtilis* cells for integration into aprE promoter locus, thereby generating *Bacillus* strain EL561 (See, FIG. 22), confirmed by DNA sequencing analysis. Transformants were selected for protease activity (i e skim milk clearing) on LA+5 ppm chloramphenicol+1.6% skim milk plates. Strains were then transferred to LA+25 ppm chloramphenicol+1.6% skim milk plates for amplification.

E. Cloning of *B. thuringiensis* nprB

Figure 23:
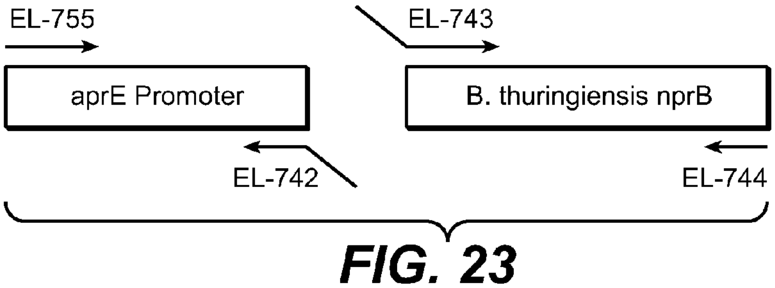
FIG. 23 provides a schematic showing the amplification of the aprE promoter and *B. thuringiensis* nprB gene fragments.

To construct the *B. thuringiensis* nprB plasmid, the amplified aprE promoter fragment (from pJHT vector) and *B. thuringiensis* nprB fragment (from plasmid pJ4:G01905) were separately prepared. FIG. 23 provides a schematic showing the amplification of the individual DNA fragments.

PCR Splice Overlap Extension (SOE) reaction was used to join the 2 separate DNA fragments together. In this reaction, the following reagents were combined: 1 ul aprE promoter DNA fragment, 1 ul *B. thuringiensis* nprB gene fragment, 1 ul Primer EL-755 (25 uM), 1 ul Primer EL-744 (25 uM), 5 ul 10× PfuUltra II Fusion HS DNA Polymerase buffer, 1 ul dNTP (10 mM), 1 ul PfuUltra II Fusion HS DNA Polymerase, and 39 ul distilled, autoclaved water, to provide a total reaction volume of 50 ul. The PCR cycles were: 95° C. for 2 minutes ($1^{st}$ cycle only), followed by 28 cycles of 95° C. for 30 seconds, 54° C. for 30 seconds, and 72° C. for 0:45 seconds.

Figure 24:
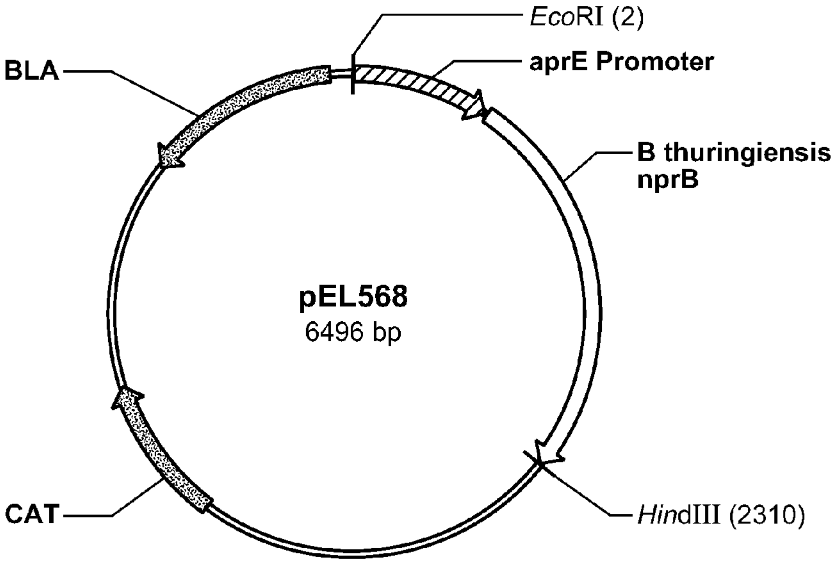
FIG. 24 provides a map of plasmid pEL568.
Figure 25:
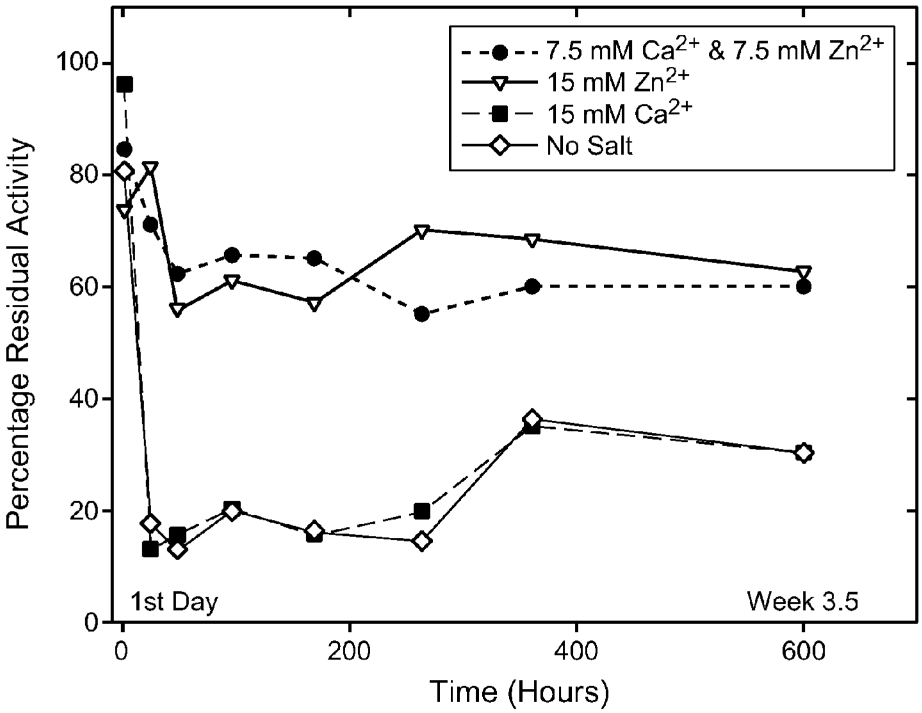
FIG. 25 provides a graph showing results from experiments designed to determine the long-term storage of 0.36 mg/ml UF concentrate of neutral metalloprotease (nprE) in TIDE® 2005 base in the presence of zinc and calcium ions at 32° C. For comparative purposes, results obtained for testing without salt and excess calcium are provided.

The PCR fusion fragment of aprE promoter-*B. thuringiensis* nprB gene+Terminator was digested with EcoRI and HindIII restriction endonucleases. The pAC vector was digested with EcoRI and HindIII restriction endonucleases. The restriction endonuclease digested aprE promoter-*B. thuringiensis* nprB DNA fragment was then ligated with the restriction endonuclease digested pAC vector. The ligation mixture was then transformed into TOP10 chemically competent *E. coli* cells. After identification of plasmids containing the correct DNA construct sequence for plasmid pEL568, transformed into competent *B. subtilis* cells. Transformants were then selected for protease activity (i e skim milk clearing) on LA+5 ppm chloramphenicol+1.6% skim milk plates. DNA plasmid preparation shows that plasmid pEL568 is stable in *B. subtilis* and does not integrate into the aprE promoter locus. FIG. 24 provides a map of plasmid pEL568.

E. Homology Modeling

In yet additional embodiments, a homology model of the mature domain of NprE from *Bacillus amyloliquefaciens* is provided. In these experiments, the protein sequence of the mature domain of the NprE sequence (SEQ ID NO:192) was run through the program BlastP (NCBI). This program matches the sequence to other known sequences of varying sequence identity. From the output, sequences for which an X-ray crystal structures are known were identified. These sequences included *S. aureus* Npr (pdb id 1BQB) *P. aeruginosa* Npr (pdb id1EZM), *B. thermolyticus* thermolysin (pdb id 1KEI) and *B. cereus* Npr (pdb id 1NPC). FIG. 5 provides a sequence alignment of the various sequences analyzed. (SEQ ID NOS:192-195)

The sequence of the *B. cereus* Npr was found to be the most identical to NprE. *B. thermolyticus* thermolysin (pdb id 1KEI) was excluded from subsequent steps as it is very similar to *B. cereus* Npr. A homology model was then prepared as detailed below, and all calculation were made using the program MOE (Chemical Computing).

First, the *S. aureus* Npr (pdb id 1BQB; SEQ ID NO:193) *P. aeruginosa* Npr (pdb id1EZM)(SEQ ID NO:194), and *B. cereus* Npr (pdb id 1NPC)(SEQ ID NO:195) sequences were aligned using known structure, in order to obtain the most accurate sequence alignment (i.e., a structure based sequence alignment was produced). Next, the NprE mature sequence was aligned to this structure based sequence alignment. Then, an initial homology model of NprE was produced using the *B. cereus* Npr (pdb id 1NPC) structure as a template, and using the sequence alignment of NprE to *B. cereus* Npr produced above. It was clear from inspection of this alignment that whereas *B. cereus* Npr contains four $Ca^{2+}$ ion binding sites, while NprE only contains two $Ca^{2+}$ ion binding sites.

Finally, after the initial homology model was built, the metal ions (i.e., $Zn^{2+}$, and two $Ca^{2+}$) were computationally fixed, as were their respective protein ligands. The rest of the model structure was computationally minimized using the CHARMM22 parameter set, resulting in the final homology model.

Example 12

Wash Performance Tests

In this Example, experiments conducted to determine the wash performance of the metalloprotease of the present invention are described. All wash performance tests were performed under American wash conditions, as indicated below:

Laundry Wash Performance Tests

| | |
|---|---|
| Equipment: | Terg-O-Tometer (US Testing) 6 pot bench top model |
| Temperature: | 15° C./ 60° F. |
| Wash Time: | 12 minutes |
| Agitation: | 100 rpm |
| Rinse Time: | 3 minutes |
| Water Hardness: | 6 grains per gallon/105 ppm as $CaCO_3$ (3/1 $Ca^{+2}/Mg^{+2}$) |
| Sud concentration: | 1.6 g/l TIDE ® 2005 liquid detergent base |
| Enzyme dosage: | 0.00-0.55-2.75-5.50 mg active protein/l wash solution |
| Swatches: | EMPA 116 Fixed, fixated at 20° C.: Blood, milk, ink on cotton (10 × 7.5 cm)<br>EMPA 116 Unfixed: Blood, milk, ink on cotton (10 × 7.5 cm)<br>Equest grass: Grass Medium scrubbed on cotton (10 × 7.5 cm)<br>CFT C-10: Pigment, oil ,milk on cotton (10 × 7.5 cm)<br>EMPA 221: Unsoiled cotton used as ballast (10 × 10 cm)<br>6 EMPA 116 fixed + 2 EMPA 221 were put in one vessel<br>6 EMPA 116 unfixed + 2 EMPA 221 were put in one vessel<br>6 Equest grass + 2 EMPA 221 were put in one vessel<br>6 CFT C-10 + 2 EMPA 221 were put in one vessel |
| Drying conditions: | Spin-drier, Grass stains were dried to the air, covered with dark clothes.<br>The other stains were ironed. |
| Measuring swatches: | Tristimulus Minolta Meter CR-300 with equation L (L*a*b), D65 Std.<br>Illuminate, on a white background. Expressed on Delta % Soil Removal.<br>3 readings per swatch (before and after washing) |

$$\% \text{ Stain Removal}=(L \text{ value after washing}-L \text{ value before washing})/(L_{0\ white\ cotton}-L \text{ value before washing})\times 100\%$$

All experiments were done in quadruplicate

The proteases were tested in a specially developed washing test, using three different cotton swatches, soiled with:

(a) milk, blood and ink (10.0×7.5 cm; EMPA), designated with the numbers 116 unfixed and fixed (the stains were fixed at 20° C.);

(b) grass medium (10.0×7.5 cm; Equest); and (c) pigment, oil and milk (10.0×7.5 cm designated with the numbers C-10 CFT).

These experiments are described in greater detail below. The washing tests were performed in a bench top model Terg-O-Tometer (US Testing), equipped with six stainless steel test vessels. The stainless steel test vessels each contained 1.6 g of TIDE® 2005 liquid detergent base, dissolved in 1000 ml water of 105 ppm/6 grains per gallon, and were each loaded with six of the same soiled cotton swatches and two extra ballast cotton swatches (EMPA 221). A selected protease (e.g., neutral metalloprotease or another protease) was added to each vessel in a concentration from 0.00 to 5.50 mg active protein per liter suds.

The tests were carried out for 12 minutes at 15° C./60° F., with an agitation of 100 rpm. After washing, the swatches were rinsed for 3 minutes under cold tap water and placed in a spin-drier. The grass swatches were air-dried and covered with dark clothing to limit the sensitivity of the grass stains to light. All other swatches were ironed. All experiments were performed in quadruplicate.

The reflectance of the tested swatches was measured with a Tristimulus Minolta Meter CR-300 using the equation L (L*a*b). Wash performance values were calculated using the following relationship:

$$\% \text{ Stain Removal}=(L \text{ value after washing}-L \text{ value before washing})/(L_{0\ white\ cotton}-L \text{ value before washing})\times 100\%$$

Figure 26A:
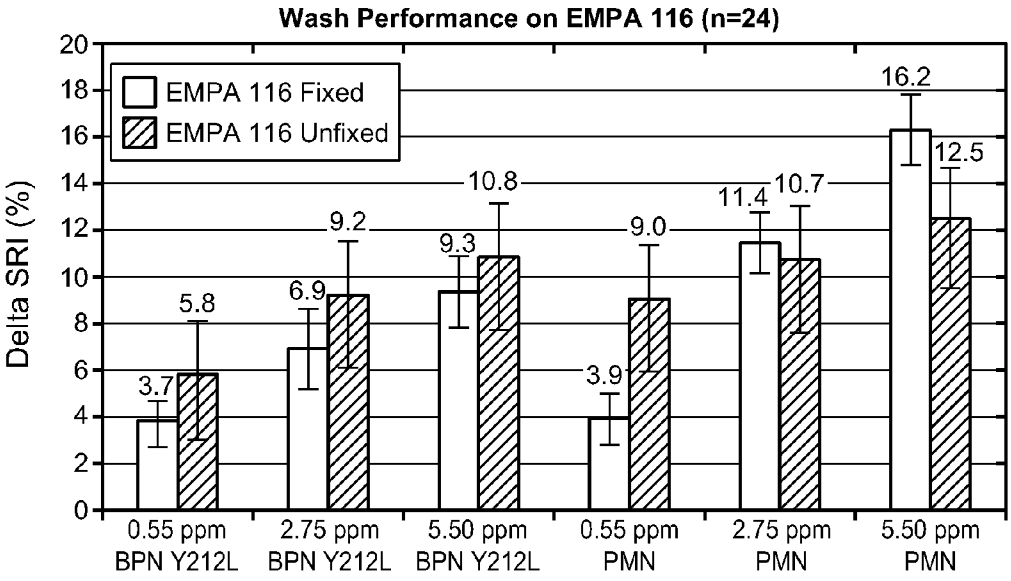
FIGS. 26A, 26B and 26C provide wash performance test data using Terg-O-Tometer (TOM) and varying soiled substrates. Panel A provides results showing the delta soil removal (%) of subtilisin (BPN' Y217L) and purified MULTIFECT® Neutral on EMPA 116 (fixed and unfixed on cotton) after washing at 15° C. in TIDE®-2005 detergent liquid. Panel B provides results showing the delta soil removal (%) of subtilisin (BPN'Y217L) and purified MULTIFECT® Neutral on Equest® grass medium soiled on cotton after washing at 15° C. in TIDE®-2005 detergent liquid. Panel C provides results showing the delta soil removal (%) of subtilisin (BPN' Y217L) and purified MULTIFECT® Neutral on CFT C-10 (pigment, oil, milk on cotton) after washing at 15° C. in TIDE®-2005 detergent liquid.
Figure 26B:
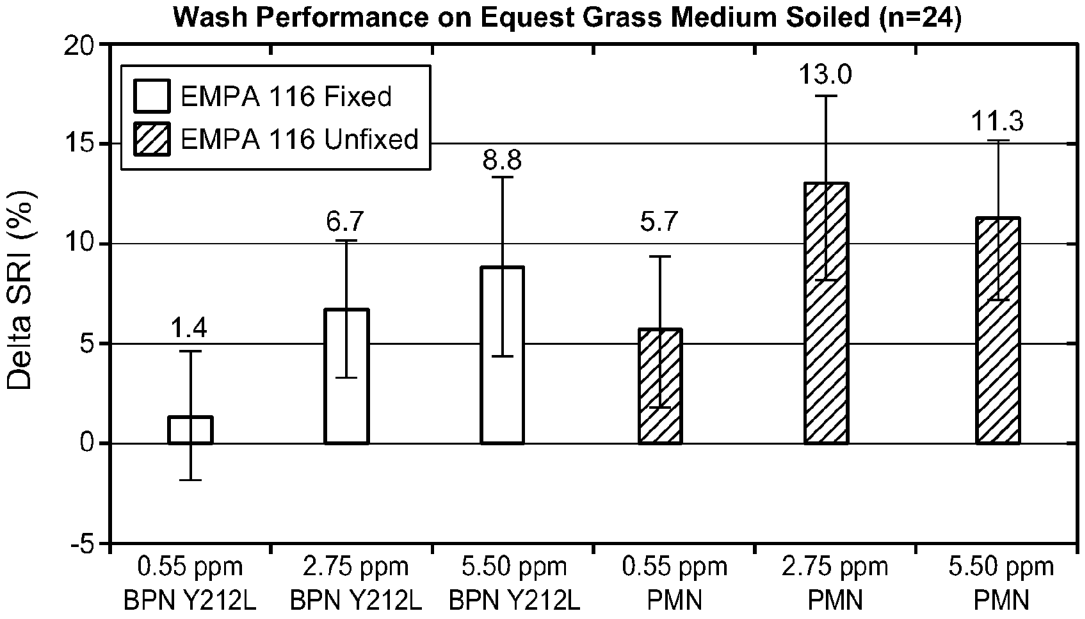
Figure 26C:
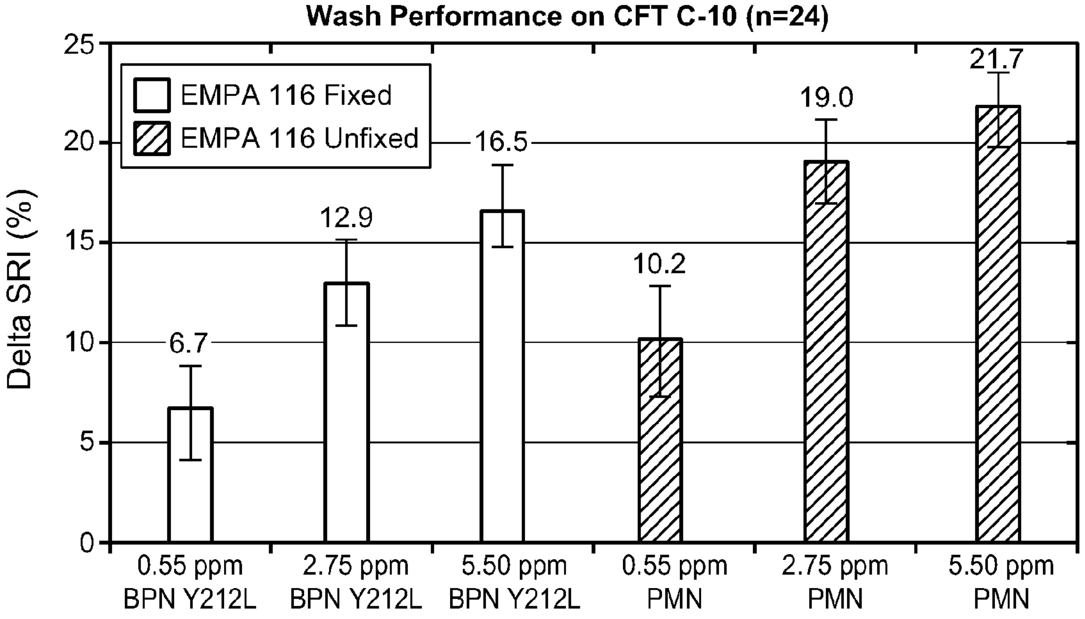

The results of the Terg-O-Tometer (TOM) assay for purified MULTIFECT® are shown in FIG. 26, and compared with those of subtilisin (BPN' Y217L), a serine alkaline protease. The TOM provided a fully operational and valid means for discriminating between the different wash performances of various proteases (e.g., serine proteases, neutral metalloprotease, and variants thereof). The TOM tests were performed on BMI and Equest medium-soiled grass surface with TIDE® 2005 as the base detergent.

As indicated in FIG. 26, it was apparent that the purified neutral metalloprotease clearly performed better in the wash test than the serine protease (BPN' Y217L). In particular, 2.75 ppm of purified neutral metalloprotease was required to show a delta soil removal of ~10% compared to only 0.55 ppm of the serine protease (BPN' Y217L) on the Equest grass stain. The wash performance of the neutral metalloprotease was also tested at low temperature and found to perform very well medium solid Equest stain fabric. Similar results were obtained with purified commercially available MULTIFECT® neutral protease as with the recombinant nprE produced as described above.

Example 13

Performance of nprE Variants in BMI-TIDE® 2× Performance Assay

In this Example, experiments conducted to assess the performance of various nprE variants in the BMI assay outlined above are described. The methods provided prior to Example 1 were used (See, "Microswatch Assay for Testing Protease Performance"). The results for multiply-substituted variants with Performance Indices greater than one (PI>1) and those with Performance Indices less than one (PI<1) are provided in the Tables below.

In Table 13.1, data obtained for selected single-substitution variants in the BMI-TIDE® 2× performance assay are provided. The Table provides performance indices, which where calculated as described above for the variants, which show improved performance compared to the WT enzyme. Those variants, which have a performance index greater than 1, have an improved performance.

In Table 13.2, data obtained for selected multiple-substitution variants in the BMI-TIDE® 2× performance assay are provided. The Table provides performance indices, which where calculated as described above for the variants, which show improved performance compared to the WT enzyme. Those variants, which have a performance index greater than 1, have an improved performance.

TABLE 13.1

Performance Assay Results for All Variants with Performance Index >1

| Variant Code | BMI Tide 2X Liquid Detergent [Perf. Index] |
|---|---|
| T004H | 1.07 |
| T004I | 1.25 |
| T004K | 1.62 |
| T004L | 1.01 |
| T004M | 1.05 |

TABLE 13.1-continued

Performance Assay Results for All Variants with Performance Index >1

| Variant Code | BMI Tide 2X Liquid Detergent [Perf. Index] |
|---|---|
| T004N | 1.03 |
| T004P | 1.18 |
| T004R | 1.65 |
| T004V | 1.18 |
| T004W | 1.21 |
| T004Y | 1.32 |
| G012I | 1.24 |
| G012K | 1.64 |
| G012L | 1.25 |
| G012M | 1.11 |
| G012Q | 1.09 |
| G012R | 1.54 |
| G012T | 1.38 |
| G012V | 1.18 |
| G012W | 1.46 |
| T014F | 1.17 |
| T014G | 1.17 |
| T014I | 1.28 |
| T014K | 1.53 |
| T014L | 1.19 |
| T014M | 1.11 |
| T014P | 1.04 |
| T014Q | 1.24 |
| T014R | 1.48 |
| T014S | 1.07 |
| T014V | 1.14 |
| T014W | 1.17 |
| T014Y | 1.11 |
| E022K | 1.79 |
| S023F | 1.30 |
| S023I | 1.20 |
| S023K | 1.67 |
| S023L | 1.27 |
| S023M | 1.04 |
| S023P | 1.23 |
| S023Q | 1.22 |
| S023R | 1.75 |
| S023V | 1.09 |
| S023W | 1.41 |
| S023Y | 1.06 |
| G024F | 1.26 |
| G024H | 1.33 |
| G024I | 1.24 |
| G024K | 1.70 |
| G024L | 1.23 |
| G024M | 1.14 |
| G024N | 1.28 |
| G024P | 1.18 |
| G024R | 1.67 |
| G024T | 1.07 |
| G024V | 1.12 |
| G024W | 1.42 |
| G024Y | 1.12 |
| K033H | 1.01 |
| Q045F | 1.25 |
| Q045H | 1.25 |
| Q045I | 1.40 |
| Q045K | 1.64 |
| Q045L | 1.24 |
| Q045N | 1.07 |
| Q045R | 1.68 |
| Q045T | 1.09 |
| Q045W | 1.60 |
| N046A | 1.06 |
| N046F | 1.11 |
| N046G | 1.07 |
| N046H | 1.32 |
| N046K | 1.61 |
| N046L | 1.14 |
| N046M | 1.13 |
| N046Q | 1.22 |
| N046R | 1.19 |
| N046S | 1.02 |
| N046T | 1.20 |

TABLE 13.1-continued

Performance Assay Results for All Variants with Performance Index >1

| Variant Code | BMI Tide 2X Liquid Detergent [Perf. Index] |
|---|---|
| N046W | 1.24 |
| N046Y | 1.21 |
| R047K | 1.15 |
| Y049F | 1.06 |
| Y049I | 1.08 |
| Y049K | 1.10 |
| Y049L | 1.06 |
| Y049R | 1.54 |
| Y049W | 1.34 |
| N050F | 1.38 |
| N050H | 1.13 |
| N050I | 1.36 |
| N050K | 1.65 |
| N050L | 1.35 |
| N050M | 1.05 |
| N050P | 1.12 |
| N050Q | 1.16 |
| N050R | 1.81 |
| N050W | 1.46 |
| N050Y | 1.27 |
| T054F | 1.16 |
| T054G | 1.12 |
| T054H | 1.17 |
| T054I | 1.34 |
| T054K | 1.47 |
| T054L | 1.26 |
| T054N | 1.25 |
| T054Q | 1.23 |
| T054R | 1.46 |
| T054S | 1.03 |
| T054V | 1.11 |
| T054W | 1.22 |
| T054Y | 1.08 |
| S058H | 1.03 |
| S058N | 1.12 |
| S058Q | 1.08 |
| T059G | 1.11 |
| T059H | 1.32 |
| T059I | 1.43 |
| T059K | 1.60 |
| T059L | 1.31 |
| T059M | 1.10 |
| T059N | 1.16 |
| T059P | 1.19 |
| T059Q | 1.31 |
| T059R | 1.56 |
| T059V | 1.13 |
| T059W | 1.32 |
| T060F | 1.07 |
| T060I | 1.09 |
| T060K | 1.49 |
| T060L | 1.13 |
| T060N | 1.07 |
| T060Q | 1.10 |
| T060R | 1.42 |
| T060V | 1.13 |
| T060W | 1.23 |
| T060Y | 1.07 |
| T065F | 1.06 |
| T065H | 1.07 |
| T065I | 1.12 |
| T065K | 1.32 |
| T065L | 1.10 |
| T065M | 1.09 |
| T065P | 1.11 |
| T065Q | 1.01 |
| T065R | 1.28 |
| T065V | 1.15 |
| T065Y | 1.09 |
| S066F | 1.05 |
| S066H | 1.06 |
| S066I | 1.24 |
| S066K | 1.44 |
| S066L | 1.09 |

TABLE 13.1-continued

Performance Assay Results for All Variants with Performance Index >1

| Variant Code | BMI Tide 2X Liquid Detergent [Perf. Index] |
|---|---|
| S066N | 1.00 |
| S066Q | 1.12 |
| S066R | 1.47 |
| S066V | 1.19 |
| S066W | 1.21 |
| S066Y | 1.06 |
| Q087H | 1.06 |
| Q087I | 1.17 |
| Q087K | 1.30 |
| Q087L | 1.07 |
| Q087M | 1.00 |
| Q087N | 1.06 |
| Q087R | 1.35 |
| Q087T | 1.08 |
| Q087V | 1.04 |
| Q087W | 1.15 |
| N090F | 1.05 |
| N090H | 1.09 |
| N090K | 1.37 |
| N090L | 1.18 |
| N090R | 1.37 |
| N096G | 1.00 |
| N096H | 1.04 |
| N096K | 1.54 |
| N096R | 1.06 |
| K097H | 1.03 |
| K097Q | 1.05 |
| K097W | 1.02 |
| K100R | 1.26 |
| R110K | 1.05 |
| D119E | 1.05 |
| D119H | 1.16 |
| D119I | 1.09 |
| D119L | 1.21 |
| D119Q | 1.17 |
| D119R | 1.14 |
| D119S | 1.10 |
| D119T | 1.23 |
| D119V | 1.24 |
| D119W | 1.09 |
| G128F | 1.10 |
| G128H | 1.27 |
| G128K | 1.90 |
| G128L | 1.20 |
| G128M | 1.11 |
| G128N | 1.23 |
| G128Q | 1.22 |
| G128R | 1.94 |
| G128W | 1.48 |
| G128Y | 1.42 |
| S129A | 1.12 |
| S129F | 1.11 |
| S129G | 1.03 |
| S129H | 1.17 |
| S129K | 1.33 |
| S129L | 1.01 |
| S129R | 1.37 |
| S129T | 1.04 |
| S129V | 1.01 |
| S129W | 1.28 |
| S129Y | 1.25 |
| F130I | 1.03 |
| F130K | 1.26 |
| F130R | 1.37 |
| F130Y | 1.31 |
| S135P | 1.03 |
| M138K | 1.36 |
| M138Q | 1.03 |
| M138V | 1.10 |
| V140C | 1.03 |
| Q151I | 1.02 |
| E152A | 1.14 |
| E152C | 1.15 |
| E152D | 1.14 |

TABLE 13.1-continued

Performance Assay Results for All Variants with Performance Index >1

| Variant Code | BMI Tide 2X Liquid Detergent [Perf. Index] |
|---|---|
| E152F | 1.09 |
| E152G | 1.03 |
| E152H | 1.15 |
| E152L | 1.15 |
| E152M | 1.12 |
| E152N | 1.11 |
| E152R | 1.19 |
| E152S | 1.02 |
| E152W | 1.06 |
| N155D | 1.13 |
| N155K | 1.05 |
| N155R | 1.14 |
| T179A | 1.03 |
| T179F | 1.15 |
| T179H | 1.20 |
| T179I | 1.21 |
| T179K | 1.62 |
| T179L | 1.20 |
| T179M | 1.12 |
| T179N | 1.04 |
| T179P | 1.04 |
| T179Q | 1.23 |
| T179R | 1.49 |
| T179S | 1.02 |
| T179V | 1.12 |
| T179W | 1.05 |
| T179Y | 1.07 |
| V190H | 1.02 |
| V190I | 1.16 |
| V190K | 1.75 |
| V190Q | 1.23 |
| V190R | 1.67 |
| S191F | 1.18 |
| S191G | 1.03 |
| S191H | 1.29 |
| S191I | 1.12 |
| S191K | 1.58 |
| S191L | 1.07 |
| S191N | 1.13 |
| S191Q | 1.13 |
| S191R | 1.74 |
| S191W | 1.16 |
| L198M | 1.19 |
| L198V | 1.05 |
| S199F | 1.10 |
| S199I | 1.08 |
| S199K | 1.64 |
| S199L | 1.15 |
| S199N | 1.14 |
| S199Q | 1.14 |
| S199R | 1.68 |
| S199V | 1.06 |
| Y204H | 1.03 |
| G205F | 1.13 |
| G205H | 1.61 |
| G205L | 1.14 |
| G205M | 1.14 |
| G205N | 1.39 |
| G205R | 2.07 |
| G205S | 1.25 |
| G205Y | 1.21 |
| K211R | 1.23 |
| K214R | 1.19 |
| L216F | 1.13 |
| L216H | 1.05 |
| L216Q | 1.05 |
| L216R | 1.64 |
| L216Y | 1.02 |
| N218K | 1.57 |
| N218P | 1.27 |
| D220E | 1.05 |
| D220H | 1.00 |
| D220N | 1.04 |
| D220P | 1.05 |

TABLE 13.1-continued

Performance Assay Results for All Variants with Performance Index >1

| Variant Code | BMI Tide 2X Liquid Detergent [Perf. Index] |
|---|---|
| A221F | 1.13 |
| A221I | 1.14 |
| A221K | 1.49 |
| A221L | 1.05 |
| A221M | 1.01 |
| A221N | 1.05 |
| A221V | 1.14 |
| A221Y | 1.17 |
| G222H | 1.01 |
| G222N | 1.01 |
| G222R | 1.04 |
| Y224F | 1.05 |
| Y224H | 1.29 |
| Y224N | 1.23 |
| Y224R | 1.12 |
| T243G | 1.13 |
| T243H | 1.48 |
| T243I | 1.06 |
| T243K | 1.87 |
| T243L | 1.11 |
| T243Q | 1.36 |
| T243R | 1.62 |
| T243W | 1.25 |
| T243Y | 1.14 |
| V260A | 1.69 |
| V260D | 1.59 |
| V260E | 1.17 |
| V260G | 2.00 |
| V260H | 1.36 |
| V260I | 2.09 |
| V260K | 1.45 |
| V260L | 1.18 |
| V260M | 1.41 |
| V260P | 1.45 |
| V260Q | 1.73 |
| V260R | 1.47 |
| V260S | 1.59 |
| V260T | 1.66 |
| V260W | 1.83 |
| V260Y | 1.20 |
| T263H | 1.06 |
| S265K | 1.30 |
| S265N | 1.04 |
| S265R | 1.28 |
| S265W | 1.00 |
| A273I | 1.19 |
| A273K | 1.47 |
| A273L | 1.14 |
| A273N | 1.10 |
| A273Q | 1.00 |
| A273R | 1.78 |
| A273Y | 1.07 |
| L282F | 1.09 |
| L282G | 1.14 |
| L282H | 1.17 |
| L282I | 1.23 |
| L282K | 1.67 |
| L282M | 1.01 |
| L282N | 1.08 |
| L282Q | 1.17 |
| L282R | 1.41 |
| L282V | 1.22 |
| S285K | 1.20 |
| S285R | 1.23 |
| Q286K | 1.22 |
| Q286R | 1.14 |
| A289K | 1.23 |
| A289R | 1.32 |
| A293R | 1.36 |
| N296K | 1.28 |
| N296R | 1.42 |
| A297K | 1.56 |
| A297N | 1.02 |
| A297Q | 1.02 |

TABLE 13.1-continued

Performance Assay Results for All Variants with Performance Index >1

| Variant Code | BMI Tide 2X Liquid Detergent [Perf. Index] |
|---|---|
| A297R | 1.50 |
| G299N | 1.02 |

TABLE 13.2

BMI Performance Assay Results for All Variants with Performance Index >1

| Variant Code | BMI TIDE ® 2X Liquid Detergent [Perf. Index] |
|---|---|
| S023W-G024M | 2.36 |
| T004V-S023W-G024W | 2.25 |
| S023W-G024Y-A288V | 2.14 |
| T004L-S023W-G024Y | 2.09 |
| N046Q-N050F-T054L | 2.03 |
| N050Y-T059R-S129Q | 1.97 |
| S023W-G024W | 1.97 |
| A273H-S285P-E292G | 1.94 |
| S023Y-G024Y | 1.93 |
| S023Y-G024W | 1.92 |
| T004S-S023Y-G024W | 1.91 |
| N046Q-T054K | 1.90 |
| S023W-G024Y | 1.90 |
| T004V-S023W | 1.89 |
| T059K-S066N | 1.88 |
| N046Q-N050W-T054H-T153A | 1.87 |
| T004V-S023W-G024Y | 1.85 |
| L282M-Q286P-A289R | 1.83 |
| N046Q-R047K-N050Y-T054K | 1.82 |
| L044Q-T263W-S285R | 1.81 |
| T004L-S023W-G024W | 1.79 |
| R047K-N050F-T054K | 1.78 |
| A273H-S285R | 1.78 |
| N050Y-T059K-S066Q | 1.78 |
| T054K-Q192K | 1.76 |
| N046Q-N050W | 1.75 |
| L282M-Q286K | 1.75 |
| T059K-S066Q | 1.74 |
| T004S-S023W | 1.74 |
| L282M-Q286R-A289R-K11N | 1.73 |
| L282M-A289R | 1.73 |
| N046Q-N050W-T054H | 1.73 |
| T059K-S129Q | 1.72 |
| T004S-S023N-G024Y-F210L | 1.71 |
| T004V-S023W-G024M-A289V | 1.70 |
| L282M-Q286K-A289R-S132T | 1.70 |
| N050W-T054H | 1.70 |
| L282M-Q286R | 1.69 |
| L282F-Q286K-A289R | 1.69 |
| T059R-S066Q | 1.68 |
| R047K-N050W-T054H | 1.68 |
| S265P-L282M-Q286K-A289R | 1.66 |
| L282M-Q286R-T229S | 1.66 |
| L282F-Q286K | 1.66 |
| T263W-S285R | 1.65 |
| S265P-L282M-Q286K | 1.65 |
| T263H-A273H-S285R | 1.65 |
| T059R-S129V | 1.64 |
| S032T-T263H-A273H-S285R | 1.64 |

TABLE 13.2-continued

BMI Performance Assay Results for All Variants with Performance Index >1

| Variant Code | BMI TIDE ® 2X Liquid Detergent [Perf. Index] |
|---|---|
| T059R-S066Q-S129Q | 1.64 |
| T004S-G024W | 1.64 |
| T004V-S023W-G024M | 1.64 |
| T059K-S066Q-S129Q | 1.63 |
| L282M-Q286K-A289R-I253V | 1.63 |
| T004V-S023Y-G024W | 1.63 |
| T059R-S066N-S129Q | 1.62 |
| N050F-T054L | 1.62 |
| T004S-S023N-G024W | 1.62 |
| T059R-S066N | 1.62 |
| T059R-S066N-S129V | 1.60 |
| Q286R-A289R | 1.60 |
| N046Q-R047K-N050F-T054K | 1.60 |
| S265P-L282M-Q286R-A289R | 1.57 |
| S265P-L282M-Q286P-A289R | 1.68 |
| Q062K-S066Q-S129I | 1.59 |
| S023N-G024W | 1.59 |
| N046Q-R047K-N050W-T054H | 1.58 |
| R047K-T054K | 1.58 |
| T004L-G024W | 1.58 |
| T014M-T059R-S129V | 1.58 |
| T059R-S066Q-N092S-S129I | 1.58 |
| R047K-N050W-T054K | 1.58 |
| T004V-G024W | 1.58 |
| N047K-N050F-T054K | 1.57 |
| S265P-L282F-Q286K-N061Y | 1.57 |
| L282F-Q286K-E159V | 1.57 |
| T004V-S023Y-G024M | 1.57 |
| S265P-L282F-A289R-T065S | 1.55 |
| T059K-F063L-S066N-S129V | 1.55 |
| T004L-S023W | 1.55 |
| N050F-T054H | 1.55 |
| T059R-S066Q-S129V | 1.54 |
| V190I-D220E-S265W-L282F | 1.54 |
| T004S-S023Y-G024M | 1.53 |
| T004L-S023N-G024Y | 1.53 |
| T059K-S066N-S129I | 1.53 |
| T059R-S066N-S129I | 1.53 |
| L282M-Q286R-A289R-P162S | 1.52 |
| N046Q-N050F-T179N | 1.52 |
| T059K-Y082C-S129V | 1.52 |
| T059K-S129I | 1.52 |
| N050Y-T054K | 1.51 |
| T059K-S066Q-V102A-S129Q | 1.51 |
| T059R-S066Q-S129I | 1.51 |
| T059W-S066N-S129V-S290R | 1.51 |
| T059R-S129I | 1.50 |
| T059K-S066Q-S129I | 1.50 |
| T059K-S066Q-S129V | 1.50 |
| S265P-L282M-Q286R-A289R-T202S-K203N | 1.49 |
| T004V-S023N-G024W | 1.49 |
| S265P-Q286K | 1.49 |
| S265P-L282F-A289R | 1.49 |
| D220P-S265W | 1.49 |
| L055F-T059W-S129V | 1.49 |
| T059R-S129Q-S191R | 1.49 |
| N050W-T054K | 1.49 |
| T004S-S023W-G024M | 1.49 |
| R047K-N050F-T054H | 1.48 |
| T059K-S066N-K088E | 1.48 |
| T059K-S066Q-S129I-V291L | 1.48 |
| L282M-Q286R-A289R | 1.48 |
| T059R-S066N-F085S-S129I | 1.47 |
| L282F-Q286P-A289R | 1.45 |
| L282F-Q286R-A289R | 1.47 |
| G099D-S265P-L282F-Q286K-A289R | 1.46 |
| N046Q-N050F | 1.46 |
| N050Y-T059W-S066N-S129V | 1.45 |
| T009I-D220P-S265N | 1.45 |
| V190F-D220P-S265W | 1.45 |
| N157Y-T263W-A273H-S285R | 1.44 |
| T263W-A273H-S285R | 1.44 |
| T263W-S285W | 1.44 |
| T004V-S023Y | 1.43 |
| N046Q-R047K-N050W | 1.42 |
| N050W-T054L | 1.42 |
| N200Y-S265P-L282F-Q286P-A289R | 1.42 |
| T059R-S066Q-P264Q | 1.42 |
| T004V-G024Y | 1.40 |
| T004L-G024Y | 1.40 |
| N050Y-S191I | 1.39 |
| N050Y-T054L | 1.39 |
| T004L-S023W-G024Y-N155K | 1.39 |
| F169I-L282F-Q286R-A289R | 1.39 |
| L282M-Q286K-A289R | 1.38 |
| F130L-M138L-E152W-D183N | 1.38 |
| N046Q-R047K-N050Y-T054H | 1.38 |
| T004V-G024M | 1.38 |
| N050Y-T059W-S066Q-S129V | 1.37 |
| S023N-G024Y | 1.37 |
| T054H-P162Q | 1.37 |
| T004S-S023W-G024Y | 1.37 |
| N050Y-T054H | 1.36 |
| L282F-Q286R-A289R-F169I | 1.35 |
| R047K-N050W | 1.35 |
| V190F-D220P | 1.35 |
| L282M-F173Y | 1.34 |
| T004L-S023Y | 1.33 |
| N050W-A288D | 1.33 |
| V190I-D220P-S265Q | 1.33 |
| S265P-L282F-Q286P-A289R | 1.24 |
| S265P-L282F-Q286R-A289R | 1.39 |
| N046Q-N050Y-T054K | 1.33 |
| T059W-S066Q | 1.31 |
| T263W-A273H-S285R | 1.44 |
| T263W-A273H-S285W | 1.27 |
| S023Y-G024M | 1.30 |
| T004L-S023N-G024W | 1.30 |
| T004V-S023N-G024Y | 1.30 |
| T059W-S066N-S129Q | 1.30 |
| T004S-S023Y | 1.29 |
| T004S-S023N-G024M | 1.29 |
| T059W-S066N-A070T | 1.29 |
| T059W-S066Q-S129Q | 1.29 |
| T263W-A273H | 1.29 |
| A273H-S285P | 1.28 |
| N046Q-R047K-N050Y-T054L | 1.28 |

TABLE 13.2-continued

| BMI Performance Assay Results for All Variants with Performance Index >1 | |
|---|---|
| Variant Code | BMI TIDE ® 2X Liquid Detergent [Perf. Index] |
| N046Q-R047K-N050Y | 1.28 |
| R047K-N050Y | 1.27 |
| T263H-S285W | 1.26 |
| R047K-N050F | 1.25 |
| N046Q-R047K-N050F-T054H | 1.25 |
| S023N-G024M | 1.25 |
| T004S-G024Y | 1.24 |
| R047K-N050Y-T054H | 1.24 |
| T059W-S066N-S129I | 1.22 |
| R047K-T054L | 1.21 |
| T004S-S023W-G024W | 1.21 |
| M138L-E152F-T146S | 1.21 |
| D220P-S265N | 1.21 |
| T004S-G024M | 1.20 |
| T004V-S023N | 1.20 |
| N046Q-N050F-T054K | 1.19 |
| N046Q-N050Y-T054H | 1.19 |
| Q062H-S066Q-S129Q | 1.19 |
| T059W-S129Q | 1.19 |
| T059W-S129V | 1.19 |
| N050F-T054K | 1.18 |
| R047K-N050F-T054L | 1.18 |
| V190I-D220P-S265W | 1.18 |
| N112I-T263H-A273H-S285R | 1.17 |
| T059W-S066N-S129V | 1.17 |
| T059W-S066Q-S129I | 1.17 |
| T059W-S129I | 1.17 |
| T263W-S285P | 1.17 |
| V190I-D220P | 1.16 |
| A289V-T263H-A273H | 1.16 |
| T263H-A273H-S285P | 1.16 |
| N90S-A273H-S285P | 1.15 |
| R047K-N050Y-T054L | 1.15 |
| T004S-S023N | 1.15 |
| T059R-S129Q | 1.14 |
| N046Q-R047K-T054H | 1.14 |
| T059W-S066Q-S129V | 1.13 |
| E152W-T179P | 1.13 |
| N050Y-S066Q-S129V | 1.13 |
| T202S-T263W-A273H | 1.13 |
| T263W-A273H-S285P | 1.13 |
| M138L-E152W-T179P | 1.11 |
| N046Q-R047K | 1.10 |
| N046Q-T054H-F176L | 1.10 |
| T004L-G024M | 1.10 |
| T004S-L282M | 1.10 |
| T263H-A273H | 1.10 |
| T263H-A273H-S285W | 1.10 |
| T004L-S023Y-G024M | 1.09 |
| L282F-Q286P | 1.09 |
| T004V-S023Y-G024Y | 1.09 |
| V190F-S265W | 1.09 |
| M138L-E152F | 1.08 |
| V190F-D220E-S265W | 1.07 |
| N046Q-N050F-T054H | 1.06 |
| N157Y-S285W | 1.06 |
| T004F-S023Y-G024M | 1.06 |
| T004V-S023N-G024M | 1.06 |
| L198I-D220E-S265Q | 1.05 |
| N046Q-N050Y-T054K-A154T | 1.05 |
| S016L-D220E-S265W | 1.05 |
| D220E-S265W | 1.04 |
| D220E-A237S-S265W | 1.04 |
| S066Q-S129Q | 1.04 |
| V190F-D220E-S265Q-T267I | 1.04 |
| L282M-F173Y-T219S | 1.04 |
| E152F-T179P | 1.04 |
| V190I-S265W | 1.03 |
| M138L-S066Q | 1.01 |
| M138L-E152W | 1.01 |
| T059W-S066Q-A070T-S129I | 1.01 |
| V190F-D220E-S265N | 1.01 |
| V190F-S265N | 1.01 |
| N046Q-N050Y | 1.01 |
| M138L-E152F-T179P | 1.00 |

Example 14

Stability of nprE Variants

In this Example, experiments conducted to determine the stability of nprE variants are described. In these experiments, the methods describe prior to Example 1 were used to determine the performance indices (See, "NprE stability assays in the presence of detergent" above). The following tables provide the results for those variants with Performance Indices greater than one (PI>1) tested with and without DTPA.

The stability was measured by determining AGLA activity before and after incubation at elevated temperature. The table contains the relative stability values compared to WT under these conditions. It is the quotient of (Variant residual activity/WT residual activity). A value greater than one indicates higher stability in the presence of detergent. In Tables 14.1 and 14.2, data are provided showing the relative stability data of single-substitution variants of NprE relative to the stability of the WT NprE stability under these conditions, with and without DTPA.

In Tables 14.3 and 14.4, data are provided showing the relative stability data of multiple-substitution variants of NprE relative to the stability of the WT NprE stability under these conditions, with and without DTPA.

TABLE 14.1

| Stability Results in the Presence of 25% TIDE ® 2X with DTPA | |
|---|---|
| Variant Code | Stability in the presence of 25% Tide 2x with DTPA |
| T004C | 1.19 |
| T004E | 1.05 |
| T004L | 1.13 |
| T004S | 1.00 |
| G012D | 1.06 |
| G012E | 1.06 |
| K013A | 1.39 |
| K013C | 1.57 |
| K013D | 1.09 |
| K013F | 1.30 |
| K013G | 1.41 |
| K013H | 1.34 |
| K013I | 1.33 |
| K013L | 1.56 |
| K013M | 1.28 |
| K013N | 1.39 |
| K013Q | 1.34 |
| K013S | 1.35 |
| K013T | 1.22 |
| K013V | 1.40 |
| K013Y | 1.34 |
| S023A | 1.01 |

TABLE 14.1-continued

Stability Results in the Presence of 25% TIDE ® 2X with DTPA

| Variant Code | Stability in the presence of 25% Tide 2x with DTPA |
|---|---|
| S023D | 1.08 |
| S023F | 1.05 |
| S023G | 1.11 |
| S023I | 1.05 |
| S023K | 1.07 |
| S023L | 1.04 |
| S023M | 1.11 |
| S023N | 1.09 |
| S023Q | 1.03 |
| S023R | 1.10 |
| S023S | 1.45 |
| S023T | 1.06 |
| S023V | 1.05 |
| S023W | 1.08 |
| S023Y | 1.15 |
| G024A | 1.01 |
| G024D | 1.05 |
| G024F | 1.08 |
| G024G | 1.46 |
| G024H | 1.05 |
| G024K | 1.08 |
| G024L | 1.06 |
| G024M | 1.10 |
| G024N | 1.11 |
| G024R | 1.07 |
| G024S | 1.02 |
| G024S | 1.02 |
| G024T | 1.04 |
| G024W | 1.11 |
| G024Y | 1.08 |
| Q045D | 1.02 |
| Q045E | 1.28 |
| N046C | 1.29 |
| N046E | 1.35 |
| N046Q | 1.07 |
| R047K | 1.09 |
| R047L | 1.13 |
| R047M | 1.00 |
| R047S | 1.21 |
| N050D | 1.04 |
| N050F | 1.07 |
| N050P | 1.03 |
| N050W | 1.04 |
| N050Y | 1.04 |
| T054C | 1.04 |
| T054D | 1.04 |
| T054E | 1.03 |
| T054F | 1.03 |
| T054H | 1.11 |
| T054I | 1.04 |
| T054K | 1.11 |
| T054L | 1.08 |
| T054M | 1.06 |
| T054N | 1.07 |
| T054Q | 1.03 |
| T054R | 1.04 |
| T054S | 1.05 |
| T054V | 1.01 |
| T054W | 1.07 |
| T054Y | 1.07 |
| T059A | 1.04 |
| T059C | 1.04 |
| T059E | 1.02 |
| T059G | 1.13 |
| T059H | 1.07 |
| T059I | 1.01 |
| T059K | 1.16 |
| T059M | 1.10 |
| T059N | 1.15 |
| T059P | 1.12 |
| T059Q | 1.04 |
| T059R | 1.28 |
| T059S | 1.04 |
| T059W | 1.26 |

TABLE 14.1-continued

Stability Results in the Presence of 25% TIDE ® 2X with DTPA

| Variant Code | Stability in the presence of 25% Tide 2x with DTPA |
|---|---|
| T060N | 1.03 |
| T065E | 1.01 |
| S066C | 1.36 |
| S066D | 1.42 |
| S066E | 1.58 |
| S066N | 1.01 |
| S066Q | 1.01 |
| Q087D | 1.25 |
| Q087E | 1.32 |
| N090C | 1.10 |
| N090D | 1.01 |
| K100H | 1.09 |
| K100P | 1.01 |
| R110A | 1.17 |
| R110C | 1.28 |
| R110E | 1.20 |
| R110H | 1.12 |
| R110K | 1.04 |
| R110L | 1.23 |
| R110M | 1.23 |
| R110N | 1.11 |
| R110Q | 1.28 |
| R110S | 1.10 |
| R110Y | 1.12 |
| D119H | 1.15 |
| G128C | 1.00 |
| S129A | 1.06 |
| S129C | 1.38 |
| S129D | 1.23 |
| S129H | 1.30 |
| S129I | 1.68 |
| S129K | 1.05 |
| S129L | 1.35 |
| S129M | 1.33 |
| S129Q | 1.44 |
| S129T | 1.36 |
| S129V | 1.55 |
| S129Y | 1.06 |
| F130I | 1.14 |
| F130K | 1.04 |
| F130L | 1.52 |
| F130M | 1.66 |
| F130Q | 1.10 |
| F130T | 1.41 |
| F130V | 1.06 |
| S137A | 1.46 |
| M138L | 1.43 |
| E152F | 1.15 |
| E152H | 1.36 |
| E152W | 1.31 |
| T179P | 1.50 |
| V190I | 1.68 |
| V190L | 1.93 |
| S199C | 1.27 |
| S199E | 1.95 |
| Y204T | 1.03 |
| K211A | 1.96 |
| K211C | 1.30 |
| K211D | 1.89 |
| K211M | 1.20 |
| K211N | 1.29 |
| K211Q | 2.00 |
| K211S | 1.43 |
| K211T | 1.18 |
| K211V | 1.52 |
| K214A | 1.74 |
| K214C | 1.62 |
| K214I | 1.17 |
| K214M | 1.27 |
| K214N | 1.35 |
| K214Q | 2.09 |
| K214V | 2.00 |
| L216C | 1.35 |
| T219D | 1.05 |

TABLE 14.1-continued

Stability Results in the Presence of 25% TIDE ® 2X with DTPA

| Variant Code | Stability in the presence of 25% Tide 2x with DTPA |
|---|---|
| D220A | 1.11 |
| D220E | 2.44 |
| D220P | 2.66 |
| A221D | 1.04 |
| A221E | 1.57 |
| G222C | 1.72 |
| T243C | 1.30 |
| T243I | 1.17 |
| K244A | 1.61 |
| K244C | 1.75 |
| K244D | 2.00 |
| K244E | 1.77 |
| K244F | 1.27 |
| K244G | 1.23 |
| K244L | 1.55 |
| K244M | 1.79 |
| K244N | 1.25 |
| K244Q | 1.82 |
| K244S | 1.87 |
| K244T | 1.65 |
| K244V | 1.82 |
| K244W | 1.01 |
| K244Y | 1.45 |
| V260E | 1.07 |
| V260K | 1.17 |
| V260L | 1.28 |
| V260M | 1.21 |
| V260P | 1.22 |
| V260S | 1.00 |
| V260T | 1.03 |
| V260W | 1.02 |
| Y261C | 1.28 |
| Y261F | 1.07 |
| Y261I | 1.20 |
| Y261L | 1.14 |
| T263E | 1.12 |
| T263F | 1.19 |
| T263H | 1.01 |
| T263L | 1.02 |
| T263Q | 1.12 |
| T263V | 1.25 |
| T263W | 1.40 |
| T263Y | 1.06 |
| S265A | 1.04 |
| S265C | 1.11 |
| S265D | 1.11 |
| S265E | 1.34 |
| S265P | 1.72 |
| S265Q | 1.00 |
| S265T | 1.15 |
| S265V | 1.17 |
| K269E | 1.61 |
| K269F | 1.21 |
| K269G | 1.32 |
| K269H | 1.63 |
| K269I | 1.73 |
| K269L | 1.53 |
| K269M | 1.52 |
| K269N | 1.60 |
| K269P | 1.47 |
| K269Q | 1.55 |
| K269S | 1.51 |
| K269T | 1.89 |
| K269V | 1.43 |
| K269W | 1.00 |
| K269Y | 1.38 |
| A273C | 1.19 |
| A273D | 1.29 |
| A273H | 1.14 |
| R280A | 1.33 |
| R280C | 1.96 |
| R280D | 1.82 |
| R280E | 1.77 |
| R280F | 1.46 |
| R280G | 1.21 |
| R280H | 1.52 |
| R280K | 1.14 |
| R280L | 1.78 |
| R280M | 1.78 |
| R280S | 1.46 |
| R280T | 1.35 |
| R280W | 1.51 |
| R280Y | 1.56 |
| L282F | 1.06 |
| L282M | 1.16 |
| L282Y | 1.04 |
| S285A | 1.16 |
| S285C | 1.27 |
| S285D | 1.39 |
| S285E | 1.59 |
| S285K | 1.00 |
| S285P | 1.30 |
| S285Q | 1.10 |
| S285R | 1.38 |
| S285W | 1.28 |
| Q286A | 1.04 |
| Q286D | 1.08 |
| Q286E | 1.31 |
| Q286K | 1.09 |
| Q286P | 1.15 |
| Q286R | 1.18 |
| A289C | 1.24 |
| A289D | 1.04 |
| A289E | 1.15 |
| A289L | 1.05 |
| A293C | 1.11 |
| N296D | 1.11 |
| N296E | 1.87 |
| N296V | 1.37 |
| A297C | 1.07 |

TABLE 14.2

Stability of Variants in Tide ® 2X Without DTPA

| Variant Code | Stability in the presence of Tide 2x without DTPA |
|---|---|
| T004C | 1.16 |
| T004V | 1.04 |
| K013A | 1.52 |
| K013C | 1.83 |
| K013D | 1.47 |
| K013F | 1.02 |
| K013G | 1.61 |
| K013H | 1.62 |
| K013I | 1.19 |
| K013L | 1.54 |
| K013M | 1.48 |
| K013N | 1.70 |
| K013Q | 1.55 |
| K013S | 1.56 |
| K013T | 1.39 |
| K013V | 1.49 |
| K013Y | 1.39 |
| S023A | 1.03 |
| S023D | 1.23 |
| S023G | 1.25 |
| S023M | 1.05 |
| S023N | 1.25 |
| S023Q | 1.10 |
| S023S | 1.50 |
| S023W | 1.02 |

TABLE 14.2-continued

Stability of Variants in Tide ® 2X Without DTPA

| Variant Code | Stability in the presence of Tide 2x without DTPA |
|---|---|
| S023Y | 1.07 |
| G024D | 1.05 |
| G024G | 1.41 |
| Q045C | 1.01 |
| Q045D | 1.02 |
| Q045E | 1.41 |
| Q045M | 1.01 |
| N046C | 1.53 |
| N046E | 1.41 |
| R047K | 1.12 |
| R047L | 1.20 |
| R047M | 1.08 |
| R047Q | 1.13 |
| R047S | 1.25 |
| Y049D | 1.16 |
| Y049H | 1.02 |
| Y049N | 1.07 |
| Y049S | 1.01 |
| N050D | 1.08 |
| N050F | 1.07 |
| N050G | 1.02 |
| N050P | 1.23 |
| N050W | 1.01 |
| T054C | 1.07 |
| T054D | 1.01 |
| T054E | 1.08 |
| T054H | 1.08 |
| T054I | 1.09 |
| T054K | 1.03 |
| T054L | 1.09 |
| T054Q | 1.09 |
| T054V | 1.14 |
| T054W | 1.02 |
| T054Y | 1.14 |
| T059A | 1.05 |
| T059C | 1.07 |
| T059E | 1.25 |
| T059M | 1.04 |
| T059P | 1.18 |
| T059Q | 1.05 |
| T059S | 1.09 |
| T065C | 1.04 |
| T065E | 1.07 |
| S066C | 1.61 |
| S066D | 1.61 |
| S066E | 1.80 |
| S066N | 1.08 |
| Q087D | 1.27 |
| Q087E | 1.30 |
| N090C | 1.09 |
| N090D | 1.00 |
| N090E | 1.03 |
| K100A | 1.00 |
| K100D | 1.07 |
| K100E | 1.03 |
| K100F | 1.07 |
| K100H | 1.16 |
| K100N | 1.06 |
| K100P | 1.06 |
| K100Q | 1.06 |
| K100S | 1.05 |
| K100Y | 1.10 |
| R110A | 1.11 |
| R110C | 1.24 |
| R110E | 1.19 |
| R110H | 1.09 |
| R110K | 1.08 |
| R110L | 1.11 |
| R110M | 1.12 |
| R110N | 1.18 |
| R110Q | 1.25 |
| R110S | 1.09 |
| R110Y | 1.16 |

TABLE 14.2-continued

Stability of Variants in Tide ® 2X Without DTPA

| Variant Code | Stability in the presence of Tide 2x without DTPA |
|---|---|
| D119H | 1.03 |
| G128C | 1.15 |
| S129A | 1.13 |
| S129C | 1.86 |
| S129D | 1.52 |
| S129H | 1.60 |
| S129I | 2.32 |
| S129K | 1.18 |
| S129L | 1.70 |
| S129M | 1.64 |
| S129Q | 1.86 |
| S129T | 1.59 |
| S129V | 2.34 |
| S129Y | 1.28 |
| F130I | 1.18 |
| F130L | 1.29 |
| F130M | 1.44 |
| F130Q | 1.17 |
| F130T | 1.32 |
| F130V | 1.05 |
| S137A | 1.37 |
| M138L | 1.11 |
| E152A | 1.01 |
| E152C | 1.16 |
| E152F | 1.32 |
| E152H | 1.53 |
| E152N | 1.12 |
| E152W | 1.32 |
| N155Q | 1.07 |
| T179P | 1.33 |
| V190I | 1.37 |
| V190L | 1.40 |
| S199C | 1.18 |
| S199D | 1.11 |
| S199E | 1.71 |
| K211A | 1.77 |
| K211C | 1.18 |
| K211D | 1.67 |
| K211G | 1.06 |
| K211M | 1.17 |
| K211N | 1.44 |
| K211Q | 1.51 |
| K211S | 1.44 |
| K211T | 1.17 |
| K211V | 1.26 |
| K214A | 1.47 |
| K214C | 1.54 |
| K214E | 1.42 |
| K214I | 1.14 |
| K214M | 1.19 |
| K214N | 1.15 |
| K214Q | 1.84 |
| K214V | 1.79 |
| L216C | 1.31 |
| D220A | 1.07 |
| D220E | 2.23 |
| D220P | 2.24 |
| A221D | 1.15 |
| A221E | 1.47 |
| G222C | 1.89 |
| T243C | 1.34 |
| T243I | 1.13 |
| K244A | 1.57 |
| K244C | 1.40 |
| K244D | 1.58 |
| K244E | 1.56 |
| K244F | 1.05 |
| K244G | 1.01 |
| K244L | 1.38 |
| K244M | 1.37 |
| K244N | 1.18 |
| K244Q | 1.42 |
| K244S | 1.55 |

TABLE 14.2-continued

Stability of Variants in Tide ® 2X Without DTPA

| Variant Code | Stability in the presence of Tide 2x without DTPA |
|---|---|
| K244T | 1.51 |
| K244V | 1.42 |
| K244Y | 1.19 |
| V260K | 1.09 |
| V260L | 1.08 |
| V260P | 1.12 |
| V260Y | 1.02 |
| Y261I | 1.19 |
| Y261L | 1.11 |
| T263F | 1.11 |
| T263H | 1.03 |
| T263M | 1.08 |
| T263Q | 1.04 |
| T263V | 1.22 |
| T263W | 1.37 |
| T263Y | 1.05 |
| S265C | 1.03 |
| S265D | 1.02 |
| S265E | 1.22 |
| S265N | 1.07 |
| S265P | 1.43 |
| S265T | 1.10 |
| S265V | 1.09 |
| K269E | 1.33 |
| K269F | 1.10 |
| K269G | 1.17 |
| K269H | 1.52 |
| K269I | 1.34 |
| K269L | 1.34 |
| K269M | 1.34 |
| K269N | 1.25 |
| K269P | 1.26 |
| K269Q | 1.39 |
| K269S | 1.50 |
| K269T | 1.32 |
| K269V | 1.39 |
| K269Y | 1.38 |
| A273C | 1.12 |
| A273D | 1.16 |
| A273H | 1.10 |
| R280A | 1.32 |
| R280C | 1.77 |
| R280D | 1.52 |
| R280E | 1.67 |
| R280F | 1.37 |
| R280G | 1.16 |
| R280H | 1.31 |
| R280K | 1.07 |
| R280L | 1.64 |
| R280M | 1.60 |
| R280S | 1.46 |
| R280T | 1.28 |
| R280V | 1.10 |
| R280W | 1.42 |
| R280Y | 1.49 |
| L282M | 1.03 |
| S285A | 1.03 |
| S285C | 1.10 |
| S285D | 1.25 |
| S285E | 1.36 |
| S285P | 1.14 |
| S285Q | 1.05 |
| S285R | 1.10 |
| S285W | 1.12 |
| Q286D | 1.05 |
| Q286E | 1.17 |
| Q286P | 1.04 |
| Q286R | 1.02 |
| A289C | 1.05 |
| A289E | 1.13 |
| A289L | 1.06 |
| N296C | 1.01 |
| N296D | 1.02 |

TABLE 14.2-continued

Stability of Variants in Tide ® 2X Without DTPA

| Variant Code | Stability in the presence of Tide 2x without DTPA |
|---|---|
| N296E | 1.67 |
| N296V | 1.32 |
| A297C | 1.02 |

TABLE 14.3

Stability Assay Results in the Presence of 25% TIDE ® 2X With DTPA

| Variant Code | Stability in the presence of TIDE ® 2X with DTPA [Perf. Index] |
|---|---|
| V190I-D220P | 3.08 |
| V190I-D220P-S265Q | 2.63 |
| V190L-D220E | 2.59 |
| V190I-D220E-S265Q | 2.57 |
| V190I-D220E-S265W-L282F | 2.52 |
| V190L-D220E-S265Q | 2.43 |
| V190I-D220E-S265W | 2.38 |
| V190L-D220E-S265N | 2.34 |
| T059R-S066Q-S129I | 2.33 |
| V190I-D220E-S265N | 2.32 |
| V190L-D220E-S265W | 2.30 |
| V190I-D220E | 2.29 |
| T059W-S066N-S129V | 2.28 |
| T059K-S066Q-S129V | 2.27 |
| T059K-Y082C-S129V | 2.27 |
| T059R-S066N-S129I | 2.27 |
| S066Q-S129V | 2.25 |
| T059R-S066Q-S129V | 2.25 |
| T059R-S129I | 2.24 |
| N050Y-T059W-S066N-S129V | 2.21 |
| D220P-S265N | 2.21 |
| S066Q-S129I | 2.21 |
| T059W-S066Q-S129V | 2.20 |
| T059K-S066Q-S129I | 2.20 |
| T059R-S129V | 2.19 |
| N050Y-S066Q-S129V | 2.19 |
| T059W-S066Q-S129I | 2.19 |
| N050Y-T059W-S066Q-S129V | 2.18 |
| T059K-S129I | 2.17 |
| D220P-S265W | 2.17 |
| F130L-M138L-T179P | 2.16 |
| S066N-S129I | 2.15 |
| T059R-S066N-S129V | 2.15 |
| F130I-M138L-T179P | 2.14 |
| T059R-S066Q-N092S-S129I | 2.13 |
| S066N-S129V | 2.11 |
| D220E-S265Q | 2.11 |
| F130L-M138L-E152W-T179P | 2.10 |
| T059W-S129V | 2.10 |
| S265P-L282M-Q286R-A289R | 2.09 |
| S265P-L282F-Q286R-A289R | 2.09 |
| T059W-S066N-S129I | 2.08 |
| V190I-D220P-S265W | 2.08 |
| F130L-E152W-T179P | 2.06 |
| F130L-M138L-E152F-T179P | 2.06 |
| Q062K-S066Q-S129I | 2.04 |
| T059K-S066N-S129I | 2.04 |
| E152H-T179P | 2.03 |

TABLE 14.3-continued

Stability Assay Results in the Presence of 25% TIDE ® 2X With DTPA

| Variant Code | Stability in the presence of TIDE ® 2X with DTPA [Perf. Index] |
|---|---|
| S265P-L282M-Q286K-A289R | 2.03 |
| F130L-M138L-E152H-T179P | 2.02 |
| T263W-A273H-S285R | 2.00 |
| D220E-S265N | 1.99 |
| F130I-M138L-E152H-T179P | 1.99 |
| F130V-M138L-E152W-T179P | 1.99 |
| F130I-M138L-E152W-T179P | 1.99 |
| T059W-S129I | 1.97 |
| D220E-S265W | 1.97 |
| F130V-M138L-T179P | 1.96 |
| F130L-E152V-T179P | 1.96 |
| T059R-S129Q | 1.95 |
| T263W-S285P | 1.94 |
| F130I-M138L-E152F-T179P | 1.93 |
| E152W-T179P | 1.93 |
| V190L-S265Q | 1.93 |
| F130L-E152F-T179P | 1.92 |
| L282M-Q286R-A289R-P162S | 1.91 |
| D220P-S265Q | 1.91 |
| M138L-E152F-T179P | 1.91 |
| F130I-E152H-T179P | 1.91 |
| M138L-E152W-T179P | 1.91 |
| F130L-T179P | 1.90 |
| F130L-M138L-E152W-T179P-Q286H | 1.90 |
| F130L-M138L-E152H | 1.89 |
| T263W-A273H-S285W | 1.89 |
| S265P-Q286K | 1.88 |
| T059W-S066Q-S129Q | 1.87 |
| T263W-S285R | 1.85 |
| T059W-S066N-S129Q | 1.83 |
| T263W-S285W | 1.83 |
| T059R-S066N-S129Q | 1.83 |
| S265P-L282M-Q286R-A289R-T202S-K203N | 1.81 |
| T059W-S129Q | 1.81 |
| Q062H-S066Q-S129Q | 1.81 |
| L282M-Q286R-A289R | 1.80 |
| V190L-D220E-S265N-V291I | 1.80 |
| V190L-S265N | 1.80 |
| F130L-M138L-E152W | 1.79 |
| N050Y-T059R-S129Q | 1.79 |
| F130I-T179P | 1.78 |
| T059K-S066Q-S129Q | 1.78 |
| T059K-S129Q | 1.78 |
| S265P-L282M-Q286P-A289R | 1.77 |
| S265P-L282F-Q286P-A289R | 1.77 |
| T263W-A273H-S285P | 1.77 |
| S265P-L282M-Q286K | 1.76 |
| S016L-D220E-S265W | 1.76 |
| S066Q-S129Q | 1.76 |
| S265P-L282M-Q286P | 1.75 |
| L282F-Q286R-A289R | 1.75 |
| F130V-E152W-T179P | 1.74 |
| L044Q-T263W-S285R | 1.74 |
| L055F-T059W-S129V | 1.74 |
| V190L-S265W | 1.74 |

TABLE 14.3-continued

Stability Assay Results in the Presence of 25% TIDE ® 2X With DTPA

| Variant Code | Stability in the presence of TIDE ® 2X with DTPA [Perf. Index] |
|---|---|
| Q286R-A289R | 1.74 |
| G99D-S265P-L282F-Q286K-A289R | 1.73 |
| F130L-M138L-E152F | 1.73 |
| T059R-S066Q-S129Q | 1.72 |
| F130L-E152H | 1.71 |
| S066N-S129Q | 1.71 |
| T004S-S023N-G024M-K269N | 1.71 |
| S265P-L282M | 1.71 |
| E152F-T179P | 1.71 |
| T059W-S066N-S129V-S290R | 1.68 |
| L282F-Q286K-A289R | 1.67 |
| F130L-M138L | 1.66 |
| F130I-M138L-E152W | 1.65 |
| S265P-L282F | 1.65 |
| F130I-M138L-E152H | 1.65 |
| F130V-M138L-E152H | 1.64 |
| V190I-S265Q | 1.64 |
| M138L-E152M | 1.61 |
| S265P-L282F-Q286P | 1.59 |
| M138L-E152H | 1.59 |
| T059K-S066N-K088E | 1.59 |
| V190I-S265W | 1.59 |
| F130L-E152W | 1.59 |
| L282M-Q286K-A289R | 1.58 |
| L282M-Q286K-A289R-I253V | 1.57 |
| T263W-A273H | 1.56 |
| V190I-S265N | 1.55 |
| M138L-E152W | 1.55 |
| A273H-S285R | 1.52 |
| F130I-M138L | 1.51 |
| F130L-E152F | 1.50 |
| F130V-M138L-E152W | 1.50 |
| T059K-S066Q-V102A-S129Q | 1.48 |
| F130V-E152H-T179P | 1.47 |
| F130I-M138L-E152F | 1.47 |
| F130V-M138L-E152F | 1.44 |
| M138L-E152F | 1.44 |
| L282M-Q286R | 1.43 |
| F130I-E152H | 1.43 |
| S265P-L282F-A289R-T065S | 1.43 |
| T263H-A273H-S285R | 1.43 |
| F130V-M138L | 1.42 |
| T014M-T059R-S129V | 1.42 |
| L282M-Q286R-A289R-K11N | 1.41 |
| A273H-S285P | 1.41 |
| L282M-Q286K-A289R-S132T | 1.40 |
| T263H-A273H-S285W | 1.39 |
| F130V-E152W | 1.38 |
| S265P-L282F-Q286K-N061Y | 1.37 |
| F130I-E152W | 1.36 |
| L198I-D220E-S265Q | 1.36 |
| V190I-S265L | 1.36 |
| T263H-S285W | 1.35 |
| S265P-L282F-A289R | 1.34 |
| M138L-S066Q | 1.32 |
| F130I-E152F | 1.32 |
| N90S-A273H-S285P | 1.31 |
| S032T-T263H-A273H-S285R | 1.31 |

TABLE 14.3-continued

| Stability Assay Results in the Presence of 25% TIDE ® 2X With DTPA | |
|---|---|
| Variant Code | Stability in the presence of TIDE ® 2X with DTPA [Perf. Index] |
| L282F-Q286P-A289R | 1.28 |
| N157Y-T263W-A273H-S285R | 1.27 |
| V105A-S129V | 1.26 |
| T263H-A273H-S285P | 1.25 |
| S129Q-L282H | 1.23 |
| T059W-S066Q | 1.23 |
| F130V-E152H | 1.21 |
| S023W-G024Y | 1.21 |
| T004V-S023N | 1.21 |
| T059R-S066Q | 1.21 |
| N050W-T054L | 1.20 |
| L282M-Q286P-A289R | 1.20 |
| A115V-V190L-S265W | 1.19 |
| L282M-Q286K | 1.19 |
| T059R-S066N | 1.18 |
| L282F-Q286P | 1.15 |
| T004V-S023W-G024M | 1.15 |
| S265P-L282F-Q286R-L78H | 1.15 |
| L282F-Q286K | 1.14 |
| T004V-S023W-G024Y | 1.14 |
| S023W-G024M | 1.13 |
| T059R-R256S | 1.13 |
| F130V-E152F | 1.12 |
| T004V-G024W | 1.12 |
| N050W-T054K | 1.11 |
| S023Y-G024M | 1.11 |
| T004V-S023Y | 1.11 |
| T004V-S023Y-G024M | 1.11 |
| N050Y-T054H | 1.10 |
| S023W-G024W | 1.10 |
| T004V-S023Y-G024Y | 1.10 |
| T004V-S023N-G024W | 1.09 |
| F130L-M138L-E152F-T179P-V291I | 1.09 |
| N050Y-T059K-S066Q | 1.09 |
| T004V-S023Y-G024W | 1.09 |
| T059K-S066N | 1.09 |
| T004V-S023N-G024Y | 1.09 |
| S023Y-G024W | 1.09 |
| N050F-T054L | 1.08 |
| R047K-T054K | 1.08 |
| S023N-G024W | 1.07 |
| L282M-A289R | 1.07 |
| S023Y-G024Y | 1.07 |
| T004V-G024M | 1.07 |
| L282F | 1.06 |
| R047K-N050F-T054K | 1.06 |
| N050F-T054K | 1.05 |
| T059K-S066Q | 1.05 |
| S023N-G024M | 1.05 |
| S023N-G024Y | 1.04 |
| T004L-S023N | 1.04 |
| R047K-N050W-T054H | 1.04 |
| T004L-S023W-G024Y | 1.04 |
| T004S-S023W | 1.03 |
| N046Q-N050W-T054H-A142T | 1.03 |
| T004L-S023Y | 1.03 |
| T004V-S023W | 1.03 |
| N050W-T054H | 1.02 |
| T004S-S023N | 1.02 |
| T004S-L282M | 1.02 |
| T004L-S023W | 1.02 |
| N050F-T054H | 1.01 |
| N050Y-T054L | 1.00 |
| R047K-N050W-T054K | 1.00 |

TABLE 14.4

| Stability Assay Results in the Presence of 25% TIDE ® 2X Without DTPA | |
|---|---|
| Variant Code | Stability Assay Results in the presence of TIDE ® 2X without DTPA [Perf. Index] |
| S066Q-S129V | 2.24 |
| S066Q-S129I | 2.19 |
| N050Y-S066Q-S129V | 2.12 |
| S066N-S129I | 2.08 |
| T059K-S066Q-S129V | 2.06 |
| S066N-S129V | 2.05 |
| F130L-E152W-T179P | 1.98 |
| S265P-L282M-Q286R-A289R | 1.96 |
| F130L-E152V-T179P | 1.96 |
| T059K-S066Q-S129I | 1.91 |
| T263W-S285P | 1.85 |
| T059K-S066N-S129I | 1.84 |
| T263W-A273H-S285P | 1.83 |
| S265P-L282F-Q286R-A289R | 1.83 |
| F130V-E152W-T179P | 1.83 |
| T263W-A273H-S285R | 1.82 |
| V190I-D220P-S265W | 1.79 |
| F130L-E152H | 1.78 |
| S066N-S129Q | 1.77 |
| S265P-L282M-Q286K-A289R | 1.77 |
| V190I-D220E | 1.76 |
| T059R-S066N-S129I | 1.76 |
| V190I-D220E-S265W | 1.75 |
| T059K-S129I | 1.75 |
| T059R-S066Q-S129I | 1.75 |
| F130I-M138L-E152H-T179P | 1.74 |
| F130I-T179P | 1.74 |
| T263W-A273H-S285W | 1.73 |
| S016L-D220E-S265W | 1.72 |
| S066Q-S129Q | 1.72 |
| V190I-D220E-S265Q | 1.72 |
| T059R-S066Q-S129V | 1.71 |

TABLE 14.4-continued

| Stability Assay Results in the Presence of 25% TIDE ® 2X Without DTPA | |
|---|---|
| Variant Code | Stability Assay Results in the presence of TIDE ® 2X without DTPA [Perf. Index] |
| D220E-S265N | 1.69 |
| V190L-D220E | 1.69 |
| D220E-S265W | 1.68 |
| V190I-D220P | 1.68 |
| V190L-D220E-S265N | 1.68 |
| L044Q-T263W-S285R | 1.67 |
| S265P-L282M-Q286P-A289R | 1.67 |
| F130L-M138L-E152H-T179P | 1.66 |
| T263W-S285R | 1.66 |
| L282M-Q286R-A289R | 1.65 |
| T263W-S285W | 1.65 |
| F130I-E152H-T179P | 1.65 |
| V190I-D220E-S265N | 1.64 |
| V190L-D220E-S265W | 1.63 |
| V190I-D220P-S265Q | 1.63 |
| T059R-S066N-S129V | 1.62 |
| V190L-D220E-S265Q | 1.62 |
| E152H-T179P | 1.62 |
| F130L-M138L-E152F-T179P | 1.61 |
| Q062H-S066Q-S129Q | 1.59 |
| T059R-S129V | 1.58 |
| V190I-D220E-S265W-L282F | 1.58 |
| V190I-S265Q | 1.58 |
| F130L-E152F-T179P | 1.58 |
| D220E-S265Q | 1.57 |
| E152W-T179P | 1.56 |
| T059K-S066Q-S129Q | 1.56 |
| F130L-M138L-T179P | 1.55 |
| F130I-M138L-E152F-T179P | 1.55 |
| F130L-M138L-E152W-T179P | 1.54 |
| N050Y-T059W-S066Q-S129V | 1.54 |
| S265P-L282M-Q286K | 1.54 |
| T059R-S129I | 1.53 |
| F130V-E152H-T179P | 1.53 |
| D220P-S265N | 1.52 |
| S265P-L282M-Q286P | 1.51 |
| F130I-E152H | 1.51 |
| T059R-S066Q-N092S-S129I | 1.51 |
| F130L-T179P | 1.49 |
| G99D-S265P-L282F-Q286K-A289R | 1.48 |
| T263W-A273H | 1.48 |
| V190I-S265N | 1.48 |
| D220P-S265W | 1.47 |
| F130L-E152W | 1.47 |

TABLE 14.4-continued

| Stability Assay Results in the Presence of 25% TIDE ® 2X Without DTPA | |
|---|---|
| Variant Code | Stability Assay Results in the presence of TIDE ® 2X without DTPA [Perf. Index] |
| F130L-M138L-E152H | 1.46 |
| S265P-L282M | 1.45 |
| V190I-S265Q | 1.45 |
| F130L-E152F | 1.45 |
| T059K-S129Q | 1.45 |
| Q286R-A289R | 1.45 |
| M138L-E152W-T179P | 1.44 |
| F130I-M138L-E152H | 1.43 |
| D220P-S265Q | 1.42 |
| V190L-S265N | 1.42 |
| F130I-M138L-E152W | 1.42 |
| S265P-Q286K | 1.41 |
| V190L-S265Q | 1.41 |
| V190I-S265W | 1.40 |
| F130L-M138L-E152F | 1.40 |
| F130V-E152H | 1.40 |
| E152F-T179P | 1.39 |
| N050Y-T059W-S066N-S129V | 1.38 |
| T059R-S066N-S129Q | 1.38 |
| F130I-E152W | 1.37 |
| F130V-E152W | 1.37 |
| T059R-S066Q-S129Q | 1.37 |
| T263H-A273H-S285P | 1.36 |
| N90S-A273H-S285P | 1.36 |
| V190L-D220E-S265N-V221I | 1.36 |
| T059R-S129Q | 1.35 |
| A273H-S285P | 1.34 |
| F130I-M138L-E152W-T179P | 1.34 |
| F130V-M138L-E152F | 1.34 |
| N050Y-T059R-S129Q | 1.34 |
| T059W-S066Q-S129I | 1.34 |
| F130V-M138L-T179P | 1.34 |
| F130V-M138L-E152W-T179P | 1.33 |
| V190L-S265W | 1.33 |
| F130V-M138L-E152W | 1.32 |
| T059W-S066Q-S129V | 1.32 |
| V190I-S265Q | 1.32 |
| F130V-M138L-E152H | 1.32 |
| F130I-E152F | 1.31 |
| N157Y-T263W-A273H-S285R | 1.31 |
| T263H-S285W | 1.30 |
| M138L-E152F-T179P | 1.30 |
| A115V-V190L-S265W | 1.29 |
| M138L-E152M | 1.29 |
| T263H-A273H-S285W | 1.29 |
| F130L-M138L-E152W | 1.28 |

TABLE 14.4-continued

| Stability Assay Results in the Presence of 25% TIDE ® 2X Without DTPA | |
|---|---|
| Variant Code | Stability Assay Results in the presence of TIDE ® 2X without DTPA [Perf. Index] |
| T059K-S066N-K088E | 1.28 |
| F130I-M138L-E152F | 1.27 |
| F130I-M138L-T179P | 1.27 |
| T004V-S023N | 1.26 |
| T059K-S066Q-V102A-S129Q | 1.26 |
| F130L-M138L | 1.26 |
| N047K-N050F-T054K | 1.24 |
| T263H-A273H-S285R | 1.24 |
| F130L-M138L-E152W-T179P-Q286H | 1.23 |
| M138L-E152H | 1.22 |
| M138L-S066Q | 1.22 |
| L282M-Q286R-A289R-P162S | 1.21 |
| L282F-Q286R-A289R | 1.21 |
| Q062K-S066Q-S129I | 1.21 |
| A273H-S285R | 1.20 |
| S265P-L282F-Q286P | 1.20 |
| S265P-L282F-Q286P-A289R | 1.20 |
| S265P-L282M-Q286R-A289R-T202S-K203N | 1.19 |
| T059W-S066N-S129I | 1.19 |
| V190I-S265L | 1.18 |
| T059W-S066N-S129V | 1.18 |
| F130I-M138L | 1.16 |
| L282M-Q286K-A289R-I253V | 1.16 |
| R047K-N050F-T054K | 1.15 |
| M138L-E152F | 1.15 |
| N050W-T054K | 1.15 |
| L198I-D220E-S265Q | 1.13 |
| L282F-Q286K-A289R | 1.13 |
| N050F-T054K | 1.13 |
| L282M-Q286R | 1.13 |
| M138L-E152W | 1.13 |
| S265P-L282F | 1.12 |
| F130V-E152F | 1.12 |
| T059W-S066N-S129Q | 1.10 |
| F130V-M138L | 1.09 |
| T263H-A273H | 1.09 |
| L282M-Q286K-A289R | 1.07 |
| N046Q-N050W-T054H-A142T | 1.07 |
| T059W-S066Q-S129Q | 1.07 |
| S265P-L282F-A289R-T065S | 1.07 |
| N050F-T054H | 1.07 |
| S129Q-L282H | 1.06 |
| L282M-Q286K-A289R-S132T | 1.03 |
| L282M-Q286R-A289R-K11N | 1.03 |
| T059K-S066N | 1.02 |
| R047K-N050W-T054K | 1.01 |
| T059K-S066Q | 1.01 |
| T004V-S023Y | 1.01 |
| T059W-S066N-S129V-S290R | 1.00 |
| N050Y-T059K-S066Q | 1.00 |
| R047K-N050Y | 1.00 |

The data in the following table (Table 14.5) represent the relative stability data of variants of NprE relative to the stability of the WT NprE stability in the citrate stability assay. The stability was measured by determining casein activity by determining AGLA activity before and after incubation at elevated temperature (See, "Citrate Stability Assay" above). The table contains the relative stability values compared to WT under these conditions. It is presented as the quotient of (Variant residual activity/WT residual activity). A value greater than one indicates higher stability in the presence of detergent.

TABLE 14.5

| Citrate Stability Assay Results | |
|---|---|
| Variant Code | Citrate Stability Relative |
| K013C | 1.22 |
| K013D | 1.32 |
| K013E | 1.07 |
| K013H | 1.50 |
| K013Q | 1.38 |
| K013S | 1.11 |
| T014G | 1.31 |
| T014H | 1.75 |
| T014K | 1.62 |
| T014M | 1.09 |
| T014P | 1.07 |
| T014Q | 2.01 |
| T014R | 1.32 |
| T014V | 1.03 |
| S023A | 1.12 |
| S023G | 1.13 |
| S023I | 1.13 |
| S023K | 1.39 |
| S023M | 1.00 |
| S023N | 1.42 |
| S023T | 1.15 |
| S023V | 1.20 |
| S023W | 1.22 |
| G024D | 1.38 |
| G024F | 1.90 |
| G024H | 1.09 |
| G024M | 1.23 |
| G024R | 1.03 |
| G024S | 1.11 |
| G024T | 1.03 |
| G024W | 1.03 |
| Q045D | 1.07 |
| Q045E | 1.12 |
| Q045M | 1.02 |

TABLE 14.5-continued

Citrate Stability Assay Results

| Variant Code | Citrate Stability Relative |
|---|---|
| Q045N | 1.16 |
| Q045P | 1.44 |
| N046G | 1.10 |
| N046H | 1.05 |
| N046I | 1.46 |
| N046P | 1.47 |
| N046V | 1.11 |
| N046Y | 1.01 |
| R047E | 1.09 |
| R047T | 1.07 |
| Y049A | 1.02 |
| Y049C | 1.03 |
| Y049D | 1.01 |
| Y049E | 1.04 |
| Y049I | 1.08 |
| Y049K | 1.04 |
| Y049T | 1.16 |
| Y049V | 1.19 |
| Y049W | 1.00 |
| T054D | 1.01 |
| T054H | 1.09 |
| T054K | 1.02 |
| T054L | 1.06 |
| T054P | 1.63 |
| T054Q | 1.17 |
| T054R | 1.11 |
| T054S | 1.09 |
| T054W | 1.02 |
| S058I | 1.23 |
| S058L | 1.71 |
| S058N | 1.08 |
| S058P | 2.53 |
| T059E | 1.08 |
| T059H | 1.19 |
| T059I | 1.02 |
| T059K | 1.21 |
| T059L | 1.16 |
| T059M | 1.04 |
| T059S | 1.07 |
| S066D | 1.03 |
| S066E | 1.03 |
| S066P | 1.13 |
| S066Q | 1.05 |
| S066T | 1.17 |
| S066V | 1.00 |
| Q087A | 1.05 |
| Q087L | 1.08 |
| Q087S | 1.15 |
| Q087T | 1.19 |
| N090D | 1.17 |
| N090F | 1.02 |
| N090G | 1.04 |
| N090L | 1.25 |
| N090T | 1.02 |
| N096G | 1.02 |
| K100D | 1.30 |
| K100N | 1.28 |
| K100P | 1.04 |
| K100V | 1.01 |
| D119H | 1.05 |
| D119T | 1.03 |
| D119W | 1.00 |
| G136I | 1.10 |
| G136L | 1.20 |
| G136P | 2.19 |
| G136V | 2.03 |
| G136W | 2.23 |
| G136Y | 1.56 |
| M138L | 1.48 |
| D139A | 2.52 |
| D139C | 2.22 |
| D139E | 1.51 |
| D139G | 2.54 |
| D139H | 1.88 |

TABLE 14.5-continued

Citrate Stability Assay Results

| Variant Code | Citrate Stability Relative |
|---|---|
| D139I | 2.40 |
| D139K | 2.27 |
| D139L | 1.53 |
| D139M | 2.49 |
| D139P | 2.21 |
| D139R | 2.54 |
| D139S | 2.22 |
| D139V | 1.51 |
| D139W | 1.94 |
| D139Y | 2.54 |
| E152C | 1.17 |
| E152F | 1.21 |
| E152G | 1.09 |
| E152H | 1.29 |
| E152R | 1.12 |
| E152S | 1.17 |
| E152W | 1.21 |
| D178A | 2.07 |
| D178C | 1.79 |
| D178G | 2.35 |
| D178H | 2.07 |
| D178K | 1.73 |
| D178L | 1.74 |
| D178M | 2.40 |
| D178N | 2.34 |
| D178P | 1.83 |
| D178Q | 1.22 |
| D178R | 2.00 |
| D178S | 2.58 |
| D178T | 1.75 |
| D178V | 1.73 |
| D178W | 1.02 |
| D178Y | 1.78 |
| E186A | 2.31 |
| E186C | 2.42 |
| E186D | 2.03 |
| E186G | 2.09 |
| E186H | 1.87 |
| E186K | 2.69 |
| E186L | 1.75 |
| E186M | 2.62 |
| E186N | 1.72 |
| E186P | 2.60 |
| E186Q | 1.92 |
| E186R | 2.69 |
| E186S | 2.57 |
| E186T | 2.69 |
| E186V | 2.10 |
| E186W | 2.47 |
| E186Y | 2.48 |
| V190I | 1.38 |
| V190L | 1.41 |
| K211A | 1.33 |
| K211M | 1.26 |
| K211Q | 1.16 |
| K211S | 1.28 |
| K214A | 1.38 |
| K214C | 1.12 |
| K214E | 1.08 |
| K214I | 1.30 |
| K214L | 1.14 |
| K214M | 1.03 |
| K214Q | 1.47 |
| K214R | 1.12 |
| K214S | 1.05 |
| K214V | 1.49 |
| L216A | 1.05 |
| L216C | 1.04 |
| L216S | 1.19 |
| D220E | 1.69 |
| D220H | 1.17 |
| D220K | 1.17 |
| D220N | 1.01 |
| D220P | 1.20 |

TABLE 14.5-continued

| Citrate Stability Assay Results | |
|---|---|
| Variant Code | Citrate Stability Relative |
| A221D | 1.11 |
| A221S | 1.05 |
| G222C | 1.01 |

Example 15 pH Performance Profile of nprE Compared to BPN' 217L

In this Example, experiments conducted to evaluate the comparative performance of nprE and BPN' Y217L are described. In these experiments, EMPA 116 (BMI) and Equest grass stains were used.

Materials:

NprE, 8 mg/mL

BPN' Y217L, 25.6 mg/mL

EMPA 116 soil cloth, 3"×4.5" (Testfabrics)

Equest grass (med.), 3"×4" (Warwick Equest)

EMPA 221 white cotton swatches, 3"×4.5"

Minolta Chromameter CR200

TIDE® 2005 (provided by Procter & Gamble)

Water hardness concentrate: 15,000 grains per gallon (gpg), 3:1 Ca:Mg

1 M Bis-TRIS-propane buffer

Conc. sulfuric acid

50 L mix tank with spigot and agitator

Terg-O-Tometer

DI Water

The swatches were prepared for treatment. Three replicates per treatment were conducted, with 18 swatches used per treatment. The grass swatches were prepared in a dark room to prevent fading. The reflectance values of about 18 soiled swatches were obtained using a Minolta Chromameter. Three readings were obtained per swatch. The L values, average L value and standard deviation were recorded. This is the $L_{initial}$ value.

The detergent solution was prepared as follows (for 40 L total). It was preferred to prepare this solution the night before testing. The solution was stored in the cold over night. The solution was prepared by adding 39.724 Kg of DI water to 50 L mix tank, starting the agitator, mixing in 60 grams of TIDE® liquid detergent, mixing in 16 mL of water hardness solution, and 200 mL of 1 M Bis-TRIS-propane. The pH was adjusted using concentrated sulfuric acid (adjusted to 0.2 pH units below desired pH, if solution was stored overnight). as pH creeps up overnight). The final concentrations were: TIDE®=1.5 g/L; water hardness=6 gpg; and Bis-TRIS-propane=5 mM.

For testing in the Terg-O-Tometer, 1 L of detergent solution was added to each Terg pot and allowed to come to temperature. Enzyme was added to the pots at varying concentrations. For BMI tests, the enzyme concentrations used were 0 mg/L, 0.275 mg/L, 0.55 mg/ml, 1.65 mg/L, 2.65 mg/L, and 5.50 mg/L. For grass stains, the nprE concentrations used were 0 mg/L, 0.1925 mg/L, 0.385 mg/L, 1.155 mg/L, 1.925 mg/L, and 3.85 mg/L (the concentrations of BPN' Y217L were the same as those used in the BMI tests). Agitation was started and the swatches were added. All replicates were run side-by-side in the same Terg-O-Tometer (e.g., 0× & ½× in the 1st run, 1× & 3× in the 2nd run, and 5× & 10× in the 3rd run). The temperature was 15° C., the agitation speed was 100 cpm, and the wash time was 12 minutes. The treated swatches were rinsed three times in 4 L tap water (~6 gpg). The swatches were air-dried overnight on paper towels. The grass swatches were covered with paper towels and allowed to dry in a darkened room. The reflectance values of the dried swatches were determined as described above. Three readings were obtained per swatch. The L values. average L value and standard deviation were recorded. This is the $L_{final}$ value.

The percentage of soil removal (% SR) was determined for each testing condition and both enzymes using the equation below:

$$\% SR = \frac{(L_{final} - L_{initial})}{(L_0 - L_{initial})} \times 100\%$$

Where:

$L_0$=reflectance of unsoiled swatches $L_{initial}$=reflectance of soiled swatches $L_{final}$=reflectance of washed swatches The delta % SR over no enzyme control was determined using the following formula:

$$\Delta\% SR = \% SR_{treatment} - \% SR_{no\ enzyme\ control}$$

BPN' Y217L was compared to nprE on EMPA 116 (BMI), at pH values of 6.7, 7.5, 8.5, and 9.5. The performance of nprE on EMPA 116 appeared to peak at about pH 8, while the performance of BPN' Y217L peaked at about pH 8.8. The results showed that nprE performed better than BPN' Y217L at pH 7.5 and 8.5, although it does not perform as well as BPN' Y217L at pH 6.7. The performance of these enzymes was equal at pH 9.5. In addition, there was no difference in the performance of these enzymes on Equest grass (med) at pH 7.8-8.4.

Example 16

Comparison of PMN and nprE Enzymes in Liquid Detergent

This Example describes cleaning experiments to determine the cleaning performance of PMN and nprE. The cleaning performance of PMN and nprE enzymes were tested in Liquid TIDE® detergent in comparison with a benchmark serine protease (Protease A) on protease sensitive stains. As shown in the table below, PMN and nprE remove stains much better than protease A, even at low enzyme levels. In the following Tables, the higher SRI values indicate a better cleaning performance.

TABLE 16.1

Comparison of Cleaning Performance of PMN vs. Protease A in Liquid TIDE ® (in full size washing machine)

| | Active Enzyme Protein in the wash solution | | | |
|---|---|---|---|---|
| | 0.55 ppm Protease A | 0.55 ppm PMN | 5.50 ppm Protease A | 5.50 ppm PMN |
| SRI on Lightly Soiled Grass Stains | 53.1 | 60.8 | 60.7 | 67.2 |
| SRI on Medium Soiled Grass Stains | 46.5 | 55.0 | 54.2 | 59.8 |
| SRI on Heavily Soiled Grass Stains | 39.1 | 45.8 | 44.5 | 51.6 |

TABLE 16.2

| Comparison of Cleaning Performance of PMP vs. Protease A in Liquid TIDE ® (in mini size washing machine) | Active Enzyme Protein in the wash solution | |
|---|---|---|
| | 0.55 ppm Protease A | 0.55 ppm PMN |
| SRI on Lightly Soiled Grass Stains | 28.1 | 52.8 |
| SRI on Medium Soiled Grass Stains | 22.8 | 33.1 |
| SRI on Heavily Soiled Grass Stains | 19.9 | 24.2 |

TABLE 16.3

| Comparison of Cleaning Performance of nprE vs. Protease A in Liquid TIDE ® (in mini-size washing machine) | Active Enzyme Protein in the wash solution | | | |
|---|---|---|---|---|
| | 0.55 ppm Protease A | 2.75 ppm Protease A | 5.50 ppm Protease A | 0.28 ppm nprE |
| SRI on Lightly Soiled Grass Stains | 26.3 | 30.8 | 30.7 | 31.5 |
| SRI on BMI Stains | 19.4 | 24.9 | 21.4 | 25.0 |
| Baby Food Beef Stains | 63.2 | 68.8 | 69.4 | 71.1 |

Example 17

Thermostability of NprE and NprE Variants

In this Example, experiments conducted to determine the thermostability of NprE and NprE variants are described. The enzymes were produced and purified as described above. The purified proteins were judged to be sufficiently homogenous, with greater than 95% purity as determined using 10% SDS-PAGE, as only one major protein was observed in the gel. This protein was approximately 32 kDa, which is the molecular weight of the mature nprE sequence. The protein was formulated for storage using the 25 mM MES buffer, pH 5.8, containing 1 mM zinc chloride, 4 mM calcium chloride, and 40% propylene glycol. The assays used in these experiments were the protease assay using fluorescence AGLA activity described above and differential scanning calorimetry (DSC), described below.

Differential Scanning calorimetry (DSC)

Excessive heat capacity curves were measured using an ultrasensitive scanning high throughput microcalorimeter VP-Cap DSC (Microcal). The standard procedure for DSC measurements and the theory of the technique is well known to those of skill in the art (See e.g., Freire, 1995) Meth. Mol. Biol., 41, 191-218 [1995]). Briefly, approx. 500 uL of 200-400 ppm pure or ultrafiltrate concentrate (UFC) protein samples were needed. Typically, 400 ppm of NprE and the variant proteins (in the absence and presence 130 mM citrate) were scanned over 20-100° C. temperature range using a scan rate of 200° C./hr in 5 mM HEPES, pH 8.0 buffer. The same sample was then rescanned to check the reversibility of the process. For NprE, the thermal unfolding process was irreversible. Scan rate dependence data of the thermal melting for NprE was assessed over a scan rate of 25 to 200° C./hr. The effect of various additives (e.g., primary and secondary alcohols, salts, cyclodextrin, PEG, sorbitol, glycerol) on the thermal melting point of NprE was also assessed.

Results

The thermal stability of wild-type NprE was determined at two different concentrations, in order to show the effect of protein concentration on the thermal melting point. The Tm values for 220 ppm and 440 ppm were determined to be 67.6±0.5 and 69.2±0.5° C., respectively. The protein concentration effect highlights a second-order event. It is contemplated that this is either aggregation or autolysis. However, it is not intended that the present invention be limited to any particular mechanism. Nonetheless, these results indicate that for an accurate determination and any comparison of thermal melting points for NprE require that the protein concentrations be well matched. The effect of the scan rate on the thermal melting point also showed a dependence where the Tm was dependent on the scan rate up to 150° C./hr, and then leveled off between 150-200° C./hr. Based on these results, 200° C./hr was selected as the upper scan rate for all studies to minimize the dependence of the Tm on scan rate.

All data collected for NprE and variants are shown in Table 4. Table 4 also includes the DSC thermal melting points obtained for NprE and variants in the presence of 130 mM citrate. In most cases, two protein concentrations were scanned. As indicated in this Table, in the case of the scans in the presence of 130 mM citrate not all proteins showed a thermal unfolding profile.

TABLE 17

DSC Results

| | DSC Thermal Concentration Concentration | | |
|---|---|---|---|
| Enzyme Tested | 220 ppm Protein | 440 ppm Protein | 440 ppm Protein with 130 mM citrate |
| Wild-type NprE | 67.6 +/− 0.5 | 69.2 +/− 0.5 | No transition |
| Thermolysin | 87.0000 | | 52.1000 |
| *B. subtilis* NprE | 68.0000 | | 55.0000 |
| FNA | 64.9000 | | 51.7000 |
| T14R | 57.0000 | | 51.7000 |
| S23K | 67.8000 | | None |
| S23R | 67.8000 | | 53.5000 |
| G24R | 63.7000 | | 50.7 |
| Q45E | 70.6000 | 70.7000 | 53.0000 |
| N46K | 63.8000 | | 50.7 |
| S58D | 63.3000 | | 50.5000 |
| T59P | 68.8000 | | 49.1000 |
| S58D, T60D | 59.0000 | | No transition |
| T60D | 66.2000 | | No transition |
| S66E | 70.3000 | 71.6000 | |
| S129I | 70.2000 | 70.7000 | 50.3000 |
| S129V | 69.9000 | 70.3000 | No transition |
| F130L | | 69.8000 | 48.5000 |
| M138I | 69.2000 | | 52.5000 |
| M138L | 67.8000 | | |
| V190I | 69.0000 | 69.4000 | 51.5 |
| L198M | 68.2000 | 68.5000 | 53.3000 |
| S199E | 70.3000 | 70.3000 | 49.1000 |
| D220P | 69.3000 | 69.9000 | 49.4000 |
| D220E | 69.4000 | 69.8000 | 50.5000 |
| K211V | | 69.8000 | |
| K214Q | | 68.9000 | |
| A221S | 59.1000 | | 52.5000 |
| G222C | 69.5000 | | No transition |
| K244S | | 67.6000 | |
| K269T | | 69.5000 | 51.5 |
| R280D | 67.4000 | 67.9000 | 49.2000 |
| N296E | 60.5000 | 69.8000 | 49.5000 |
| N50W, N296E | | 62.4000 | 47.2000 |
| G5C, N61C | 67.8000 | | 48.4 |
| Q45K, S199E | | 67.7000 | 51.3000 |
| F130L, D220P | 62.7000 | 70.3000 | 50.8000 |
| M138L, D220P | 63.2000 | 68.2000 | 50.8000 |
| S129I, V190I | | 70.3000 | 55.8000 |
| S129V, V190I | | 69.9000 | 55.3000 |
| S129V, D220P | | 70.6000 | 55.7000 |
| S129I, D220P | | 70.7000 | 53.5000 |

TABLE 17-continued

DSC Results

| Enzyme Tested | DSC Thermal Concentration Concentration 220 ppm Protein | 440 ppm Protein | 440 ppm Protein with 130 mM citrate |
|---|---|---|---|
| S129V, R280L | | 69.5000 | 54.9000 |
| V190I, D220P | | 69.8000 | 52.8000 |
| Q45K, S199E | | 67.7000 | 51.3000 |
| N50W, N296E | | 62.4000 | 47.2000 |
| G24K K269T D220E | | 65.0000 | 51.5000 |
| S129I, F130L, D220P | | 68.9000 | 56.6000 |
| nprE-T004S-S023N-G024M(+K269N) | | 64.6000 | None |
| nprE-T004V-S023N | | 71.2000 | 49.0000 |
| nprE-S023W-G024Y | | 64.0000 | None |
| nprE-T004V-S023W-G024M | | 65.5000 | 49.3000 |
| nprE-T059K-S66Q-S129I | | 70.5000 | 49.3000 |
| nprE-T059R-S66N-S129I | | 70.2000 | 54.0000 |
| nprE-T059R-S129I | | 69.4000 | 54.0000 |
| nprE-T059K-S66Q-S129V | | 70.3000 | 56.0000 |

Figure 27:
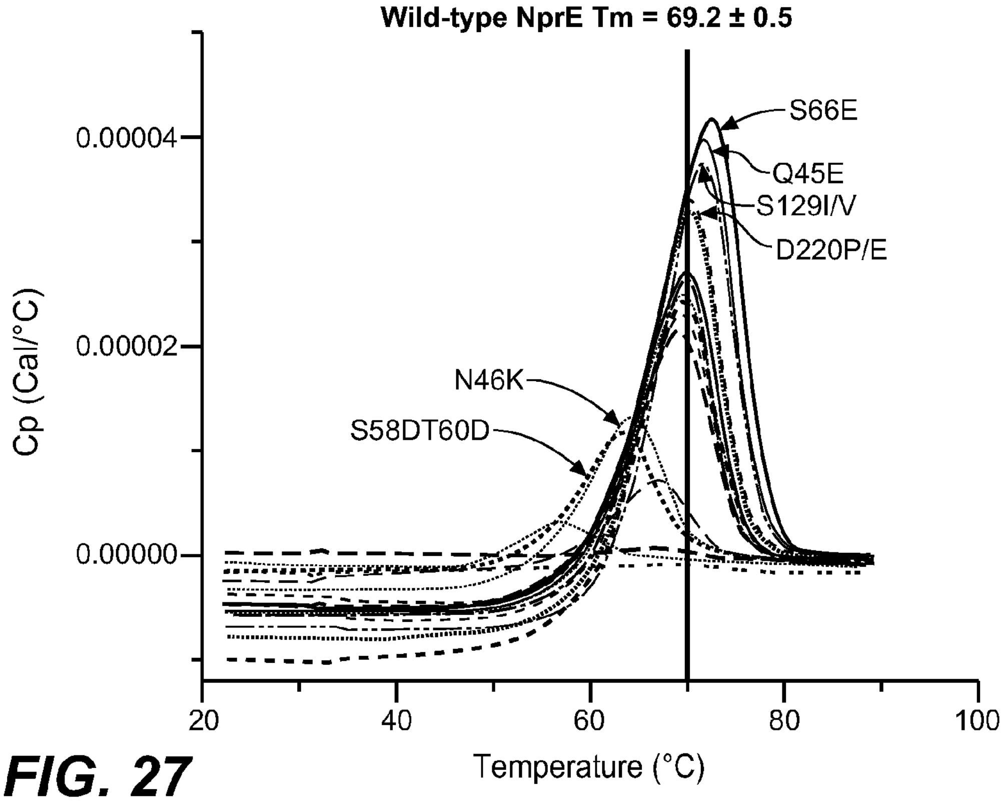
FIG. 27 provides a graph showing the results of DSC scans for 440 ppm NprE and variants obtained using the VP-Cap DSC (MicroCal™).

A representative Figure of the thermal unfolding profiles (DSC scans) for wild type and various mutants of NprE are shown in FIG. 27. The unfolding profiles indicate the wild-type midpoint and show selective mutants that display increased thermal melting points relative to wild-type and those that display decreased melting points relative to wild-type. This Figure clearly highlights that the DSC distinguished between stable and less stable NprE variants, and is useful as a secondary screen. A general trend is observed between the thermal melting points of the variants and their stability in detergent. For example, the variants S66E, S199E, D220P/E, S129I/V are all winners in TIDE® and show an approximate 1° C. increase in thermal melting point relative to wild type NprE. This 1° C. increase in thermal melting point is small yet significant, as thermal stability typically requires multiple amino acid substitutions.

Figure 28:
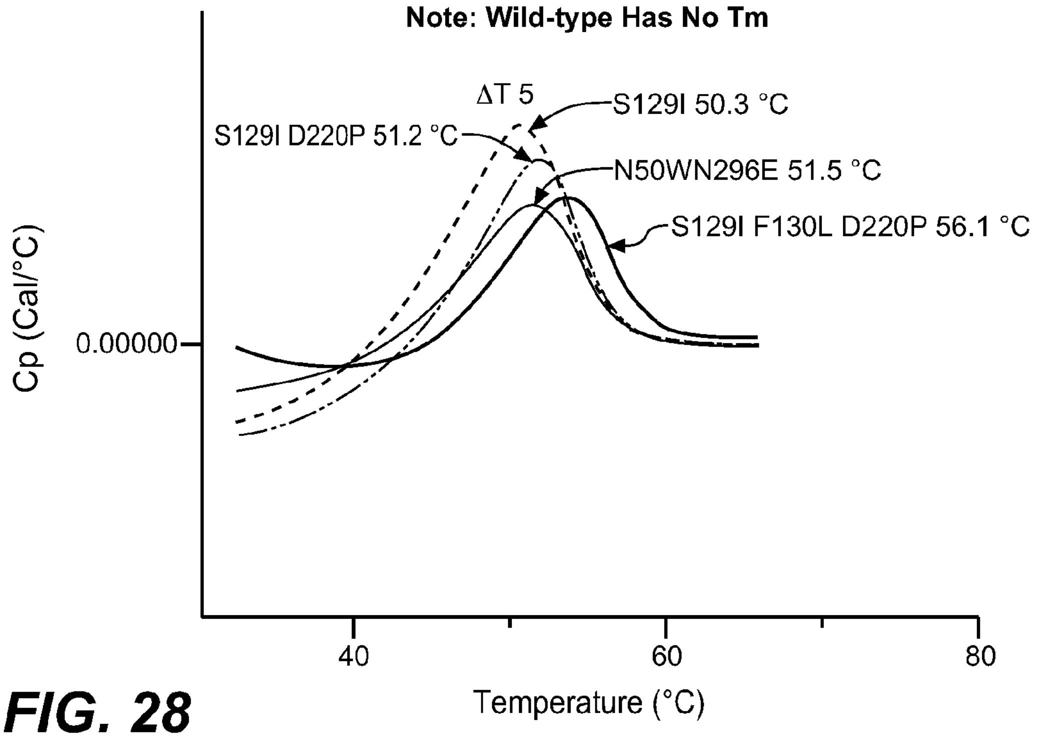
FIG. 28 provides a graph showing the results for DSC scans for 440 ppm NprE and variants in the presence of 130 mM citrate were obtained using the VP-Cap DSC (MicroCal™).

FIG. 28 shows the thermal unfolding of NprE variants that display a thermal unfolding profile in the presence of 130 mM citrate. Citrate is a detergent component that rapidly causes the autolysis of NprE, in the absence of calcium. For wild-type NprE, there is no thermal unfolding profile in the presence of citrate, which is consistent with a protein that is already unfolded or lacks a well-formed hydrophobic core. Mutants that display a thermal unfolding profile in the presence of citrate are included in Table 17. These variants have thermal melting points in the range of 47-56° C. The DSC scans in the presence of 130 mM citrate indicated variants that are more stable than wild-type NprE to citrate. For example, citrate-stable variants are show to contain either S129I or S129V and combinatorials containing either of these substitutions show a +5° C. increase in thermal melting point.

Figure 29:
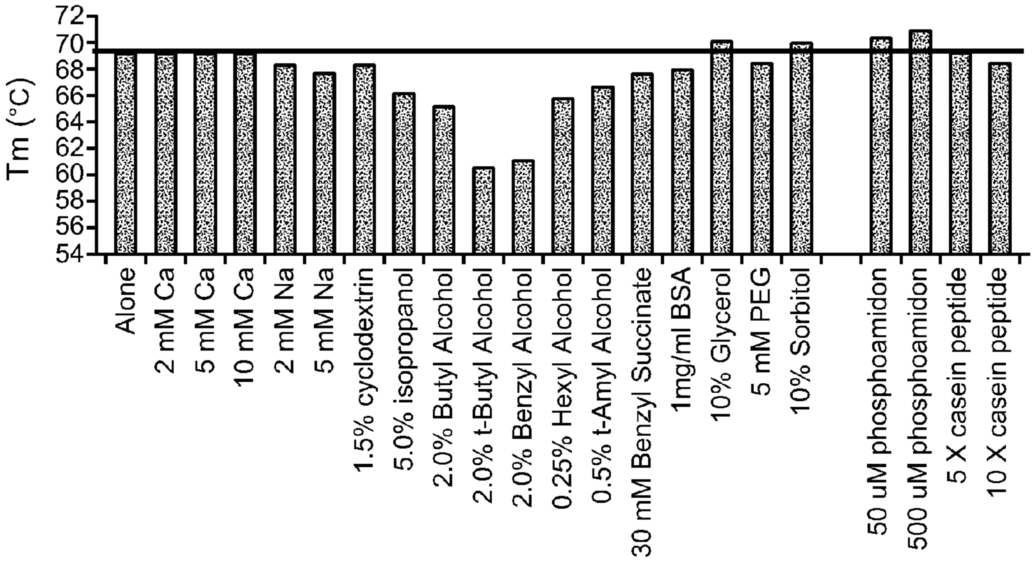
FIG. 29 provides a graph showing the thermal melting points for 440 ppm NprE in the presence of various additives and obtained using the VP-Cap DSC (MicroCal™). In this Figure, the horizontal line represents the Tm for wild-type NprE with no additives.

Effect of Additives on the Thermal Melting Points of NprE:

FIG. 29 shows the results of experiments including various additives. The buffer was 5 mM HEPES, pH 8.0. The samples were scanned from 20-100° C. using a scan rate of 200° C./hr. In this Figure, the horizontal line represents the Tm for wild-type NprE with no additive. In these experiments, the data showed little or no effect on the thermal melting point (Tm) of NprE in the presence of these reagents. The inclusion of an inhibitor of NprE activity, namely phosphoramidon, was shown to increase the Tm by approx. 1° C., suggesting that the inhibitor may impart some stabilization to NprE against the thermal unfolding process. None of the conditions above assisted in making the thermal unfolding process reversible. However, it is not intended that the present invention be limited to any particular mechanism.

Example 18

NprE Homologue Stability in TIDE® and Homolog BMI Wash Performance

Figure 30:
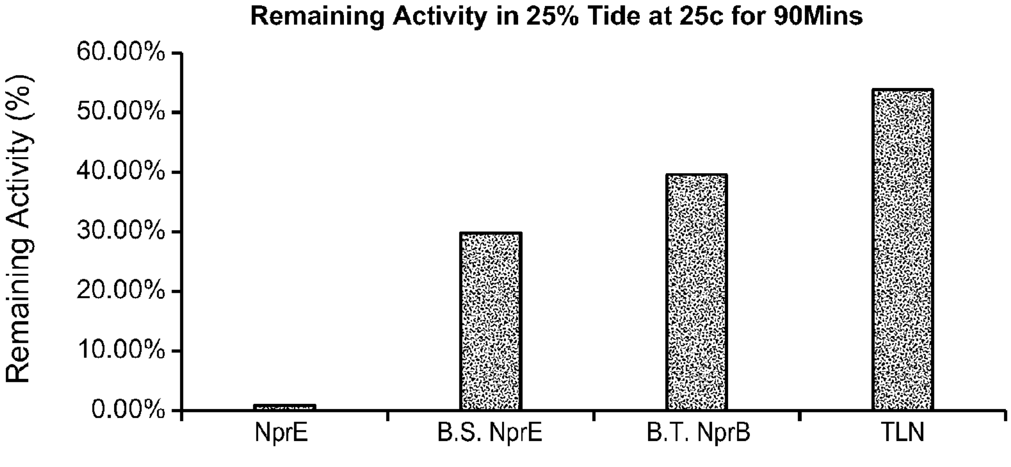
FIG. 30 provides a graph showing the remaining activity of nprE and nprE homologs in 25% TIDE® at 25° C., after 90 minutes.

In this Example, experiments conducted to assess the stability of nprE homologs in TIDE®, as well as the wash performance of these homologs are described. Purified NprE ("NprE"), *Bacillus subtilis* NprE (B.S. NprE), *Bacillus thuringiensis* NprB (B.T. NprB) and *Bacillus* thermoproteolyticus thermolysin (TLN) were incubated in 200 ul 25% tide in 10 mM HEPES, pH8 at 10 ug/ml at 25° C. for 90 mins. The initial activities and remaining activities were measured using the AGLA assay, as described above. Briefly, 10 ul of sample were added into 200 ul of AGLA buffer (50 mM MES, pH6.5, 0.005% TWEEN®-80, 2.5 mM $CaCl_2$), then 10 ul of diluted sample was added into 200 ul of AGLA substrate (2.4 mM Abz-AGLA-Nba in AGLA buffer). The excitation at 350 nm and emission at 415 nm were monitored for first 100 seconds, the initial slope was recorded as enzyme activity. The percent of remaining activity was calculated by dividing the remaining activity over initial activity. FIG. 30 provides a graph showing the remaining activity after 90 minutes.

Figure 31:
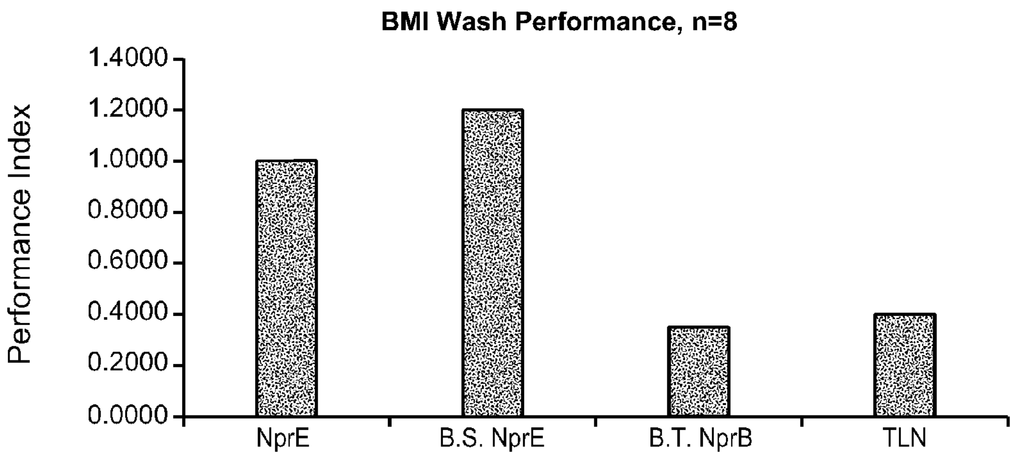
FIG. 31 provides a graph showing the BMI wash performance of nprE and nprE homologs.
Figure 32:
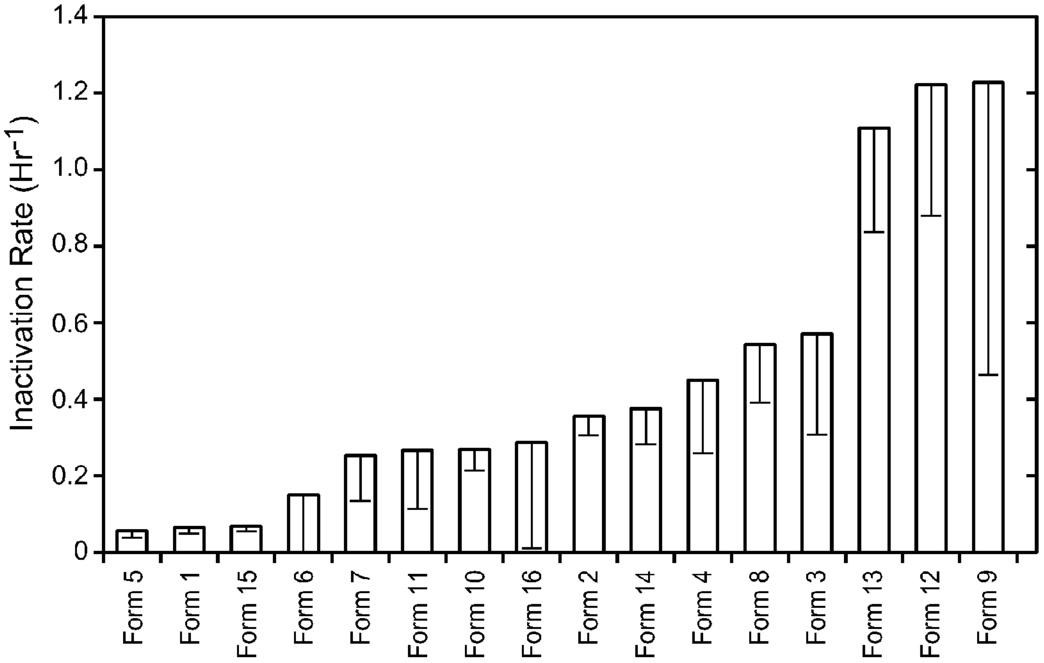
FIG. 32 provides a graph showing the results of NprE stability measurements in various formulation mixes.

To determine the wash performance of these homologues in TIDE®, one pre-washed BMI microswatch was first added into each well of a 96-well plate. Then, 190 ul of 1× compact TIDE® (780 ug/ml compact TIDE®, 5 mM HEPES, pH8, 6 gpg water hardness) were added. Then, 10 ul of purified NprE, *Bacillus subtilis* NprE, *Bacillus thuringiensis* NprB and *Bacillus thermoproteolyticus* thermolysin were added to the wells to produce a final enzyme concentration is 0.25 ug/ml. The plate was incubated at 25° C. for 30 mins with shaking at 1400 rpm on Thermomixer. At the end of incubation, 100 ul of supernatant were transferred into a new 96-well plate. The OD at 405 nm of supernatant was then measured. The supernatant OD was subtracted with the OD of a blank control without enzyme addition. The performance index was calculated by dividing the OD of each homologue to the OD of NprE. FIG. 31 provides a graph showing the BMI was performance of NprE, as well as the nprE homologs described herein.

Example 19

Metal Analysis of Wild-Type nprE and Variants

In this Example, experiments conducted to determine the zinc and calcium content of nprE and nprE variants are described. In these experiments, total trace metal analysis by inductively coupled plasma—mass spectrometry (ICPMS) and particle induced X-ray emission with a microfocused beam (micro-PIXE) were performed to confirm the zinc and calcium content of NprE. Overall, one zinc and two calcium ions are tightly bound.

All ICPMS and micro-PIXE samples were prepared in metal free buffer to remove any exogenous metal contaminants. Typically, 250 uL of 40 mg/mL NprE samples were buffer exchanged three times with 20 mM HEPES, pH 8.2 using YM-10 microdialysis apparatus. Metal free buffer was generated by passing the buffer through a column packed with Chelax 100 resin. The final protein concentration was determined using Bicinchoninic acid protein determination assay kit (BCA assay) from Sigma. ICPMS samples were analyzed at the West Coast Analytical Services, Inc. MicroPIXE samples were analyzed at the Ion Beam Analysis Laboratory.

Table 19-1 shows ICPMS metal analysis results for calcium and zinc ions from NprE wild type. Relative to protein concentration, two calcium ions and two zinc ions were found to be present in the sample.

TABLE 19-1

ICPMS Metal Analysis of Wild-Type NprE

| | Ca (ppm) | Zn (ppm) |
|---|---|---|
| ICPMS | 73.8 | 156 |
| Mol w (g/mol) | 40.08 | 65.37 |
| Protein (ppm) | 833 | 833 |
| Ratio/protein | 1.4 | 1.9 |

The MicroPIXE elemental composition analysis plot measured the metal contents relative to a protein internal standard. All peaks detected using Micro-PIXE were calculated relative to the sulfur peak arising from three methionines in the case of NprE. An observed large chloride ion peak was due to the presence of salt in buffer.

Table 18-2 shows the metal content determined by MicroPIXE, which indicates that in general, NprE contains two tightly bound calcium and one zinc ion per protein molecule. Wild type NprE showed 1 zinc ion with 2 calcium ions. It is contemplated that calcium ions may have shown a low occupancy rate due to preparation of the sample. S58D and T60D showed close to two zinc ions per protein indicating a possible extra zinc ion binding to the site. The double variant has two added cysteines adding the accuracy of the technique. However, it is not intended that the present invention be limited to any particular embodiment with a specific number of ions.

TABLE 19-2

Micro-PIXE Metal Determination Showing Ca and Zn Contents for NprE Native and Variants

| | #S | Ca/S | Ca/prot | Zn/S | Zn/prot | Ca/Zn |
|---|---|---|---|---|---|---|
| S58D | 3 | 0.72 | 2.2 | 0.52 | 1.6 | 1.4 |
| T60D | 3 | 0.68 | 2.0 | 0.57 | 1.7 | 1.2 |
| S58D.T60D | 5 | 0.41 | 2.1 | 0.22 | 1.1 | 1.9 |
| N46K | 3 | 0.59 | 1.8 | 0.42 | 1.3 | 1.4 |
| S23K | 3 | 0.62 | 1.9 | 0.33 | 1.0 | 1.9 |
| A221S | 3 | 0.76 | 2.3 | 0.5 | 1.5 | 1.5 |
| WT | 3 | 0.54 | 1.6 | 0.34 | 1.0 | 1.6 |

Consistent with other well-characterized calcium and zinc dependent neutral proteases such as thermolysin or thermolysin-like proteases (TLPs)(See e.g., Dahlquist et al., Biochem., 15:1103-1111 [1976]; Srpingman et al., (1995) Biochemistry 34, 15713-15720 [1995]; and Willenbrock et al., (1995) FEBS Lett. 358:189-192 [1995]), NprE was found to contain at least two tightly bound calcium ions and one zinc ion per molecule. A potential third calcium binding site is proposed but expected to be very weak. Since all samples were desalted to remove any exogenous metals, these weakly bounding calcium sites are expected to be unoccupied.

Example 20

Stabilizing NprE with Calcium Formate in TIDE® Compact HDL Detergent

In this Example, experiments conducted to develop means to stabilize NprE in TIDE® compact HDL detergent are described. In these experiments, means to stabilize NprE by increasing the calcium formate level at a fixed citrate concentration while lowering DTPA content in experimental TIDE® compact formulation ("TIDE® 2x") were investigated. A statistical design of experiments (DOE) methodology was used in order to simplify the experiments as well as data analyses. It was shown that DTPA present in TIDE® adversely affects NprE stability, while addition of calcium formate helps overcome the detrimental effect in the full strength TIDE® compact formulation.

A full central composite response surface model with duplicate center points was used as a DOE method. A total of 16 unique formulations varying four components were premade according to the composition variations listed in Table 19.1. LAS was varied from 0-6% (w/w) with DTPA (0-0.25%) and calcium-formate (0-0.2%) at a fixed concentration of citric acid (1.9%). All other components of the TIDE® detergent were held constant. The component concentration boundary conditions were determined based on phase stability of the various mixes. The protein stability tests were conducted with 780 ppm nprE in the full strength (~100%) formulation mixes and incubated at 32° C. Inactivation was measured up to 24 hours. All assays were done using red fluorescent labeled casein assay kit (Invitrogen) with 0.5 ppm protein concentration. Rates of NprE inactivation were measured in three independent experiments. DOE data were analyzed using DOE Fusion Pro (S-Matrix).

TABLE 20.1

Composition of the 16 TIDE ® Formulations Used for DOE Studies

| | HLAS | Citric acid | DTPA | Ca formate |
|---|---|---|---|---|
| Form 1 | 3 | 1.9 | 0 | 0.1 |
| Form 2 | 3 | 1.9 | 0.125 | 0.1 |
| Form 3 | 3 | 1.9 | 0.25 | 0.1 |
| Form 4 | 6 | 1.9 | 0.25 | 0.2 |
| Form 5 | 0 | 1.9 | 0 | 0.2 |
| Form 6 | 6 | 1.9 | 0 | 0.2 |
| Form 7 | 0 | 1.9 | 0.25 | 0.2 |
| Form 8 | 6 | 1.9 | 0.125 | 0.1 |
| Form 9 | 6 | 1.9 | 0.25 | 0 |
| Form 10 | 0 | 1.9 | 0.125 | 0.1 |
| Form 11 | 6 | 1.9 | 0 | 0 |
| Form 12 | 3 | 1.9 | 0.125 | 0 |
| Form 13 | 0 | 1.9 | 0.25 | 0 |
| Form 14 | 3 | 1.9 | 0.125 | 0.1 |
| Form 15 | 0 | 1.9 | 0 | 0 |
| Form 16 | 3 | 1.9 | 0.125 | 0.2 |

Table 20.2 and FIG. 31 show the results of NprE stability measurements in various formulation mixes. Average rates and the standard deviation were the averaged NprE inactivation rate ($hour^{-1}$) from three independent measurements. Qualitatively, formulations with low DTPA content with high calcium load tend to be more stable in the full strength compact TIDE®. As an example, Formulation #5, with no addition of DTPA and high calcium formate level showed the lowest inactivation rate, indicating high NprE stability. In contrast, Formulation #9, with high DTPA concentration with no added calcium formate showed lowest stability. In Table 20.2, the ranking is based on measured stability (i.e., averaged rates). Runs are from three independent stability experiments.

TABLE 20.2

NprE Inactivation Rates in 16 Formulation Mixes

| | Ranking | Run 1 | Run 2 | Run 3 | Average Rate ($hour^{-1}$) | Standard Deviation |
|---|---|---|---|---|---|---|
| Form 5 | 1 | 0.031 | 0.053 | 0.067 | 0.050 | 0.019 |
| Form 1 | 2 | 0.060 | 0.044 | 0.081 | 0.062 | 0.019 |
| Form 15 | 3 | 0.050 | 0.079 | 0.060 | 0.063 | 0.015 |
| Form 6 | 4 | 0.312 | 0.057 | 0.059 | 0.143 | 0.147 |
| Form 7 | 5 | 0.364 | 0.254 | 0.128 | 0.249 | 0.118 |
| Form 11 | 6 | 0.099 | 0.288 | 0.395 | 0.261 | 0.150 |
| Form 10 | 7 | 0.337 | 0.238 | 0.226 | 0.267 | 0.061 |
| Form 16 | 8 | 0.063 | 0.593 | 0.188 | 0.281 | 0.277 |
| Form 2 | 9 | 0.392 | 0.372 | 0.296 | 0.354 | 0.051 |
| Form 14 | 10 | 0.387 | 0.451 | 0.269 | 0.369 | 0.093 |
| Form 4 | 11 | 0.665 | 0.333 | 0.336 | 0.445 | 0.191 |
| Form 8 | 12 | 0.682 | 0.554 | 0.378 | 0.538 | 0.153 |
| Form 3 | 13 | 0.864 | 0.440 | 0.389 | 0.566 | 0.261 |
| Form 13 | 14 | 1.417 | 0.931 | 0.964 | 1.104 | 0.272 |
| Form 12 | 15 | 1.005 | 1.620 | 1.029 | 1.218 | 0.349 |
| Form 9 | 16 | 0.875 | 2.099 | 0.694 | 1.223 | 0.764 |

Figure 33A:
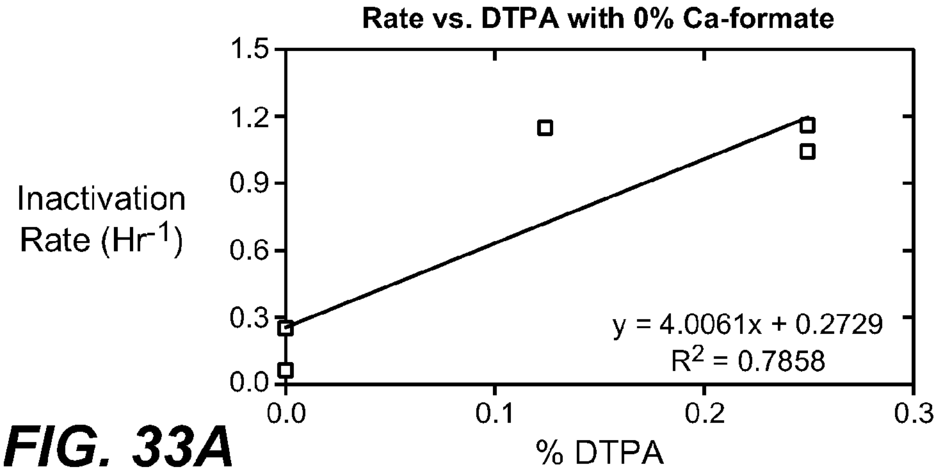
FIGS. 33A, 33B and 33C provide graphs (Panels A, B and C showing the rate of NprE inactivation with different % DTPA concentrations at a fixed calcium formate concentration.
Figure 33B:
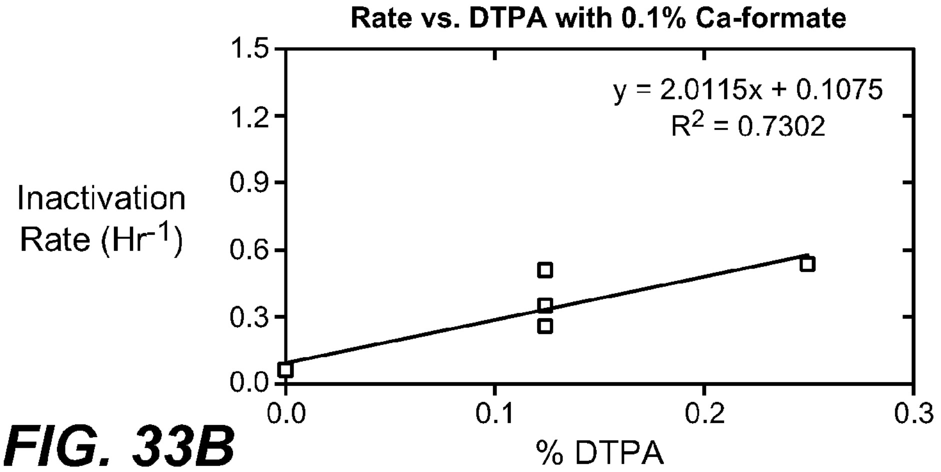
Figure 33C:
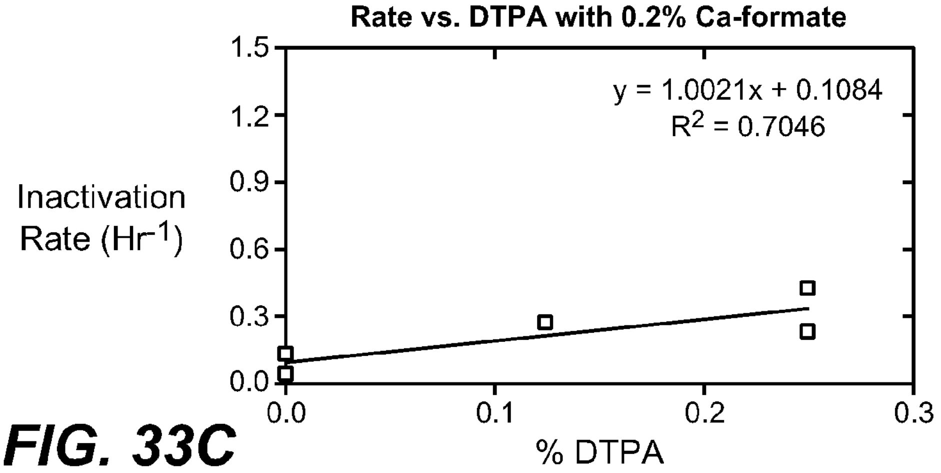

FIG. 33 shows NprE inactivation effects by DTPA at varying levels of fixed calcium formate concentration. Panel A shows rate of NprE inactivation by DTPA without any added calcium formate. The correlation shows that DTPA has significant detrimental effect. Panel B shows some decreased effect of DTPA with 0.1% calcium formate. Panel C shows significantly decreased effect of DTPA with 0.2% calcium formate.

Figure 34A:
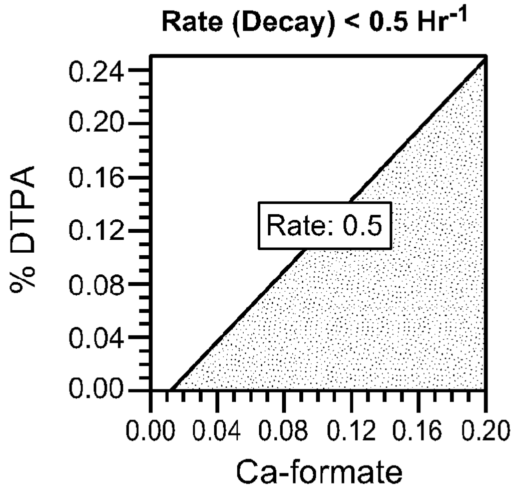
FIGS. 34A, 34B and 34C provide graphs (Panels A, B and C) showing the DOE analysis software generated prediction profiles of a DTPA and calcium formate composition based on response goal (decay rate).
Figure 34B:
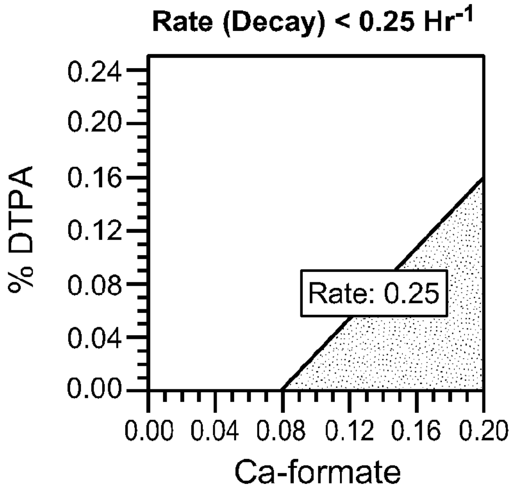
Figure 34C:
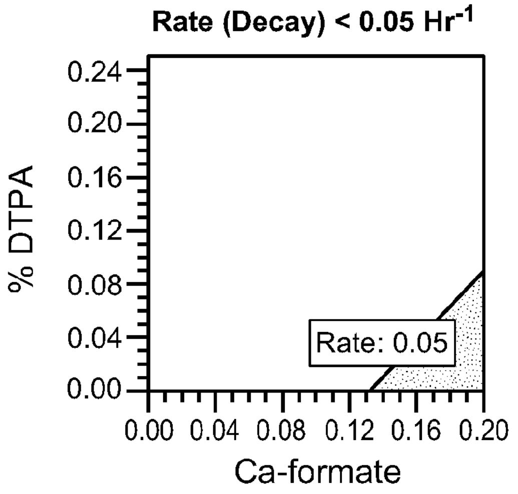

FIG. 34 shows DOE analysis software (Fusion Pro) generated prediction profile of DTPA and calcium formate composition based on response goal (decay rate) of less than 0.5 $hr^{-1}$ (Panel A), 0.25 $hr^{-1}$ (Panel B) and 0.05 $hr^{-1}$ (Panel C). The shaded areas indicate DTPA and calcium formate composition ratios that are predicted to show stability with decay rate below the set goal. For example, 0.16% calcium formate in the presence of 0.04% DTPA would provide NprE stability with decay rate of less than 0.25 $hour^{-1}$ as shown in Panel B of FIG. 34. On the other hand, 0.08% calcium formate cannot sustain NprE stability with decay rate of at least 0.25 $hour^{-1}$ in the presence of 0.16% DTPA.

Example 21

Identification of the Citrate-Induced Autolytic Sites for *B. amyloliquefaciens* Neutral Metalloprotease NprE In this Example, methods used to assess the citrate-induced autolysis of wild-type and recombinant variant nprE (e.g., *B. subtilis* variant) are described. In these experiments, autolysis of the neutral metalloprotease from *B. amyloliquefaciens* (natural and the recombinant variant expressed in *B. subtilis*) was induced using sodium citrate (Sigma). The autolysis process was controlled by performing the reaction at 4° C. in 25 mM MES, pH 6.5, buffer. In these experiments, the autolysis of 0.4 mg/ml NprE was optimized by varying either: (a) the time of incubation (10-100 minutes) in 10 mM citrate; or (b) the citrate concentration (10-100 mM) over 100 minutes. A control of neutral metalloprotease diluted in buffer alone (i.e., no citrate) was incubated under similar conditions. The autolytic reactions were terminated by addition of an equal volume of 1N HCl, the samples were precipitated using TCA and the pellet was washed and dried using acetone. The resultant pellet was resuspended in 20 uL buffer, pH 6.5, and 4× LDS sample buffer (NuPage, Invitrogen)

The autolytic fragments were resolved by 10% (w/v) SDS-PAGE and electroblotted onto a PVDF membrane. The first 10 amino acid residues were sequenced by Edman degradation (Argo Bioanalytica). The partial amino acid sequences of the autolytic fragments were determined using trypsin in-gel digestion and analyzed using LCQ-MS (Agilent). The in-gel digestion process involved macerating the gel piece that contained the protein, removal of the Coomassie blue stain followed by re-hydration of the gel pieces in 25 mM $NH_4CO_3$ containing 2 M urea. Trypsin was added to the re-hydrated gel pieces for approx. 6 hours at 37° C. Following the digestion, the peptides were extracted using acetonitrile and TCA. The peptides were separated on a C4-hydrophobic column (Vydac) using an acetonitrile-water gradient. The resultant peptide maps were searched with the SEQUEST® database search program against a database containing Genencor enzymes.

The amino acid sequences of the first 10 amino acids of each of the fragments were compared with the known amino acid sequence for *B. amyloliquefaciens* NprE. This enabled the identification of the amino acid at the N-termini and hence the cleavage site(s).

The generation of the citrate-induced fragments and their resolution was shown on 10% SDS-PAGE. The sizes of the fragments were identified using a standard molecular weight marker from Invitrogen. In the presence of 10 mM citrate, two fragments in addition to remaining intact NprE were observed over the 100 minute time range. The two fragments formed at the low citrate concentration were found to be 24 kDa and 9 kDa in size. The intact nprE is 32 kDa. The 100-minute time range results in a good proportion of cleaved protein (i.e., the primary autolysis fragments). No additional fragments were observed or detected under these conditions. A study over 100 minutes in the presence of increasing citrate was performed to obtain the secondary autolytic fragments. In this experiment, when concentrations between 10-30 mM citrate were used, the two fragments described above were observed. At 40 mM citrate, less of the larger 24-kDa fragments were apparent however a 15-kDa fragment was also apparent. Between 50-100 mM citrate, the 24 kDa fragment and the 9-kDa fragments were no longer detected but three other fragments, of sizes 21 kDa, 15 kDa and 11 kDa, were observed.

The identity of the N-termini of the 24 kDa, 9 kDa (first two fragments), and the 21 kDa, 15 kDa and 11 kDa (the next autolytic fragments) were determined using Edman degradation (Argo Bioanalytica).

TABLE 21

N-Terminal Sequence of Fragments

| Sample Name | N-terminal Amino acid sequence (5'-3') (SEQ ID NO:) | | Corresponding molecule weight on SDS-PAGE (kDa) |
|---|---|---|---|
| Band A1 | AATTGTGTTL | (SEQ ID NO: 215) | 24 |
| Band A2 | DAGDYGGVHT | (SEQ ID NO: 216) | 9 |
| | AGDYGGVHTN | (SEQ ID NO: 217) | |
| | GDYGGVHTN | (SEQ ID NO: 218) | |
| Band A3 | AATTGTGTTL | (SEQ ID NO: 219) | 21 |
| Band A4 | AATTGTGTTL | (SEQ ID NO: 220) | 15 |
| Band A5 | LSNPTKYGQP | (SEQ ID NO: 221) | 11 |

Bands A1, A 3 and A4 have the native N-terminal sequence that matches the N-terminus for the intact NprE. The sequencing report for Band A2 showed three fragments where the least intense sequence appeared to be identical to the more intense sequence, except that it was two residues and one residue shorter than the more intense sequences, respectively. This was consistent with a fraying of that particular protein fragment. The pattern and the sizes of the gel fragments suggest that the 15 kDa (Band A4) may be derived from the 21-kDa fragment (Band A3) and hence the C-terminus is deduced to be at or near position 198. However, it is not intended that the present invention be limited to this particular embodiment.

FIG. 35 provides the amino acid sequences for the various fragments (1-5 or A1-5 for N-terminal sequencing purposes). Fragment 1 (A1) has the N-terminal residues equivalent to that for the intact native protein (SEQ ID NO:222), fragment 2 (Ad2) N-terminus starts at or near D220 (SEQ ID NO:223). The following two amino acid residues (A221 and G222) are also highlighted because this fragment was identified as being frayed. Fragment 3 (A3) (SEQ ID NO:224) and fragment 4 (A4) (SEQ ID NO:225) have the N-terminus of the intact protein, and fragment 5 (A5) (SEQ ID NO:226) starts at L198. The C-terminus of fragment 4 is likely to be at or near M138 (based on the size difference between A3 and A4). The corresponding fragment for A3 was not detected.

Trypsin digestion followed by LCQ-MS of the peptide maps for fragments 1 through 5 positively identified several amino acid peptides within the respective fragments. These are highlighted in FIG. 35. The LCQ-MS provided a positive control for the identity of the fragments.

Based on the N-terminal and LCQ-MS analysis of the cleavage fragments, primary cleavage sites were identified at amino acid positions D220, A221, G222, M138, and L198. These sites were targeted using site-directed mutagenesis and site-evaluation libraries of D220, A221, G222, L198, and M138, D139 were created. The mutant proteins were screened for increasing stability in detergent and for BMI-wash performance, as indicated herein. In some instances, the amino acids alongside these sites were also selected for protein engineering, in order to ensure that the clip site was indeed targeted.

The protein engineering results clearly indicated that amino acid substitutions of either Pro or Glu at D220 generated an NprE molecule that is more stable in detergent. In addition, additional stability was afforded to the NprE molecule by replacing G222 with Cys, and M138 with either Ile or Leu. In general, these specific amino acid substitutions provided the NprE with detergent stability advantages without the BMI-wash performance being compromised. Thus, these experiments provide important mapping data for the citrate-induced autolysis sites, facilitating the identification of key amino acid residues that alter and affect the overall stability of NprE. Citrate (a builder added to detergent matrices) destabilizes and autolyses NprE and is suggested to do so by chelating the essential calcium-bound atoms. The application of NprE in extreme detergent conditions requires that a more stable NprE molecule be used in these settings. In these experiments, substitutions of one or more of the autolytic sites of NprE have resulted in a more detergent-stable nprE molecule for use in these extreme detergents.

Example 22

Liquid Laundry Detergent Compositions

In this Example, various formulations for liquid laundry detergent compositions are provided. The following liquid laundry detergent compositions of the present invention are prepared:

| | Formulations | | | | |
|---|---|---|---|---|---|
| Compound | I | II | III | IV | V |
| LAS | 24.0 | 32.0 | 6.0 | 3.0 | 6.0 |
| $NaC_{16}$-$C_{17}$ HSAS | — | — | — | 5.0 | — |
| $C_{12}$-$C_{15}$ $AE_{1.8}S$ | — | — | 8.0 | 7.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | — | 17.0 | — | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | | — |
| Cellulase | — | — | 0.0002 | | 0.0001 |
| Lipase | 0.1 | — | 0.1 | — | 0.1 |
| nprE | 0.05 | 0.3 | — | 0.5 | 0.2 |
| PMN | — | — | 0.08 | — | — |
| Protease A | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

#1: Add 1N HCl aq. soln to adjust the neat pH of the formula in the range from about 3 to about 5.

The pH of Examples above 22(I)-(II) is about 5 to about 7, and of 22(III)-(V) is about 7.5 to about 8.5.

Example 23

Hand Dish Liquid Detergent Compositions

In this Example, various hand dish liquid detergent formulations are provided. The following hand dish liquid detergent compositions of the present invention:

| | Formulations | | | | | |
|---|---|---|---|---|---|---|
| Compound | I | II | III | IV | V | VI |
| $C_{12}$-$C_{15}$ $AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |

-continued

| Compound | Formulations | | | | | |
|---|---|---|---|---|---|---|
| | I | II | III | IV | V | VI |
| Diamine | 1.0 | 5.0 | 7.0 | 1.0 | 5.0 | 7.0 |
| $MgCl_2$ | 0.25 | — | — | 1.0 | — | — |
| nprE | 0.02 | 0.01 | — | 0.01 | — | 0.05 |
| PMN | — | — | 0.03 | — | 0.02 | — |
| Protease A | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples 23(I)-(VI) is about 8 to about 11

Example 24

Liquid Automatic Dishwashing Detergent Compositions

In this Example, various liquid automatic dishwashing detergent formulations are provided. The following hand dish liquid detergent compositions of the present invention:

| Compound | Formulations | | | | |
|---|---|---|---|---|---|
| | I | II | III | IV | V |
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| nprE | 0.1 | 0.03 | — | 0.03 | — |
| PMN | — | — | 0.05 | — | 0.06 |
| Protease B | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 25

Granular and/or Tablet Laundry Compositions

This Example provides various formulations for granular and/or tablet laundry detergents. The following laundry compositions of present invention, which may be in the form of granules or tablet, are prepared.

| Compound | Formulations | | | | |
|---|---|---|---|---|---|
| Base Product | I | II | III | IV | V |
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |

-continued

| Compound | Formulations | | | | |
|---|---|---|---|---|---|
| Base Product | I | II | III | IV | V |
| MA/AA | 2.0 | 2.0 | 2.0 | — | — |
| AA | — | — | — | — | 4.0 |
| 3Na Citrate $2H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE | 0.03 | — | 0.1 | 0.06 | — |
| PMN | — | 0.05 | — | — | 0.1 |
| Protease B | — | 0.01 | — | — | — |
| Protease C | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/$MgSO_4$/PVPVI/suds suppressor/high molecular PEG/clay.

Example 26

Liquid Laundry Detergents

This Example provides various formulations for liquid laundry detergents. The following liquid laundry detergent formulations of the present invention are prepared:

| Compound | Formulations | | | | | |
|---|---|---|---|---|---|---|
| | I | I | II | III | IV | V |
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}$ S | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethan-olamine | 3.0 | 3.0 | 1.5 | 1.0 | 2.5 | 1.0 |
| TEPAE | 2.0 | 2.0 | — | 1.0 | 1.0 | 1.0 |
| nprE | 0.03 | 0.05 | — | 0.03 | — | 0.02 |
| PMN | — | — | 0.01 | — | 0.08 | — |
| Protease A | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | | — | — |

-continued

| | Formulations | | | | | |
|---|---|---|---|---|---|---|
| Compound | I | I | II | III | IV | V |
| Aldose Oxidase | 0.05 | — | — | 0.05 | — | 0.02 |
| Galactose oxidase | — | 0.04 | | | | |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 27

High Density Dishwashing Detergents

This Example provides various formulations for high density dishwashing detergents. The following compact high density dishwashing detergents of the present invention are prepared:

| | Formulations | | | | | |
|---|---|---|---|---|---|---|
| Compound | I | II | III | IV | V | VI |
| STPP | — | 45.0 | 45.0 | — | — | 40.0 |
| 3Na Citrate $2H_2O$ | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE | 0.072 | 0.053 | — | 0.026 | — | 0.01 |
| PMN | — | — | 0.053 | — | 0.059 | — |
| Protease B | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarb-oxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/$MgSO_4$/PVPVI/suds suppressor/high molecular PEG/clay.

The pH of Examples 27(1) through (VI) is from about 9.6 to about 11.3.

Example 28

Tablet Detergent Compositions

This Example provides various tablet detergent formulations. The following tablet detergent compositions of the present invention are prepared by compression of a granular dishwashing detergent composition at a pressure of 13 $KN/cm^2$ using a standard 12 head rotary press:

| | Formulations | | | | | | | |
|---|---|---|---|---|---|---|---|---|
| Compound | I | II | III | IV | V | VI | VII | VIII |
| STPP | — | 48.8 | 44.7 | 38.2 | — | 42.4 | 46.1 | 46.0 |
| 3Na Citrate $2H_2O$ | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B | 0.01 | — | — | — | — | — | — | — |
| Protease C | — | — | — | — | — | 0.01 | — | — |
| nprE | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |

-continued

| | Formulations | | | | | | | |
|---|---|---|---|---|---|---|---|---|
| Compound | I | II | III | IV | V | VI | VII | VIII |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/$MgSO_4$/PVPVI/suds suppressor/high molecular PEG/clay.

The pH of Examples 28(1) through 28(VII) is from about 10 to about 11.5; pH of 15(VIII) is from 8-10. The tablet weight of Examples 28(1) through 28(VIII) is from about 20 grams to about 30 grams.

Example 29

Liquid Hard Surface Cleaning Detergents

This Example provides various formulations for liquid hard surface cleaning detergents. The following liquid hard surface cleaning detergent compositions of the present invention are prepared:

| | Formulations | | | | | | |
|---|---|---|---|---|---|---|---|
| Compound | I | II | III | IV | V | VI | VII |
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate $2H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE | 0.07 | — | 0.08 | 0.03 | — | 0.01 | 0.04 |
| PMN | — | 0.05 | — | — | 0.06 | — | — |
| Protease B | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples 29(1) through (VII) is from about 7.4 to about 9.5.

While particular embodiments of the present invention have been illustrated and described, it will be apparent to those skilled in the art that various other changes and modifications can be made without departing from the spirit and scope of the invention. It is therefore intended to cover in the appended claims all such changes and modifications that are within the scope of this invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. An isolated *Bacillus* neutral metalloprotease variant comprising multiple mutations selected from F130L/M138L, wherein said variant has at least 95% sequence identity to SEQ ID No: 18, wherein the variant has improved storage stability compared to the parental polypeptide.

2. The isolated neutral metalloprotease variant of claim 1, wherein said variant further comprises at least one substitution at a position selected from at least one position equivalent to positions 1, 3, 4, 5, 6, 11, 12, 13, 14, 16, 21, 23, 24, 25, 31, 32, 33, 35, 36, 38, 44, 45, 46, 47, 48, 49, 50, 51, 54, 55, 58, 59, 60, 61, 62, 63, 65, 66, 69, 70, 76, 85, 86, 87, 88, 90, 91, 92, 96, 97, 98, 99, 100, 102, 109, 110, 111, 112, 113, 115, 117, 119, 127, 128, 129, 132, 135, 136, 137, 139, 140, 146, 148, 151, 152, 153, 154, 155, 157, 158, 159, 161, 162, 169, 173, 178, 179, 180, 181, 183, 184, 186, 190, 191, 192, 196, 198, 199, 200, 202, 203, 204, 205, 210, 211, 214, 215, 216, 217, 218, 219, 220, 221, 222, 223, 224, 228, 229, 237, 239, 240, 243, 244, 245, 248, 252, 253, 260, 261, 263, 264, 265, 267, 269, 270, 273, 277, 280, 282, 283, 284, 285, 286, 288, 289, 290, 292, 293, 296, 297, and 299, of a neutral metalloprotease comprising the amino acid sequence set forth in SEQ ID NO:18.

3. The isolated variant neutral metalloprotease of claim 2, wherein said variant comprises at least one mutation selected from T004C, T004E, T004H, T004I, T004K, T004L, T004M, T004N, T004P, T004R, T004S, T004V, T004W, T004Y, G012D, G012E, G012I, G012K, G012L, G012M, G012Q, G012R, G012T, G012V, G012W, K013A, K013C, K013D, K013E, K013F, K013G, K013H, K013I, K013L, K013M, K013N, K013Q, K013S, K013T, K013V, K013Y, T014F, T014G, T014H, T014I, T014K, T014L, T014M, T014P, T014Q, T014R, T014S, T014V, T014W, T014Y, S023A, S023D, S023F, S023G, S023I, S023K, S023L, S023M, S023N, S023P, S023Q, S023R, S023S, S023T, S023V, S023W, S023Y, G024A, G024D, G024F, G024G, G024H, G024I, G024K, G024L, G024M, G024N, G024P, G024R, G024S, G024T, G024V, G024W, G024Y, K033H, Q045C, Q045D, Q045E, Q045F, Q045H, Q045I, Q045K, Q045L, Q045M, Q045N, Q045P, Q045R, Q045T, Q045W, N046A, N046C, N046E, N046F, N046G, N046H, N046I, N046K, N046L, N046M, N046P, N046Q, N046R, N046S, N046T, N046V, N046W, N046Y, R047E, R047K, R047L, R047M, R47Q, R047S, R047T, Y049A, Y049C, Y049D, Y049E, Y049F, Y049H, Y049I, Y049K, Y049L, Y049N, Y049R, Y049S, Y049T, Y049V, Y049W, N050D, N050F, N050G, N050H, N050I, N050K, N050L, N050M, N050P, N050Q, N050R, N050W, N050Y, T054C, T054D, T054E, T054F, T054G, T054H, T054I T054K, T054L, T054M, T054N, T054P, T054Q, T054R, T054S, T054V, T054W, T054Y, S058D, S058H, S058I, S058L, S058N, S058P, S058Q, T059A, T059C, T059E, T059G, T059H, T059I, T059K, T059L T059M, T059N, T059P, T059Q, T059R, T059S, T059V, T059W, T060D, T060F, T060I, T060K, T060L, T060N, T060Q, T060R, T060V, T060W, T060Y, T065C, T065E, T065F, T065H, T065I, T065K, T065L, T065M, T065P, T065Q, T065R, T065V, T065Y, S066C, S066D, S066E, S066F, S066H, S066I, S066K, S066L, S066N, S066P, S066Q, S066R, S066T, S066V, S066W, S066Y, Q087A, Q087D, Q087E, Q087H, Q087I, Q087K, Q087L, Q087M, Q087N, Q087R, Q087S, Q087T, Q087V, Q087W, N090C, N090D, N090E, N090F, N090G, N090H, N090K, N090L, N090R, N090T, N096G, N096H, N096K, N096R, K097H, K097Q, K097W, K100A, K100D, K100E, K100F, K100H, K100N, K100P, K100Q, K100R, K100S, K100V, K100Y, R110A, R110C, R110E, R110H, R110K, R110L, R110M, R110N, R110Q, R110S, R110Y, D119E, D119H, D119I, D119L, D119Q, D119R, D119S, D119T, D119V, D119W, G128C, G128F, G128H, G128K, G128L, G128M, G128N, G128Q, G128R, G128W, G128Y, S129A, S129C, S129D, S129F, S129G, S129H, S129I, S129K, S129L, S129M, S129Q, S129R, S129T, S129V, S129W, S129Y, S135P, G136I, G136L, G136P, G136V, G136W, G136Y, S137A, D139A, D139C, D139E, D139G, D139H, D139I, D139K, D139L, D139M, D139P, D139R, D139S, D139V, D139W, D139Y, V140C, Q151I, E152A, E152C, E152D, E152F, E152G, E152H, E152L, E152M, E152N, E152R, E152S, E152W, N155D, N155K, N155Q, N155R, D178A, D178C, D178G, D178H, D178K, D178L, D178M, D178N, D178P, D178Q, D178R, D178S, D178T, D178V, D178W, D178Y, T179A, T179F, T179H, T179I, T179K, T179L, T179M, T179N, T179P, T179Q, T179R, T179S, T179V, T179W, T179Y, E186A, E186C, E186D, E186G, E186H, E186K, E186L, E186M, E186N, E186P, E186Q, E186R, E186S, E186T, E186V, E186W, E186Y, V190H, V190I, V190K, V190L, V190Q, V190R, S191F, S191G, S191H, S191I, S191K, S191L, S191N, S191Q, S191R, S191W, L198M, L198V, S199C, S199D, S199E, S199F, S199I, S199K, S199L, S199N, S199Q, S199R, S199V, Y204H, Y204T, G205F, G205H, G205L, G205M, G205N, G205R, G205S, G205Y, K211A, K211C, K211D, K211G, K211M, K211N, K211Q, K211R, K211S, K211T, K211V, K214A, K214C, K214E, K214I, K214L, K214M, K214N, K214Q, K214R, K214S, K214V, L216A, L216C, L216F, L216H, L216Q, L216R, L216S, L216Y, N218K, N218P, T219D, D220A, D220E, D220H, D220K, D220N, D220P, A221D, A221E, A221F, A221I, A221K, A221L, A221M, A221N, A221S, A221V, A221Y, G222C, G222H, G222N, G222R, Y224F, Y224H, Y224N, Y224R, T243C, T243G, T243H, T243I, T243K, T243L, T243Q, T243R, T243W, T243Y, K244A, K244C, K244D, K244E, K244F, K244G, K244L, K244M, K244N, K244Q, K244S, K244T, K244V, K244W, K244Y, V260A, V260D, V260E, V260G, V260H, V260I, V260K, V260L, V260M, V260P, V260Q, V260R V260S, V260T, V260W, V260Y, Y261C, Y261F, Y261I, Y261L, T263E, T263F, T263H, T263I, T263L, T263M, T263Q, T263V, T263W, T263Y, S265A, S265C, S265D, S265E, S265K, S265N, S265P, S265Q, S265R, S265T, S265V, S265W, K269E, K269F, K269G, K269H, K269I, K269L, K269M, K269N, K269P, K269Q, K269S, K269T, K269V, K269W, K269Y, A273C, A273D, A273H, A273I, A273K, A273L, A273N, A273Q, A273R, A273Y, R280A, R280C, R280D, R280E, R280F, R280G, R280H, R280K, R280L, R280M, R280S, R280T, R280V, R280W, R280Y, L282F, L282G, L282H, L282I, L282K, L282M, L282N, L282Q, L282R, L282V, L282Y, S285A, S285C, S285D, S285E, S285K, S285P, S285Q, S285R, S285W, Q286A, Q286D, Q286E, Q286K, Q286P, Q286R, A289C, A289D, A289E, A289K, A289L, A289R, A293C, A293R, N296C, N296D, N296E, N296K, N296R, N296V, A297C, A297K, A297N, A297Q, A297R, and G299N.

4. The isolated variant neutral metalloprotease of claim 1, wherein said variant further comprises multiple mutations selected from S023W/G024M, T004V/S023W/G024W, S023W/G024Y/A288V, T004L/S023W/G024Y, N046Q/N050F/T054L, N050Y/T059R/S129Q, S023W/G024W, A273H/S285P/E292G, S023Y/G024Y, S023Y/G024W, T004S/S023Y/G024W, N046Q/T054K, S023W/G024Y, T004V/S023W, T059K/S066N, N046Q/N050W/T054H/T153A, T004V/S023W/G024Y, L282M/Q286P/A289R, N046Q/R047K/N050Y/T054K, L044Q/T263W/S285R, T004L/S023W/G024W, R047K/N050F/T054K, A273H/S285R, N050Y/T059K/S066Q, T054K/Q192K, N046Q/N050W, L282M/Q286K, T059K/S066Q, T004S/S023W, L282M/Q286R/A289R/K011N, L282M/A289R, N046Q/N050W/T054H, T059K/S129Q, T004S/S023N/G024Y/F210L, T004V/S023W/G024M/A289V, L282M/Q286K/A289R/S132T, N050W/T054H, L282M/Q286R, L282F/Q286K/A289R, T059R/S066Q, R047K/N050W/T054H, S265P/L282M/Q286K/A289R, L282M/Q286R/T229S, L282F/Q286K, T263W/S285R, S265P/L282M/Q286K, T263H/A273H/S285R, T059R/S129V, S032T/T263H/A273H/S285R, T059R/S066Q/S129Q, T004S/G024W, T004V/S023W/G024M, T059K/S066Q/S129Q, L282M/Q286K/A289R/I253V, T004V/S023Y/G024W, T059R/S066N/S129Q, N050F/T054L, T004S/S023N/G024W, T059R/S066N, T059R/S066N/S129V, Q286R/A289R, N046Q/R047K/N050F/T054K, S265P/L282M/Q286P/A289R, S265P/L282M/Q286R/A289R Q062K/S066Q/S129I, S023N/G024W, N046Q/R047K/N050W/T054H, R047K/T054K, T004L/G024W, T014M/T059R/S129V, T059R/S066Q/N092S/S129I, R047K/N050W/T054K, T004V/G024W, N047K/N050F/T054K, S265P/L282F/Q286K/N061Y, L282F/Q286K/E159V, T004V/S023Y/G024M, S265P/L282F/A289R/T065S, T059K/F063L/S066N/S129V, T004L/S023W, N050F/T054H, T059R/S066Q/S129V, V190I/D220E/S265W/L282F, T004S/S023Y/G024M, T004L/S023N/G024Y, T059K/S066N/S129I, T059R/S066N/S129I, L282M/Q286R/A289R/P162S, N046Q/N050F/T179N, T059K/Y082C/S129V, T059K/S129I, N050Y/T054K, T059K/S066Q/V102A/S129Q, T059R/S066Q/S129I, T059W/S066N/S129V/S290R, T059R/S129I, T059K/S066Q/S129I, T059K/S066Q/S129V, S265P/L282M/Q286R/A289R/T202S/K203N, T004V/S023N/G024W, S265P/Q286K, S265P/L282F/A289R, D220P/S265W, L055F/T059W/S129V, T059R/S129Q/S191R, N050W/T054K, T004S/S023W/G024M, R047K/N050F/T054H, T059K/S066N/K088E, T059K/S066Q/S129I/V291L, L282M/Q286R/A289R, T059R/S066N/F085S/S129I, L282F/Q286P/A289R, L282F/Q286R/A289R, G099D/S265P/L282F/Q286K/A289R, N046Q/N050F, N050Y/T059W/S066N/S129V, T009I/D220P/S265N, V190F/D220P/S265W, N157Y/T263W/A273H/S285R, T263W/A273H/S285R, T263W/S285W, T004V/S023Y, N046Q/R047K/N050W, N050W/T054L, N200Y/S265P/L282F/Q286P/A289R, T059R/S066Q/P264Q, T004V/G024Y, T004L/G024Y, N050Y/S191I, N050Y/T054L, T004L/S023W/G024Y/N155K, F169I/L282F/Q286R/A289R, L282M/Q286K/A289R, N046Q/R047K/N050Y/T054H, T004V/G024M, N050Y/T059W/S066Q/S129V, S023N/G024Y, T054H/P162Q, T004S/S023W/G024Y, N050Y/T054H, L282F/Q286R/A289R/F169I, R047K/N050W, V190F/D220P, L282M/F173Y, T004L/S023Y, N050W/A288D, V190I/D220P/S265Q, S265P/L282F/Q286P/A289R, S265P/L282F/Q286R/A289R, N046Q/N050Y/T054K, T059W/S066Q, T263W/A273H/S285W T263W/A273H/S285P, S023Y/G024M, T004L/S023N/G024W, T004V/S023N/G024Y, T059W/S066N/S129Q, T004S/S023Y, T004S/S023N/G024M, T059W/S066N/A070T, T059W/S066Q/S129Q, T263W/A273H, A273H/285P, N046Q/R047K/N050Y/T054L, N046Q/R047K/N050Y, R047K/N050Y, T263H/S285W, R047K/N050F, N046Q/R047K/N050F/T054H, S023N/G024M, T004S/G024Y, R047K/N050Y/T054H, T059W/S066N/S129I, R047K/T054L, T004S/S023W/G024W, D220P/S265N, T004S/G024M, T004V/S023N, N046Q/N050F/T054K, N046Q/N050Y/T054H, Q062H/S066Q/S129Q, T059W/S129Q, T059W/S129V, N050F/T054K, R047K/N050F/T054L, V190I/D220P/S265W, N112I/T263H/A273H/S285R, T059W/S066N/S129V, T059W/S066Q/S129I, T059W/S129I, T263W/S285P, V190I/D220P, A289V/T263H/A273H, T263H/A273H/S285P, N90S/A273H/S285P, R047K/N050Y/T054L, T004S/S023N, T059R/S129Q, N046Q/R047K/T054H, T059W/S066Q/S129V, E152W/T179P, N050Y/S066Q/S129V, T202S/T263W/A273H, T263W/A273H/S285P, N046Q/R047K, N046Q/T054H/F176L, T004L/G024M, T004S/L282M, T263H/A273H, T263H/A273H/S285W, T004L/S023Y/G024M, L282F/Q286P, T004V/S023Y/G024Y, V190F/S265W, V190F/D220E/S265W, N046Q/N050F/T054H, N157Y/S285W, T004F/S023Y/G024M, T004V/S023N/G024M, L198I/D220E/S265Q, N046Q/N050Y/T054K/A154T, S016L/D220E/S265W, D220E/S265W, D220E/A237S/S265W, S066Q/S129Q, V190F/D220E/S265Q/T267I, L282M/F173Y/T219S, E152F/T179P, V190I/S265W, T059W/S066Q/A070T/S129I, V190F/D220E/S265N, V190F/S265N, and N046Q/N050Y.

5. The isolated variant neutral metalloprotease of claim 1, wherein said variant further comprises multiple mutations selected from V190I/D220P, V190I/D220P/S265Q, V190L/D220E, V190I/D220E/S265Q, V190I/D220E/S265W/L282F, V190L/D220E/S265Q, V190I/D220E/S265W, V190L/D220E/S265N, T059R/S066Q/S129I, V190I/D220E/S265N, V190L/D220E/S265W, V190I/D220E, T059W/S066N/S129V, T059K/S066Q/S129V, T059K/Y082C/S129V, T059R/S066N/S129I, S066Q/S129V, T059R/S066Q/S129V, T059R/S129I, N050Y/T059W/S066N/S129V, D220P/S265N, S066Q/S129I, T059W/S066Q/S129V, T059K/S066Q/S129I, T059R/S129V, N050Y/S066Q/S129V, T059W/S066Q/S129I, N050Y/T059W/S066Q/S129V, T059K/S129I, D220P/S265W, S066N/S129I, T059R/S066N/S129V, T059R/S066Q/N092S/S129I, S066N/S129V, D220E/S265Q, T059W/S129V, S265P/L282M/Q286R/A289R, S265P/L282F/Q286R/A289R, T059W/S066N/S129I, V190I/D220P/S265W, Q062K/S066Q/S129I, T059K/S066N/S129I, E152H/T179P, S265P/L282M/Q286K/A289R, T263W/A273H/S285R, D220E/S265N, T059W/S129I, D220E/S265W, T059R/S129Q, T263W/S285P, E152W/T179P, V190L/S265Q, L282M/Q286R/A289R/P162S, D220P/S265Q, M138L/E152F/T179P, T263W/A273H/S285W, S265P/Q286K, T059W/S066Q/S129Q, T263W/S285R, T059W/S066N/S129Q, T263W/S285W, T059R/S066N/S129Q, S265P/L282M/Q286R/A289R/T202S/K203N, T059W/S129Q, Q062H/S066Q/S129Q, L282M/Q286R/A289R, V190L/D220E/S265N/V291I, V190L/S265N, N050Y/T059R/S129Q, T059K/S066Q/S129Q, T059K/S129Q, S265P/L282M/Q286P/A289R, S265P/L282F/Q286P/A289R, T263W/A273H/S285P, S265P/L282M/Q286K, S016L/D220E/S265W, S066Q/S129Q, S265P/L282M/Q286P, L282F/Q286R/A289R, L044Q/T263W/S285R L055F/T059W/S129V, V190L/S265W, Q286R/A289R, G99D/S265P/L282F/Q286K/A289R, T059R/S066Q/S129Q, S066N/S129Q, T004S/S023N/G024M/K269N, S265P/L282M, E152F/T179P, T059W/S066N/S129V/S290R, L282F/Q286K/A289R, S265P/L282F, V190I/S265Q, S265P/L282F/Q286P, T059K/S066N/K088E, V190I/S265W, L282M/Q286K/A289R, L282M/Q286K/A289R/I253V, T263W/A273H, V190I/S265N, A273H/S285R, T059K/S066Q/V102A/S129Q, L282M/Q286R, S265P/L282F/A289R/T065S, T263H/A273H/S285R, T014M/T059R/S129V, L282M/Q286R/A289R/K11N, A273H/S285P, L282M/Q286K/A289R/S132T, T263H/A273H/S285W, S265P/L282F/Q286K/N061Y, L198I/D220E/S265Q, V190I/S265L, T263H/S285W, S265P/L282F/A289R, N90S/A273H/S285P, S032T/T263H/A273H/S285R, L282F/Q286P/A289R, N157Y/T263W/A273H/S285R, V105A/S129V, T263H/A273H/S285P, S129Q/L282H, T059W/S066Q, S023W/G024Y, T004V/S023N, T059R/S066Q, N050W/T054L, L282M/Q286P/A289R, A115V/V190L/S265W, L282M/Q286K, T059R/S066N, L282F/Q286P, T004V/S023W/G024M, S265P/L282F/Q286R/L78H, L282F/Q286K, T004V/S023W/G024Y, S023W/G024M, T059R/R256S, T004V/G024W, N050W/T054K, S023Y/G024M, T004V/S023Y, T004V/S023Y/G024M, N050Y/T054H, S023W/G024W, T004V/S023Y/G024Y, T004V/S023N/G024W, N050Y/T059K/S066Q, T004V/S023Y/G024W, T059K/S066N, T004V/S023N/G024Y, S023Y/G024W, N050F/T054L, R047K/T054K, S023N/G024W, L282M/A289R, S023Y/G024Y, T004V/G024M, R047K/N050F/T054K, N050F/T054K, T059K/S066Q, S023N/G024M, S023N/G024Y, T004L/S023N, R047K/N050W/T054H, T004L/S023W/G024Y, T004S/S023W, N046Q/N050W/T054H/A142T, T004L/S023Y, T004V/S023W, N050W/T054H, T004S/S023N, T004S/L282M, T004L/S023W, N050F/T054H, N050Y/T054L, and R047K/N050W/T054K.

6. The isolated variant neutral metalloprotease of claim 1, wherein said variant further comprises multiple mutations selected from S066Q/S129V, S066Q/S129I, N050Y/S066Q/S129V, S066N/S129I, T059K/S066Q/S129V, S066N/S129V, S265P/L282M/Q286R/A289R, T059K/S066Q/S129I, T263W/S285P, T059K/S066N/S129I, T263W/A273H/S285P, S265P/L282F/Q286R/A289R, T263W/A273H/S285R, V190I/D220P/S265W, S066N/S129Q, S265P/L282M/Q286K/A289R, V190I/D220E, T059R/S066N/S129I, V190I/D220E/S265W, T059K/S129I, T059R/S066Q/S129I, T263W/A273H/S285W, S016L/D220E/S265W, S066Q/S129Q, V190I/D220E/S265Q, T059R/S066Q/S129V, D220E/S265N, V190L/D220E, D220E/S265W, V190I/D220P, V190L/D220E/S265N, L044Q/T263W/S285R, S265P/L282M/Q286P/A289R, T263W/S285R, L282M/Q286R/A289R, T263W/S285W, V190I/D220E/S265N, V190L/D220E/S265W, V190I/D220P/S265Q, T059R/S066N/S129V, V190L/D220E/S265Q, E152H/T179P, Q062H/S066Q/S129Q, T059R/S129V, V190I/D220E/S265W/L282F, V190I/S265Q, F130L/E152F/T179P, D220E/S265Q, E152W/T179P, T059K/S066Q/S129Q, N050Y/T059W/S066Q/S129V, S265P/L282M/Q286K, T059R/S129I, D220P/S265N, S265P/L282M/Q286P, T059R/S066Q/N092S/S129I, G99D/S265P/L282F/Q286K/A289R, T263W/A273H, V190I/S265N, D220P/S265W, S265P/L282M, V190I/S265Q, T059K/S129Q, Q286R/A289R, D220P/S265Q, V190L/S265N, S265P/Q286K, V190L/S265Q, V190I/S265W, N050Y/T059W/S066N/S129V, T059R/S066N/S129Q, T059R/S066Q/S129Q, T263H/A273H/S285P, N90S/A273H/S285P, V190L/D220E/S265N/V291I, T059R/S129Q, A273H/S285P, N050Y/T059R/S129Q, T059W/S066Q/S129I, V190L/S265W, T059W/S066Q/S129V, V190I/S265Q, N157Y/T263W/A273H/S285R, T263H/S285W, A115V/V190L/S265W, T263H/A273H/S285W, T059K/S066N/K088E, T004V/S023N, T059K/S066Q/V102A/S129Q, N047K/N050F/T054K, T263H/A273H/S285R, L282M/Q286R/A289R/P162S, L282F/Q286R/A289R, Q062K/S066Q/S129I, A273H/S285R, S265P/L282F/Q286P, S265P/L282F/Q286P/A289R, S265P/L282M/Q286R/A289R/T202S/K203N, T059W/S066N/S129I, V190I/S265L, T059W/S066N/S129V, L282M/Q286K/A289R/I253V, R047K/N050F/T054K, N050W/T054K, L198I/D220E/S265Q, L282F/Q286K/A289R, N050F/T054K, L282M/Q286R, S265P/L282F, T059W/S066N/S129Q, T263H/A273H, L282M/Q286K/A289R, N046Q/N050W/T054H/A142T, T059W/S066Q/S129Q, S265P/L282F/A289R/T065S, N050F/T054H, S129Q/L282H, L282M/Q286K/A289R/S132T, L282M/Q286R/A289R/K11N, T059K/S066N, R047K/N050W/T054K, T059K/S066Q, T004V/S023Y, T059W/S066N/S129V/S290R, N050Y/T059K/S066Q, and R047K/N050Y.

7. A variant neutral metalloprotease according to claim 1, wherein the variant metalloprotease further has improved performance as compared to wild-type *B. amyloliquefaciens* neutral metalloprotease.

8. The variant neutral metalloprotease of claim 7, wherein said improved performance comprises improved thermostability, improved performance under lower or higher pH conditions or autolytic stability, as compared to wild-type *B. amyloliquefaciens* neutral metalloprotease.

9. A method for producing the variant of claim 1 comprising: transforming an isolated host cell with an expression vector comprising a polynucleotide encoding the amino acid sequence of the variant of claim 1; and cultivating said transformed host cell under conditions suitable for the production of said variant.

10. The method of claim 9, wherein said host cell is a *Bacillus* species.

11. A composition comprising at least one neutral metalloprotease according to claim 1 obtained from *B. amyloliquefaciens*, wherein said composition further comprises at least one stabilizer.

12. The composition of claim 11, wherein said stabilizer is selected from the group consisting of borax, glycerol, zinc ions, calcium ions, and calcium formate.

13. The composition of claim 11, wherein said stabilizer is at least one competitive inhibitor that stabilizes said at least one neutral metalloprotease in the presence of an anionic surfactant.

14. A cleaning composition comprising the isolated neutral metalloprotease of claim 1.

15. The cleaning composition of claim 14, wherein said cleaning composition is a detergent.

16. The cleaning composition of claim 14, further comprising at least one additional enzymes or enzyme derivatives selected from proteases, amylases, lipases, mannanases, pectinases, cutinases, oxidoreductases, hemicellulases, and cellulases.

17. The cleaning composition of claim 15, wherein said composition comprises at least 0.0001 weight percent of said neutral metalloprotease.

18. A method of cleaning, comprising the step of contacting a surface and/or an article comprising a fabric with the cleaning composition of claim 14.

19. The method of claim 18, further comprising the step of rinsing said surface and/or material after contacting said surface or material with said cleaning composition.

* * * * *

SEQUENCE LISTING

<160> NUMBER OF SEQ ID NOS: 226

<210> SEQ ID NO 1
<211> LENGTH: 713
<212> TYPE: DNA
<213> ORGANISM: Bacillus subtilis

<400> SEQUENCE: 1
gagctgggta aagcctatga attctccatt ttcttctgct atcaaaataa cagactcgtg 60
attttccaaa cgagctttca aaaaagcctc tgccccttgc aaatcggatg cctgtctata 120
aaattcccga tattggttaa acagcggcgc aatggcggcc gcatctgatg tctttgcttg 180
gcgaatgttc atcttatttc ttcctccctc tcaataattt tttcattcta tcccttttct 240
gtaaagttta tttttcagaa tacttttatc atcatgcttt gaaaaaatat cacgataata 300
tccattgttc tcacggaagc acacgcaggt catttgaacg aatttttttcg acaggaattt 360 gccgggactc aggagcattt aacctaaaaa agcatgacat ttcagcataa tgaacattta 420
ctcatgtcta ttttcgttct tttctgtatg aaaatagtta tttcgagtct ctacggaaat 480
agcgagagat gatataccta aatagagata aaatcatctc aaaaaaatgg gtctactaaa 540
atattattcc atctattaca ataaattcac agaatagtct tttaagtaag tctactctga 600 attttttttaa aaggagaggg taaagagtga gaagcaaaaa attgtggatc agcttgttgt 660
ttgcgttaac gttaatcttt acgatggcgt tcagcaacat gtctgcgcag gct 713

<210> SEQ ID NO 2
<211> LENGTH: 1578
<212> TYPE: DNA
<213> ORGANISM: Bacillus amyloliquefaciens

<400> SEQUENCE: 2
gctgagaatc ctcagcttaa agaaaacctg acgaattttg taccgaagca ttctttggtg 60
caatcagaat tgccttctgt cagtgacaaa gctatcaagc aatacttgaa acaaaacggc 120
aaagtcttta aaggcaatcc ttctgaaaga ttgaagctga ttgaccaaac gaccgatgat 180
ctcggctaca agcacttccg ttatgtgcct gtcgtaaacg gtgtgcctgt gaaagactct 240
caagtcatta ttcacgtcga taaatccaac aacgtctatg cgattaacgg tgaattaaac 300
aacgatgttt ccgccaaaac ggcaaacagc aaaaaattat ctgcaaatca ggcgctggat 360
catgcttata aagcgatcgg caaatcacct gaagccgttt ctaacggaac cgttgcaaac 420
aaaaacaaag ccgagctgaa agcagcagcc acaaaagacg gcaaataccg cctcgcctat 480
gatgtaacca tccgctacat cgaaccggaa cctgcaaact gggaagtaac cgttgatgcg 540
gaaacaggaa aaatcctgaa aaagcaaaac aaagtggagc atgccgccac aaccggaaca 600
ggtacgactc ttaaaggaaa aacggtctca ttaaatattt cttctgaaag cggcaaatat 660
gtgctgcgcg atctttctaa acctaccgga acacaaatta ttacgtacga tctgcaaaac 720
cgcgagtata acctgccggg cacactcgta tccagcacca caaaccagtt tacaacttct 780
tctcagcgcg ctgccgttga tgcgcattac aacctcggca aagtgtatga ttatttctat 840
cagaagttta atcgcaacag ctacgacaat aaaggcggca agatcgtatc ctccgttcat 900
tacggcagca gatacaataa cgcagcctgg atcggcgacc aaatgattta cggtgacggc 960
gacggttcat tcttctcacc tctttccggt tcaatggacg taaccgctca tgaaatgaca 1020
catggcgtta cacaggaaac agccaacctg aactacgaaa atcagccggg cgctttaaac 1080
gaatccttct ctgatgtatt cgggtacttc aacgatactg aggactggga tatcggtgaa 1140

```
gatattacgg tcagccagcc ggctctccgc agcttatcca atccgacaaa atacggacag   1200

cctgataatt tcaaaaatta caaaaacctt ccgaacactg atgccggcga ctacggcggc   1260

gtgcatacaa acagcggaat cccgaacaaa gccgcttaca atacgattac aaaaatcggc   1320

gtgaacaaag cggagcagat ttactatcgt gctctgacgg tatacctcac tccgtcatca   1380

acttttaaag atgcaaaagc cgctttgatt caatctgcgc gggaccttta cggctctcaa   1440

gatgctgcaa gcgtagaagc tgcctggaat gcagtcggat tgtaaacaag aaaagagacc   1500

ggaaatccgg tctctttttt atatctaaaa acatttcaca gtggcttcac catgatcata   1560

tatgtcaagc ttgggggg                                                 1578


<210> SEQ ID NO 3
<211> LENGTH: 520
<212> TYPE: PRT
<213> ORGANISM: Bacillus amyloliquefaciens

<400> SEQUENCE: 3

Met Gly Leu Gly Lys Lys Leu Ser Val Ala Val Ala Ala Ser Phe Met
1               5                   10                  15

Ser Leu Thr Ile Ser Leu Pro Gly Val Gln Ala Ala Glu Asn Pro Gln
            20                  25                  30

Leu Lys Glu Asn Leu Thr Asn Phe Val Pro Lys His Ser Leu Val Gln
        35                  40                  45

Ser Glu Leu Pro Ser Val Ser Asp Lys Ala Ile Lys Gln Tyr Leu Lys
    50                  55                  60

Gln Asn Gly Lys Val Lys Gly Asn Pro Ser Glu Arg Leu Lys Leu Ile
65                  70                  75                  80

Asp Gln Thr Thr Asp Asp Leu Gly Tyr Lys His Phe Arg Tyr Val Pro
                85                  90                  95

Val Val Asn Gly Val Pro Val Lys Asp Ser Gln Val Ile Ile His Val
            100                 105                 110

Asp Lys Ser Asn Asn Val Tyr Ala Ile Asn Gly Glu Leu Asn Asn Asp
        115                 120                 125

Val Ser Ala Lys Thr Ala Asn Ser Lys Lys Leu Ser Ala Asn Gln Ala
    130                 135                 140

Leu Asp His Ala Tyr Lys Ala Ile Gly Lys Ser Pro Glu Ala Val Ser
145                 150                 155                 160

Asn Gly Thr Val Ala Asn Lys Asn Lys Ala Glu Leu Lys Ala Ala Ala
                165                 170                 175

Thr Lys Asp Gly Lys Tyr Arg Leu Ala Tyr Asp Val Thr Ile Arg Tyr
            180                 185                 190

Ile Glu Pro Glu Pro Ala Asn Trp Glu Val Thr Val Asp Ala Glu Thr
        195                 200                 205

Gly Lys Ile Leu Lys Lys Gln Asn Lys Val Glu His Ala Ala Thr Thr
    210                 215                 220

Gly Thr Gly Thr Thr Leu Lys Gly Lys Thr Val Ser Leu Asn Ile Ser
225                 230                 235                 240

Ser Glu Ser Gly Lys Tyr Val Leu Arg Asp Leu Ser Lys Pro Thr Gly
                245                 250                 255

Thr Gln Ile Ile Thr Tyr Asp Leu Gln Asn Arg Glu Tyr Asn Leu Pro
            260                 265                 270

Gly Thr Leu Val Ser Ser Thr Thr Asn Gln Phe Thr Thr Ser Ser Gln
        275                 280                 285
```

-continued

```
Arg Ala Ala Val Asp Ala His Tyr Asn Leu Gly Lys Val Tyr Asp Tyr
    290                 295                 300

Phe Tyr Gln Lys Phe Asn Arg Asn Ser Tyr Asp Asn Lys Gly Gly Lys
305                 310                 315                 320

Ile Val Ser Ser Val His Tyr Gly Ser Arg Tyr Asn Asn Ala Ala Trp
                325                 330                 335

Ile Gly Asp Gln Met Ile Tyr Gly Asp Gly Asp Gly Ser Phe Phe Ser
            340                 345                 350

Pro Leu Ser Gly Ser Met Asp Val Thr Ala His Glu Met Thr His Gly
        355                 360                 365

Val Thr Gln Glu Thr Ala Asn Leu Asn Tyr Glu Asn Gln Pro Gly Ala
    370                 375                 380

Leu Asn Glu Ser Phe Ser Asp Val Phe Gly Tyr Phe Asn Asp Thr Glu
385                 390                 395                 400

Asp Trp Asp Ile Gly Glu Asp Ile Thr Val Ser Gln Pro Ala Leu Arg
                405                 410                 415

Ser Leu Ser Asn Pro Thr Lys Tyr Gly Gln Pro Asp Asn Phe Lys Asn
            420                 425                 430

Tyr Lys Asn Leu Pro Asn Thr Asp Ala Gly Asp Tyr Gly Gly Val His
        435                 440                 445

Thr Asn Ser Gly Ile Pro Asn Lys Ala Ala Tyr Asn Thr Ile Thr Lys
    450                 455                 460

Ile Gly Val Asn Lys Ala Glu Gln Ile Tyr Tyr Arg Ala Leu Thr Val
465                 470                 475                 480

Tyr Leu Thr Pro Ser Ser Thr Phe Lys Asp Ala Lys Ala Ala Leu Ile
                485                 490                 495

Gln Ser Ala Arg Asp Leu Tyr Gly Ser Gln Asp Ala Ala Ser Val Glu
            500                 505                 510

Ala Ala Trp Asn Ala Val Gly Leu
        515                 520
```

<210> SEQ ID NO 4
<211> LENGTH: 523
<212> TYPE: PRT
<213> ORGANISM: Unknown
<220> FEATURE:
<223> OTHER INFORMATION: NpreE homolog

<400> SEQUENCE: 4

```
Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Asn
            20                  25                  30

Pro Gln Leu Lys Glu Asn Leu Thr Asn Phe Val Pro Lys His Ser Leu
        35                  40                  45

Val Gln Ser Glu Leu Pro Ser Val Ser Asp Lys Ala Ile Lys Gln Tyr
    50                  55                  60

Leu Lys Gln Asn Gly Lys Val Phe Lys Gly Asn Pro Ser Glu Arg Leu
65                  70                  75                  80

Lys Leu Ile Asp Gln Thr Thr Asp Asp Leu Gly Tyr Lys His Phe Arg
                85                  90                  95

Tyr Val Pro Val Val Asn Gly Val Pro Val Lys Asp Ser Gln Val Ile
            100                 105                 110

Ile His Val Asp Lys Ser Asn Asn Val Tyr Ala Ile Asn Gly Glu Leu
        115                 120                 125
```

-continued

```
Asn Asn Asp Val Ser Ala Lys Thr Ala Asn Ser Lys Lys Leu Ser Ala
    130                 135                 140

Asn Gln Ala Leu Asp His Ala Tyr Lys Ala Ile Gly Lys Ser Pro Glu
145                 150                 155                 160

Ala Val Ser Asn Gly Thr Val Ala Asn Lys Asn Lys Ala Glu Leu Lys
                165                 170                 175

Ala Ala Ala Thr Lys Asp Gly Lys Tyr Arg Leu Ala Tyr Asp Val Thr
            180                 185                 190

Ile Arg Tyr Ile Glu Pro Glu Pro Ala Asn Trp Glu Val Thr Val Asp
        195                 200                 205

Ala Glu Thr Gly Lys Ile Leu Lys Lys Gln Asn Lys Val Glu His Ala
    210                 215                 220

Ala Thr Thr Gly Thr Gly Thr Thr Leu Lys Gly Lys Thr Val Ser Leu
225                 230                 235                 240

Asn Ile Ser Ser Glu Ser Gly Lys Tyr Val Leu Arg Asp Leu Ser Lys
                245                 250                 255

Pro Thr Gly Thr Gln Ile Ile Thr Tyr Asp Leu Gln Asn Arg Glu Tyr
            260                 265                 270

Asn Leu Pro Gly Thr Leu Val Ser Ser Thr Thr Asn Gln Phe Thr Thr
        275                 280                 285

Ser Ser Gln Arg Ala Ala Val Asp Ala His Tyr Asn Leu Gly Lys Val
    290                 295                 300

Tyr Asp Tyr Phe Tyr Gln Lys Phe Asn Arg Asn Ser Tyr Asp Asn Lys
305                 310                 315                 320

Gly Gly Lys Ile Val Ser Ser Val His Tyr Gly Ser Arg Tyr Asn Asn
                325                 330                 335

Ala Ala Trp Ile Gly Asp Gln Met Ile Tyr Gly Asp Gly Asp Gly Ser
            340                 345                 350

Phe Phe Ser Pro Leu Ser Gly Ser Met Asp Val Thr Ala His Glu Met
        355                 360                 365

Thr His Gly Val Thr Gln Glu Thr Ala Asn Leu Asn Tyr Glu Asn Gln
    370                 375                 380

Pro Gly Ala Leu Asn Glu Ser Phe Ser Asp Val Phe Gly Tyr Phe Asn
385                 390                 395                 400

Asp Thr Glu Asp Trp Asp Ile Gly Glu Asp Ile Thr Val Ser Gln Pro
                405                 410                 415

Ala Leu Arg Ser Leu Ser Asn Pro Thr Lys Tyr Gly Gln Pro Asp Asn
            420                 425                 430

Phe Lys Asn Tyr Lys Asn Leu Pro Asn Thr Asp Ala Gly Asp Tyr Gly
        435                 440                 445

Gly Val His Thr Asn Ser Gly Ile Pro Asn Lys Ala Ala Tyr Asn Thr
    450                 455                 460

Ile Thr Lys Ile Gly Val Asn Lys Ala Glu Gln Ile Tyr Tyr Arg Ala
465                 470                 475                 480

Leu Thr Val Tyr Leu Thr Pro Ser Ser Thr Phe Lys Asp Ala Lys Ala
                485                 490                 495

Ala Leu Ile Gln Ser Ala Arg Asp Leu Tyr Gly Ser Gln Asp Ala Ala
            500                 505                 510

Ser Val Glu Ala Ala Trp Asn Ala Val Gly Leu
        515                 520
```

<210> SEQ ID NO 5
<211> LENGTH: 22
<212> TYPE: DNA

<213> ORGANISM: Artificial Sequence
<220> FEATURE:
<223> OTHER INFORMATION: primer

<400> SEQUENCE: 5
gagctgggta aagcctatga at 22

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
gttcagcaac atgtctgcgc aggct 25

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gctgagaatc ctcagcttaa agaaaacctg 30

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
ggcttcacca tgatcatata tgtcaagctt gggggg 36

<210> SEQ ID NO 9
<211> LENGTH: 55
<212> TYPE: DNA
<213> ORGANISM: Artificial Sequence
<220> FEATURE:
<223> OTHER INFORMATION: primer

<400> SEQUENCE: 9
caggttttct ttaagctgag gattctcagc agcctgcgca gacatgttgc tgaac 55

<210> SEQ ID NO 10
<211> LENGTH: 55
<212> TYPE: DNA
<213> ORGANISM: Artificial Sequence
<220> FEATURE:
<223> OTHER INFORMATION: primer

<400> SEQUENCE: 10
gttcagcaac atgtctgcgc aggctgctga gaatcctcag cttaaagaaa acctg 55

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
ccccccaagc ttgacatata tgatcatggt gaagcc 36

<210> SEQ ID NO 12
<211> LENGTH: 1566
<212> TYPE: DNA
<213> ORGANISM: Bacillus amyloliquefaciens

<400> SEQUENCE: 12
gtgggtttag gtaagaaatt gtctgttgct gtcgccgctt cctttatgag tttaaccatc 60
agtctgccgg gtgttcaggc cgctgagaat cctcagctta aagaaaacct gacgaatttt 120
gtaccgaagc attctttggt gcaatcagaa ttgccttctg tcagtgacaa agctatcaag 180
caatacttga aacaaaacgg caaagtcttt aaaggcaatc cttctgaaag attgaagctg 240
attgaccaaa cgaccgatga tctcggctac aagcacttcc gttatgtgcc tgtcgtaaac 300
ggtgtgcctg tgaaagactc tcaagtcatt attcacgtcg ataaatccaa caacgtctat 360
gcgattaacg gtgaattaaa caacgatgtt tccgccaaaa cggcaaacag caaaaaatta 420
tctgcaaatc aggcgctgga tcatgcttat aaagcgatcg gcaaatcacc tgaagccgtt 480
tctaacggaa ccgttgcaaa caaaaacaaa gccgagctga aagcagcagc cacaaaagac 540
ggcaaatacc gcctcgccta tgatgtaacc atccgctaca tcgaaccgga acctgcaaac 600
tgggaagtaa ccgttgatgc ggaaacagga aaaatcctga aaaagcaaaa caaagtggag 660
catgccgcca caaccggaac aggtacgact cttaaaggaa aaacggtctc attaaatatt 720
tcttctgaaa gcggcaaata tgtgctgcgc gatctttcta aacctaccgg aacacaaatt 780
attacgtacg atctgcaaaa ccgcgagtat aacctgccgg gcacactcgt atccagcacc 840
acaaaccagt ttacaacttc ttctcagcgc gctgccgttg atgcgcatta caacctcggc 900
aaagtgtatg attatttcta tcagaagttt aatcgcaaca gctacgacaa taaaggcggc 960
aagatcgtat cctccgttca ttacggcagc agatacaata acgcagcctg gatcggcgac 1020
caaatgattt acggtgacgg cgacggttca ttcttctcac ctctttccgg ttcaatggac 1080
gtaaccgctc atgaaatgac acatggcgtt acacaggaaa cagccaacct gaactacgaa 1140
aatcagccgg gcgctttaaa cgaatccttc tctgatgtat tcgggtactt caacgatact 1200
gaggactggg atatcggtga agatattacg gtcagccagc cggctctccg cagcttatcc 1260
aatccgacaa aatacggaca gcctgataat ttcaaaaatt acaaaaacct tccgaacact 1320
gatgccggcg actacggcgg cgtgcataca aacagcggaa tcccgaacaa agccgcttac 1380
aatacgatta caaaaatcgg cgtgaacaaa gcggagcaga tttactatcg tgctctgacg 1440
gtatacctca ctccgtcatc aacttttaaa gatgcaaaag ccgctttgat tcaatctgcg 1500
cgggaccttt acggctctca agatgctgca agcgtagaag ctgcctggaa tgcagtcgga 1560
ttgtaa 1566

<210> SEQ ID NO 13
<211> LENGTH: 521
<212> TYPE: PRT
<213> ORGANISM: Bacillus amyloliquefaciens

<400> SEQUENCE: 13

Met Gly Leu Gly Lys Lys Leu Ser Val Ala Val Ala Ala Ser Phe Met
1               5                   10                  15

Ser Leu Thr Ile Ser Leu Pro Gly Val Gln Ala Ala Glu Asn Pro Gln
            20                  25                  30

Leu Lys Glu Asn Leu Thr Asn Phe Val Pro Lys His Ser Leu Val Gln
        35                  40                  45

-continued

```
Ser Glu Leu Pro Ser Val Ser Asp Lys Ala Ile Lys Gln Tyr Leu Lys
    50                  55                  60

Gln Asn Gly Lys Val Phe Lys Gly Asn Pro Ser Glu Arg Leu Lys Leu
65                  70                  75                  80

Ile Asp Gln Thr Thr Asp Asp Leu Gly Tyr Lys His Phe Arg Tyr Val
                85                  90                  95

Pro Val Val Asn Gly Val Pro Val Lys Asp Ser Gln Val Ile Ile His
            100                 105                 110

Val Asp Lys Ser Asn Asn Val Tyr Ala Ile Asn Gly Glu Leu Asn Asn
        115                 120                 125

Asp Val Ser Ala Lys Thr Ala Asn Ser Lys Lys Leu Ser Ala Asn Gln
    130                 135                 140

Ala Leu Asp His Ala Tyr Lys Ala Ile Gly Lys Ser Pro Glu Ala Val
145                 150                 155                 160

Ser Asn Gly Thr Val Ala Asn Lys Asn Lys Ala Glu Leu Lys Ala Ala
                165                 170                 175

Ala Thr Lys Asp Gly Lys Tyr Arg Leu Ala Tyr Asp Val Thr Ile Arg
            180                 185                 190

Tyr Ile Glu Pro Glu Pro Ala Asn Trp Glu Val Thr Val Asp Ala Glu
        195                 200                 205

Thr Gly Lys Ile Leu Lys Lys Gln Asn Lys Val Glu His Ala Ala Thr
    210                 215                 220

Thr Gly Thr Gly Thr Thr Leu Lys Gly Lys Thr Val Ser Leu Asn Ile
225                 230                 235                 240

Ser Ser Glu Ser Gly Lys Tyr Val Leu Arg Asp Leu Ser Lys Pro Thr
                245                 250                 255

Gly Thr Gln Ile Ile Thr Tyr Asp Leu Gln Asn Arg Glu Tyr Asn Leu
            260                 265                 270

Pro Gly Thr Leu Val Ser Ser Thr Thr Asn Gln Phe Thr Thr Ser Ser
        275                 280                 285

Gln Arg Ala Ala Val Asp Ala His Tyr Asn Leu Gly Lys Val Tyr Asp
    290                 295                 300

Tyr Phe Tyr Gln Lys Phe Asn Arg Asn Ser Tyr Asp Asn Lys Gly Gly
305                 310                 315                 320

Lys Ile Val Ser Ser Val His Tyr Gly Ser Arg Tyr Asn Asn Ala Ala
                325                 330                 335

Trp Ile Gly Asp Gln Met Ile Tyr Gly Asp Gly Asp Gly Ser Phe Phe
            340                 345                 350

Ser Pro Leu Ser Gly Ser Met Asp Val Thr Ala His Glu Met Thr His
        355                 360                 365

Gly Val Thr Gln Glu Thr Ala Asn Leu Asn Tyr Glu Asn Gln Pro Gly
    370                 375                 380

Ala Leu Asn Glu Ser Phe Ser Asp Val Phe Gly Tyr Phe Asn Asp Thr
385                 390                 395                 400

Glu Asp Trp Asp Ile Gly Glu Asp Ile Thr Val Ser Gln Pro Ala Leu
                405                 410                 415

Arg Ser Leu Ser Asn Pro Thr Lys Tyr Gly Gln Pro Asp Asn Phe Lys
            420                 425                 430

Asn Tyr Lys Asn Leu Pro Asn Thr Asp Ala Gly Asp Tyr Gly Gly Val
        435                 440                 445

His Thr Asn Ser Gly Ile Pro Asn Lys Ala Ala Tyr Asn Thr Ile Thr
    450                 455                 460
```

-continued

```
Lys Ile Gly Val Asn Lys Ala Glu Gln Ile Tyr Tyr Arg Ala Leu Thr
465                 470                 475                 480

Val Tyr Leu Thr Pro Ser Ser Thr Phe Lys Asp Ala Lys Ala Ala Leu
                485                 490                 495

Ile Gln Ser Ala Arg Asp Leu Tyr Gly Ser Gln Asp Ala Ala Ser Val
            500                 505                 510

Glu Ala Ala Trp Asn Ala Val Gly Leu
        515                 520


<210> SEQ ID NO 14

<400> SEQUENCE: 14

000


<210> SEQ ID NO 15

<400> SEQUENCE: 15

000


<210> SEQ ID NO 16

<400> SEQUENCE: 16

000


<210> SEQ ID NO 17
<211> LENGTH: 194
<212> TYPE: PRT
<213> ORGANISM: Bacillus amyloliquefaciens

<400> SEQUENCE: 17

Ala Glu Asn Pro Gln Leu Lys Glu Asn Leu Thr Asn Phe Val Pro Lys
1               5                   10                  15

His Ser Leu Val Gln Ser Glu Leu Pro Ser Val Ser Asp Lys Ala Ile
            20                  25                  30

Lys Gln Tyr Leu Lys Gln Asn Gly Lys Val Phe Lys Gly Asn Pro Ser
        35                  40                  45

Glu Arg Leu Lys Leu Ile Asp Gln Thr Thr Asp Asp Leu Gly Tyr Lys
    50                  55                  60

His Phe Arg Tyr Val Pro Val Val Asn Gly Val Pro Val Lys Asp Ser
65                  70                  75                  80

Gln Val Ile Ile His Val Asp Lys Ser Asn Asn Val Tyr Ala Ile Asn
                85                  90                  95

Gly Glu Leu Asn Asn Asp Val Ser Ala Lys Thr Ala Asn Ser Lys Lys
            100                 105                 110

Leu Ser Ala Asn Gln Ala Leu Asp His Ala Tyr Lys Ala Ile Gly Lys
        115                 120                 125

Ser Pro Glu Ala Val Ser Asn Gly Thr Val Ala Asn Lys Asn Lys Ala
    130                 135                 140

Glu Leu Lys Ala Ala Ala Thr Lys Asp Gly Lys Tyr Arg Leu Ala Tyr
145                 150                 155                 160

Asp Val Thr Ile Arg Tyr Ile Glu Pro Glu Pro Ala Asn Trp Glu Val
                165                 170                 175

Thr Val Asp Ala Glu Thr Gly Lys Ile Leu Lys Lys Gln Asn Lys Val
            180                 185                 190

Glu His
```

<210> SEQ ID NO 18
<211> LENGTH: 300
<212> TYPE: PRT
<213> ORGANISM: Bacillus amyloliquefaciens

<400> SEQUENCE: 18

```
Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300
```

<210> SEQ ID NO 19
<211> LENGTH: 46
<212> TYPE: DNA
<213> ORGANISM: Artificial Sequence
<220> FEATURE:
<223> OTHER INFORMATION: primer

<400> SEQUENCE: 19

```
ctgcaggaat tcagatctta acatttttcc cctatcattt ttcccg                    46
```

<210> SEQ ID NO 20

-continued

<211> LENGTH: 46
<212> TYPE: DNA
<213> ORGANISM: Artificial Sequence
<220> FEATURE:
<223> OTHER INFORMATION: primer

<400> SEQUENCE: 20
ggatccaagc ttcccgggaa aagacatata tgatcatggt gaagcc 46

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
gtcagtcaga tcttccttca ggttatgacc 30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
gtctcgaaga tctgattgct taactgcttc 30

<210> SEQ ID NO 23
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 23
gtggagcatg ccgccacann sggaacaggt acgactctta a 41

<210> SEQ ID NO 24
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 24
caggtacgac tcttaaanns aaaacggtct cattaaatat 40

<210> SEQ ID NO 25
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 25
gtacgactct taaagganns acggtctcat taaatatttc 40

<210> SEQ ID NO 26
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 26
cgactcttaa aggaaaanns gtctcattaa atatttc 37

<210> SEQ ID NO 27
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 27
cattaaatat ttcttctgaa nnsggcaaat atgtgctgcg 40

<210> SEQ ID NO 28
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 28
taaatatttc ttctgaaagc nnsaaatatg tgctgcgcga tc 42

<210> SEQ ID NO 29
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 29
gtgctgcgcg atctttctnn scctaccgga acacaaatta t 41

<210> SEQ ID NO 30
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 30
aaattattac gtacgatctg nnsaaccgcg agtataacct g 41

<210> SEQ ID NO 31
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 31
ttattacgta cgatctgcaa nnscgcgagt ataacctgcc 40

<210> SEQ ID NO 32
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 32
cgtacgatct gcaaaacnns gagtataacc tgccggg 37

<210> SEQ ID NO 33
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 33
gatctgcaaa accgcgagnn saacctgccg ggcacactc 39

<210> SEQ ID NO 34
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 34
ctgcaaaacc gcgagtatnn sctgccgggc acactcgtat c 41

<210> SEQ ID NO 35
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 35
gagtataacc tgccgggcnn sctcgtatcc agcaccac 38

<210> SEQ ID NO 36
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 36
cgggcacact cgtatccnns accacaaacc agtttac 37

<210> SEQ ID NO 37
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 37
gcacactcgt atccagcnns acaaaccagt ttacaac 37

<210> SEQ ID NO 38
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 38
cactcgtatc cagcaccnns aaccagttta caacttc 37

<210> SEQ ID NO 39
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 39
ccacaaacca gtttacanns tcttctcagc gcgctgc 37

<210> SEQ ID NO 40
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)

<223> OTHER INFORMATION: n is a, c, g, or t

<400> SEQUENCE: 40
caaaccagtt tacaactnns tctcagcgcg ctgccgttg 39

<210> SEQ ID NO 41
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 41
gtgtatgatt atttctatnn saagtttaat cgcaacag 38

<210> SEQ ID NO 42
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 42
attatttcta tcagaagttt nnscgcaaca gctacgacaa taa 43

<210> SEQ ID NO 43
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 43
ttaatcgcaa cagctacgac nnsaaaggcg gcaagatcgt atc 43

<210> SEQ ID NO 44
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 44
gcaacagcta cgacaatnns ggcggcaaga tcgtatc 37

<210> SEQ ID NO 45
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 45
ctacgacaat aaaggcggcn nsatcgtatc ctccgttcat ta 42

<210> SEQ ID NO 46
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 46
gaggactggg atatcggtnn sgatattacg gtcagccag 39

<210> SEQ ID NO 47
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 47
gtcagccagc cggctctcnn sagcttatcc aatccgac 38

<210> SEQ ID NO 48
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 48
gacagcctga taatttcnns aattacaaaa accttcc 37

<210> SEQ ID NO 49
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 49
gataatttca aaaattacnn saaccttccg aacactgatg 40

<210> SEQ ID NO 50
<211> LENGTH: 37
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (18)..(19)
<223> OTHER INFORMATION: n is a, c, g, or t

<400> SEQUENCE: 50
gcgactacgg cggcgtgnns acaaacagcg gaatccc 37

<210> SEQ ID NO 51
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 51
ctttgattca atctgcgnns gacctttacg gctctcaag 39

<210> SEQ ID NO 52
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 52
ttaagagtcg tacctgttcc snntgtggcg gcatgctcca c 41

<210> SEQ ID NO 53
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 53
atatttaatg agaccgtttt snntttaaga gtcgtacctg 40

<210> SEQ ID NO 54
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 54
gaaatattta atgagaccgt snntccttta agagtcgtac 40

<210> SEQ ID NO 55
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 55
gaaatattta atgagacsnn ttttccttta agagtcg 37

<210> SEQ ID NO 56
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 56
cgcagcacat atttgccsnn ttcagaagaa atatttaatg 40

<210> SEQ ID NO 57
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 57
gatcgcgcag cacatattts nngctttcag aagaaatatt ta 42

<210> SEQ ID NO 58
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 58
ataatttgtg ttccggtagg snnagaaaga tcgcgcagca c 41

<210> SEQ ID NO 59
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 59
caggttatac tcgcggttsn ncagatcgta cgtaataatt t 41

<210> SEQ ID NO 60
<211> LENGTH: 40
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 60
ggcaggttat actcgcgsnn ttgcagatcg tacgtaataa 40

<210> SEQ ID NO 61
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 61
cccggcaggt tatactcsnn gttttgcaga tcgtacg 37

<210> SEQ ID NO 62
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 62
gagtgtgccc ggcaggttsn nctcgcggtt ttgcagatc 39

<210> SEQ ID NO 63
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 63
gatacgagtg tgcccggcag snnatactcg cggttttgca g 41

<210> SEQ ID NO 64
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 64
gtggtgctgg atacgagsnn gcccggcagg ttatactc 38

<210> SEQ ID NO 65
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 65
gtaaactggt ttgtggtsnn ggatacgagt gtgcccg 37

<210> SEQ ID NO 66
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 66
gttgtaaact ggtttgtsnn gctggatacg agtgtgc 37

<210> SEQ ID NO 67
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 67
gaagttgtaa actggttsnn ggtgctggat acgagtg 37

<210> SEQ ID NO 68
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 68
gcagcgcgct gagaagasnn tgtaaactgg tttgtgg 37

<210> SEQ ID NO 69
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 69
caacggcagc gcgctgagas nnagttgtaa actggtttg 39

<210> SEQ ID NO 70
<211> LENGTH: 38
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 70
ctgttgcgat taaacttsnn atagaaataa tcatacac 38

<210> SEQ ID NO 71
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 71
ttattgtcgt agctgttgcg snnaaacttc tgatagaaat aat 43

<210> SEQ ID NO 72
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 72
gatacgatct tgccgccttt snngtcgtag ctgttgcgat taa 43

<210> SEQ ID NO 73
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 73
gatacgatct tgccgccsnn attgtcgtag ctgttgc 37

<210> SEQ ID NO 74
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 74
taatgaacgg aggatacgat snngccgcct ttattgtcgt ag 42

<210> SEQ ID NO 75
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 75
ctggctgacc gtaatatcsn naccgatatc ccagtcctc 39

<210> SEQ ID NO 76
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 76
gtcggattgg ataagctsnn gagagccggc tggctgac 38

<210> SEQ ID NO 77
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 77
ggaaggtttt tgtaattsnn gaaattatca ggctgtc 37

<210> SEQ ID NO 78
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 78
catcagtgtt cggaaggtts nngtaatttt tgaaattatc 40

<210> SEQ ID NO 79
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 79
gggattccgc tgtttgtsnn cacgccgccg tagtcgc 37

<210> SEQ ID NO 80

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 80
cttgagagcc gtaaaggtcs nncgcagatt gaatcaaag 39

<210> SEQ ID NO 81
<211> LENGTH: 44
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 81
gtggagcatg ccgccacann sggaacaggt acgactctta aagg 44

<210> SEQ ID NO 82
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 82
ccggaacagg tacgactctt aaannsaaaa cggtctcatt aaatatttct tctgaaagc 59

<210> SEQ ID NO 83
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (29)..(30)
<223> OTHER INFORMATION: n is a, c, g, or t

<400> SEQUENCE: 83
cggaacacaa attattacgt acgatctgnn saaccgcgag tataacctgc c 51

<210> SEQ ID NO 84
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 84
gtacgatctg caaaaccgcg agnnsaacct gccgggcaca ctcgtatcc 49

<210> SEQ ID NO 85
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 85
gtacgatctg caaaaccgcg agtatnnsct gccgggcaca ctcgtatcca g 51

<210> SEQ ID NO 86
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 86
ccagcaccac aaaccagttt acannstctt ctcagcgcgc tgccgttg 48

<210> SEQ ID NO 87
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(31)
<223> OTHER INFORMATION: n is a, c, g, or t

<400> SEQUENCE: 87
gcagatacaa taacgcagcc tggatcggcn nscaaatgat ttacggtgac ggcgac 56

<210> SEQ ID NO 88
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 88
ccaaatgatt tacggtgacg gcgacnnstc attcttctca cctctttccg gttc 54

<210> SEQ ID NO 89
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 89
ggtgacggcg acggttcann sttctcacct ctttccggtc c 41

-continued

<210> SEQ ID NO 90
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 90
catgaaatga cacatggcgt tacannsgaa acagccaacc tgaactac 48

<210> SEQ ID NO 91
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t

<400> SEQUENCE: 91
catgaaatga cacatggcgt tacacagnns acagccaacc tgaactacg 49

<210> SEQ ID NO 92
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 92
catggcgtta cacaggaaac agccnnsctg aactacgaaa atcagccg 48

<210> SEQ ID NO 93
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (27)..(28)
<223> OTHER INFORMATION: n is a, c, g, or t

<400> SEQUENCE: 93
ctgatgtatt cgggtacttc aacgatnnsg aggactggga tatcggtg 48

<210> SEQ ID NO 94
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 94
gcagcttatc caatccgaca aaannsggac agcctgataa tttcaaaaat tac 53

-continued

<210> SEQ ID NO 95
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (27)..(28)
<223> OTHER INFORMATION: n is a, c, g, or t

<400> SEQUENCE: 95
gcagcttatc caatccgaca aaatacnnsc agcctgataa tttcaaaaat tacaaaaacc 60

<210> SEQ ID NO 96
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 96
gaacactgat gccggcgacn nsggcggcgt gcatacaaac 40

<210> SEQ ID NO 97
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 97
gaacaaagcc gcttacaata cgattnnsaa aatcggcgtg aacaaagcg 49

<210> SEQ ID NO 98
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 98
gcagatttac tatcgtgctc tgacgnnsta cctcactccg tcatcaactt ttaaag 56

<210> SEQ ID NO 99
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 99
gatttactat cgtgctctga cggtannsct cactccgtca tcaactttta aag 53

<210> SEQ ID NO 100
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 100
gtgctctgac ggtatacctc nnsccgtcat caacttttaa agatgc 46

<210> SEQ ID NO 101
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t

<400> SEQUENCE: 101
ccgtcatcaa cttttaaaga tgcaaaanns gctttgattc aatctgcgcg g 51

<210> SEQ ID NO 102
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 102
gattcaatct gcgcgggacn nstacggctc tcaagatgct gc 42

<210> SEQ ID NO 103
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 103
cgcgggacct ttacggcnns caagatgctg caagcgtag 39

<210> SEQ ID NO 104
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 104
cctttacggc tctcaagatg ctnnsagcgt agaagctgcc tggaatg 47

<210> SEQ ID NO 105
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 105
ctcaagatgc tgcaagcgta gaannsgcct ggaatgcagt cggattg 47

<210> SEQ ID NO 106
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 106
gcaagcgtag aagctgcctg gnnsgcagtc ggattgtaaa caagaaaag 49

<210> SEQ ID NO 107
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 107
gaagctgcct ggaatgcagt cnnsttgtaa acaagaaaag agaccggaaa tcc 53

<210> SEQ ID NO 108
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 108
cacactcgta tccagcaccn nsaaccagtt tacaacttct tctcag 46

<210> SEQ ID NO 109
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 109
ctccgttcat tacggcagcn nstacaataa cgcagcctgg atc 43

<210> SEQ ID NO 110
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 110
ctcacctctt tccggttcaa tgnnsgtaac cgctcatgaa atgacac 47

<210> SEQ ID NO 111
<211> LENGTH: 44
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 111
cctttaagag tcgtacctgt tccsnntgtg gcggcatgct ccac 44

<210> SEQ ID NO 112
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (35)..(36)
<223> OTHER INFORMATION: n is a, c, g, or t

<400> SEQUENCE: 112
gctttcagaa gaaatattta atgagaccgt tttsnnttta agagtcgtac ctgttccgg 59

<210> SEQ ID NO 113
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 113
ggcaggttat actcgcggtt snncagatcg tacgtaataa tttgtgttcc g 51

<210> SEQ ID NO 114
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 114
ggatacgagt gtgcccggca ggttsnnctc gcggttttgc agatcgtac 49

<210> SEQ ID NO 115
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 115
ctggatacga gtgtgcccgg cagsnnatac tcgcggtttt gcagatcgta c 51

<210> SEQ ID NO 116
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 116
caacggcagc gcgctgagaa gasnntgtaa actggtttgt ggtgctgg 48

<210> SEQ ID NO 117
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 117
gtcgccgtca ccgtaaatca tttgsnngcc gatccaggct gcgttattgt atctgc 56

<210> SEQ ID NO 118
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t

<400> SEQUENCE: 118
gaaccggaaa gaggtgagaa gaatgasnng tcgccgtcac cgtaaatcat ttgg 54

<210> SEQ ID NO 119
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)

<223> OTHER INFORMATION: n is a, c, g, or t

<400> SEQUENCE: 119
ggaccggaaa gaggtgagaa snntgaaccg tcgccgtcac c 41

<210> SEQ ID NO 120
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 120
gtagttcagg ttggctgttt csnntgtaac gccatgtgtc atttcatg 48

<210> SEQ ID NO 121
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 121
cgtagttcag gttggctgts nnctgtgtaa cgccatgtgt catttcatg 49

<210> SEQ ID NO 122
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 122
cggctgattt tcgtagttca gsnnggctgt ttcctgtgta acgccatg 48

<210> SEQ ID NO 123
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 123
caccgatatc ccagtcctcs nnatcgttga agtacccgaa tacatcag 48

<210> SEQ ID NO 124
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (29)..(30)
<223> OTHER INFORMATION: n is a, c, g, or t

<400> SEQUENCE: 124
gtaatttttg aaattatcag gctgtccsnn ttttgtcgga ttggataagc tgc 53

<210> SEQ ID NO 125
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (33)..(34)
<223> OTHER INFORMATION: n is a, c, g, or t

<400> SEQUENCE: 125
ggtttttgta atttttgaaa ttatcaggct gsnngtattt tgtcggattg gataagctgc 60

<210> SEQ ID NO 126
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 126
gtttgtatgc acgccgccsn ngtcgccggc atcagtgttc 40

<210> SEQ ID NO 127
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 127
cgctttgttc acgccgattt tsnnaatcgt attgtaagcg gctttgttc 49

<210> SEQ ID NO 128
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(31)
<223> OTHER INFORMATION: n is a, c, g, or t

<400> SEQUENCE: 128
ctttaaaagt tgatgacgga gtgaggtasn ncgtcagagc acgatagtaa atctgc 56

<210> SEQ ID NO 129
<211> LENGTH: 53
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (27)..(28)
<223> OTHER INFORMATION: n is a, c, g, or t

<400> SEQUENCE: 129
ctttaaaagt tgatgacgga gtgagsnnta ccgtcagagc acgatagtaa atc 53

<210> SEQ ID NO 130
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 130
gcatctttaa aagttgatga cggsnngagg tataccgtca gagcac 46

<210> SEQ ID NO 131
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 131
ccgcgcagat tgaatcaaag csnnttttgc atctttaaaa gttgatgacg g 51

<210> SEQ ID NO 132
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 132
gcagcatctt gagagccgta snngtcccgc gcagattgaa tc 42

<210> SEQ ID NO 133
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 133
ctacgcttgc agcatcttgs nngccgtaaa ggtcccgcg 39

<210> SEQ ID NO 134
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 134
cattccaggc agcttctacg ctsnnagcat cttgagagcc gtaaagg 47

<210> SEQ ID NO 135
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 135
caatccgact gcattccagg csnnttctac gcttgcagca tcttgag 47

<210> SEQ ID NO 136
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (27)..(28)
<223> OTHER INFORMATION: n is a, c, g, or t

<400> SEQUENCE: 136
cttttcttgt ttacaatccg actgcsnncc aggcagcttc tacgcttgc 49

<210> SEQ ID NO 137
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (31)..(32)
<223> OTHER INFORMATION: n is a, c, g, or t

<400> SEQUENCE: 137
ggatttccgg tctcttttct tgtttacaas nngactgcat tccaggcagc ttc 53

<210> SEQ ID NO 138
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 138
ctgagaagaa gttgtaaact ggttsnnggt gctggatacg agtgtg 46

<210> SEQ ID NO 139
<211> LENGTH: 43
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 139
gatccaggct gcgttattgt asnngctgcc gtaatgaacg gag 43

<210> SEQ ID NO 140
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 140
gtgtcatttc atgagcggtt acsnncattg aaccggaaag aggtgag 47

<210> SEQ ID NO 141
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (27)..(28)
<223> OTHER INFORMATION: n is a, c, g, or t

<400> SEQUENCE: 141
gcgacggttc attcttctca cctcttnnsg gttcaatgga cgtaaccgct c 51

<210> SEQ ID NO 142
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(31)
<223> OTHER INFORMATION: n is a, c, g, or t

<400> SEQUENCE: 142
gcgacggttc attcttctca cctctttccn nstcaatgga cgtaaccgct catg 54

<210> SEQ ID NO 143
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 143
cttctcacct ctttccggtn nsatggacgt aaccgctcat g 41

<210> SEQ ID NO 144
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 144
cctctttccg gttcaatgga cnnsaccgct catgaaatga cac 43

<210> SEQ ID NO 145
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 145
cagccagccg gctctccgcn nsttatccaa tccgacaaaa tacggacag 49

<210> SEQ ID NO 146
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 146
cagccagccg gctctccgca gcnnstccaa tccgacaaaa tacggacag 49

<210> SEQ ID NO 147
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 147
cagccagccg gctctccgca gcttannsaa tccgacaaaa tacggacagc c 51

<210> SEQ ID NO 148
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (31)..(32)
<223> OTHER INFORMATION: n is a, c, g, or t

<400> SEQUENCE: 148
cagcctgata atttcaaaaa ttacaaaaac nnsccgaaca ctgatgccgg cgac 54

<210> SEQ ID NO 149
<211> LENGTH: 54
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g, or t

<400> SEQUENCE: 149
cagcctgata atttcaaaaa ttacaaaaac cttnnsaaca ctgatgccgg cgac 54

<210> SEQ ID NO 150
<211> LENGTH: 57
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (37)..(38)
<223> OTHER INFORMATION: n is a, c, g, or t

<400> SEQUENCE: 150
cagcctgata atttcaaaaa ttacaaaaac cttccgnnsa ctgatgccgg cgactac 57

<210> SEQ ID NO 151
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (40)..(41)
<223> OTHER INFORMATION: n is a, c, g, or t

<400> SEQUENCE: 151
cagcctgata atttcaaaaa ttacaaaaac cttccgaacn nsgatgccgg cgactacgg 59

<210> SEQ ID NO 152
<211> LENGTH: 64
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t

<400> SEQUENCE: 152
cagcctgata atttcaaaaa ttacaaaaac cttccgaaca ctnnsgccgg cgactacggc 60
ggcg 64

<210> SEQ ID NO 153
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (46)..(47)
<223> OTHER INFORMATION: n is a, c, g, or t

<400> SEQUENCE: 153
cagcctgata atttcaaaaa ttacaaaaac cttccgaaca ctgatnnsgg cgactacggc 60
ggcgtg 66

<210> SEQ ID NO 154
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 154
ccttccgaac actgatgccn nsgactacgg cggcgtgcat ac 42

<210> SEQ ID NO 155
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 155
cgggaccttt acggctctnn sgatgctgca agcgtagaag ctg 43

<210> SEQ ID NO 156
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 156
gcgtagaagc tgcctggaat nnsgtcggat tgtaaacaag aaaagagacc gg 52

<210> SEQ ID NO 157
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 157
gagcggttac gtccattgaa ccsnnaagag gtgagaagaa tgaaccgtcg c 51

<210> SEQ ID NO 158
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 158

-continued catgagcggt tacgtccatt gasnnggaaa gaggtgagaa gaatgaaccg tcgc 54

<210> SEQ ID NO 159
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 159
catgagcggt tacgtccats nnaccggaaa gaggtgagaa g 41

<210> SEQ ID NO 160
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 160
gtgtcatttc atgagcggts nngtccattg aaccggaaag agg 43

<210> SEQ ID NO 161
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (29)..(30)
<223> OTHER INFORMATION: n is a, c, g, or t

<400> SEQUENCE: 161
ctgtccgtat tttgtcggat tggataasnn gcggagagcc ggctggctg 49

<210> SEQ ID NO 162
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t

<400> SEQUENCE: 162
ctgtccgtat tttgtcggat tggasnngct gcggagagcc ggctggctg 49

<210> SEQ ID NO 163
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 163
ggctgtccgt attttgtcgg attsnntaag ctgcggagag ccggctggct g 51

<210> SEQ ID NO 164
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 164
gtcgccggca tcagtgttcg gsnngttttt gtaatttttg aaattatcag gctg 54

<210> SEQ ID NO 165
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 165
gtcgccggca tcagtgttsn naaggttttt gtaatttttg aaattatcag gctg 54

<210> SEQ ID NO 166
<211> LENGTH: 57
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 166
gtagtcgccg gcatcagtsn ncggaaggtt tttgtaattt ttgaaattat caggctg 57

<210> SEQ ID NO 167
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 167
ccgtagtcgc cggcatcsnn gttcggaagg tttttgtaat ttttgaaatt atcaggctg 59

<210> SEQ ID NO 168
<211> LENGTH: 64
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 168
cgccgccgta gtcgccggcs nnagtgttcg gaaggttttt gtaatttttg aaattatcag 60
gctg 64

<210> SEQ ID NO 169
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 169
cacgccgccg tagtcgccsn natcagtgtt cggaaggttt ttgtaatttt tgaaattatc 60
aggctg 66

<210> SEQ ID NO 170
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 170
gtatgcacgc cgccgtagtc snnggcatca gtgttcggaa gg 42

<210> SEQ ID NO 171
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 171
cagcttctac gcttgcagca tcsnnagagc cgtaaaggtc ccg 43

<210> SEQ ID NO 172
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (31)..(32)
<223> OTHER INFORMATION: n is a, c, g, or t

<400> SEQUENCE: 172
ccggtctctt ttcttgttta caatccgacs nnattccagg cagcttctac gc 52

<210> SEQ ID NO 173
<211> LENGTH: 521
<212> TYPE: PRT
<213> ORGANISM: Bacillus amyloliquefaciens

<400> SEQUENCE: 173

-continued

```
Met Gly Leu Gly Lys Lys Leu Ser Val Ala Val Ala Ala Ser Phe Met
1               5                   10                  15

Ser Leu Thr Ile Ser Leu Pro Gly Val Gln Ala Ala Glu Asn Pro Gln
            20                  25                  30

Leu Lys Glu Asn Leu Thr Asn Phe Val Pro Lys His Ser Leu Val Gln
        35                  40                  45

Ser Glu Leu Pro Ser Val Ser Asp Lys Ala Ile Lys Gln Tyr Leu Lys
    50                  55                  60

Gln Asn Gly Lys Val Phe Lys Gly Asn Pro Ser Glu Arg Leu Lys Leu
65                  70                  75                  80

Ile Asp Gln Thr Thr Asp Asp Leu Gly Tyr Lys His Phe Arg Tyr Val
                85                  90                  95

Pro Val Val Asn Gly Val Pro Val Lys Asp Ser Gln Val Ile Ile His
            100                 105                 110

Val Asp Lys Ser Asn Asn Val Tyr Ala Ile Asn Gly Glu Leu Asn Asn
        115                 120                 125

Asp Val Ser Ala Lys Thr Ala Asn Ser Lys Lys Leu Ser Ala Asn Gln
    130                 135                 140

Ala Leu Asp His Ala Tyr Lys Ala Ile Gly Lys Ser Pro Glu Ala Val
145                 150                 155                 160

Ser Asn Gly Thr Val Ala Asn Lys Asn Lys Ala Glu Leu Lys Ala Ala
                165                 170                 175

Ala Thr Lys Asp Gly Lys Tyr Arg Leu Ala Tyr Asp Val Thr Ile Arg
            180                 185                 190

Tyr Ile Glu Pro Glu Pro Ala Asn Trp Glu Val Thr Val Asp Ala Glu
        195                 200                 205

Thr Gly Lys Ile Leu Lys Lys Gln Asn Lys Val Glu His Ala Ala Thr
    210                 215                 220

Thr Gly Thr Gly Thr Thr Leu Lys Gly Lys Thr Val Ser Leu Asn Ile
225                 230                 235                 240

Ser Ser Glu Ser Gly Lys Tyr Val Leu Arg Asp Leu Ser Lys Pro Thr
                245                 250                 255

Gly Thr Gln Ile Ile Thr Tyr Asp Leu Gln Asn Arg Glu Tyr Asn Leu
            260                 265                 270

Pro Gly Thr Leu Val Ser Ser Thr Thr Asn Gln Phe Thr Thr Ser Ser
        275                 280                 285

Gln Arg Ala Ala Val Asp Ala His Tyr Asn Leu Gly Lys Val Tyr Asp
    290                 295                 300

Tyr Phe Tyr Gln Lys Phe Asn Arg Asn Ser Tyr Asp Asn Lys Gly Gly
305                 310                 315                 320

Lys Ile Val Ser Ser Val His Tyr Gly Ser Arg Tyr Asn Asn Ala Ala
                325                 330                 335

Trp Ile Gly Asp Gln Met Ile Tyr Gly Asp Gly Asp Gly Ser Phe Phe
            340                 345                 350

Ser Pro Leu Ser Gly Ser Met Asp Val Thr Ala His Glu Met Thr His
        355                 360                 365

Gly Val Thr Gln Glu Thr Ala Asn Leu Asn Tyr Glu Asn Gln Pro Gly
    370                 375                 380

Ala Leu Asn Glu Ser Phe Ser Asp Val Phe Gly Tyr Phe Asn Asp Thr
385                 390                 395                 400

Glu Asp Trp Asp Ile Gly Glu Asp Ile Thr Val Ser Gln Pro Ala Leu
                405                 410                 415
```

-continued

```
Arg Ser Leu Ser Asn Pro Thr Lys Tyr Gly Gln Pro Asp Asn Phe Lys
            420                 425                 430

Asn Tyr Lys Asn Leu Pro Asn Thr Asp Ala Gly Asp Tyr Gly Gly Val
        435                 440                 445

His Thr Asn Ser Gly Ile Pro Asn Lys Ala Ala Tyr Asn Thr Ile Thr
    450                 455                 460

Lys Ile Gly Val Asn Lys Ala Glu Gln Ile Tyr Tyr Arg Ala Leu Thr
465                 470                 475                 480

Val Tyr Leu Thr Pro Ser Ser Thr Phe Lys Asp Ala Lys Ala Ala Leu
                485                 490                 495

Ile Gln Ser Ala Arg Asp Leu Tyr Gly Ser Gln Asp Ala Ala Ser Val
            500                 505                 510

Glu Ala Ala Trp Asn Ala Val Gly Leu
        515                 520


<210> SEQ ID NO 174
<211> LENGTH: 521
<212> TYPE: PRT
<213> ORGANISM: Bacillus subtilis

<400> SEQUENCE: 174

Met Gly Leu Gly Lys Lys Leu Ser Val Arg Val Ala Ala Ser Phe Met
1               5                   10                  15

Ser Leu Ser Ile Ser Leu Pro Gly Val Gln Ala Ala Glu Gly His Gln
            20                  25                  30

Leu Lys Glu Asn Gln Thr Asn Phe Leu Ser Lys Lys Pro Ile Ala Gln
        35                  40                  45

Ser Glu Leu Ser Ala Pro Asn Asp Lys Ala Val Lys Gln Phe Leu Lys
    50                  55                  60

Lys Asn Ser Asn Ile Phe Lys Gly Asp Pro Ser Lys Ser Val Lys Leu
65                  70                  75                  80

Val Glu Ser Thr Thr Asp Ala Leu Gly Tyr Lys His Phe Arg Tyr Ala
                85                  90                  95

Pro Val Val Asn Gly Val Pro Ile Lys Asp Ser Gln Val Ile Val His
            100                 105                 110

Val Asp Lys Ser Asp Asn Val Tyr Ala Val Asn Gly Glu Leu His Asn
        115                 120                 125

Gln Ser Ala Ala Lys Thr Asp Asn Ser Gln Lys Val Ser Ser Glu Lys
    130                 135                 140

Ala Leu Ala Leu Ala Phe Lys Ala Ile Gly Lys Ser Pro Asp Ala Val
145                 150                 155                 160

Ser Asn Gly Ala Ala Lys Asn Ser Asn Lys Ala Glu Leu Lys Ala Ile
                165                 170                 175

Glu Thr Lys Asp Gly Ser Tyr Arg Leu Ala Tyr Asp Val Thr Ile Arg
            180                 185                 190

Tyr Val Glu Pro Glu Pro Ala Asn Trp Glu Val Leu Val Asp Ala Glu
        195                 200                 205

Thr Gly Ser Ile Leu Lys Gln Gln Asn Lys Val Glu His Ala Ala Ala
    210                 215                 220

Thr Gly Ser Gly Thr Thr Leu Lys Gly Ala Thr Val Pro Leu Asn Ile
225                 230                 235                 240

Ser Tyr Glu Gly Gly Lys Tyr Val Leu Arg Asp Leu Ser Lys Pro Thr
                245                 250                 255

Gly Thr Gln Ile Ile Thr Tyr Asp Leu Gln Asn Arg Gln Ser Arg Leu
            260                 265                 270
```

```
Pro Gly Thr Leu Val Ser Ser Thr Thr Lys Thr Phe Thr Ser Ser Ser
        275                 280                 285

Gln Arg Ala Ala Val Asp Ala His Tyr Asn Leu Gly Lys Val Tyr Asp
    290                 295                 300

Tyr Phe Tyr Ser Asn Phe Lys Arg Asn Ser Tyr Asp Asn Lys Gly Ser
305                 310                 315                 320

Lys Ile Val Ser Ser Val His Tyr Gly Thr Gln Tyr Asn Asn Ala Ala
                325                 330                 335

Trp Thr Gly Asp Gln Met Ile Tyr Gly Asp Gly Asp Gly Ser Phe Phe
            340                 345                 350

Ser Pro Leu Ser Gly Ser Leu Asp Val Thr Ala His Glu Met Thr His
        355                 360                 365

Gly Val Thr Gln Glu Thr Ala Asn Leu Ile Tyr Glu Asn Gln Pro Gly
    370                 375                 380

Ala Leu Asn Glu Ser Phe Ser Asp Val Phe Gly Tyr Phe Asn Asp Thr
385                 390                 395                 400

Glu Asp Trp Asp Ile Gly Glu Asp Ile Thr Val Ser Gln Pro Ala Leu
                405                 410                 415

Arg Ser Leu Ser Asn Pro Thr Lys Tyr Asn Gln Pro Asp Asn Tyr Ala
            420                 425                 430

Asn Tyr Arg Asn Leu Pro Asn Thr Asp Glu Gly Asp Tyr Gly Gly Val
        435                 440                 445

His Thr Asn Ser Gly Ile Pro Asn Lys Ala Ala Tyr Asn Thr Ile Thr
    450                 455                 460

Lys Leu Gly Val Ser Lys Ser Gln Gln Ile Tyr Tyr Arg Ala Leu Thr
465                 470                 475                 480

Thr Tyr Leu Thr Pro Ser Ser Thr Phe Lys Asp Ala Lys Ala Ala Leu
                485                 490                 495

Ile Gln Ser Ala Arg Asp Leu Tyr Gly Ser Thr Asp Ala Ala Lys Val
            500                 505                 510

Glu Ala Ala Trp Asn Ala Val Gly Leu
        515                 520
```

<210> SEQ ID NO 175
<211> LENGTH: 509
<212> TYPE: PRT
<213> ORGANISM: Staphylococcus aureos

<400> SEQUENCE: 175

```
Met Arg Lys Phe Ser Arg Tyr Ala Phe Thr Ser Met Ala Thr Val Thr
1               5                   10                  15

Leu Leu Ser Ser Leu Thr Pro Ala Ala Leu Ala Ser Asp Thr Asn His
            20                  25                  30

Lys Pro Ala Thr Ser Asp Ile Asn Phe Glu Ile Thr Gln Lys Ser Asp
        35                  40                  45

Ala Val Lys Ala Leu Lys Glu Leu Pro Lys Ser Glu Asn Val Lys Asn
    50                  55                  60

His Tyr Gln Asp Tyr Ser Val Thr Asp Val Lys Thr Asp Lys Lys Gly
65                  70                  75                  80

Phe Thr His Tyr Thr Leu Gln Pro Ser Val Asp Gly Val His Ala Pro
                85                  90                  95

Asp Lys Glu Val Lys Val His Ala Asp Lys Ser Gly Lys Val Val Leu
            100                 105                 110

Ile Asn Gly Asp Thr Asp Ala Lys Lys Val Lys Pro Thr Asn Lys Val
```

```
        115                 120                 125

Thr Leu Ser Lys Asp Glu Ala Ala Asp Lys Ala Phe Asn Ala Val Lys
    130                 135                 140

Ile Asp Lys Asn Lys Ala Lys Asn Leu Gln Asp Asp Val Ile Lys Glu
145                 150                 155                 160

Asn Lys Val Glu Ile Asp Gly Asp Ser Asn Lys Tyr Ile Tyr Asn Ile
                165                 170                 175

Glu Leu Ile Thr Val Thr Pro Glu Ile Ser His Trp Lys Val Lys Ile
            180                 185                 190

Asp Ala Asp Thr Gly Ala Val Val Glu Lys Thr Asn Leu Val Lys Glu
        195                 200                 205

Ala Ala Ala Thr Gly Thr Gly Lys Gly Val Leu Gly Asp Thr Lys Asp
    210                 215                 220

Ile Asn Ile Asn Ser Ile Asp Gly Gly Phe Ser Leu Glu Asp Leu Thr
225                 230                 235                 240

His Gln Gly Lys Leu Ser Ala Tyr Asn Phe Asn Asp Gln Thr Gly Gln
                245                 250                 255

Ala Thr Leu Ile Thr Asn Glu Asp Glu Asn Phe Val Lys Asp Asp Gln
            260                 265                 270

Arg Ala Gly Val Asp Ala Asn Tyr Tyr Ala Lys Gln Thr Tyr Asp Tyr
        275                 280                 285

Tyr Lys Asn Thr Phe Gly Arg Glu Ser Tyr Asp Asn His Gly Ser Pro
    290                 295                 300

Ile Val Ser Leu Thr His Val Asn His Tyr Gly Gly Gln Asp Asn Arg
305                 310                 315                 320

Asn Asn Ala Ala Trp Ile Gly Asp Lys Met Ile Tyr Gly Asp Gly Asp
                325                 330                 335

Gly Arg Thr Phe Thr Asn Leu Ser Gly Ala Asn Asp Val Val Ala His
            340                 345                 350

Glu Leu Thr His Gly Val Thr Gln Glu Thr Ala Asn Leu Glu Tyr Lys
        355                 360                 365

Asp Gln Ser Gly Ala Leu Asn Glu Ser Phe Ser Asp Val Phe Gly Tyr
    370                 375                 380

Phe Val Asp Asp Glu Asp Phe Leu Met Gly Glu Asp Val Tyr Thr Pro
385                 390                 395                 400

Gly Lys Glu Gly Asp Ala Leu Arg Ser Met Ser Asn Pro Glu Gln Phe
                405                 410                 415

Gly Gln Pro Ser His Met Lys Asp Tyr Val Tyr Thr Glu Lys Asp Asn
            420                 425                 430

Gly Gly Val His Thr Asn Ser Gly Ile Pro Asn Lys Ala Ala Tyr Asn
        435                 440                 445

Val Ile Gln Ala Ile Gly Lys Ser Lys Ser Glu Gln Ile Tyr Tyr Arg
    450                 455                 460

Ala Leu Thr Glu Tyr Leu Thr Ser Asn Ser Asn Phe Lys Asp Cys Lys
465                 470                 475                 480

Asp Ala Leu Tyr Gln Ala Ala Lys Asp Leu Tyr Asp Glu Gln Thr Ala
                485                 490                 495

Glu Gln Val Tyr Glu Ala Trp Asn Glu Val Gly Val Glu
            500                 505
```

<210> SEQ ID NO 176
<211> LENGTH: 548
<212> TYPE: PRT
<213> ORGANISM: Bacillus stearothermophilis

<400> SEQUENCE: 176

```
Met Asn Lys Arg Ala Met Leu Gly Ala Ile Gly Leu Ala Phe Gly Leu
1               5                   10                  15

Leu Ala Ala Pro Ile Gly Ala Ser Ala Lys Gly Glu Ser Ile Val Trp
            20                  25                  30

Asn Glu Gln Trp Lys Thr Pro Ser Phe Val Ser Gly Ser Leu Leu Asn
        35                  40                  45

Gly Gly Glu Gln Ala Leu Glu Glu Leu Val Tyr Gln Tyr Val Asp Arg
    50                  55                  60

Glu Asn Gly Thr Phe Arg Leu Gly Gly Arg Ala Arg Asp Arg Leu Ala
65                  70                  75                  80

Leu Ile Gly Lys Gln Thr Asp Glu Leu Gly His Thr Val Met Arg Phe
                85                  90                  95

Glu Gln Arg His His Gly Ile Pro Val Tyr Gly Thr Met Leu Ala Ala
            100                 105                 110

His Val Lys Asp Gly Glu Leu Ile Ala Leu Ser Gly Ser Leu Ile Pro
        115                 120                 125

Asn Leu Asp Gly Gln Pro Arg Leu Lys Lys Ala Lys Thr Val Thr Val
    130                 135                 140

Gln Gln Ala Glu Ala Ile Ala Glu Gln Asp Val Thr Glu Thr Val Thr
145                 150                 155                 160

Lys Glu Arg Pro Thr Thr Glu Asn Gly Glu Arg Thr Arg Leu Val Ile
                165                 170                 175

Tyr Pro Thr Asp Gly Thr Ala Arg Leu Ala Tyr Glu Val Asn Val Arg
            180                 185                 190

Phe Leu Thr Pro Val Pro Gly Asn Trp Val Tyr Ile Ile Asp Ala Thr
        195                 200                 205

Asp Gly Ala Ile Leu Asn Lys Phe Asn Gln Ile Asp Ser Arg Gln Pro
    210                 215                 220

Gly Gly Gly Gln Pro Val Ala Gly Ala Ser Thr Val Gly Val Gly Arg
225                 230                 235                 240

Gly Val Leu Gly Asp Gln Lys Tyr Ile Asn Thr Thr Tyr Ser Ser Tyr
                245                 250                 255

Tyr Gly Tyr Tyr Tyr Leu Gln Asp Asn Thr Arg Gly Ser Gly Ile Phe
            260                 265                 270

Thr Tyr Asp Gly Arg Asn Arg Thr Val Leu Pro Gly Ser Leu Trp Thr
        275                 280                 285

Asp Gly Asp Asn Gln Phe Thr Ala Ser Tyr Asp Ala Ala Ala Val Asp
    290                 295                 300

Ala His Tyr Tyr Ala Gly Val Val Tyr Asp Tyr Tyr Lys Asn Val His
305                 310                 315                 320

Gly Arg Leu Ser Tyr Asp Gly Ser Asn Ala Ala Ile Arg Ser Thr Val
                325                 330                 335

His Tyr Gly Arg Gly Tyr Asn Asn Ala Phe Trp Asn Gly Ser Gln Met
            340                 345                 350

Val Tyr Gly Asp Gly Asp Gly Gln Thr Phe Leu Pro Phe Ser Gly Gly
        355                 360                 365

Ile Asp Val Val Gly His Glu Leu Thr His Ala Val Thr Asp Tyr Thr
    370                 375                 380

Ala Gly Leu Val Tyr Gln Asn Glu Ser Gly Ala Ile Asn Glu Ala Met
385                 390                 395                 400

Ser Asp Ile Phe Gly Thr Leu Val Glu Phe Tyr Ala Asn Arg Asn Pro
```

```
                405                 410                 415

Asp Trp Glu Ile Gly Glu Asp Ile Tyr Thr Pro Gly Val Ala Gly Asp
            420                 425                 430

Ala Leu Arg Ser Met Ser Asp Pro Ala Lys Tyr Gly Asp Pro Asp His
        435                 440                 445

Tyr Ser Lys Arg Tyr Thr Gly Thr Gln Asp Asn Gly Gly Val His Thr
    450                 455                 460

Asn Ser Gly Ile Ile Asn Lys Ala Ala Tyr Leu Leu Ser Gln Gly Gly
465                 470                 475                 480

Val His Tyr Gly Val Ser Val Asn Gly Ile Gly Arg Asp Lys Met Gly
                485                 490                 495

Lys Ile Phe Tyr Arg Ala Leu Val Tyr Tyr Leu Thr Pro Thr Ser Asn
            500                 505                 510

Phe Ser Gln Leu Arg Ala Ala Cys Val Gln Ala Ala Ala Asp Leu Tyr
        515                 520                 525

Gly Ser Thr Ser Gln Glu Val Asn Ser Val Lys Gln Ala Phe Asn Ala
    530                 535                 540

Val Gly Val Tyr
545


<210> SEQ ID NO 177
<211> LENGTH: 544
<212> TYPE: PRT
<213> ORGANISM: Bacillus caldolyticus

<400> SEQUENCE: 177

Met Asn Lys Arg Ala Met Leu Gly Ala Ile Gly Leu Ala Phe Gly Leu
1               5                   10                  15

Met Ala Trp Pro Phe Gly Ala Ser Ala Lys Gly Lys Ser Met Val Trp
            20                  25                  30

Asn Glu Gln Trp Lys Thr Pro Ser Phe Val Ser Gly Ser Leu Leu Gly
        35                  40                  45

Arg Cys Ser Gln Glu Leu Val Tyr Arg Tyr Leu Asp Gln Glu Lys Asn
    50                  55                  60

Thr Phe Gln Leu Gly Gly Gln Ala Arg Glu Arg Leu Ser Leu Ile Gly
65                  70                  75                  80

Asn Lys Leu Asp Glu Leu Gly His Thr Val Met Arg Phe Glu Gln Ala
                85                  90                  95

Ile Ala Ala Ser Leu Cys Met Gly Ala Val Leu Val Ala His Val Asn
            100                 105                 110

Asp Gly Glu Leu Ser Ser Leu Ser Gly Thr Leu Ile Pro Asn Leu Asp
        115                 120                 125

Lys Arg Thr Leu Lys Thr Glu Ala Ala Ile Ser Ile Gln Gln Ala Glu
    130                 135                 140

Met Ile Ala Lys Gln Asp Val Ala Asp Arg Val Thr Lys Glu Arg Pro
145                 150                 155                 160

Ala Ala Glu Glu Gly Lys Pro Thr Arg Leu Val Ile Tyr Pro Asp Glu
                165                 170                 175

Glu Thr Pro Arg Leu Ala Tyr Glu Val Asn Val Arg Phe Leu Thr Pro
            180                 185                 190

Val Pro Gly Asn Trp Ile Tyr Met Ile Asp Ala Ala Asp Gly Lys Val
        195                 200                 205

Leu Asn Lys Trp Asn Gln Met Asp Glu Ala Lys Pro Gly Gly Ala Gln
    210                 215                 220
```

Pro Val Ala Gly Thr Ser Thr Val Gly Val Gly Arg Gly Val Leu Gly
225 230 235 240

Asp Gln Lys Tyr Ile Asn Thr Thr Tyr Ser Ser Tyr Tyr Gly Tyr Tyr
245 250 255

Tyr Leu Gln Asp Asn Thr Arg Gly Ser Gly Ile Phe Thr Tyr Asp Gly
260 265 270

Arg Asn Arg Thr Val Leu Pro Gly Ser Leu Trp Ala Asp Gly Asp Asn
275 280 285

Gln Phe Phe Ala Ser Tyr Asp Ala Ala Ala Val Asp Ala His Tyr Tyr
290 295 300

Ala Gly Val Val Tyr Asp Tyr Tyr Lys Asn Val His Gly Arg Leu Ser
305 310 315 320

Tyr Asp Gly Ser Asn Ala Ala Ile Arg Ser Thr Val His Tyr Gly Arg
325 330 335

Gly Tyr Asn Asn Ala Phe Trp Asn Gly Ser Gln Met Val Tyr Gly Asp
340 345 350

Gly Asp Gly Gln Thr Phe Leu Pro Phe Ser Gly Gly Ile Asp Val Val
355 360 365

Gly His Glu Leu Thr His Ala Val Thr Asp Tyr Thr Ala Gly Leu Val
370 375 380

Tyr Gln Asn Glu Ser Gly Ala Ile Asn Glu Ala Met Ser Asp Ile Phe
385 390 395 400

Gly Thr Leu Val Glu Phe Tyr Ala Asn Arg Asn Pro Asp Trp Glu Ile
405 410 415

Gly Glu Asp Ile Tyr Thr Pro Gly Val Ala Gly Asp Ala Leu Arg Ser
420 425 430

Met Ser Asp Pro Ala Lys Tyr Gly Asp Pro Asp His Tyr Ser Lys Arg
435 440 445

Tyr Thr Gly Thr Gln Asp Asn Gly Gly Val His Thr Asn Ser Gly Ile
450 455 460

Ile Asn Lys Ala Ala Tyr Leu Leu Ser Gln Gly Gly Val His Tyr Gly
465 470 475 480

Val Ser Val Thr Gly Ile Gly Arg Asp Lys Met Gly Lys Ile Phe Tyr
485 490 495

Arg Ala Leu Val Tyr Tyr Leu Thr Pro Thr Ser Asn Phe Ser Gln Leu
500 505 510

Arg Ala Ala Cys Val Gln Ala Ala Ala Asp Leu Tyr Gly Ser Thr Ser
515 520 525

Gln Glu Val Asn Ser Val Lys Gln Ala Phe Asn Ala Val Gly Val Tyr
530 535 540

<210> SEQ ID NO 178
<211> LENGTH: 566
<212> TYPE: PRT
<213> ORGANISM: Bacillus thuringiensis

<400> SEQUENCE: 178

Met Lys Lys Lys Ser Leu Ala Leu Val Leu Ala Thr Gly Met Ala Val
1 5 10 15

Thr Thr Phe Gly Gly Thr Gly Ser Ala Phe Ala Asp Ser Lys Asn Val
20 25 30

Leu Ser Thr Lys Lys Tyr Asn Glu Thr Val Gln Ser Pro Glu Phe Val
35 40 45

Ser Gly Asp Leu Thr Glu Ala Thr Gly Lys Lys Ala Glu Ser Val Val
50 55 60

-continued

```
Phe Asp Tyr Leu Asn Ala Ala Lys Gly Asp Tyr Lys Leu Gly Glu Lys
65                  70                  75                  80

Ser Ala Gln Asp Cys Phe Lys Val Lys Gln Ala Lys Lys Asp Ala Val
                85                  90                  95

Thr Asp Ser Thr Val Leu Arg Leu Gln Gln Val Tyr Glu Gly Val Pro
            100                 105                 110

Val Trp Gly Ser Thr Gln Val Ala His Val Ser Lys Asp Gly Ser Leu
        115                 120                 125

Lys Val Leu Ser Gly Thr Val Ala Pro Asp Leu Asp Lys Lys Glu Lys
    130                 135                 140

Leu Lys Asn Lys Asn Lys Ile Glu Gly Ala Lys Ala Ile Glu Ile Ala
145                 150                 155                 160

Gln Lys Asp Leu Gly Ile Thr Pro Lys Tyr Glu Val Glu Pro Lys Ala
                165                 170                 175

Asp Leu Tyr Val Tyr Gln Asn Gly Glu Glu Thr Thr Tyr Ala Tyr Val
            180                 185                 190

Val Asn Leu Asn Phe Leu Asp Pro Ser Pro Gly Asn Tyr Tyr Tyr Phe
        195                 200                 205

Ile Glu Ala Asp Ser Gly Lys Val Leu Asn Lys Tyr Asn Lys Leu Asp
    210                 215                 220

His Val Ala Asn Glu Asp Lys Ser Pro Val Lys Gln Glu Ala Pro Lys
225                 230                 235                 240

Gln Glu Val Lys Pro Ala Val Lys Pro Val Thr Gly Thr Asn Ala Val
                245                 250                 255

Gly Thr Gly Lys Gly Val Leu Gly Asp Thr Lys Ser Leu Asn Thr Thr
            260                 265                 270

Leu Ser Ser Ser Ser Tyr Tyr Leu Gln Asp Asn Thr Arg Gly Ala Thr
        275                 280                 285

Ile Phe Thr Tyr Asp Ala Lys Asn Arg Thr Thr Leu Pro Gly Thr Leu
    290                 295                 300

Trp Val Asp Ala Asp Asn Val Phe Asn Ala Ala Tyr Asp Ala Ala Ala
305                 310                 315                 320

Val Asp Ala His Tyr Tyr Ala Gly Lys Thr Tyr Asp Tyr Tyr Lys Ala
                325                 330                 335

Thr Phe Asn Arg Asn Ser Ile Asn Asp Ala Gly Ala Pro Leu Lys Ser
            340                 345                 350

Thr Val His Tyr Gly Ser Lys Tyr Asn Asn Ala Phe Trp Asn Gly Ser
        355                 360                 365

Gln Met Val Tyr Gly Asp Gly Asp Gly Val Thr Phe Thr Ser Leu Ser
    370                 375                 380

Gly Gly Ile Asp Val Ile Gly His Glu Leu Thr His Ala Val Thr Glu
385                 390                 395                 400

Tyr Ser Ser Asp Leu Ile Tyr Gln Asn Glu Ser Gly Ala Leu Asn Glu
                405                 410                 415

Ala Ile Ser Asp Val Phe Gly Thr Leu Val Glu Phe Tyr Asp Asn Arg
            420                 425                 430

Asn Pro Asp Trp Glu Ile Gly Glu Asp Ile Tyr Thr Pro Gly Lys Ala
        435                 440                 445

Gly Asp Ala Leu Arg Ser Met Ser Asp Pro Thr Lys Tyr Gly Asp Pro
    450                 455                 460

Asp His Tyr Ser Lys Arg Tyr Thr Gly Thr Ser Asp Asn Gly Gly Val
465                 470                 475                 480
```

```
His Thr Asn Ser Gly Ile Ile Asn Lys Gln Ala Tyr Leu Leu Ala Asn
                485                 490                 495

Gly Gly Thr His Tyr Gly Val Thr Val Thr Gly Ile Gly Lys Asp Lys
            500                 505                 510

Leu Gly Ala Ile Tyr Tyr Arg Ala Asn Thr Gln Tyr Phe Thr Gln Ser
        515                 520                 525

Thr Thr Phe Ser Gln Ala Arg Ala Gly Ala Val Gln Ala Ala Ala Asp
    530                 535                 540

Leu Tyr Gly Ala Asn Ser Ala Glu Val Asn Ala Val Lys Gln Ser Phe
545                 550                 555                 560

Ser Ala Val Gly Ile Asn
                565


<210> SEQ ID NO 179
<211> LENGTH: 566
<212> TYPE: PRT
<213> ORGANISM: Bacillus cereus

<400> SEQUENCE: 179

Met Lys Lys Lys Ser Leu Ala Leu Val Leu Ala Thr Gly Met Ala Val
1               5                   10                  15

Thr Thr Phe Gly Gly Thr Gly Ser Ala Phe Ala Asp Ser Lys Asn Val
            20                  25                  30

Leu Ser Thr Lys Lys Tyr Asn Glu Thr Val Gln Ser Pro Glu Phe Ile
        35                  40                  45

Ser Gly Asp Leu Thr Glu Ala Thr Gly Lys Lys Ala Glu Ser Val Val
    50                  55                  60

Phe Asp Tyr Leu Asn Ala Ala Lys Gly Asp Tyr Lys Leu Gly Glu Lys
65                  70                  75                  80

Ser Ala Gln Asp Ser Phe Lys Val Lys Gln Val Lys Lys Asp Ala Val
                85                  90                  95

Thr Asp Ser Thr Val Val Arg Met Gln Gln Val Tyr Glu Gly Val Pro
            100                 105                 110

Val Trp Gly Ser Thr Gln Val Ala His Val Ser Lys Asp Gly Ser Leu
        115                 120                 125

Lys Val Leu Ser Gly Thr Val Ala Pro Asp Leu Asp Lys Lys Glu Lys
    130                 135                 140

Leu Lys Asn Lys Asn Lys Ile Glu Gly Ala Lys Ala Ile Glu Ile Ala
145                 150                 155                 160

Gln Gln Asp Leu Gly Val Thr Pro Lys Tyr Glu Val Glu Pro Lys Ala
                165                 170                 175

Asp Leu Tyr Val Tyr Gln Asn Gly Glu Glu Thr Thr Tyr Ala Tyr Val
            180                 185                 190

Val Asn Leu Asn Phe Leu Asp Pro Ser Pro Gly Asn Tyr Tyr Tyr Phe
        195                 200                 205

Ile Glu Ala Asp Ser Gly Lys Val Leu Asn Lys Phe Asn Thr Ile Asp
    210                 215                 220

His Val Thr Asn Asp Asp Lys Ser Pro Val Lys Gln Glu Ala Pro Lys
225                 230                 235                 240

Gln Asp Ala Lys Ala Val Val Lys Pro Val Thr Gly Thr Asn Lys Val
                245                 250                 255

Gly Thr Gly Lys Gly Val Leu Gly Asp Thr Lys Ser Leu Asn Thr Thr
            260                 265                 270

Leu Ser Gly Ser Ser Tyr Tyr Leu Gln Asp Asn Thr Arg Gly Ala Thr
        275                 280                 285
```

Ile Phe Thr Tyr Asp Ala Lys Asn Arg Ser Thr Leu Pro Gly Thr Leu
    290                 295                 300

Trp Ala Asp Ala Asp Asn Val Phe Asn Ala Ala Tyr Asp Ala Ala Ala
305                 310                 315                 320

Val Asp Ala His Tyr Tyr Ala Gly Lys Thr Tyr Asp Tyr Tyr Lys Ala
                325                 330                 335

Thr Phe Asn Arg Asn Ser Ile Asn Asp Ala Gly Ala Pro Leu Lys Ser
            340                 345                 350

Thr Val His Tyr Gly Ser Asn Tyr Asn Asn Ala Phe Trp Asn Gly Ser
        355                 360                 365

Gln Met Val Tyr Gly Asp Gly Asp Gly Val Thr Phe Thr Ser Leu Ser
    370                 375                 380

Gly Gly Ile Asp Val Ile Gly His Glu Leu Thr His Ala Val Thr Glu
385                 390                 395                 400

Asn Ser Ser Asn Leu Ile Tyr Gln Asn Glu Ser Gly Ala Leu Asn Glu
                405                 410                 415

Ala Ile Ser Asp Ile Phe Gly Thr Leu Val Glu Phe Tyr Asp Asn Arg
            420                 425                 430

Asn Pro Asp Trp Glu Ile Gly Glu Asp Ile Tyr Thr Pro Gly Lys Ala
        435                 440                 445

Gly Asp Ala Leu Arg Ser Met Ser Asp Pro Thr Lys Tyr Gly Asp Pro
    450                 455                 460

Asp His Tyr Ser Lys Arg Tyr Thr Gly Ser Ser Asp Asn Gly Gly Val
465                 470                 475                 480

His Thr Asn Ser Gly Ile Ile Asn Lys Gln Ala Tyr Leu Leu Ala Asn
                485                 490                 495

Gly Gly Thr His Tyr Gly Val Thr Val Thr Gly Ile Gly Lys Asp Lys
            500                 505                 510

Leu Gly Ala Ile Tyr Tyr Arg Ala Asn Thr Gln Tyr Phe Thr Gln Ser
        515                 520                 525

Thr Thr Phe Ser Gln Ala Arg Ala Gly Ala Val Gln Ala Ala Ala Asp
    530                 535                 540

Leu Tyr Gly Ala Asn Ser Ala Glu Val Ala Ala Val Lys Gln Ser Phe
545                 550                 555                 560

Ser Ala Val Gly Val Asn
                565

<210> SEQ ID NO 180
<211> LENGTH: 538
<212> TYPE: PRT
<213> ORGANISM: Bacillus subtilis

<400> SEQUENCE: 180

Met Arg Asn Leu Thr Lys Thr Ser Leu Leu Leu Ala Gly Leu Cys Thr
1               5                   10                  15

Ala Ala Gln Met Val Phe Val Thr His Ala Ser Ala Glu Glu Ser Ile
            20                  25                  30

Glu Tyr Asp His Thr Tyr Gln Thr Pro Ser Tyr Ile Ile Glu Lys Ser
        35                  40                  45

Pro Gln Lys Pro Val Gln Asn Thr Thr Gln Lys Glu Ser Leu Phe Ser
    50                  55                  60

Tyr Leu Asp Lys His Gln Thr Gln Phe Lys Leu Lys Gly Asn Ala Asn
65                  70                  75                  80

Ser His Phe Arg Val Ser Lys Thr Ile Lys Asp Pro Lys Thr Lys Gln

-continued

```
                85                  90                  95

Thr Phe Phe Lys Leu Thr Glu Val Tyr Lys Gly Ile Pro Ile Tyr Gly
            100                 105                 110

Phe Glu Gln Ala Val Ala Met Lys Glu Asn Lys Gln Val Lys Ser Phe
        115                 120                 125

Phe Gly Lys Val His Pro Gln Ile Lys Asp Val Ser Val Thr Pro Ser
    130                 135                 140

Ile Ser Glu Lys Lys Ala Ile His Thr Ala Arg Arg Glu Leu Glu Ala
145                 150                 155                 160

Ser Ile Gly Lys Ile Glu Tyr Leu Asp Gly Glu Pro Lys Gly Glu Leu
                165                 170                 175

Tyr Ile Tyr Pro His Asp Gly Glu Tyr Asp Leu Ala Tyr Leu Val Arg
            180                 185                 190

Leu Ser Thr Ser Glu Pro Glu Pro Gly Tyr Trp His Tyr Phe Ile Asp
        195                 200                 205

Ala Lys Asn Gly Lys Val Ile Glu Ser Phe Asn Ala Ile His Glu Ala
    210                 215                 220

Ala Gly Thr Gly Ile Gly Val Ser Gly Asp Glu Lys Ser Phe Asp Val
225                 230                 235                 240

Thr Glu Gln Asn Gly Arg Phe Tyr Leu Ala Asp Glu Thr Arg Gly Lys
                245                 250                 255

Gly Ile Asn Thr Phe Asp Ala Lys Asn Leu Asn Glu Thr Leu Phe Thr
            260                 265                 270

Leu Leu Ser Gln Leu Ile Gly Tyr Thr Gly Lys Glu Ile Val Ser Gly
        275                 280                 285

Thr Ser Val Phe Asn Glu Pro Ala Ala Val Asp Ala His Ala Asn Ala
    290                 295                 300

Gln Ala Val Tyr Asp Tyr Tyr Ser Lys Thr Phe Gly Arg Asp Ser Phe
305                 310                 315                 320

Asp Gln Asn Gly Ala Arg Ile Thr Ser Thr Val His Val Gly Lys Gln
                325                 330                 335

Trp Asn Asn Ala Ala Trp Asn Gly Val Gln Met Val Tyr Gly Asp Gly
            340                 345                 350

Asp Gly Ser Lys Phe Lys Pro Leu Ser Gly Ser Leu Asp Ile Val Ala
        355                 360                 365

His Glu Ile Thr His Ala Val Thr Gln Tyr Ser Ala Gly Leu Leu Tyr
    370                 375                 380

Gln Gly Glu Pro Gly Ala Leu Asn Glu Ser Ile Ser Asp Ile Met Gly
385                 390                 395                 400

Ala Met Ala Asp Arg Asp Asp Trp Glu Ile Gly Glu Asp Val Tyr Thr
                405                 410                 415

Pro Gly Ile Ala Gly Asp Ser Leu Arg Ser Leu Glu Asp Pro Ser Lys
            420                 425                 430

Gln Gly Asn Pro Asp His Tyr Ser Asn Arg Tyr Thr Gly Thr Glu Asp
        435                 440                 445

Tyr Gly Gly Val His Ile Asn Ser Ser Ile His Asn Lys Ala Ala Tyr
    450                 455                 460

Leu Leu Ala Glu Gly Gly Val His His Gly Val Gln Val Glu Gly Ile
465                 470                 475                 480

Gly Arg Glu Ala Ser Glu Gln Ile Tyr Tyr Arg Ala Leu Thr Tyr Tyr
                485                 490                 495

Val Thr Ala Ser Thr Asp Phe Ser Met Met Lys Gln Ala Ala Ile Glu
            500                 505                 510
```

Ala Ala Asn Asp Leu Tyr Gly Glu Gly Ser Lys Gln Ser Ala Ser Val
515 520 525

Glu Lys Ala Tyr Glu Ala Val Gly Ile Leu
530 535

<210> SEQ ID NO 181
<211> LENGTH: 568
<212> TYPE: PRT
<213> ORGANISM: Bacillus cereus

<400> SEQUENCE: 181

Met Lys Asn Lys Lys Asn Phe Val Lys Ile Gly Leu Thr Thr Gly Val
1 5 10 15

Met Leu Ser Val Ile Met Pro Tyr Gly Asp Ala Tyr Ala Ala Thr Glu
20 25 30

Asp Leu Lys Val Glu Thr Lys Glu Asp Thr Phe Arg Thr Gly Asn Leu
35 40 45

Thr Val Pro Ser Gln Lys Ser Ala Glu Asn Val Ala Lys Asp Ala Leu
50 55 60

Lys Gly Lys Thr Glu Gln Ala Leu Ser Ser Lys Gln Val Asn Thr Glu
65 70 75 80

Ser Lys Val Asn Tyr Asn Val Thr Gln Ser Arg Lys Ser Tyr Asp Gly
85 90 95

Thr Thr Leu Val Arg Leu Gln Gln Thr Tyr Glu Gly Arg Asp Val Tyr
100 105 110

Gly Tyr Gln Leu Thr Ala His Ile Asn Asp Asp Gly Val Leu Thr Ser
115 120 125

Val Ser Gly Asp Ser Ala Gln Asp Leu Gln Gln Gln Glu Asp Leu Lys
130 135 140

Gln Pro Ile Thr Leu Ser Glu Glu Asp Ala Lys Lys Gln Leu Phe Lys
145 150 155 160

Ile Tyr Gly Asp Asn Leu Thr Phe Val Glu Glu Pro Glu Ile Lys Gln
165 170 175

Val Val Tyr Val Asp Glu Asn Thr Asn Lys Ala Thr Ser Ala Tyr Gln
180 185 190

Ile Thr Phe Ser Ala Ser Thr Pro Glu Tyr Val Ser Gly Thr Val Leu
195 200 205

Ile Asp Ala Phe Val Gly Asp Leu Leu Lys Glu Leu Val Gln Lys Leu
210 215 220

Gly Ile Gln Val Asp Ser Ser Ile Val Gln Ser Ala Thr Ser Asn Lys
225 230 235 240

Ser Gln Asp Pro Ser Lys Leu Thr Gly Thr Gly Lys Asp Asp Leu Gly
245 250 255

Met Asn Arg Thr Phe Gly Ile Ser Gln Arg Ser Asp Gly Thr Tyr Thr
260 265 270

Leu Ala Asp Tyr Ser Arg Gly Lys Gly Ile Glu Thr Tyr Thr Ala Asn
275 280 285

Tyr Lys Asp Tyr Asn Asn Tyr Arg Arg Asn Ile Trp Gly Tyr Leu Asp
290 295 300

Asp Leu Val Thr Ser Asn Ser Thr Asn Phe Thr Asp Pro Lys Ala Val
305 310 315 320

Ser Ala His Tyr Leu Ala Thr Lys Val Tyr Asp Phe Tyr Gln Glu Lys
325 330 335

Tyr Ser Arg Asn Ser Phe Asp Asn Asn Gly Gln Lys Val Ile Ser Val

```
            340                 345                 350

Val His Gly Trp Asn Thr Asn Gly Thr Asn Lys Gly Asn Pro Lys Gln
        355                 360                 365

Trp Phe Asn Ala Phe Ser Asn Gly Ala Met Leu Val Tyr Gly Asp Pro
    370                 375                 380

Ile Val Arg Ala Phe Asp Val Ala Gly His Glu Phe Thr His Ala Val
385                 390                 395                 400

Thr Arg Asn Glu Ser Gly Leu Glu Tyr Ala Gly Glu Ala Gly Ala Ile
                405                 410                 415

Asn Glu Ala Ile Ser Asp Ile Leu Gly Val Ala Val Glu Lys Tyr Ala
            420                 425                 430

Asn Asn Gly Lys Phe Asn Trp Thr Met Gly Glu Gln Ser Gly Arg Ile
        435                 440                 445

Phe Arg Asp Met Lys Asn Pro Ser Ser Ile Ser Ser Arg Tyr Pro Glu
    450                 455                 460

Asp Tyr Arg His Tyr Asn Asn Leu Pro Ile Asp Ala Ala His Asp His
465                 470                 475                 480

Gly Gly Val His Thr Asn Ser Ser Ile Ile Asn Lys Val Ala Tyr Leu
                485                 490                 495

Ile Ala Ser Gly Gly Asn His Asn Gly Val Asn Val Gln Gly Ile Gly
            500                 505                 510

Glu Asp Lys Met Phe Asp Ile Phe Tyr Tyr Ala Asn Thr Asp Glu Leu
        515                 520                 525

Asn Met Thr Ser Asp Phe Lys Glu Leu Lys Glu Ala Cys Ile Arg Val
    530                 535                 540

Ala Thr Asn Leu Tyr Gly Lys Asp Ser Ser Glu Val Gln Ala Val Gln
545                 550                 555                 560

Gln Ala Phe Lys Ala Ala Tyr Ile
                565


<210> SEQ ID NO 182
<211> LENGTH: 316
<212> TYPE: PRT
<213> ORGANISM: Bacillus thermoproteolyticus

<400> SEQUENCE: 182

Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Tyr Leu Gln Asp
            20                  25                  30

Asn Thr Arg Gly Asn Gly Ile Phe Thr Tyr Asp Ala Lys Tyr Arg Thr
        35                  40                  45

Thr Leu Pro Gly Ser Leu Trp Ala Asp Ala Asp Asn Gln Phe Phe Ala
    50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95

Asn Ala Ala Ile Arg Ser Ser Val His Tyr Ser Gln Gly Tyr Asn Asn
            100                 105                 110

Ala Phe Trp Asn Gly Ser Gln Met Val Tyr Gly Asp Gly Asp Gly Gln
        115                 120                 125

Thr Phe Ile Pro Leu Ser Gly Gly Ile Asp Val Val Ala His Glu Leu
    130                 135                 140
```

Thr His Ala Val Thr Asp Tyr Thr Ala Gly Leu Ile Tyr Gln Asn Glu
145 150 155 160

Ser Gly Ala Ile Asn Glu Ala Ile Ser Asp Ile Phe Gly Thr Leu Val
165 170 175

Lys Phe Tyr Ala Asn Lys Asn Pro Asp Trp Glu Ile Gly Glu Asp Val
180 185 190

Tyr Thr Pro Gly Ile Ser Gly Asp Ser Leu Arg Ser Met Ser Asp Pro
195 200 205

Ala Lys Tyr Gly Asp Pro Asp His Tyr Ser Lys Arg Tyr Thr Gly Thr
210 215 220

Gln Asp Asn Gly Gly Val His Ile Asn Ser Gly Ile Ile Asn Lys Ala
225 230 235 240

Ala Tyr Leu Ile Ser Gln Gly Gly Thr His Tyr Gly Val Ser Val Val
245 250 255

Gly Ile Gly Arg Asp Lys Leu Gly Lys Ile Phe Tyr Arg Ala Leu Thr
260 265 270

Gln Tyr Leu Thr Pro Thr Ser Asn Phe Ser Gln Leu Arg Ala Ala Ala
275 280 285

Val Gln Ser Ala Thr Asp Leu Tyr Gly Ser Thr Ser Gln Glu Val Ala
290 295 300

Ser Val Lys Gln Ala Phe Asp Ala Val Gly Val Lys
305 310 315

<210> SEQ ID NO 183
<211> LENGTH: 316
<212> TYPE: PRT
<213> ORGANISM: Bacillus stearothermophilis

<400> SEQUENCE: 183

Ile Thr Gly Thr Ser Thr Val Gly Val Gly Arg Gly Val Leu Gly Asp
1 5 10 15

Gln Lys Asn Ile Asn Thr Thr Tyr Ser Thr Tyr Tyr Tyr Leu Gln Asp
20 25 30

Asn Thr Arg Gly Asn Gly Ile Phe Thr Tyr Asp Ala Lys Tyr Arg Thr
35 40 45

Thr Leu Pro Gly Ser Leu Trp Ala Asp Ala Asp Asn Gln Phe Phe Ala
50 55 60

Ser Tyr Asp Ala Pro Ala Val Asp Ala His Tyr Tyr Ala Gly Val Thr
65 70 75 80

Tyr Asp Tyr Tyr Lys Asn Val His Asn Arg Leu Ser Tyr Asp Gly Asn
85 90 95

Asn Ala Ala Ile Arg Ser Ser Val His Tyr Ser Gln Gly Tyr Asn Asn
100 105 110

Ala Phe Trp Asn Gly Ser Gln Met Val Tyr Gly Asp Gly Asp Gly Gln
115 120 125

Thr Phe Ile Pro Leu Ser Gly Gly Ile Asp Val Val Ala His Glu Leu
130 135 140

Thr His Ala Val Thr Asp Tyr Thr Ala Gly Leu Ile Tyr Gln Asn Glu
145 150 155 160

Ser Gly Ala Ile Asn Glu Ala Ile Ser Asp Ile Phe Gly Thr Leu Val
165 170 175

Glu Phe Tyr Ala Asn Lys Asn Pro Asp Trp Glu Ile Gly Glu Asp Val
180 185 190

Tyr Thr Pro Gly Ile Ser Gly Asp Ser Leu Arg Ser Met Ser Asp Pro
195 200 205

```
Ala Lys Tyr Gly Asp Pro Asp His Tyr Ser Lys Arg Tyr Thr Gly Thr
    210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
        275                 280                 285

Val Gln Ser Ala Thr Asp Leu Tyr Gly Ser Thr Ser Gln Glu Val Ala
    290                 295                 300

Ser Val Lys Gln Ala Phe Asp Ala Val Gly Val Lys
305                 310                 315


<210> SEQ ID NO 184
<211> LENGTH: 319
<212> TYPE: PRT
<213> ORGANISM: Bacillus caldoyticus

<400> SEQUENCE: 184

Val Ala Gly Thr Ser Thr Val Gly Val Gly Arg Gly Val Leu Gly Asp
1               5                   10                  15

Gln Lys Tyr Ile Asn Thr Thr Tyr Ser Ser Tyr Tyr Gly Tyr Tyr Tyr
            20                  25                  30

Leu Gln Asp Asn Thr Arg Gly Ser Gly Ile Phe Thr Tyr Asp Gly Arg
        35                  40                  45

Asn Arg Thr Val Leu Pro Gly Ser Leu Trp Ala Asp Gly Asp Asn Gln
    50                  55                  60

Phe Phe Ala Ser Tyr Asp Ala Ala Ala Val Asp Ala His Tyr Tyr Ala
65                  70                  75                  80

Gly Val Val Tyr Asp Tyr Tyr Lys Asn Val His Gly Arg Leu Ser Tyr
                85                  90                  95

Asp Gly Ser Asn Ala Ala Ile Arg Ser Thr Val His Tyr Gly Arg Gly
            100                 105                 110

Tyr Asn Asn Ala Phe Trp Asn Gly Ser Gln Met Val Tyr Gly Asp Gly
        115                 120                 125

Asp Gly Gln Thr Phe Leu Pro Phe Ser Gly Gly Ile Asp Val Val Gly
    130                 135                 140

His Glu Leu Thr His Ala Val Thr Asp Tyr Thr Ala Gly Leu Val Tyr
145                 150                 155                 160

Gln Asn Glu Ser Gly Ala Ile Asn Glu Ala Met Ser Asp Ile Phe Gly
                165                 170                 175

Thr Leu Val Glu Phe Tyr Ala Asn Arg Asn Pro Asp Trp Glu Ile Gly
            180                 185                 190

Glu Asp Ile Tyr Thr Pro Gly Val Ala Gly Asp Ala Leu Arg Ser Met
        195                 200                 205

Ser Asp Pro Ala Lys Tyr Gly Asp Pro Asp His Tyr Ser Lys Arg Tyr
    210                 215                 220

Thr Gly Thr Gln Asp Asn Gly Gly Val His Thr Asn Ser Gly Ile Ile
225                 230                 235                 240

Asn Lys Ala Ala Tyr Leu Leu Ser Gln Gly Gly Val His Tyr Gly Val
                245                 250                 255

Ser Val Thr Gly Ile Gly Arg Asp Lys Met Gly Lys Ile Phe Tyr Arg
```

```
        260                 265                 270

Ala Leu Val Tyr Tyr Leu Thr Pro Thr Ser Asn Phe Ser Gln Leu Arg
        275                 280                 285

Ala Ala Cys Val Gln Ala Ala Ala Asp Leu Tyr Gly Ser Thr Ser Gln
    290                 295                 300

Glu Val Asn Ser Val Lys Gln Ala Phe Asn Ala Val Gly Val Tyr
305                 310                 315


<210> SEQ ID NO 185
<211> LENGTH: 317
<212> TYPE: PRT
<213> ORGANISM: Bacillus cereus

<400> SEQUENCE: 185

Val Thr Gly Thr Asn Lys Val Gly Thr Gly Lys Gly Val Leu Gly Asp
1               5                   10                  15

Thr Lys Ser Leu Asn Thr Thr Leu Ser Gly Ser Ser Tyr Tyr Leu Gln
            20                  25                  30

Asp Asn Thr Arg Gly Ala Thr Ile Phe Thr Tyr Asp Ala Lys Asn Arg
        35                  40                  45

Ser Thr Leu Pro Gly Thr Leu Trp Ala Asp Ala Asp Asn Val Phe Asn
    50                  55                  60

Ala Ala Tyr Asp Ala Ala Ala Val Asp Ala His Tyr Tyr Ala Gly Lys
65                  70                  75                  80

Thr Tyr Asp Tyr Tyr Lys Ala Thr Phe Asn Arg Asn Ser Ile Asn Asp
                85                  90                  95

Ala Gly Ala Pro Leu Lys Ser Thr Val His Tyr Gly Ser Asn Tyr Asn
            100                 105                 110

Asn Ala Phe Trp Asn Gly Ser Gln Met Val Tyr Gly Asp Gly Asp Gly
        115                 120                 125

Val Thr Phe Thr Ser Leu Ser Gly Gly Ile Asp Val Ile Gly His Glu
    130                 135                 140

Leu Thr His Ala Val Thr Glu Asn Ser Ser Asn Leu Ile Tyr Gln Asn
145                 150                 155                 160

Glu Ser Gly Ala Leu Asn Glu Ala Ile Ser Asp Ile Phe Gly Thr Leu
                165                 170                 175

Val Glu Phe Tyr Asp Asn Arg Asn Pro Asp Trp Glu Ile Gly Glu Asp
            180                 185                 190

Ile Tyr Thr Pro Gly Lys Ala Gly Asp Ala Leu Arg Ser Met Ser Asp
        195                 200                 205

Pro Thr Lys Tyr Gly Asp Pro Asp His Tyr Ser Lys Arg Tyr Thr Gly
    210                 215                 220

Ser Ser Asp Asn Gly Gly Val His Thr Asn Ser Gly Ile Ile Asn Lys
225                 230                 235                 240

Gln Ala Tyr Leu Leu Ala Asn Gly Gly Thr His Tyr Gly Val Thr Val
                245                 250                 255

Thr Gly Ile Gly Lys Asp Lys Leu Gly Ala Ile Tyr Tyr Arg Ala Asn
            260                 265                 270

Thr Gln Tyr Phe Thr Gln Ser Thr Thr Phe Ser Gln Ala Arg Ala Gly
        275                 280                 285

Ala Val Gln Ala Ala Ala Asp Leu Tyr Gly Ala Asn Ser Ala Glu Val
    290                 295                 300

Ala Ala Val Lys Gln Ser Phe Ser Ala Val Gly Val Asn
305                 310                 315
```

<210> SEQ ID NO 186
<211> LENGTH: 304
<212> TYPE: PRT
<213> ORGANISM: Bacillus brevis

<400> SEQUENCE: 186

Val Thr Ala Thr Gly Lys Gly Val Leu Gly Asp Thr Lys Gln Phe Glu
1 5 10 15

Thr Thr Lys Gln Gly Ser Thr Tyr Met Leu Lys Asp Thr Thr Arg Gly
20 25 30

Lys Gly Ile Glu Thr Tyr Thr Ala Asn Asn Arg Thr Ser Leu Pro Gly
35 40 45

Thr Leu Met Thr Asp Ser Asp Asn Tyr Trp Thr Asp Gly Ala Ala Val
50 55 60

Asp Ala His Ala His Ala Gln Lys Thr Tyr Asp Tyr Phe Arg Asn Val
65 70 75 80

His Asn Arg Asn Ser Tyr Asp Gly Asn Gly Ala Val Ile Arg Ser Thr
85 90 95

Val His Tyr Ser Thr Arg Tyr Asn Asn Ala Phe Trp Asn Gly Ser Gln
100 105 110

Met Val Tyr Gly Asp Gly Asp Gly Thr Thr Phe Leu Pro Leu Ser Gly
115 120 125

Gly Leu Asp Val Val Ala His Glu Leu Thr His Ala Val Thr Glu Arg
130 135 140

Thr Ala Gly Leu Val Tyr Gln Asn Glu Ser Gly Ala Leu Asn Glu Ser
145 150 155 160

Met Ser Asp Ile Phe Gly Ala Met Val Asp Asn Asp Asp Trp Leu Met
165 170 175

Gly Glu Asp Ile Tyr Thr Pro Gly Arg Ser Gly Asp Ala Leu Arg Ser
180 185 190

Leu Gln Asp Pro Ala Ala Tyr Gly Asp Pro Asp His Tyr Ser Lys Arg
195 200 205

Tyr Thr Gly Ser Gln Asp Asn Gly Gly Val His Thr Asn Ser Gly Ile
210 215 220

Asn Asn Lys Ala Ala Tyr Leu Leu Ala Glu Gly Gly Thr His Tyr Gly
225 230 235 240

Val Arg Val Asn Gly Ile Gly Arg Thr Asp Thr Ala Lys Ile Tyr Tyr
245 250 255

His Ala Leu Thr His Tyr Leu Thr Pro Tyr Ser Asn Phe Ser Ala Met
260 265 270

Arg Arg Ala Ala Val Leu Ser Ala Thr Asp Leu Phe Gly Ala Asn Ser
275 280 285

Arg Gln Val Gln Ala Val Asn Ala Ala Tyr Asp Ala Val Gly Val Lys
290 295 300

<210> SEQ ID NO 187
<211> LENGTH: 302
<212> TYPE: PRT
<213> ORGANISM: Bacillus polymyxa

<400> SEQUENCE: 187

Ala Thr Gly Lys Gly Val Leu Gly Asp Ser Lys Ser Phe Thr Thr Thr
1 5 10 15

Ala Ser Gly Ser Ser Tyr Gln Leu Lys Asp Thr Thr Arg Gly Asn Gly
20 25 30

```
Ile Val Thr Tyr Thr Ala Ser Asn Arg Gln Ser Ile Pro Gly Thr Leu
        35                  40                  45

Leu Thr Asp Ala Asp Asn Val Trp Asn Asp Pro Ala Gly Val Asp Ala
    50                  55                  60

His Ala Tyr Ala Ala Lys Thr Tyr Asp Tyr Tyr Lys Ser Lys Phe Gly
65                  70                  75                  80

Arg Asn Ser Ile Asp Gly Arg Gly Leu Gln Leu Arg Ser Thr Val His
                85                  90                  95

Tyr Gly Ser Arg Tyr Asn Asn Ala Phe Trp Asn Gly Ser Gln Met Thr
            100                 105                 110

Tyr Gly Asp Gly Asp Gly Asp Gly Ser Thr Phe Ile Ala Phe Ser Gly
        115                 120                 125

Asp Pro Asp Val Val Gly His Glu Leu Thr His Gly Val Thr Glu Tyr
    130                 135                 140

Thr Ser Asn Leu Glu Tyr Tyr Gly Glu Ser Gly Ala Leu Asn Glu Ala
145                 150                 155                 160

Phe Ser Asp Val Ile Gly Asn Asp Ile Gln Arg Lys Asn Trp Leu Val
                165                 170                 175

Gly Asp Asp Ile Tyr Thr Pro Asn Ile Cys Gly Asp Ala Leu Arg Ser
            180                 185                 190

Met Ser Asn Pro Thr Leu Tyr Asp Gln Pro His His Tyr Ser Asn Leu
        195                 200                 205

Tyr Lys Gly Ser Ser Asp Asn Gly Gly Val His Thr Asn Ser Gly Ile
    210                 215                 220

Ile Asn Lys Ala Tyr Tyr Leu Leu Ala Gln Gly Gly Thr Phe His Gly
225                 230                 235                 240

Val Thr Val Asn Gly Ile Gly Arg Asp Ala Ala Val Gln Ile Tyr Tyr
                245                 250                 255

Ser Ala Phe Thr Asn Tyr Leu Thr Ser Ser Ser Asp Phe Ser Asn Ala
            260                 265                 270

Arg Ala Ala Val Ile Gln Ala Ala Lys Asp Leu Tyr Gly Ala Asn Ser
        275                 280                 285

Ala Glu Ala Thr Ala Ala Ala Lys Ser Phe Asp Ala Val Gly
    290                 295                 300


<210> SEQ ID NO 188
<211> LENGTH: 300
<212> TYPE: PRT
<213> ORGANISM: Bacillus pumilus

<400> SEQUENCE: 188

Ala Ala Ala Thr Gly Ser Gly Thr Thr Leu Lys Gly Ala Thr Val Pro
1               5                   10                  15

Leu Asn Ile Ser Tyr Glu Gly Gly Lys Tyr Val Leu Arg Asp Leu Ser
            20                  25                  30

Lys Pro Thr Gly Thr Gln Ile Ile Thr Tyr Asp Leu Gln Asn Arg Gln
        35                  40                  45

Ser Arg Leu Pro Gly Thr Leu Val Ser Ser Thr Thr Lys Thr Phe Thr
    50                  55                  60

Ser Ser Ser Gln Arg Ala Ala Val Asp Ala His Tyr Asn Leu Gly Lys
65                  70                  75                  80

Val Tyr Asp Tyr Phe Tyr Ser Asn Phe Lys Arg Asn Ser Tyr Asp Asn
                85                  90                  95

Lys Gly Ser Lys Ile Val Ser Ser Val His Tyr Gly Thr Gln Tyr Asn
            100                 105                 110
```

```
Asn Ala Ala Trp Thr Gly Asp Gln Met Ile Tyr Gly Asp Gly Asp Gly
        115                 120                 125

Ser Phe Phe Ser Pro Leu Ser Gly Ser Leu Asp Val Thr Ala His Glu
    130                 135                 140

Met Thr His Gly Val Thr Gln Glu Thr Ala Asn Leu Ile Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Asn Gln Pro Asp
        195                 200                 205

Asn Tyr Ala Asn Tyr Arg Asn Leu Pro Asn Thr Asp Glu Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Leu Gly Val Ser Lys Ser Gln Gln Ile Tyr Tyr Arg
                245                 250                 255

Ala Leu Thr Thr Tyr Leu Thr Pro Ser Ser Thr Phe Lys Asp Ala Lys
            260                 265                 270

Ala Ala Leu Ile Gln Ser Ala Arg Asp Leu Tyr Gly Ser Thr Asp Ala
        275                 280                 285

Ala Lys Val Glu Ala Ala Trp Asn Ala Val Gly Leu
    290                 295                 300


<210> SEQ ID NO 189
<211> LENGTH: 300
<212> TYPE: PRT
<213> ORGANISM: Bacillus subtilis var.

<400> SEQUENCE: 189

Ala Ala Ala Thr Gly Ser Gly Thr Thr Leu Lys Gly Ala Thr Val Pro
1               5                   10                  15

Leu Asn Ile Ser Tyr Glu Gly Gly Lys Tyr Val Leu Arg Asp Leu Ser
            20                  25                  30

Lys Pro Thr Gly Thr Gln Ile Ile Thr Tyr Asp Leu Gln Asn Arg Gln
        35                  40                  45

Ser Arg Leu Pro Gly Thr Leu Val Ser Ser Thr Thr Lys Thr Phe Thr
    50                  55                  60

Ser Ser Ser Gln Arg Ala Ala Val Asp Ala His Tyr Asn Leu Gly Lys
65                  70                  75                  80

Val Tyr Asp Tyr Phe Tyr Ser Asn Phe Lys Arg Asn Ser Tyr Asp Asn
                85                  90                  95

Lys Gly Ser Lys Ile Val Ser Ser Val His Tyr Gly Thr Gln Tyr Asn
            100                 105                 110

Asn Ala Ala Trp Thr Gly Asp Gln Met Ile Tyr Gly Asp Gly Asp Gly
        115                 120                 125

Ser Phe Phe Ser Pro Leu Ser Gly Ser Leu Asp Val Thr Ala His Glu
    130                 135                 140

Met Thr His Gly Val Thr Gln Glu Thr Ala Asn Leu Ile Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
```

-continued

```
            180                 185                 190

Pro Ala Leu Arg Ser Leu Ser Asn Pro Thr Lys Tyr Asn Gln Pro Asp
        195                 200                 205

Asn Tyr Ala Asn Tyr Arg Asn Leu Pro Asn Thr Asp Glu Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Leu Gly Val Ser Lys Ser Gln Gln Ile Tyr Tyr Arg
                245                 250                 255

Ala Leu Thr Thr Tyr Leu Thr Pro Ser Ser Thr Phe Lys Asp Ala Lys
            260                 265                 270

Ala Ala Leu Ile Gln Ser Ala Arg Asp Leu Tyr Gly Ser Thr Asp Ala
        275                 280                 285

Ala Lys Val Glu Ala Ala Trp Asn Ala Val Gly Leu
    290                 295                 300


<210> SEQ ID NO 190
<211> LENGTH: 230
<212> TYPE: PRT
<213> ORGANISM: Bacillus subtilis

<400> SEQUENCE: 190

Ala Val Asp Ala His Tyr Asn Leu Gly Lys Val Tyr Asp Tyr Phe Tyr
1               5                   10                  15

Ser Asn Phe Lys Arg Asn Ser Tyr Asp Asn Lys Gly Ser Lys Ile Val
            20                  25                  30

Ser Ser Val His Tyr Gly Thr Gln Tyr Asn Asn Ala Ala Trp Thr Gly
        35                  40                  45

Asp Gln Met Ile Tyr Gly Asp Gly Asp Gly Ser Phe Phe Ser Pro Leu
    50                  55                  60

Ser Gly Ser Leu Asp Val Thr Ala His Glu Met Thr His Gly Val Thr
65                  70                  75                  80

Gln Glu Thr Ala Asn Leu Ile Tyr Glu Asn Gln Pro Gly Ala Leu Asn
                85                  90                  95

Glu Ser Phe Ser Asp Val Phe Gly Tyr Phe Asn Asp Thr Glu Asp Trp
            100                 105                 110

Asp Ile Gly Glu Asp Ile Thr Val Ser Gln Pro Ala Leu Arg Ser Leu
        115                 120                 125

Ser Asn Pro Thr Lys Tyr Asn Gln Pro Asp Asn Tyr Ala Asn Tyr Arg
    130                 135                 140

Asn Leu Pro Asn Thr Asp Glu Gly Asp Tyr Gly Gly Val His Thr Asn
145                 150                 155                 160

Ser Gly Ile Pro Asn Lys Ala Ala Tyr Asn Thr Ile Thr Lys Leu Gly
                165                 170                 175

Val Ser Lys Ser Gln Gln Ile Tyr Tyr Arg Ala Leu Thr Thr Tyr Leu
            180                 185                 190

Thr Pro Ser Ser Thr Phe Lys Asp Ala Lys Ala Ala Leu Ile Gln Ser
        195                 200                 205

Ala Arg Asp Leu Tyr Gly Ser Thr Asp Ala Ala Lys Val Glu Ala Ala
    210                 215                 220

Trp Asn Ala Val Gly Leu
225                 230


<210> SEQ ID NO 191
<211> LENGTH: 300
```

```
<212> TYPE: PRT
<213> ORGANISM: Bacillus amyloliquefaciens

<400> SEQUENCE: 191

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300


<210> SEQ ID NO 192
<211> LENGTH: 300
<212> TYPE: PRT
<213> ORGANISM: Bacillus amyloliquefaciens

<400> SEQUENCE: 192

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45
```

-continued

```
Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300


<210> SEQ ID NO 193
<211> LENGTH: 301
<212> TYPE: PRT
<213> ORGANISM: Staphylococcus aureos

<400> SEQUENCE: 193

Ala Ala Ala Thr Gly Thr Gly Lys Gly Val Leu Gly Asp Thr Lys Asp
1               5                   10                  15

Ile Asn Ile Asn Ser Ile Asp Gly Gly Phe Ser Leu Glu Asp Leu Thr
            20                  25                  30

His Gln Gly Lys Leu Ser Ala Tyr Asn Phe Asn Asp Gln Thr Gly Gln
        35                  40                  45

Ala Thr Leu Ile Thr Asn Glu Asp Glu Asn Phe Val Lys Asp Asp Gln
    50                  55                  60

Arg Ala Gly Val Asp Ala Asn Tyr Tyr Ala Lys Gln Thr Tyr Asp Tyr
65                  70                  75                  80

Tyr Lys Asn Thr Phe Gly Arg Glu Ser Tyr Asp Asn His Gly Ser Pro
                85                  90                  95

Ile Val Ser Leu Thr His Val Asn His Tyr Gly Gly Gln Asp Asn Arg
            100                 105                 110

Asn Asn Ala Ala Trp Ile Gly Asp Lys Met Ile Tyr Gly Asp Gly Asp
        115                 120                 125
```

```
Gly Arg Thr Phe Thr Asn Leu Ser Gly Ala Asn Asp Val Val Ala His
    130                 135                 140

Glu Ile Thr His Gly Val Thr Gln Gln Thr Ala Asn Leu Glu Tyr Lys
145                 150                 155                 160

Asp Gln Ser Gly Ala Leu Asn Glu Ser Phe Ser Asp Val Phe Gly Tyr
                165                 170                 175

Phe Val Asp Asp Glu Asp Phe Leu Met Gly Glu Asp Val Tyr Thr Pro
            180                 185                 190

Gly Lys Glu Gly Asp Ala Leu Arg Ser Met Ser Asn Pro Glu Gln Phe
        195                 200                 205

Gly Gln Pro Ser His Met Lys Asp Tyr Val Tyr Thr Glu Lys Asp Asn
    210                 215                 220

Gly Gly Val His Thr Asn Ser Gly Ile Pro Asn Lys Ala Ala Tyr Asn
225                 230                 235                 240

Val Ile Gln Ala Ile Gly Lys Ser Lys Ser Glu Gln Ile Tyr Tyr Arg
                245                 250                 255

Ala Leu Thr Glu Tyr Leu Thr Ser Asn Ser Asn Phe Lys Asp Leu Lys
            260                 265                 270

Asp Ala Leu Tyr Gln Ala Ala Lys Asp Leu Tyr Glu Gln Gln Thr Ala
        275                 280                 285

Glu Gln Val Tyr Glu Ala Trp Asn Glu Val Gly Val Glu
    290                 295                 300


<210> SEQ ID NO 194
<211> LENGTH: 298
<212> TYPE: PRT
<213> ORGANISM: Pseudomonas aeruginosa

<400> SEQUENCE: 194

Ala Glu Ala Gly Gly Pro Gly Gly Asn Gln Lys Ile Gly Lys Tyr Thr
1               5                   10                  15

Tyr Gly Ser Asp Tyr Gly Pro Leu Ile Val Asn Asp Arg Cys Glu Met
            20                  25                  30

Asp Asp Gly Asn Val Ile Thr Val Asp Met Asn Ser Ser Thr Asp Asp
        35                  40                  45

Ser Lys Thr Thr Pro Phe Arg Phe Ala Cys Pro Thr Asn Thr Tyr Lys
    50                  55                  60

Gln Val Asn Gly Ala Tyr Ser Pro Leu Asn Asp Ala His Phe Phe Gly
65                  70                  75                  80

Gly Val Val Phe Lys Leu Tyr Arg Asp Trp Phe Gly Thr Ser Pro Leu
                85                  90                  95

Thr His Lys Leu Tyr Met Lys Val His Tyr Gly Arg Ser Val Glu Asn
            100                 105                 110

Ala Tyr Trp Asp Gly Thr Ala Met Leu Phe Gly Asp Gly Ala Thr Met
        115                 120                 125

Phe Tyr Pro Leu Val Ser Leu Asp Val Ala Ala His Glu Val Ser His
    130                 135                 140

Gly Phe Thr Glu Gln Asn Ser Gly Leu Ile Tyr Arg Gly Gln Ser Gly
145                 150                 155                 160

Gly Met Asn Glu Ala Phe Ser Asp Met Ala Gly Glu Ala Ala Glu Phe
                165                 170                 175

Tyr Met Arg Gly Lys Asn Asp Phe Leu Ile Gly Tyr Asp Ile Lys Lys
            180                 185                 190

Gly Ser Gly Ala Leu Arg Tyr Met Asp Gln Pro Ser Arg Asp Gly Arg
```

```
        195                 200                 205

Ser Ile Asp Asn Ala Ser Gln Tyr Tyr Asn Gly Ile Asp Val His His
    210                 215                 220

Ser Ser Gly Val Tyr Asn Arg Ala Phe Tyr Leu Leu Ala Asn Ser Pro
225                 230                 235                 240

Gly Trp Asp Thr Arg Lys Ala Phe Glu Val Phe Val Asp Ala Asn Arg
                245                 250                 255

Tyr Tyr Trp Thr Ala Thr Ser Asn Tyr Asn Ser Gly Ala Cys Gly Val
            260                 265                 270

Ile Arg Ser Ala Gln Asn Arg Asn Tyr Ser Ala Ala Asp Val Thr Arg
        275                 280                 285

Ala Phe Ser Thr Val Gly Val Thr Cys Pro
    290                 295


<210> SEQ ID NO 195
<211> LENGTH: 317
<212> TYPE: PRT
<213> ORGANISM: Bacillus cereus

<400> SEQUENCE: 195

Val Thr Gly Thr Asn Lys Val Gly Thr Gly Lys Gly Val Leu Gly Asp
1               5                   10                  15

Thr Lys Ser Leu Asn Thr Thr Leu Ser Gly Ser Ser Tyr Tyr Leu Gln
            20                  25                  30

Asp Asn Thr Arg Gly Ala Thr Ile Phe Thr Tyr Asp Ala Lys Asn Arg
        35                  40                  45

Ser Thr Leu Pro Gly Thr Leu Trp Ala Asp Ala Asp Asn Val Phe Asn
    50                  55                  60

Ala Ala Tyr Asp Ala Ala Ala Val Asp Ala His Tyr Tyr Ala Gly Lys
65                  70                  75                  80

Thr Tyr Asp Tyr Tyr Lys Ala Thr Phe Asn Arg Asn Ser Ile Asn Asp
                85                  90                  95

Ala Gly Ala Pro Leu Lys Ser Thr Val His Tyr Gly Ser Asn Tyr Asn
            100                 105                 110

Asn Ala Phe Trp Asn Gly Ser Gln Met Val Tyr Gly Asp Gly Asp Gly
        115                 120                 125

Val Thr Phe Thr Ser Leu Ser Gly Gly Ile Asp Val Ile Gly His Glu
    130                 135                 140

Leu Thr His Ala Val Thr Glu Asn Ser Ser Asn Leu Ile Tyr Gln Asn
145                 150                 155                 160

Glu Ser Gly Ala Leu Asn Glu Ala Ile Ser Asp Ile Phe Gly Thr Leu
                165                 170                 175

Val Glu Phe Tyr Asp Asn Arg Asn Pro Asp Trp Glu Ile Gly Glu Asp
            180                 185                 190

Ile Tyr Thr Pro Gly Lys Ala Gly Asp Ala Leu Arg Ser Met Ser Asp
        195                 200                 205

Pro Thr Lys Tyr Gly Asp Pro Asp His Tyr Ser Lys Arg Tyr Thr Gly
    210                 215                 220

Ser Ser Asp Asn Gly Gly Val His Thr Asn Ser Gly Ile Ile Asn Lys
225                 230                 235                 240

Gln Ala Tyr Leu Leu Ala Asn Gly Gly Thr His Tyr Gly Val Thr Val
                245                 250                 255

Thr Gly Ile Gly Lys Asp Lys Leu Gly Ala Ile Tyr Tyr Arg Ala Asn
            260                 265                 270
```

-continued

```
Thr Gln Tyr Phe Thr Gln Ser Thr Thr Phe Ser Gln Ala Arg Ala Gly
        275                 280                 285

Ala Val Gln Ala Ala Ala Asp Leu Tyr Gly Ala Asn Ser Ala Glu Val
    290                 295                 300

Ala Ala Val Lys Gln Ser Phe Ser Ala Val Gly Val Asn
305                 310                 315


<210> SEQ ID NO 196
<211> LENGTH: 30
<212> TYPE: DNA
<213> ORGANISM: Artificial Sequence
<220> FEATURE:
<223> OTHER INFORMATION: primer

<400> SEQUENCE: 196

cgtcttcaac aattgtccat tttcttctgc                                        30


<210> SEQ ID NO 197
<211> LENGTH: 53
<212> TYPE: DNA
<213> ORGANISM: Artificial Sequence
<220> FEATURE:
<223> OTHER INFORMATION: primer

<400> SEQUENCE: 197

cagacaattt cttacctaaa cccactcttt accctctcct tttaaaaaaa ttc               53


<210> SEQ ID NO 198
<211> LENGTH: 53
<212> TYPE: DNA
<213> ORGANISM: Artificial Sequence
<220> FEATURE:
<223> OTHER INFORMATION: primer

<400> SEQUENCE: 198

gaattttttt aaaaggagag ggtaaagagt gggtttaggt aagaaattgt ctg               53


<210> SEQ ID NO 199
<211> LENGTH: 32
<212> TYPE: DNA
<213> ORGANISM: Artificial Sequence
<220> FEATURE:
<223> OTHER INFORMATION: primer

<400> SEQUENCE: 199

gcttatggat cccgtcgttt cagctgagag ag                                      32


<210> SEQ ID NO 200
<211> LENGTH: 51
<212> TYPE: DNA
<213> ORGANISM: Artificial Sequence
<220> FEATURE:
<223> OTHER INFORMATION: primer

<400> SEQUENCE: 200

gatgtcttgg tcaagttgcg cactctttac cctctccttt taaaaaaatt c                 51


<210> SEQ ID NO 201
<211> LENGTH: 51
<212> TYPE: DNA
<213> ORGANISM: Artificial Sequence
<220> FEATURE:
<223> OTHER INFORMATION: primer

<400> SEQUENCE: 201
```

gaattttttt aaaaggagag ggtaaagagt gcgcaacttg accaagacat c 51

<210> SEQ ID NO 202
<211> LENGTH: 50
<212> TYPE: DNA
<213> ORGANISM: Artificial Sequence
<220> FEATURE:
<223> OTHER INFORMATION: primer

<400> SEQUENCE: 202
ccaaggccgg ttttttatgt aagcttatag aatgccgaca gcctcatacg 50

<210> SEQ ID NO 203
<211> LENGTH: 50
<212> TYPE: DNA
<213> ORGANISM: Artificial Sequence
<220> FEATURE:
<223> OTHER INFORMATION: primer

<400> SEQUENCE: 203
cgtatgaggc tgtcggcatt ctataagctt acataaaaaa ccggccttgg 50

<210> SEQ ID NO 204
<211> LENGTH: 24
<212> TYPE: DNA
<213> ORGANISM: Artificial Sequence
<220> FEATURE:
<223> OTHER INFORMATION: primer

<400> SEQUENCE: 204
aatggtgcat gcaaggagat ggcg 24

<210> SEQ ID NO 205
<211> LENGTH: 31
<212> TYPE: DNA
<213> ORGANISM: Artificial Sequence
<220> FEATURE:
<223> OTHER INFORMATION: primer

<400> SEQUENCE: 205
cgtcttcaag aattcctcca ttttcttctg c 31

<210> SEQ ID NO 206
<211> LENGTH: 54
<212> TYPE: DNA
<213> ORGANISM: Artificial Sequence
<220> FEATURE:
<223> OTHER INFORMATION: primer

<400> SEQUENCE: 206
gcacccaaca ttgcacgttt attcactctt taccctctcc ttttaaaaaa attc 54

<210> SEQ ID NO 207
<211> LENGTH: 54
<212> TYPE: DNA
<213> ORGANISM: Artificial Sequence
<220> FEATURE:
<223> OTHER INFORMATION: primer

<400> SEQUENCE: 207
gaattttttt aaaaggagag ggtaaagagt gaataaacgt gcaatgttgg gtgc 54

<210> SEQ ID NO 208
<211> LENGTH: 32
<212> TYPE: DNA
<213> ORGANISM: Artificial Sequence
<220> FEATURE:
<223> OTHER INFORMATION: primer

<400> SEQUENCE: 208
gcttataagc ttaatatact ccaaccgcgt tg 32

<210> SEQ ID NO 209
<211> LENGTH: 50
<212> TYPE: DNA
<213> ORGANISM: Artificial Sequence
<220> FEATURE:
<223> OTHER INFORMATION: primer

<400> SEQUENCE: 209
ccagcatagc gcgtttgttc actctttacc ctctcctttt aaaaaaattc 50

<210> SEQ ID NO 210
<211> LENGTH: 50
<212> TYPE: DNA
<213> ORGANISM: Artificial Sequence
<220> FEATURE:
<223> OTHER INFORMATION: primer

<400> SEQUENCE: 210
gaattttttt aaaaggagag ggtaaagagt gaacaaacgc gctatgctgg 50

<210> SEQ ID NO 211
<211> LENGTH: 38
<212> TYPE: DNA
<213> ORGANISM: Artificial Sequence
<220> FEATURE:
<223> OTHER INFORMATION: primer

<400> SEQUENCE: 211
gcttataagc ttaatagaca cccacggcat taaacgcc 38

<210> SEQ ID NO 212
<211> LENGTH: 58
<212> TYPE: DNA
<213> ORGANISM: Artificial Sequence
<220> FEATURE:
<223> OTHER INFORMATION: primer

<400> SEQUENCE: 212
caggacaaga gctaaggact ttttttcac tctttaccct ctccttttaa aaaaattc 58

<210> SEQ ID NO 213
<211> LENGTH: 58
<212> TYPE: DNA
<213> ORGANISM: Artificial Sequence
<220> FEATURE:
<223> OTHER INFORMATION: primer

<400> SEQUENCE: 213
gaattttttt aaaaggagag ggtaaagagt gaaaaaaaag tccttagctc ttgtcctg 58

<210> SEQ ID NO 214
<211> LENGTH: 30
<212> TYPE: DNA
<213> ORGANISM: Artificial Sequence
<220> FEATURE:
<223> OTHER INFORMATION: primer

<400> SEQUENCE: 214
gcttataagc ttaattaatg ccgacggcac 30

<210> SEQ ID NO 215
<211> LENGTH: 10
<212> TYPE: PRT
<213> ORGANISM: Bacillus amyloliquefaciens

<400> SEQUENCE: 215

Ala Ala Thr Thr Gly Thr Gly Thr Thr Leu
1 5 10

<210> SEQ ID NO 216
<211> LENGTH: 10
<212> TYPE: PRT
<213> ORGANISM: Bacillus amyloliquefaciens

<400> SEQUENCE: 216

Asp Ala Gly Asp Tyr Gly Gly Val His Thr
1 5 10

<210> SEQ ID NO 217
<211> LENGTH: 10
<212> TYPE: PRT
<213> ORGANISM: Bacillus amyloliquefaciens

<400> SEQUENCE: 217

Ala Gly Asp Tyr Gly Gly Val His Thr Asn
1 5 10

<210> SEQ ID NO 218
<211> LENGTH: 9
<212> TYPE: PRT
<213> ORGANISM: Bacillus amyloliquefaciens

<400> SEQUENCE: 218

Gly Asp Tyr Gly Gly Val His Thr Asn
1 5

<210> SEQ ID NO 219
<211> LENGTH: 10
<212> TYPE: PRT
<213> ORGANISM: Bacillus amyloliquefaciens

<400> SEQUENCE: 219

Ala Ala Thr Thr Gly Thr Gly Thr Thr Leu
1 5 10

<210> SEQ ID NO 220
<211> LENGTH: 10
<212> TYPE: PRT
<213> ORGANISM: Bacillus amyloliquefaciens

<400> SEQUENCE: 220

Ala Ala Thr Thr Gly Thr Gly Thr Thr Leu
1 5 10

<210> SEQ ID NO 221
<211> LENGTH: 10
<212> TYPE: PRT
<213> ORGANISM: Bacillus amyloliquefaciens

<400> SEQUENCE: 221

Leu Ser Asn Pro Thr Lys Tyr Gly Gln Pro
1 5 10

<210> SEQ ID NO 222

<211> LENGTH: 219
<212> TYPE: PRT
<213> ORGANISM: Bacillus amyloliquefaciens

<400> SEQUENCE: 222

```
Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr
    210                 215
```

<210> SEQ ID NO 223
<211> LENGTH: 81
<212> TYPE: PRT
<213> ORGANISM: Bacillus amyloliquefaciens

<400> SEQUENCE: 223

```
Asp Ala Gly Asp Tyr Gly Gly Val His Thr Asn Ser Gly Ile Pro Asn
1               5                   10                  15

Lys Ala Ala Tyr Asn Thr Ile Thr Lys Ile Gly Val Asn Lys Ala Glu
            20                  25                  30

Gln Ile Tyr Tyr Arg Ala Leu Thr Val Tyr Leu Thr Pro Ser Ser Thr
        35                  40                  45

Phe Lys Asp Ala Lys Ala Ala Leu Ile Gln Ser Ala Arg Asp Leu Tyr
    50                  55                  60

Gly Ser Gln Asp Ala Ala Ser Val Glu Ala Ala Trp Asn Ala Val Gly
65                  70                  75                  80

Leu
```

<210> SEQ ID NO 224
<211> LENGTH: 197
<212> TYPE: PRT
<213> ORGANISM: Bacillus amyloliquefaciens

<400> SEQUENCE: 224

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser
        195

<210> SEQ ID NO 225
<211> LENGTH: 140
<212> TYPE: PRT
<213> ORGANISM: Bacillus amyloliquefaciens

<400> SEQUENCE: 225

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val
    130                 135                 140

<210> SEQ ID NO 226
<211> LENGTH: 103

-continued

```
<212> TYPE: PRT
<213> ORGANISM: Bacillus amyloliquefaciens

<400> SEQUENCE: 226

Leu Ser Asn Pro Thr Lys Tyr Gly Gln Pro Asp Asn Phe Lys Asn Tyr
1               5                   10                  15

Lys Asn Leu Pro Asn Thr Asp Ala Gly Asp Tyr Gly Gly Val His Thr
            20                  25                  30

Asn Ser Gly Ile Pro Asn Lys Ala Ala Tyr Asn Thr Ile Thr Lys Ile
        35                  40                  45

Gly Val Asn Lys Ala Glu Gln Ile Tyr Tyr Arg Ala Leu Thr Val Tyr
    50                  55                  60

Leu Thr Pro Ser Ser Thr Phe Lys Asp Ala Lys Ala Ala Leu Ile Gln
65                  70                  75                  80

Ser Ala Arg Asp Leu Tyr Gly Ser Gln Asp Ala Ala Ser Val Glu Ala
                85                  90                  95

Ala Trp Asn Ala Val Gly Leu
            100
```